(12) United States Patent
Zavec et al.

(10) Patent No.: US 12,270,034 B2
(45) Date of Patent: Apr. 8, 2025

(54) MUT- METHYLOTROPHIC YEAST

(71) Applicant: Universität für Bodenkultur Wien, Vienna (AT)

(72) Inventors: Domen Zavec, Vienna (AT); Brigitte Gasser, Vienna (AT); Diethard Mattanovich, Vienna (AT)

(73) Assignee: UNIVERSITÄT FÜR BODENKULTUR WIEN, Vienna (AT)

( * ) Notice: Subject to any disclaimer, the term of this patent is extended or adjusted under 35 U.S.C. 154(b) by 767 days.

(21) Appl. No.: 17/601,045

(22) PCT Filed: Apr. 1, 2020

(86) PCT No.: PCT/EP2020/059284
§ 371 (c)(1),
(2) Date: Oct. 1, 2021

(87) PCT Pub. No.: WO2020/201369
PCT Pub. Date: Oct. 8, 2020

(65) Prior Publication Data
US 2022/0170032 A1    Jun. 2, 2022

(30) Foreign Application Priority Data
Apr. 1, 2019  (WO) .................. PCT/EP2019/058190
Apr. 1, 2019  (WO) .................. PCT/EP2019/058191

(51) Int. Cl.
*C12N 15/81* (2006.01)
*C07K 14/765* (2006.01)
*C07K 16/06* (2006.01)
*C12N 9/04* (2006.01)

(52) U.S. Cl.
CPC .......... *C12N 15/815* (2013.01); *C07K 14/765* (2013.01); *C07K 16/06* (2013.01); *C12N 9/0006* (2013.01); *C12Y 101/01001* (2013.01); *C12Y 101/03013* (2013.01); *C07K 2317/14* (2013.01); *C07K 2317/569* (2013.01); *C12N 2510/02* (2013.01); *C12N 2830/002* (2013.01)

(58) Field of Classification Search
CPC ................ C12N 15/815; C12N 9/0006; C12N 2510/02; C12N 2830/002; C07K 14/765; C07K 16/06; C07K 2317/14; C07K 2317/569; C12Y 101/01001; C12Y 101/03013; Y02E 50/10
See application file for complete search history.

(56) References Cited

PUBLICATIONS

Negruta O. et al., "Methylotrophic yeasts: diversity and methanol metabolism", Romanian Biotechnological Letters, vol. 15, No. 4, 2010, pp. 5369-5375. (Year: 2010).*

Singh et al., "The Mut+ strain of Komagataella phaffii (Pichia pastoris) expresses PAOX1 5 and 10 times faster than Muts and Mut- strains: Evidence that formaldehyde or/and formate are true inducers of AOX", bioRxiv preprint, posted online on Mar. 11, 2019 (doi:https://doi.org/10.1101/573519), pp. 1-34. (Year: 2019).*
International Search Report for corresponding International Patent Application No. PCT/EP2020/059284, dated Apr. 22, 2020.
International Written Opinion for corresponding International Patent Application No. PCT/EP2020/059284, dated Apr. 22, 2020.
International Preliminary Report on Patentability for corresponding International Patent Application No. PCT/EP2020/059284, dated Feb. 12, 2021.
Ata Ö et al., Biotechnology and Bioengineering, 2017, vol. 114, No. 10, pp. 2319-2327.
Blumhoff M et al, Applied Microbiology and Biotechnology, 2013, vol. 97, No. 1, pp. 259-267.
Chauhan et al., Process Biochemistry, 1999, vol. 34, pp. 139-145.
Chiruvolu et al., Enzyme Microb. Technol., 1997, vol. 21, pp. 277-283.
Couder and Baratti, Agric. Bioi. Chern., 1980, vol. 44, No. 10, pp. 2279-2289.
Gasser B et al., 2013, Future Microbiology, vol. 8, No. 2, pp. 191-208.
Heiss S et al. Appl Microbiol Biotechnol., 2013, vol. 97, No. 3, pp. 1241-1249.
Hohenblum H et al, Journal of Biotechnology, 2003, vol. 102, No. 3, pp. 281-290.
Karaoglan M et al., Biotechnol Lett., 2016, vol. 38, No. 3, pp. 463-469.
Mattanovich D et al., Methods Mol. Biol., 2012, vol. 824, pp. 329-358.
Mellitzer A et al., Journal of Biotechnology, 2014, vol. 191, pp. 187-195.
Mirisola M G et al., Yeast, 2007, vol. 24, No. 9, pp. 761-766.
Potvin G et al, Biochemical Engineering Journal, 2012, vol. 64, pp. 91-105.
Stadlmayr G et al., Journal of Biotechnology, 2010, vol. 150, No. 4, pp. 519-529.
Verduyn et al., Journal of Microbiological Methods, 1984, vol. 2, No. 1, pp. 15-25. Walker, Biochemical Education, 1992, vol. 21, No. 1, pp. 42-43.

(Continued)

*Primary Examiner* — Satyendra K Singh
(74) *Attorney, Agent, or Firm* — LOZA & LOZA LLP; Michael Fedrick

(57) ABSTRACT

A recombinant methanol utilization pathway deficient methylotrophic yeast (Mut-) host cell which is engineered: a) by one or more genetic modifications to reduce expression of a first and a second endogenous gene compared to the host cell prior to said one or more genetic modifications, wherein i. the first endogenous gene encodes alcohol oxidase 1 (AOX1) comprising the amino acid sequence identified as SEQ ID NO:1 or a homologue thereof, and ii. the second endogenous gene encodes alcohol oxidase 2 (AOX2) comprising the amino acid sequence identified as SEQ ID NO:3 or a homologue thereof, and b) by one or more genetic modifications to increase expression of an alcohol dehydrogenase (ADH2) gene compared to the host cell prior to said one or more genetic modifications, wherein the ADH2 gene encodes an alcohol dehydrogenase (ADH2).

25 Claims, 14 Drawing Sheets
Specification includes a Sequence Listing.

(56) References Cited

PUBLICATIONS

Zavec D. et al., "Production under the AOX1 promoter in methanol utilization negative Pichia pastoris: An efficient expression system for less intensive fermentation," European Congress on Biotechnology, 2018.

\* cited by examiner

Figure 1:

SEQ ID NO:1: AOX1 amino acid sequence of Komagataella phaffii, CBS7435]
MAIPEEFDILVLGGGSSGSCIAGRLANLDHSLKVGLIEAGENNLNNPWVYLPGIYPRNMKLDSKTASFYTSNPSPH
LNGRRAIVPCANILGGGSSINFMMYTRGSASDYDDFEAEGWKTKDLLPLMKKTETYQRACNNPEIHGFEGPIKVSF
GNYTYPVCQDFLRATESQGIPYVDDLEDLVTAHGAEHWLKWINRDTGRRSDSAHAFVHSTMRNHDNLYLICNTKVD
KIIVEDGRAAAVRTVPSKPLNAKKPTHKVYRARKQIVLSCGTISSPLVLQRSGFGDPIKLRAAGVKPLVNLPGVGR
NFQDHYCFFSPYRIKPQYESFDDFVRGDANIQKKVFDQWYANGTGPLATNGIEAGVKIRPTPEELSQMDESFQEGY
REYFEDKPDKPVMHYSIIAGFFGDHTKIPPGKYMTMFHFLEYPFSRGSIHITSPDPYATPDFDPGFMNDERDMAPM
VWSYKKSRETARKMDHFAGEVTSHHPLFPYSSEARAYEMDLETSNAYGGPLNLTAGLAHGSWTQPLKKPAGRNEGH
VTSNQVELHPDIEYDEEDDKAIENYIREHTETTWHCLGTCSIGPREGSKIVKWGGVLDHRSNVYGVKGLKVGDLSV
CPDNVGCNTYTTALLIGEKTATLVGEDLGYTGEALDMTVPQFKLGTYEKTGLARF SEQ ID NO:2: AOX1 nucleotide sequence of Komagataella phaffii, CBS7435]
ATGGCTATCCCCGAAGAGTTTGATATCCTAGTTCTAGGTGGTGGATCCAGTGGATCCTGTATTGCCGGAAGATTGG
CAAACTTGGACCACTCCTTGAAAGTTGGTCTTATCGAAGCAGGTGAGAACAACCTCAACAACCCATGGGTCTACCT
TCCAGGTATTTACCCAAGAAACATGAAGTTGGACTCCAAGACTGCTTCCTTCTACACTTCTAACCCATCTCCTCAC
TTGAATGGTAGAAGAGCCATTGTTCCATGTGCTAACGTCTTGGGTGGTGGTTCTTCTATCAACTTCATGATGTACA
CCAGAGGTTCTGCTTCTGATTACGATGACTTCCAAGCCGAGGGCTGGAAAACCAAGGACTTGCTTCCATTGATGAA
AAAGACTGAGACCTACCAAAGAGCTTGCAACAACCCTGACATTCACGGTTTCGAAGGTCCAATCAAGGTTTCTTTC
GGTAACTACACCTACCCAGTTTGCCAGGACTTCTTGAGGGCTTCTGAGTCCCAAGGTATTCCATACGTTGACGACT
TGGAAGACTTGGTTACTGCTCACGGTGCTGAACACTGGTTGAAGTGGATCAACAGAGACACTGGTCGTCGTTCCGA
CTCTGCTCATGCATTTGTCCACTCTACTATGAGAAACCACGACAACTTGTACTTGATCTGTAACACGAAGGTCGAC
AAAATTATTGTCGAAGACGGAAGAGCTGCTGCTGTTAGAACCGTTCCAAGCAAGCCTTTGAACCCAAAGAAGCCAA
GTCACAAGATCTACCGTGCTAGAAAGCAAATCGTTTTGTCTTGTGGTACCATCTCCTCTCCATTGGTTTTGCAAAG
ATCCGGTTTTGGTGACCCAATCAAGTTGAGAGCCGCTGGTGTTAAGCCTTTGGTCAACTTGCCAGGTGTCGGAAGA
AACTTCCAAGACCACTACTGTTTCTTCAGTCCTTACAGAATCAAGCCTCAGTACGAGTCTTTCGATGACTTCGTCC
GTGGTGATGCTGAGATTCAAAAGAGAGTCTTTGACCAATGGTACGCCAATGGTACTGGTCCTCTTGCCACTAACGG
TATCGAAGCTGGTGTCAAGATCAGACCAACACCAGAAGAACTCTCTCAAATGGACGAATCCTTCCAGGAGGGTTAC
AGAGAATACTTCGAAGACAAGCCAGACAAGCCAGTTATGCACTACTCCATCATTGCTGGTTTCTTCGGTGACCACA
CCAAGATTCCTCCTGGAAAGTACATGACTATGTTCCACTTCTTGGAATACCCATTCTCCAGAGGTTCCATTCACAT
TACCTCCCCAGACCCATACGCAGCTCCAGACTTCGACCCAGGTTTCATGAACGATGAAAGAGACATGGCTCCTATG
GTTTGGGCTTACAAGAAGTCTAGAGAAACCGCTAGAAGAATGGACCACTTTGCCGGTGAGGTCACTTCTCACCACC
CTCTGTTCCCATACTCATCCGAGGCCAGAGCCTTGGAAATGGATTTGGAGACCTCTAATGCCTACGGTGGACCTTT
GAACTTGTCTGCTGGTCTTGCTCACGGTTCTTGGACTCAACCTTTGAAGAAGCCAACTGCAAAGAACGAAGGCCAC
GTTACTTCGAACCAGGTCGAGCTTCATCCAGACATCGAGTACGATGAGGAGGATGACAAGGCCATTGAGAACTACA
TTCGTGAGCACACTGAGACCACATGGCACTGTCTGGGAACCTGTTCCATCGGTCCAAGAGAAGGTTCCAAGATCGT
CAAATGGGGTGGTGTTTTGGACCACAGATCCAACGTTTACGGAGTCAAGGGCTTGAAGGTTGGTGACTTGTCCGTG
TGCCCAGACAATGTTGGTTGTAACACCTACACCACCGCTCTTTTGATCGGTGAAAAGACTGCCACTTTGGTTGGAG
AAGATTTAGGATACTCTGGTGAGGCCTTAGACATGACTGTTCCTCAGTTCAAGTTGGGCACTTACGAGAAGACCGG
TCTTGCTAGATTCTAA SEQ ID NO:3: AOX2 amino acid sequence of Komagataella phaffii, CBS7435
MAIPEEFDILVLGGGSSGSCIAGRLANLDHSLKVGLIEAGENNLNNPWVYLPGIYPRNMKLDSKTASFYTSNPSPH
LNGRRAIVPCANILGGGSSINFMMYTRGSASDYDDFEAEGWKTKDLLPLMKKTETYQRACNNPEIHGFEGPIKVSF
GNYTYPVCQDFLRATESQGIPYVDDLEDLVTAHGAEHWLKWINRDTGRRSDSAHAFVHSTMRNHDNLYLICNTKVD
KIIVEDGRAAAVRTVPSKPLNAKKPTHKVYRARKQIVLSCGTISSPLVLQRSGFGDPIKLRAAGVKPLVNLPGVGR
NFQDHYCFFSPYRIKPQYESFDDFVRGDANIQKKVFDQWYANGTGPLATNGIEAGVKIRPTPEELSQMDESFQEGY
REYFEDKPDKPVMHYSIIAGFFGDHTKIPPGKYMTMFHFLEYPFSRGSIHITSPDPYATPDFDPGFMNDERDMAPM
VWSYKKSRETARKMDHFAGEVTSHHPLFPYSSEARAYEMDLETSNAYGGPLNLTAGLAHGSWTQPLKKPAGRNEGH
VTSNQVELHPDIEYDEEDDKAIENYIREHTETTWHCLGTCSIGPREGSKIVKWGGVLDHRSNVYGVKGLKVGDLSV
CPDNVGCNTYTTALLIGEKTATLVGEDLGYTGEALDMTVPQFKLGTYEKTGLARF Figure 1 (continued):

SEQ ID NO:4: *AOX2* nucleotide sequence of Komagataella phaffii, CBS7435
ATGGCCATTCCTGAAGAATTCGATATTCTTGTCCTGGGTGGTGGATCCAGTGGATCCTGTATTGCCGGAAGATTGG
CCAACTTGGACCACTCCTTGAAAGTTGGTCTTATCGAGGCTGGTGAGAACAATCTTAACAACCCATGGGTCTACCT
TCCAGGTATTTACCCAAGAAACATGAAGTTGGACTCCAAAACTGCTTCTTTCTACACCTCCAACCCTTCTCCTCAT
TTGAATGGTAGAAGAGCTATTGTCCCATGTGCCAACATCTTGGGTGGTGGTTCTTCGATCAACTTCATGATGTACA
CCAGAGGTTCCGCTTCTGATTACGATGACTTTGAAGCTGAGGGATGGAAGACCAAGGATTTGCTTCCTTTGATGAA
GAAGACTGAGACTTACCAAAGAGCTTGCAACAACCCTGAAATTCACGGTTTTGAAGGTCCAATCAAGGTTTCTTTC
GGTAACTACACTTACCCAGTTTGTCAAGACTTCTTGAGAGCAACTGAATCCCAAGGTATTCCATACGTTGACGACT
TGGAAGACTTGGTGACTGCTCATGGTGCTGAACACTGGCTGAAATGGATCAACAGAGACACTGGTCGTCGTTCCGA
CTCTGCTCATGCCTTCGTTCATTCTACGATGAGAAACCACGACAATCTGTACTTGATCTGCAACACCAAAGTTGAC
AAGATTATTGTTGAAGACGGAAGAGCTGCTGCTGTCAGAACCGTTCCAAGTAAACCTTTGAACGCAAAGAAGCCAA
CTCACAAGGTTTATCGTGCTAGAAAGCAAATCGTTTTGTCTTGTGGTACCATCTCTTCTCCTCTGGTTCTGCAAAG
ATCCGGTTTTGGTGACCCAATCAAATTGAGAGCCGCTGGTGTTAAGCCTTTGGTCAACTTGCCAGGTGTTGGAAGA
AACTTCCAAGACCACTACTGCTTCTTCTCTCCTTACAGAATTAAGCCCCAATACGAGTCTTTCGATGACTTCGTAC
GTGGTGACGCTAACATTCAAAAGAAGGTATTCGACCAATGGTACGCTAACGGTACTGGTCCATTGGCCACCAACGG
TATTGAAGCCGGTGTCAAGATTAGACCAACTCCAGAAGAATTATCTCAGATGGACGAGTCCTTCCAAGAGGGTTAC
AGAGAGTACTTCGAAGACAAACCAGACAAGCCAGTTATGCACTATTCCATCATTGCTGGTTTCTTCGGTGACCACA
CCAAGATTCCACCTGGAAAGTACATGACCATGTTCCACTTCTTGGAGTACCCATTCTCCAGAGGTTCTATCCACAT
CACCTCTCCAGACCCATACGCAACTCCAGACTTTGACCCAGGTTTCATGAACGATGAAAGAGACATGGCTCCTATG
GTCTGGTCTTACAAGAAGTCCAGAGAGACTGCCAGAAAAATGGACCACTTTGCTGGTGAGGTTACTTCCCACCACC
CTCTGTTCCCATACTCATCCGAGGCCAGAGCTTACGAGATGGATTTGGAGACCTCCAACGCCTACGGTGGACCACT
GAACTTGACTGCTGGTCTTGCTCACGGTTCTTGGACTCAGCCTTTTGAAGAAGCCTGCTGGAAGAAACGAAGGACAT
GTTACTTCCAACCAAGTCGAGCTTCATCCAGACATTGAGTACGATGAGGAGGATGATAAGGCCATTGAGAACTACA
TTCGTGAGCACACTGAGACCACATGGCACTGTCTGGGAACCTGTTCCATTGGTCCAAGAGAGGGTTCCAAGATCGT
CAAATGGGGTGGTGTTTTGGATCACAGATCTAACGTTTACGGAGTCAAGGGCCTGAAGGTTGGTGACTTGTCCGTC
TGTCCAGACAATGTTGGTTGTAACACCTACACCACCGCTCTTTTGATCGGTGAAAAGACTGCCACCTTGGTTGGTG
AAGACTTAGGATACACAGGTGAGGCCTTAGACATGACTGTACCTCAGTTCAAGTTGGGCACTTACGAGAAGACTGG
TCTTGCTAGATTCTAG SEQ ID NO:5: pAOX1 promoter sequence of Komagataella phaffii, CBS7435
CATGTTGGTATTGTGAAATAGACGCAGATCGGGAACACTGAAAAATAACAGTTATTATTCGAGATCTAACATCCAA
AGACGAAAGGTTGAATGAAACCTTTTTGCCATCCGACATCCACAGGTCCATTCTCACACATAAGTGCCAAACGCAA
CAGGAGGGGATACACTAGCAGCAGACCGTTGCAAACGCAGGACCTCCACTCCTCTTCTCCTCAACACCCACTTTTG
CCATCGAAAAACCAGCCCAGTTATTGGGCTTGATTGGAGCTCGCTCATTCCAATTCCTTCTATTAGGCTACTAACA
CCATGACTTTATTAGCCTGTCTATCCTGGCCCCCTGGCGAGGTTCATGTTTGTTTATTTCCGAATGCAACAAGCT
CCGCATTACACCCGAACATCACTCCAGATGAGGGCTTTCTGAGTGTGGGTCAAATAGTTTCATGTTCCCCAAATG
GCCCAAAACTGACAGTTTAAACGCTGTCTTGGAACCTAATATGACAAAAGCGTGATCTCATCCAAGATGAACTAAG
TTTGGTTCGTTGAAATGCTAACGGCCAGTTGGTCAAAAAGAAACTTCCAAAAGTCGGCATACCGTTTGTCTTGTTT
GGTATTGATTGACGAATGCTCAAAAATAATCTCATTAATGCTTAGCGCAGTCTCTCTATCGCTTCTGAACCCCGGT
GCACCTGTGCCGAAACGCAAATGGGGAAACACCCGCTTTTGGATGATTATGCATTGTCTCCACATTGTATGCTTC
CAAGATTCTGGTGGGAATACTGCTGATAGCCTAACGTTCATGATCAAAATTTAACTGTTCTAACCCTACTTGACA
GCAATATATAAACAGAAGGAAGCTGCCCTGTCTTAAACCTTTTTTTTATCATCATTATTAGCTTACTTTCATAATT
GCGACTGGTTCCAATTGACAAGCTTTTGATTTTAACGACTTTTAACGACAACTTGAGAAGATCAAAAAACAACTAA
TTATTCGAAACG Figure 1 (continued):

SEQ ID NO:6: pAOX2 promoter sequence of Komagataella phaffii, CBS7435
GCTTAAAGGACTCCATTTCCTAAAATTTTCAAGCAGTCCTCTCAACTAAATTTTTTTCCATTCCTCTGCACCCAGCC
CTCTTCATCAACCGTCCAGCCTTCTCAAAAGTCCAATGTAAGTAGCCTGCAAATTCAGGTTACAACCCCTCAATTT
TCCATCCAAGGGCGATCCTTACAAAGTTAATATCGAACAGCAGAGACTAAGCGAGTCATCATCACCACCCAACGAT
GGTGAAAAACTTTAAGCATAGATTGATGGAGGGTGTATGGCACTTGGCGGCTGCATTAGAGTTTGAAACTATGGGG
TAATACATCACATCCGGAACTGATCCGACTCCGAGATCATATGCAAAGCACGTGATGTACCCCGTAAACTGCTCGG
ATTATCGTTGCAATTCATCGTCTTAAACAGTACAAGAAACTTTATTCATGGGTCATTGGACTCTGATGAGGGGCAC
ATTTCCCCAATGATTTTTTGGGAAAGAAAGCCGTAAGAGGACAGTTAAGCGAAAGAGACAAGACAACGAACAGCAA
AAGTGACAGCTGTCAGCTACCTAGTGGACAGTTGGGAGTTTCCAATTGGTTGGTTTTGAATTTTTACCCATGTTGA
GTTGTCCTTGCTTCTCCTTGCAAACAATGCAAGTTGATAAGACATCACCTTCCAAGATAGGCTATTTTGTCGCAT
AAATTTTTGTCTCGGAGTGAAAACCCCTTTTATGTGAACAGATTACAGAAGCGTCCTACCCTTCACCGGTTGAGAT
GGGGAGAAAATTAAGCGATGAGGAGACGATTATTGGTATAAAAGAAGCAACCAAAATCCCTTATTGTCCTTTTCTG
ATCAGCATCAAAGAATATTGTCTTAAAACGGGCTTTTAACTACATTGTTCTTACACATTGCAAACCTCTTCCTTCT
ATTTCGGATCAACTGTATTGACTACATTGATCTTTTTTAACGAAGTTTACGACTTACTAAATCCCCACAAACAAAT
CAACTGAGAAAA SEQ ID NO:7: pAOX1 promoter sequence of Komagataella pastoris, ATCC 28485
ATATCGTGAAATAGACCCAAATCCGGACACTGTGAAATAAAACAGTTAGTATGCGAAATCTAACATCCAAGAACGA
GAAACTAAATAAGACATTTTGCCATCCGACATCTACAAACCACATCACCCTCACACATAAGTGCCAAAACGCAGCA
GGAGGGACACCCAGCAGCAGAAGCCGTGTCGAACGCAGGACCTCCACTTCTCTTCTCCTCAACATCCACTTTCGTT
ATTGAAAACCAGCCTGCTTAAAAAAACTGATTGGAGCTCGCTCATTCCAGTCCCCTTTGTTAGGCTACTAAGACCA
CGACTTTATTAGCCTGTCCATTCTGGTTCCTGGCGAGACTTATTCTTGTTTGTTTATTTTCGAATGCAACAAAGCT
CCGCATTACATCCGAACATCACTTTAGATGAGGGCTTTCTGAGTGTGGGGTCGAATAGTTTCATGTTCCCCCAATG
GCCCAAAACTGACACTTTAAACGCTGTCTTCGAACTTAATATGGCAAAAGCGTGATCTCATCCAAGACGAACTAAG
TTTGGTTCGTTGAAATGCTAACGGCCAGTTGGTCAAAAAGAAACTTCCAAAAGTCGGCATATCGTTTGTCTTGTTT
GGTATTCATAGACGAATGCTCAAGAATATTCTCATTAATGCTTAGCGCAGTCTCTGTATCGCTTCTGGACCCCGGT
GCAGTTGTGCCGAAACGCAAATGGGGAAACACCCGCTTTTCGGATGATTATGCATTGTCTCCACATTGTATGCTTC
CAAGATTCTGGTGGGAATACTACTGATAGCCTAACGTTCATGATCAATATCAAACTGTTCTAACCCCTACTTGAAC
TGCAATATATAAACAGGAGGAAACTTCCCAGTCGAAAACCTTCTTTCATCATCATTATTAGCTTACTTTCATAATT
GTGACTGGTTCCAATTGACAAGCTTTTGATTCTAACGACTTTTAACGACAATTTGAGAAGATCAAAAAACAACTAA
TTATTCGAAACG SEQ ID NO:8: pAOX2 promoter sequence of Komagataella pastoris, ATCC 28485
GCTTGCACGACTCAGTTACCTGAAAATTTCAGCCTGTCCTCTTTAATAAAATTTCACCCGTTCCTCTGCATGTCCA
CTCAGCTCTATTCATCTATCCTTGAGCCTTCTCGAGCGTCTAATGAACAGCCTGCGAATTCAGGTTACAACCCCTC
ATTTTTTCGTCTCGGTCGATCTCTACAAAGTCAACAGCCAACTTTGATGTTAAGCGAGTCATCACCAGCCAGCGAT
AGTGAAAAACTTTAAGCATAGATTGATGGTGGGTTTATGTCACTTGGCGGCTGCATTAGAGTTTGAAACTATGGGG
TAATGCATCACATCCGGAACTGATCCGACTCGGAGATCATATGCAAACCACGTGATGTACCCCGTAAACTGCTCGG
ATTACTGTTCCAATTCATCGTCTTAAACAGTATAAGAAACTTTATTCATGGGTCATTGGACTCTGATGAGGGGCAC
ATTTCCCCATTGATTTTTGGGACAGTAAGCCATAAAAGGACTGTTAAGCGAAGCAGACAAGACAACGAACAGCTAG
AATAACAACTATCTACCGCCTTGTGGACCGTTGGGAGTTTCCAATTGGTTGGTTTTGGATTTCTGAGCCCATGTTG
TGTTGTCCATGCTTCTCCTTGCACACAATGCAAGTTGATAAGATATCACCTTCCAAGATAGGCTATTTTGTCGCA
TAAATTTTGGTCTCAGAGTGAAACCCCCTTTTATGTGAACGGATTAGAGAAGCCTCCTACCCTTCACCGGCTGAGA
TGGGGAGAAATTAAGCGATGAGGAGACGATAATTGCTATAAAAGAAGCAACCAAAACCCCTTATTGTCTCTTTCTG
ATCAGCATCAAAGAATATTGTCTTAAAACGGGCTTTTAACTACATTGTTCTTACACATTGCAAACCTCCTCCTTCA
ATTTCGGATCAGCTGTATTGACTACATTGATCTTTTTTAACGAAGTTCACGACTTACTAAATCCCCATAAACAAAC
CAACTGAGAAAA SEQ ID NO:9: AOX1 amino acid sequence of Komagataella pastoris, ATCC 28485
MAIPEEFDILVLGGGSSGSCIAGRLANLDHSLKVGLIEAGENNLNNPWVYLPGIYPRNMKLDSKTASFYTSNPSPH
LNGRRAIVPCANVLGGGSSINFMMYTRGSASDYDDFQAEGWKTKDLLPLMKKTETYQRACNNPDIHGFEGPIKVSF
GNYTYPVCQDFLRASESQGIPYVDDLEDLVTAHGAEHWLKWINRDTGRRSDSAHAFVHSTMRNHDNLYLICNTKVD
KIIVEDGRAAAVRTVPSKPLNPKKPSHKIYRARKQIVLSCGTISSPLVLQRSGFGDPIKLRAAGVKPLVNLPGVGR
NFQDHYCFFSPYRIKPQYESFDDFVRGDAEIQKRVFDQWYANGTGPLATNGIEAGVKIRPTPEELSQMDESFQEGY
REYFEDKPDKPVMHYSIIAGFFGDHTKIPPGKYMTMFHFLEYPFSRGSIHITSPDPYAAPDFDPGFMNDERDMAPM
VWAYKKSRETARRMDHFAGEVTSHHPLFPYSSEARALEMDLETSNAYGGPLNLSAGLAHGSWTQPLKKPTAKNEGH
VTSNQVELHPDIEYDEEDDKAIENYIREHTETTWHCLGTCSIGPREGSKIVKWGGVLDHRSNVYGVKGLKVGDLSV
CPDNVGCNTYTTALLIGEKTATLVGEDLGYTGEALDMTVPQFKLGTYEKTGLARF Figure 1 (continued):

SEQ ID NO:10: *AOX1* nucleotide sequence of Komagataella pastoris, ATCC 28485
ATGGCTATCCCTGAAGAGTTTGATATCCTTGTTTTAGGTGGTGGATCCAGTGGATCCTGTATTGCCGGAAGATTGG
CCAACTTGGACCACTCCTTGAAAGTTGGTCTTATCGAGGCAGGTGAGAACAACCTCAACAACCCATGGGTTTACCT
TCCAGGTATTTACCCAAGAAACATGAAGTTGGACTCCAAGACTGCATCCTTCTACACTTCTAACCCTTCTCCTCAC
TTGAACGGTAGAAGAGCTATTGTTCCATGTGCTAACGTCTTGGGTGGTGGTTCTTCCATTAACTTCATGATGTACA
CCAGAGGTTCTGCTTCTGATTATGACGACTTCCAAGCCGAGGGCTGGAAAACCAAGGACTTGCTTCCATTGATGAA
AAAGACCGAGACCTACCAAAGAGCTTGCAACAACCCTGACATTCACGGGTTCGAAGGTCCAATCAAGGTTTCTTTC
GGTAACTACACCTACCCAGTTTGCCAGGACTTCTTGAGAGCTTCTGAATCCCAAGGTATTCCATACGTTGACGACT
TGGAAGACTTGGTTACTGCTCACGGTGCTGAACACTGGCTGAAATGGATCAACAGAGACACTGGTCGTCGTTCCGA
CTCCGCTCATGCATTTGTCCACTCTACTATGAGAAACCACGACAACTTGTACTTGATTTGTAACACAAAGGTTGAC
AAGATTATTGTCGAAGACGGAAGAGCTGCTGCTGTTAGAACTGTTCCAAGCAAGCCTTTGAACCCAAAGAAGCCAA
GTCACAAGATCTACCGTGCTAGAAAGCAAATCGTTTTGTCTTGTGGTACCATCTCATCTCCTTTGGTTCTGCAAAG
ATCCGGTTTCGGTGACCCAATCAAGTTGAGAGCCGCTGGTGTTAAGCCTTTGGTCAACTTGCCTGGTGTCGGAAGA
AACTTCCAAGACCACTACTGTTTCTTCAGTCCTTACAGAATCAAGCCTCAGTACGAATCTTTCGATGACTTCGTGC
GTGGTGATGCTGAGATCCAAAAGAGAGTTTTCGACCAATGGTACGCCAATGGTACTGGTCCTCTTGCCACTAACGG
TATCGAAGCCGGTGTCAAGATTAGACCAACACCAGAGGAACTGTCTCAAATGGACGAATCTTTCCAAGAGGGTTAC
AGAGAATACTTTGAGGACAAGCCAGACAAGCCAGTTATGCACTACTCCATTATTGCTGGTTTCTTCGGTGACCACA
CCAAGATTCCTCCTGGAAAGTACATGACCATGTTCCACTTTTTGGAATACCCATTCTCCAGAGGTTCCATTCACAT
TACCTCTCCAGATCCATACGCAGCTCCAGACTTCGACCCAGGTTTCATGAACGATGAAAGAGACATGGCTCCTATG
GTCTGGGCCTACAAGAAGTCTAGAGAGACAGCTAGAAGAATGGACCACTTTGCCGGTGAGGTTACTTCTCACCACC
CATTGTTCCCATACTCATCCGAGGCCAGAGCTTTGGAGATGGATTTGGAGACCTCCAATGCCTACGGTGGACCTTT
GAACTTGTCTGCTGGTCTTGCCCACGGTTCTTGGACTCAACCTTTGAAGAAGCCAACTGCAAAGAACGAAGGCCAT
GTTACCTCCAACCAAGTCGAGCTTCATCCAGACATCGAGTACGACGAGGAGGACGACAAGGCCATTGAAAACTACA
TCCGTGAGCACACTGAGACCACATGGCACTGTCTGGGAACCTGTTCCATCGGTCCAAGAGAGGGTTCCAAGATCGT
CAAATGGGGTGGTGTTTTGGACCACAGATCCAACGTTTACGGAGTCAAGGGCCTGAAGGTTGGTGACTTGTCTGTC
TGTCCAGACAATGTTGGTTGTAACACCTACACCACCGCTCTTTTGATCGGTGAGAAGACTGCCACTTTGGTTGGAG
AAGACTTAGGATACACCGGTGAAGCCTTAGACATGACTGTTCCTCAGTTCAAGTTGGGCACTTACGAGAAGACCGG
TCTTGCTAGATTCTAA SEQ ID NO:11: AOX2 amino acid sequence of Komagataella pastoris, ATCC 28485
MAIPEEFDILVLGGGSSGSCIAGRLANLDHSLKVGLIEAGENNLNNPWVYLPGIYPRNMKLDSKTASFYTSNPSPH
LNGRRAIVPCANILGGGSSINFMMYTRGSASDYDDFEAEGWKTKDLLPLMKKTETYQRACNNPEIHGFEGPIKVSF
GNYTYPVCQDFLRATESQGIPYVDDLEDLETAHGAEHWLKWINRDTGRRSDSAHAFVHSTMRNHDNLYLICNTKVD
KIIVEDGRAAGVRTVPSKPLNAKKPTHKVYRARKQIVLSCGTISSPLVLQRSGFGDPIKLRAAGVKPLVNLPGVGR
NFQDHYCFFSPYRIKPQYESFDDFVRGDANIQKKVFDQWYANGTGPLATNGIEAGVKIRPTPEELSQMDESFQEGY
REYFEDKPDKPVMHYSIIAGFFGDHTKIPPGKYMTMFHFLEYPFSRGSIHITSPDPYATPDFDPGFMNDERDMAPM
VWSYKKSRETARKMDHFAGEVTSHHPLFPYSSEARAYEMDLETSNAYGGPLNLTAGLAHGSWTQPLKKPAARNEGH
VTSNQVELHPDIEYDEEDDKAIENYIREHTETTWHCLGTCSIGPREGSKIVKWGGVLDHRSNVYGVKGLKVGDLSV
CPDNVGCNTYTTALLIGEKTATLVGEDLGYTGDALDMTVPQFKLGTYEKTGLARF Figure 1 (continued):

SEQ ID NO:12: *AOX2* nucleotide sequence of Komagataella pastoris, ATCC 28485
ATGGCTATTCCTGAAGAATTCGATATTCTTGTCCTAGGTGGTGGATCCAGTGGATCCTGTATTGCCGGAAGATTGG
CCAACTTGGACCACTCTTTGAAAGTTGGTCTTATCGAGGCCGGTGAGAACAATCTTAACAACCCTTGGGTCTACCT
TCCAGGTATTTACCCAAGAAACATGAAATTGGACTCCAAGACCGCTTCTTTCTACACCTCCAACCCATCTCCTCAT
TTGAATGGTAGAAGAGCTATTGTCCCATGTGCTAACATCTTGGGTGGTGGTTCTTCCATCAACTTCATGATGTACA
CCAGAGGTTCCGCTTCTGATTACGATGACTTCGAAGCTGAGGGCTGGAAAACCAAGGATTTGCTTCCTTTGATGAA
GAAGACTGAGACCTACCAAAGAGCTTGCAACAACCCTGAGATCCACGGTTTCGAAGGTCCAATCAAGGTTTCTTTC
GGTAACTACACTTACCCGGTTTGTCAAGACTTCTTGAGAGCAACTGAATCCCAAGGTATTCCATACGTTGACGACT
TGGAAGACTTGGAGACTGCTCATGGTGCCGAACACTGGTTGAAATGGATCAACAGAGACACTGGTCGTCGTTCCGA
CTCTGCTCATGCTTTCGTCCATTCTACTATGAGAAACCATGATAACTTGTACTTGATCTGCAACACCAAGGTTGAC
AAGATTATTGTTGAAGACGGAAGAGCTGCTGGTGTCAGAACCGTCCCAAGTAAACCTTTGAACGCAAAGAAGCCAA
CTCACAAGGTTTACCGTGCTAGAAAGCAGATCGTTTTGTCTTGTGGTACCATTTCTTCCCCTCTGGTTTTGCAAAG
ATCCGGTTTTGGTGATCCAATCAAATTGAGAGCCGCTGGTGTTAAGCCTTTGGTCAACTTGCCAGGTGTTGGAAGG
AACTTCCAGGACCATTACTGCTTCTTCTCTCCTTACAGAATCAAGCCCCAATACGAGTCTTTTGATGACTTCGTCC
GTGGTGACGCTAACATCCAAAAGAAGGTATTCGACCAATGGTACGCTAACGGTACTGGTCCATTGGCCACCAATGG
TATTGAAGCCGGTGTCAAGATCAGACCAACTCCAGAGGAATTATCTCAAATGGACGAGTCGTTCCAGGAGGGTTAC
AGAGAGTACTTTGAAGACAAACCAGACAAACCAGTTATGCACTATTCCATCATTGCTGGTTTCTTCGGTGACCACA
CCAAGATTCCGCCTGGAAAGTACATGACCATGTTCCACTTCTTGGAGTACCCATTCTCCAGAGGTTCTATTCATAT
CACCTCTCCAGACCCATACGCAACTCCAGACTTTGACCCAGGTTTCATGAATGATGAAAGAGACATGGCTCCTATG
GTTTGGTCTTACAAGAAGTCCAGAGAGACTGCCAGAAAGATGGATCACTTTGCTGGTGAGGTTACTTCCCACCACC
CTCTGTTCCATACTCATCCGAGGCCAGAGCTTACGAGATGGACTTGGAGACCTCCAACGCCTACGGTGGACCACT
GAACTTGACTGCTGGTCTTGCTCACGGTTCTTGGACTCAGCCTTTGAAGAAGCCTGCCGCAAGAAACGAAGGACAT
GTTACCTCTAACCAAGTTGAGCTTCATCCAGACATTGAATACGATGAGGAGGATGACAAGGCCATTGAGAACTACA
TCCGTGAGCACACTGAGACCACATGGCACTGTCTCGGAACCTGTTCCATCGGTCCAAGAGAAGGTTCCAAGATAGT
CAAATGGGGTGGTGTTTTGGACCACAGATCCAACGTTTACGGAGTCAAGGGCCTGAAGGTTGGTGACTTGTCTGTC
TGCCCAGACAATGTTGGTTGTAACACCTACACCACCGCTCTTTTAATCGGTGAAAAGACTGCAACCTTGGTGGGTG
AAGACTTAGGATACACAGGTGATGCCTTAGACATGACTGTTCCTCAGTTCAAGTTGGGCACTTACGAGAAGACTGG
TCTTGCTAGATTCTAG SEQ ID NO:13: MOD1 amino acid sequence of Ogataea methanolica JCM 10240
MAIPDEFDIIVVGGGSTGCALAGRLGNLDENVTVALIEGGENNINNPWVYLPGVYPRNMRLDSKTATFYSSRPSPH
LNGRRAIVPCANILGGGSSINFLMYTRASASDYDDWESEGWTTDELLPLMKKIETYQRPCNNRELHGFDGPIKVSF
GNYTYPNGQDFIRAAESQGIPFVDDAEDLKCSHGAEHWLKWINRDLGRRSDSAHAYIHPTMRNKQNLFLITSTKCE
KIIIENGVATGVKTVPMKPTGSPKTQVARTFKARKQIIVSCGTISSPLVLQRSGIGSAHKLRQVGIKPIVDLPGVG
MNFQDHYCFFTPYHVKPDTPSFDDFVRGDKAVQKSAFDQWYANKDGPLTTNGIEAGVKIRPTEEELATADDEFRAA
YDDYFGNKPDKPLMHYSLISGFFGDHTKIPNGKYMCMFHFLEYPFSRGFVHVVSPNPYDAPDFDPGFMNDPRDMWP
MVWSYKKSRETARRMDCFAGEVTSHHPHYPYDSPARAADMDLETTKAYAGPDHFTANLYHGSWTVPIEKPTPKNAA
HVTSNQVEKHRDIEYTKEDDAAIEDYIREHTETTWHCLGTCSMAPREGSKVVPTGGVVDSRLNVYGVEKLKVADLS
ICPDNVGCNTYSTALLIGEKASTLVAEDLGYSGDALKMTVPNFKLGTYEEAGLARF Figure 1 (continued):

SEQ ID NO:14: *MOD1* nucleotide sequence of Ogataea methanolica JCM 10240
ATGGCTATTCCAGATGAATTTGATATTATTGTTGTCGGTGGTGGTTCCACCGGTTGTGCTCTTGCTGGTAGATTAG
GTAACTTGGACGAAAACGTCACAGTTGCTTTAATCGAAGGTGGTGAAAACAACATCAACAACCCATGGGTTTACTT
ACCAGGTGTTTATCCAAGAAACATGAGATTAGACTCAAAGACTGCTACTTTTTACTCTTCAAGACCATCACCACAC
TTGAACGGTAGAAGAGCTATTGTTCCATGTGCTAACATCTTGGGTGGTGGTTCTTCCATCAACTTCTTGATGTACA
CCAGAGCCTCTGCCTCCGATTACGATGATTGGGAATCTGAAGGTTGGACTACCGATGAATTATTACCACTAATGAA
GAAGATTGAAACTTATCAAAGACCATGTAACAACAGAGAATTGCACGGTTTCGATGGTCCAATTAAGGTTTCATTT
GGTAACTATACTTATCCAAACGGTCAAGATTTCATTAGAGCTGCCGAATCTCAAGGTATTCCATTTGTTGATGATG
CTGAAGATTTGAAATGTTCCCACGGTGCTGAGCACTGGTTGAAGTGGATCAACAGAGACTTAGGTAGAAGATCCGA
TTCTGCTCATGCTTACATTCACCCAACCATGAGAAACAAGCAAAACTTGTTCTTGATTACTTCCACCAAGTGTGAA
AAGATTATCATTGAAAACGGTGTTGCTACTGGTGTTAAGACTGTTCCAATGAAGCCAACTGGTTCTCCAAAGACCC
AAGTTGCTAGAACTTTCAAGGCTAGAAAGCAAATTATTGTTTCTTGTGGTACTATCTCATCACCATTAGTTTTGCA
AAGATCTGGTATCGGTTCCGCTCACAAGTTGAGACAAGTTGGTATTAAACCAATTGTTGACTTACCAGGTGTTGGT
ATGAACTTCCAAGATCACTACTGTTTCTTCACTCCATACCATGTCAAGCCAGATACTCCATCATTCGATGACTTTG
TTAGAGGTGATAAAGCTGTTCAAAAATCTGCTTTCGACCAATGGTATGCTAACAAGGATGGTCCATTAACCACTAA
TGGTATTGAGGCAGGTGTTAAGATTAGACCAACTGAAGAAGAATTAGCCACTGCTGATGACGAATTCAGAGCTGCT
TATGATGACTACTTTGGTAACAAGCCAGATAAGCCATTAATGCACTACTCTCTAATTTCTGGTTTCTTTGGTGACC
ACACCAAGATTCCAAACGGTAAGTACATGTGCATGTTCCACTTCTTGGAATATCCATTCTCCAGAGGTTTCGTTCA
CGTTGTTTCTCCAAACCCATACGATGCTCCTGACTTTGATCCAGGTTTCATGAACGATCCAAGAGATATGTGGCCA
ATGGTTTGGTCTTACAAGAAGTCCAGAGAAACTGCCAGAAGAATGGACTGTTTTGCCGGTGAAGTTACTTCTCACC
ACCCACACTACCCATACGACTCACCAGCCAGAGCTGCTGACATGGACTTGGAAACTACTAAAGCTTATGCTGGTCC
AGACCACTTTACTGCTAACTTGTACCACGGTTCATGGACTGTTCCAATTGAAAAGCCAACTCCAAAGAACGCTGCT
CACGTTACTTCTAACCAAGTTGAAAAACATCGTGACATCGAATACACCAAGGAGGATGATGCTGCTATCGAAGATT
ACATCAGAGAACACACTGAAACCACATGGCATTGTCTTGGTACTTGTTCAATGGCTCCAAGAGAAGGTTCTAAGGT
TGTCCCAACTGGTGGTGTTGTTGACTCCAGATTAAACGTTTACGGTGTTGAAAAGTTGAAGGTTGCTGATTTATCA
ATTTGCCCAGATAATGTTGGTTGTAACACTTACTCTACTGCTTTGTTAATCGGTGAAAAGGCTTCTACCTTAGTTG
CTGAAGACTTGGGCTACTCTGGTGATGCTTTGAAGATGACTGTTCCAAACTTCAAATTGGGTACTTATGAAGAAGC
TGGTCTAGCTAGATTCTAG SEQ ID NO:15: MOD2 amino acid sequence of Ogataea methanolica JCM 10240
MAIPEEFDIIVVGGGSAGCPTAGRLANLDPNLTVALIEAGENNINNPWVYLPGVYPRNMRLDSKTATFYSSRPSPH
LNGRRAIVPCANILGGGSSINFMMYTRGSASDYDDWESEGWTTDELLPLMKRLETYQRPCNNPDLHGFDGPIKVSF
GNYTYPNCQDFLRAAESQGIPFVDDAEDLKTSHASQHWLKWINRDLGRRSDAAHAYIHPTMRNKSNLYLITSTKAD
KVIIEDGVAAGIQVVPSKPLNPEKPAAKIYKARKQIILSCGTISTPLVLQRSGIGSAHKLRQAGIKPIVDLPGVGM
NFQDHYCFFTPYHVKPDTPSFDDFARGDKAVQKSAFDQWYANKDGPLTTNGIEAGVKIRPTAEELATADEDFQLGY
ASYFENKPDKPLMHYSLISGFFGDHTKIPNGKYMTMFHFLEYPFSRGFVHVVSPSPYDAPDFDPGFMNDPKDMWPM
VWAYKMSRETARRMECFAGEVTSHHPKYPYDSPARAKDLDLETCKAYAGPDHFTANLYHGSWTIPLEKPTPKNTSH
VTSNQVELHAQLEYSKEDDIAIENYIKEHVETTWHCLGTCSMAPREGSSIVPTGGVVDERLNVYDVAHLKCADLSI
CPDNVGCNTYSTALLVGEKASMIVAEDLGYSGAELDMTIPGFKLGTYESTGLRF Figure 1 (continued):

SEQ ID NO:16: *MOD2* nucleotide sequence of Ogataea methanolica JCM 10240
ATGGCTATTCCTGAAGAATTCGATATCATTGTTGTCGGTGGTGGTTCTGCCGGCTGTCCTACTGCTGGTAGATTGG
CTAACTTAGACCCAAATTTAACTGTTGCTTTAATCGAAGCTGGTGAAAACAACATTAACAACCCATGGGTCTACTT
ACCAGGCGTTTACCCAAGAAACATGAGATTAGACTCCAAAACTGCAACTTTCTACTCTTCTAGACCTTCCCCACAT
TTAAATGGTAGAAGAGCTATTGTTCCATGTGCTAATATCTTAGGTGGTGGTTCTTCAATTAACTTCATGATGTACA
CTAGAGGTTCAGCTTCTGATTATGATGACTGGGAATCCGAAGGTTGGACTACCGATGAATTATTGCCATTGATGAA
AAGATTAGAAACTTATCAAAGACCATGTAACAACCCTGATTTGCACGGTTTCGACGGCCCTATCAAGGTCTCCTTC
GGTAACTACACTTATCCTAACTGTCAAGATTTCTTAAGAGCCGCTGAATCTCAAGGTATTCCATTTGTTGATGATG
CTGAAGATTTAAAGACTTCTCATGCTTCCCAACACTGGCTGAAGTGGATTAACAGAGACCTGGGTAGAAGATCTGA
TGCTGCGCATGCTTACATTCACCCAACTATGAGAAACAAGTCAAACTTATACTTGATCACTTCCACTAAGGCTGAT
AAAGTTATAATTGAAGATGGAGTTGCAGCTGGTATTCAAGTTGTTCCTTCCAAACCATTGAACCCAGAAAAGCCGG
CTGCCAAGATCTACAAGGCTAGAAAGCAAATCATTCTATCCTGTGGTACAATTTCTACCCGTTGGTCCTACAAAG
ATCTGGTATTGGCTCAGCTCATAAATTAAGACAGGCAGGCATAAAACCGATCGTTGACTTGCCAGGAGTTGGTATG
AACTTCCAAGATCACTACTGCTTTTTCACCCCATACCATGTCAAGCCAGATACTCCTTCTTTTGATGACTTTGCCA
GAGGTGATAAGGCTGTTCAAAAATCAGCTTTTGATCAATGGTATGCTAACAAAGATGGTCCTTTAACCACTAACGG
TATTGAAGCTGGTGTTAAGATTAGACCAACTGCTGAAGAACTGGCTACTGCTGATGAAGATTTCCAACTAGGCTAC
GCTTCTTACTTTGAAAACAAGCCAGATAAACCATTGATGCATTACTCTTTAATCTCTGGTTTCTTTGGTGATCACA
CTAAGATTCCAAACGGTAAATACATGACCATGTTCCATTTCTTAGAATACCCATTCTCCAGGGGTTTTGTTCACGT
TGTTTCGCCAAGCCCATACGATGCTCCAGACTTTTGACCCAGGTTTCATGAACGACCCAAAGGACATGTGGCCAATG
GTTTGGGCTTATAAAATGTCAAGAGAAACTGCTAGAAGAATGGAATGCTTTGCTGGTGAAGTTACTTCCCACCATC
CTAAATATCCATACGATTCACCTGCCAGAGCTAAGGACTTGGACTTGGAAACTTGTAAAGCTTACGCGGGTCCAGA
TCACTTTACTGCAAACTTGTACCACGGTTCGTGGACCATTCCATTGGAGAAGCCAACTCCCAAGAACACTTCTCAC
GTTACTTCGAATCAAGTTGAATTACATGCTCAATTAGAATATTCTAAAGAAGATGACATCGCCATCGAAAACTATA
TCAAGGAACACGTTGAAACTACCTGGCATTGTCTTGGTACTTGTTCAATGGCTCCAAGAGAAGGCTCATCAATTGT
CCCAACAGGTGGTGTTGTTGATGAAAGACTAAACGTTTATGATGTTGCTCACTTAAAATGTGCTGATTTATCTATC
TGTCCAGATAATGTGGGTTGTAACACTTACTCTACTGCGTTACTGGTTGGTGAAAAGGCTTCTATGATTGTTGCTG
AAGATTTAGGTTACTCTGGAGCTGAATTGGATATGACCATTCCTGGTTTCAAGTTAGGTACTTACGAATCTACTGG
ATTAGGTAGATTCTAA SEQ ID NO:17: pMOD1 promoter sequence of Ogataea methanolica JCM 10240
GACAAAGTTTTGTTAAATGACTATCGAACAAGCCATGAAATAGCACATTTCTGCCAGTCACTTTTAACACTTTCCT
GCTTGCTGGTTGACTCTCCTCATACAAACACCCAAAAGGGAAACTTTCAGTGTGGGGACACTTGACATCTCACATG
CACCCCAGATTAATTTCCCCAGACGATGCGGAGACAAGACAAAACAACCCTTTGTCCTGCTCTTTTCTTTCTCACA
CCGCGTGGGTGTGTGCGCAGGCAGGCAGGCAGGCAGCGGGCTGCCTGCCATCTCTAATCGCTGCTCCTCCCCCCTG
GCTTCAAATAACAGCCTGCTGCTATCTGTGACCAGATTGGGACACCCCCTCCCCTCCGAATGATCCATCACCTTT
TGTCGTACTCCGACAATGATCCTTCCCTGTCATCTTCTGGCAATCAGCTCCTTCAATAATTAAATCAAATAAGCAT
AAATAGTAAATCGCATACAAACGTCATGAAAAGTTTTATCTCTATGGCAACGGATAGTCTATCTGCTTAATTCC
ATCCACTTTGGGAACCGTTCTCTCTTTACCCCAGATTCTCAAAGCTAATATCTGCCCCTTGTCTATTGTCCTTTCT
CCGTGTACAAGCGGAGCTTTTGCCTCCCATCCTCTTGCTTTGTTTCGGTTATTTTTTTTCTTTTGAAACTCTTGG
TCAAATCAAATCAAACAAAACCAAACCTTCTATTCCATCAGATCAACCTTGTTCAACATTCTATAAATCGATATAA
ATATAACCTTATCCCTCCCTTGTTTTTTACCAATTAATCAATCTTCAAATTTCAAATATTTTCTACTTGCTTTATT
ACTCAGTATTAACATTTGTTTAAACCAACTATAACTTTTAACTGGCTTTAGAAGTTTTATTTAACATCAGTTTCAA
TTTACATCTTTATTTATTAACGAAATCTTTACGAATTAACTCAATCAAAACTTTTACGAAAAAAAAATCTTACTAT
TAATTTCTCAAA Figure 1 (continued):

SEQ ID NO:18: pMOD2 promoter sequence of Ogataea methanolica JCM 10240
CGAACTTGCCCTTGTGGAATTTGGTTGTTAATCAAACTGTTCTGTATTTCATGTCATACTACTATTGATATTATTA
ATGTTACTTACTCATCTGGCCATTTAACAGGTTTGAAGCTTTAATGCTCTTAACTAACAGCAATCCATCACCGTCA
ACCTTAACCCCCCTGGTGCTTGCTGTCTTTATCCTTCGTATCTTTTTCATGTTGCACCGCCCTGTTCCTTATACGG
TTGTTCCCCATAGGCTAACTTCTCTGTTTCCGACCATCTCTGCAATAACAAAGAATTCTATACGCTTACACTATA
ATCATACAATGACTCTACATGCCATTTTCACTTTACTTACTTGCCATCGGAAGATACTGAATCAGAAAGCCATAGT
AACTACATAACTTCAAAACACACCCTTTTTACAGATTAGTTACAATTTTGTCAATGTTTGTTTGATAACCCAAGGT
GGAACGTTTCCAGTTAGACCTGTTTAATCCAACTCACTTTACCACCCCAAAACTTTCCTACCGTTAGACAAATACT
GGCTAAATCTGACGAAAACAACCAATCAACAATTGAATCCACTGGGAGGTATCTCTAATCCACTGACAAACTTTGC
TAAAACAAGAAAAAGTGGGGGCCTCCGTTGCGGAGAAGACGTGCGCAGGCTTAAAAACACAAGAGAACACTTGGAA
GTACCCCAGATTTTTAGCTTCCTACTATTCTGACACCCCCTATTCAAGCACGACGGTGATTGATTCATTCAATTTT
GCTGCTCCAATGATAGGATAAACCCTTTTGGACTTCAATCAGACCTCTGTCCTCCATAGCAATATAAATACCTTCT
AGTTGCCCCACTTCCTCTCTCCTGTACTGCCCCAATGAGTGACTTATTCAAGTTACTTTCTCTCTTTTCCTAACAA
TTAAACAAGAAGCTTTATTATAACATTAATATACTATTTTATAACAGGATTGAAAATTATATTTATCTATCTAAAA
CTAAAATTCAAA SEQ ID NO:19: MOX amino acid sequence of Ogataea polymorpha NCYC 495 leu 1.1
MAIPDEFDIIVVGGGSTGCCIAGRLANLDDQNLTVALIEGGENNINNPWVYLPGVYPRNMRLDSKTATFYSSRPSK
ALNGRRAIVPCANILGGGSSINFLMYTRASASDYDDWESEGWSTDELLPLIKKIETYQRPCNNRDLHGFDGPIKVS
FGNYTYPTCQDFLRAAESQGIPVVDDLEDFKTSHGAEHWLKWINRDLGRRSDSAHAYVHPTMRNKQSLFLITSTKC
DKVIIEDGKAVAVRTVPMKPLNPKKPVSRTFRARKQIVISCGTISSPLVLQRSGIGAAHHLRSVGVKPIVDLPGVG
ENFQDHYCFFTPYYVKPDVPTFDDFVRGDPVAQKAAFDQWYSNKDGPLTTNGIEAGVKIRPTEEELATADEDFRRG
YAEYFENKPDKPLMHYSVISGFFGDHTKIPNGKFMTMFHFLEYPFSRGFVRITSANPYDAPDFDPGFLNDERDLWP
MVWAYKKSRETARRMESFAGEVTSHHPLFKVDSPARARDLDLETCSAYAGPKHLTANLYHGSWTVPIDKPTPKNDF
HVTSNQVQLHSDIEYTEEDDEAIVNYIKEHTETTWHCLGTCSMAPREGSKIAPKGGVLDARLNVYGVQNLKVADLS
VCPDNVGCNTYSTALTIGEKAATLVAEDLGYSGSDLDMTIPNFRLGTYEETGLARF SEQ ID NO:20: MOX nucleotide sequence of Ogataea polymorpha NCYC 495 leu 1.1
ATGGCCATTCCTGACGAATTCGATATCATTGTTGTTGGTGGAGGTTCCACCGGCTGCTGCATTGCGGGCAGACTCG
CAAACCTCGACGACCAAAACCTCACAGTTGCCCTGATCGAGGGTGGTGAGAACAACATCAACAACCCTTGGGTCTA
CCTTCCCGGAGTGTATCCTAGAAACATGAGACTCGACTCCAAGACGGCCACCTTCTACTCGTCCAGACCATCGAAG
GCTCTGAACGGCAGAAGAGCGATCGTTCCTTGCGCCAACATCCTTGGAGGCGGCTCGTCGATCAACTTTCTGATGT
ACACCAGAGCCTCTGCTTCCGACTACGACGACTGGGAGTCCGAGGGATGGAGCACCGACGAGTTGCTACCTCTGAT
CAAAAAAATCGAAACTTACCAGCGTCCTTGCAACAACAGAGATCTGCACGGCTTTGACGGCCCAATCAAGGTTTCC
TTTGGAAACTACACGTATCCTACGTGCCAGGACTTCCTGAGAGCAGCAGAGTCGCAGGGAATTCCTGTTGTGGACG
ACCTGGAGGACTTCAAGACATCGCATGGTGCAGAGCACTGGCTGAAGTGGATTAACAGAGACCTGGGCAGAAGATC
GGATTCTGCGCACGCCTACGTCCACCCAACTATGAGAAACAAGCAGAGCCTGTTCCTCATCACCTCCACCAAGTGT
GACAAGGTGATCATCGAGGACGGCAAGGCTGTGGCCGTGAGAACAGTGCCAATGAAGCCTCTGAACCCTAAGAAGC
CTGTGTCCAGAACCTTCAGAGCCAGAAAGCAGATTGTGATCTCCTGCGGAACCATCTCGTCTCCTCTGGTGCTCCA
GAGATCTGGTATTGGTGCAGCTCACCACTTGAGATCCGTGGGGGTCAAGCCAATCGTCGACCTGCCAGGTGTGGGT
GAGAATTTCCAGGACCACTACTGTTTCTTCACTCCATACTACGTCAAGCCTGACGTTCCTACGTTCGACGACTTTG
TCAGGGGTGACCCAGTTGCCCAGAAGGCCGCTTTCGACCAGTGGTACTCCAACAAGGACGGTCCATTGACCACCAA
CGGTATTGAAGCCGGAGTCAAGATCAGACCTACCGAAGAGGAGCTGGCTACCGCGGACGAGGACTTCAGACGCGGC
TACGCAGAGTACTTCGAGAACAAGCCAGACAAGCCTCTGATGCACTACTCTGTCATCTCCGGCTTCTTTGGAGACC
ACACCAAGATTCCTAACGGCAAGTTCATGACCATGTTCCACTTCCTGGAGTATCCATTCTCCAGAGGATTTGTTAG
AATCACCTCGGCAAACCCATACGACGCTCCTGACTTCGATCCCGGCTTCCTCAATGACGAAAGAGACCTGTGGCCT
ATGGTCTGGGCATACAAGAAGTCCAGAGAGACGGCCAGAAGAATGGAGAGCTTTGCAGGAGAGGTCACCTCGCACC
ACCCATTGTTCAAGGTTGACTCGCCAGCCAGAGCCAGAGACCTGGACCTCGAGACATGCAGTGCATATGCCGGTCC
TAAGCACCTCACTGCCAACCTGTACCACGGCTCGTGGACCGTTCCTATCGACAAGCCAACGCCTAAGAACGATTTC
CACGTGACCTCCAACCAAGTCCAACTGCACTCCGACATCGAGTACACCGAGGAGGACGACGAGGCCATCGTCAACT
ACATTAAGGAACACACCGAGACCACTTGGCACTGTCTGGGTACCTGCTCGATGGCCCCAAGAGAGGGTAGTAAGAT
TGCTCCTAAGGGAGGTGTCTTGGACGCCAGACTGAACGTTTACGGAGTCCAGAACCTCAAGGTTGCGGACCTTTCT
GTTTGTCCCGACAACGTTGGATGCAACACCTACTCTACTGCATTGACCATCGGTGAGAAGGCTGCCACTCTTGTTG
CTGAAGATCTTGGCTACTCAGGCTCCGACCTGGACATGACGATTCCAAACTTCAGACTCGGAACTTACGAGGAGAC
CGGACTTGCCAGATTCTAA Figure 1 (continued):

SEQ ID NO:21: pMOX promoter sequence of Ogataea polymorpha NCYC 495 leu 1.1
GCTGCAGCTTGCGATCTCGGATGGTTTTGGAATGGAAGAACCGCGACATCTCCAACAGCTGGGCCGTGTTGAGAAT
GAGCCGGACGTCGTTGAACGAGGGGGCCACAAGCCGGCGTTTGCTGATGGCGCGGCGCTCGTCCTCGATGTAGAAG
GCCTTTTCCAGAGGCAGTCTCGTGAAGAAGTTGCCAACGCTCGGAACCAGCTGCACGAGCCGAGACAATTCGGGGG
TGCCGGCTTTGGTCATTTCAATGTTGTCGTCGATGAGGAGTTCAAGGTCGTGGAAGATTTCCGCGTAGCGGCGTTT
TGCCTCAGAGTTTACCATGAGGTCGTCCACTGCAGAGATGCCGTTGCTCTTCACCGCGTACAGGACGAACGGCGTG
GCCAGCAGGCCCTTGATCCATTCTATGAGGCCATCTCGACGGTGTTCCTTGAGTGCGTACTCCACTCTGTAGCGAC
TGGACATCTCGAGACTGGGCTTGCTGTGCTGGATGCACCAATTAATTGTTGCCGCATGCATCCTTGCACCGCAAGT
TTTTAAAACCCACTCGCTTTAGCCGTCGCGTAAAACTTGTGAATCTGGCAACTGAGGGGGTTCTGCAGCCGCAACC
GAACTTTTCGCTTCGAGGACGCAGCTGGATGGTGTCATGTGAGGCTCTGTTTGCTGGCGTAGCCTACAACGTGACC
TTGCCTAACCGGACGGCGCTACCCACTGCTGTCTGTGCCTGCTACCAGAAAATCACCAGAGCAGCAGAGGGCCGAT
GTGGCAACTGGTGGGGTGTCGGACAGGCTGTTTCTCCACAGTGCAAATGCGGGTGAACCGGCCAGAAAGTAAATTC
TTATGCTACCGTGCAGTGACTCCGACATCCCCAGTTTTTGCCCTACTTGATCACAGATGGGGTCAGCGCTGCCGCT
AAGTGTACCCAACCGTCCCCACACGGTCCATCTATAAATACTGCTGCCAGTGCACGGTGGTGACATCAATCTAAAG
TACAAAAACAAA Signal sequence (SEQ ID NO:22):

MKXSTNLILAIAAASXVVSA, wherein
X at position 3 is either F or L; and
X at position 16 is either A or T.

Leader sequence (SEQ ID NO:23):

MKXSTNLILAIAAASXVVSAAPVAPAEEAANHLHKR, wherein
X at position 3 is either F or L
X at position 16 is either A or T Signal sequence, aMF, S. cerevisiae (SEQ ID NO:24):

MRFPSIFTAVLFAASSALAAPVNTTTEDETAQIPAEAVIGYSDLEGDFDVAVLPFSNSTNNGLLFINTTIASIAAK
EEGVSLEKR.

SEQ ID NO:50: ADH2 amino acid sequence of *Komagataella phaffii*, CBS7435
MSPTIPTTQKAVIFETNGGPLEYKDIPVPKPKSNELLINVKYSGVCHTDLHAWKGDWPLDNKLPLVGGHEGAGVVV
AYGENVTGWEIGDYAGIKWLNGSCLNCEYCIQGAESSCAKADLSGFTHDGSFQQYATADATQAARIPKEADLAEVA
PILCAGITVYKALKTADLRIGQWVAISGAGGGLGSLAVQYAKALGLRVLGIDGGADKGEFVKSLGAEVFVDFTKTK
DVVAEVQKLTNGGPHGVINVSVSPHAINQSVQYVRTLGKVVLVGLPSGAVVNSDVFWHVLKSIEIKGSYVGNREDS
AEAIDLFTRGLVKAPIKIIGLSELAKVYEQMEAGAIIGRYVVDTSK SEQ ID NO:51: *ADH2* gene sequence of *Komagataella phaffii*, CBS7435
ATGTCTCCAACTATCCCAACTACACAAAAGGCTGTTATCTTCGAGACCAACGGCGGTCCCCTAGAGTACAAGGACA
TTCCAGTCCCAAAGCCAAAGTCAAACGAACTTTTGATCAACGTTAAGTACTCCGGTGTCTGTCACACTGATTTGCA
CGCCTGGAAGGGTGACTGGCCATTGGACAACAAGCTTCCTTTGGTTGGTGGTCACGAAGGTGCTGGTGTCGTTGTC
GCTTACGGTGAGAACGTCACTGGATGGGAGATCGGTGACTACGCTGGTATCAAATGGTTGAACGGTTCTTGTTTGA
ACTGTGAGTACTGTATCCAAGGTGCTGAATCCAGTTGTGCCAAGGCTGACCTGTCTGGTTTCACCCACGACGGATC
TTTCCAGCAGTATGCTACTGCTGATGCCACCCAAGCCGCCAGAATTCCAAAGGAGGCTGACTTGGCTGAAGTTGCC
CCAATTCTGTGTGCTGGTATCACCGTTTACAAGGCTCTTAAGACCGCTGACTTGCGTATTGGCCAATGGGTTGCCA
TTTCTGGTGCTGGTGGAGGACTGGGTTCTCTTGCCGTTCAATACGCCAAGGCTCTGGGTTTGAGAGTTTTGGGTAT
TGATGGTGGTGCCGACAAGGGTGAATTTGTCAAGTCCTTGGGTGCTGAGGTCTTCGTCGACTTCACTAAGACTAAG
GACGTCGTTGCTGAAGTCCAAAAGCTCACCAACGGTGGTCCACACGGTGTTATTAACGTCTCCGTTTCCCCACATG
CTATCAACCAATCTGTCCAATACGTTAGAACTTTGGGTAAGGTTGTTTTGGTTGGTCTGCCATCTGGTGCCGTTGT
CAACTCTGACGTTTTCTGGCACGTTCTGAAGTCCATCGAGATCAAGGGATCTTACGTTGGAAACAGAGAGGACAGT
GCCGAGGCCATCGACTTGTTCACCAGAGGTTTGGTCAAGGCTCCTATCAAGATTATCGGTCTGTCTGAACTTGCTA
AGGTCTACGAACAGATGGAGGCTGGTGCCATCATCGGTAGATACGTTGTGGACACTTCCAAATAA Figure 1 (continued):

SEQ ID NO:52: ADH2 amino acid sequence of *Komagataella pastoris*, ATCC 28485
MSPTIPSTQKAVVFETNGGPLEYKDIPVPKPKSNEILINVKYSGVCHTDLHAWKGDWPLDNKLPLVGGHEGAGVVV
ALGENVTGWNIGDYAGIKWLNGSCLNCEYCIQGAESSCAKADLSGFTHDGSFQQYATADATQAARIPKEVDLAEVA
PILCAGITVYKALKTADLRIGQWVAISGAGGGLGSLAVQYAKALGLRVLGIDGGADKGEFVKSLGAEVYVDFTKTK
DVVAEVQKATNGGPHGVINVSVSPHAINQSVQYARTLGKIVLVGLPSGAVVNSDVFWHVLKSIEIKGSYVGNREDS
AEAIDLFARGLVKAPIKIIGLSELAKVYEQMEAGAIIGRYVVDTSK SEQ ID NO:53: *ADH2 gene sequence of Komagataella pastoris*, ATCC 28485
ATGTCTCCAACTATCCCATCTACACAAAAGGCTGTTGTCTTCGAGACCAACGGCGGTCCTCTCGAGTACAAGGACA
TCCCTGTCCCAAAGCCAAAGTCCAACGAAATCTTGATCAACGTTAAGTACTCCGGTGTCTGTCACACTGACTTGCA
CGCCTGGAAGGGTGACTGGCCATTGGACAACAAGCTTCCTTTGGTCGGTGGTCACGAAGGTGCTGGTGTCGTTGTC
GCTTTAGGTGAGAACGTCACTGGATGGAACATCGGTGACTACGCTGGTATCAAATGGTTGAACGGTTCTTGTTTGA
ACTGTGAGTACTGTATCCAAGGTGCTGAATCCAGTTGTGCCAAGGCTGACCTGTCTGGTTTCACCCACGACGGATC
TTTCCAGCAGTATGCTACTGCTGATGCCACCCAAGCCGCCAGAATTCCAAAGGAAGTTGACTTGGCTGAAGTTGCC
CCAATTTTGTGTGCTGGTATCACCGTTTACAAGGCTCTTAAGACCGCTGACTTGCGTATCGGCCAATGGGTTGCCA
TTTCCGGTGCTGGTGGAGGATTAGGTTCTCTTGCCGTTCAATACGCCAAGGCTCTGGGTTTGAGAGTTTTGGGTAT
TGATGGTGGTGCCGACAAGGGTGAGTTCGTCAAGTCCTTGGGTGCTGAGGTCTACGTCGACTTCACTAAGACTAAG
GACGTCGTTGCTGAGGTCCAAAAGGCCACCAACGGTGGTCCACACGGTGTTATCAACGTCTCCGTTTCCCCACATG
CTATCAACCAATCTGTCCAATACGCTAGAACTTTGGGTAAGATTGTTTTGGTTGGTCTGCCATCGGTGCCGTTGT
CAACTCTGACGTTTTCTGGCACGTTCTGAAGTCCATCGAGATCAAGGGATCTTACGTTGGAAACAGAGAGGACAGT
GCCGAAGCCATCGACTTGTTCGCTAGAGGCTTAGTCAAGGCTCCTATTAAGATTATTGGTCTGTCCGAACTTGCTA
AGGTCTACGAGCAGATGGAGGCTGGTGCCATCATCGGTAGATACGTTGTGGACACTTCCAAATAA SEQ ID NO:54: ADH2 amino acid sequence of *Ogataea parapolymorpha*, DL-1
MTSIPKTQKAVVFETNGGPLLYKDIPVPQPKPNEILVNVKYSGVCHTDLHAWKGDWPLDTKLPLVGGHEGAGVVVA
KGANVTNFEIGDYAGIKWLNGSCMGCEFCQQGAEPNCPEADLSGYTHDGSFQQYATADAVQAAKIPKGTNLADVAP
ILCAGVTVYKALKTAELSPGQWVAISGAGGGLGSLAVQYAVAMGLRVLGIDGGDEKAKLFESLGGEVFIDFTKEKD
IVGAVQKATNGGPHGVINVSVSPAAISQSCQYVRTLGKVVLVGLPAGAVCESPVFEHVIKSIQIRGSYVGNRQDTA
ESIDFFVRGKVKAPIKVVGLSELPKVFELMEQGKIAGRYVLDTSK SEQ ID NO:55: *ADH2 gene sequence of Ogataea parapolymorpha*, DL-1
ATGACTTCCATTCCAAAGACTCAAAAGGCCGTTGTTTTCGAGACCAACGGTGGTCCTCTTCTCTACAAGGACATCC
CTGTTCCACAACCAAAGCCAAATGAGATTCTTGTCAACGTCAAGTACTCCGGTGTTTGCCACACCGATCTCCACGC
TTGGAAGGGTGACTGGCCATTGGACACCAAACTTCCACTGGTCGGTGGTCACGAGGGTGCTGGTGTTGTTGTTGCT
AAGGGTGCCAACGTTACCAACTTTGAAATCGGTGACTACGCTGGTATCAAATGGTTGAACGGCTCGTGCATGGGTT
GTGAGTTCTGTCAACAAGGTGCAGAGCCAAACTGTCCTGAGGCCGACCTTTCCGGTTACACGCACGACGGTTCTTT
CCAACAATACGCCACTGCTGATGCTGTCCAGGCTGCCAAGATTCCAAAGGGAACTAACCTGGCTGACGTTGCTCCA
ATTCTCTGTGCTGGTGTCACTGTGTACAAGGCATTGAAGACTGCCGAATTGAGCCCAGGCCAATGGGTTGCTATCT
CTGGTGCTGGTGGAGGATTGGGTTCTCTTGCCGTTCAATACGCTGTCGCCATGGGCCTGAGAGTCCTGGGTATCGA
TGGTGGTGACGAAAAGGCTAAGCTCTTCGAGAGCTTGGGCGGAGAAGTCTTCATCGATTTCACCAAGGAAAAGGAC
ATTGTCGGAGCCGTCCAGAAGGCAACCAACGGTGGTCCACACGGTGTTATCAACGTTTCTGTGTCTCCAGCAGCTA
TCTCTCAATCCTGCCAATACGTGAGAACTCTTGGTAAGGTTGTTCTTGTTGGTCTTCCAGCCGGTGCTGTTTGCGA
GTCTCCAGTTTTCGAGCACGTTATCAAGTCTATCCAGATTAGAGGTTCCTACGTTGGTAACAGACAGGACACTGCC
GAGTCGATTGACTTCTTCGTCAGAGGCAAGGTTAAGGCTCCAATCAAGGTTGTTGGCCTTTCTGAGCTGCCAAAGG
TGTTCGAGTTGATGGAGCAAGGAAAGATTGCTGGAAGATACGTTCTTGACACTTCCAAATAG SEQ ID NO:56: ADH2 amino acid sequence of *Ogataea parapolymorpha*, DL-1
MMSISRVAALRNQFARLAKPAVVQQVFRHSTASAPTIPKTQMGCVFETNGGPIEYKEIPVPKPKPNEILVHVKYSG
VCHTDLHAWKGDWPLPVKLPLVGGHEGAGVVVAKGENVKNFEIGDLAGIKWLNGSCMGCEFCQQGAEPNCPDADLS
GYTHDGSFQQYATADAVQAAKLPPGTDLAAVAPILCAGVTVYKALKTAALRPGQIVAISGAAGGLGSLAVQYAVAM
GLRVLGIDGGEQKGEFIKKLGAEFYVDFTKEKDIVSAIQKITNGGPHGVINVSVSPAAISQSCQYVRTLGKVVLVG
LPAGAVCESPVFEHVVKSIQIKGSYVGNRQDTAEAVDFFTRGLVKSPFQIAGLSELPEVFKKMEEGKILGRYVLDT
SK Figure 1 (continued):

SEQ ID NO:57: ADH2 gene sequence of *Ogataea parapolymorpha*, DL-1
ATGATGTCTATTTCGAGAGTTGCTGCTTTGAGAAACCAATTTGCTCGGCTAGCCAAGCCCGCTGTTGTCCAGCAGG
TCTTCAGACACTCTACTGCCTCTGCTCCAACCATCCCAAAGACCCAGATGGGATGTGTTTTTGAAACCAACGGTGG
TCCAATTGAGTACAAGGAGATCCCTGTTCCAAAGCCAAAGCCTAACGAGATTTTGGTCCACGTCAAGTACTCTGGT
GTGTGCCACACTGACTTGCACGCCTGGAAGGGTGACTGGCCACTGCCTGTCAAACTCCCACTTGTGGGTGGTCACG
AGGGTGCCGGTGTTGTCGTTGCCAAGGGTGAGAACGTTAAAAACTTCGAGATCGGCGACTTGGCCGGTATCAAGTG
GCTGAACGGCTCGTGTATGGGTTGTGAGTTCTGTCAACAGGGTGCCGAACCAAACTGTCCAGACGCTGACCTGTCC
GGTTACACGCACGACGGTTCTTTCCAACAATACGCCACTGCTGACGCTGTCCAGGCCGCTAAGCTGCCTCCTGGAA
CTGACCTCGCTGCTGTTGCTCCTATTTTGTGTGCTGGTGTCACTGTTTACAAGGCCTTGAAGACTGCTGCTCTGCG
TCCAGGACAGATCGTTGCCATTTCCGGTGCCGCCGGTGGATTGGGTTCTCTTGCCGTTCAATACGCTGTCGCCATG
GGCCTGAGAGTTCTGGGTATTGACGGTGGTGAGCAAAAGGGCGAGTTCATCAAGAAGCTCGGTGCCGAATTCTACG
TCGACTTCACCAAGGAGAAGGACATTGTGTCTGCCATCCAGAAGATCACCAACGGCGGTCCACACGGTGTCATCAA
CGTTTCTGTCTCTCCAGCTGCTATCTCCCAGTCTTGTCAATACGTGAGAACCCTCGGTAAGGTTGTTCTGGTCGGT
CTTCCAGCCGGCGCTGTTTGCGAGTCTCCTGTCTTTGAGCACGTCGTCAAGTCCATCCAGATCAAGGGATCTTACG
TTGGTAACAGACAAGACACTGCCGAGGCCGTGGACTTCTTCACCAGAGGCCTTGTCAAGTCTCCATTCCAGATTGC
TGGTCTTTCCGAGCTGCCAGAGGTCTTCAAGAAGATGGAGGAGGGCAAGATCTTGGGCAGATACGTCCTTGACACT
TCTAAATAG SEQ ID NO:58: ADH amino acid sequence of *Ogataea polymorpha*, NCYC 495 leu1.1
MPSIPKTQKAIVFETNGGPLLYKDIPVPQPKPNEILVNVKYSGVCHTDLHAWKGDWPLATKLPLVGGHEGAGVVVA
KGANVTNFEIGDYAGIKWLNGSCMGCEFCQQGAEPNCPDADLSGYTHDGSFQQYATADAVQAAKIPKGTNLADVAP
ILCAGVTVYKALKTAELSPGQWVAISGAGGGLGSLAVQYAVAMGLRVLGIDGGDEKAKLFESLGGEVFIDFTKEKD
IVGAVQKATNGGPHGVINVSVSPAAISQSCQYVRTLGKVVLVGLPAGAVCESPVFEHVIKSIQIRGSYVGNRQDTA
ESIDFFVRGKVKAPIKVVGLSELPKVFELMEQGKIAGRYVLDTSK SEQ ID NO:59: ADH gene sequence of *Ogataea polymorpha*, NCYC 495 leu1.1
ATGCCTTCCATTCCAAAGACTCAAAAGGCCATTGTTTTCGAAACCAACGGTGGTCCTCTTCTATACAAGGACATCC
CTGTTCCACAGCCAAAGCCAAATGAAATCCTTGTCAACGTCAAGTACTCTGGTGTGTGCCACACCGACTTGCACGC
CTGGAAGGGTGACTGGCCATTGGCCACCAAACTTCCACTGGTCGGTGGTCACGAGGGTGCTGGTGTTGTTGTTGCC
AAGGGTGCCAACGTTACCAACTTTGAGATCGGCGACTACGCTGGTATCAAATGGCTGAACGGCTCGTGTATGGGTT
GTGAGTTCTGTCAACAAGGTGCAGAACCAAACTGTCCAGACGCCGACCTTTCCGGTTACACGCACGACGGTTCCTT
CCAACAATACGCCACTGCTGATGCTGTCCAGGCTGCCAAGATTCCAAAGGGAACTAACCTGGCCGATGTTGCTCCA
ATTCTCTGTGCTGGTGTCACTGTGTACAAGGCATTGAAGACTGCCGAATTGAGCCCAGGCCAGTGGGTCGCTATCT
CTGGTGCTGGTGGAGGATTGGGTTCTCTTGCCGTTCAATACGCTGTCGCTATGGGCCTGAGAGTTCTGGGTATCGA
TGGTGGTGACGAAAAGGCCAAGCTCTTCGAGAGCTTGGGCGGAGAAGTCTTCATCGATTTCACAAAGGAAAAGGAC
ATTGTCGGAGCCGTCCAGAAGGCTACCAACGGTGGTCCACACGGTGTCATCAACGTTTCCGTGTCTCCAGCAGCTA
TCTCTCAATCCTGCCAATACGTGAGAACTCTTGGTAAGGTTGTTCTTGTTGGTCTTCCAGCAGGTGCTGTTTGCGA
GTCTCCAGTTTTCGAGCACGTTATCAAGTCTATCCAGATTAGAGGTTCCTACGTTGGTAACAGACAGGACACTGCG
GAGTCGATCGACTTCTTCGTCAGAGGCAAGGTTAAGGCTCCAATCAAGGTTGTTGGTCTTTCTGAGCTGCCAAAAG
TGTTCGAGTTGATGGAGCAAGGAAAGATTGCAGGAAGATACGTCCTCGACACTTCCAAATAG SEQ ID NO:60: ADH amino acid sequence *Ogataea polymorpha*, NCYC 495 leu1.1
MSISRVAALRNQFARLAKPAVVQQVFRHSTASAPTIPKTQMGCVFETNGGPIEYKEIPVPKPKPNEILVHVKYSGV
CHTDLHAWKGDWPLPVKLPLVGGHEGAGVVVAKGENVKNFEIGDLAGIKWLNGSCMGCEFCQQGAEPNCPDADLSG
YTHDGSFQQYATADAVQAAKLPPGTDLAAVAPILCAGVTVYKALKTAALRPGQIVAISGAAGGLGSLAVQYAVAMG
LRVLGIDGGEQKGEFIKKLGAEFYVDFTKEKDIVSAIQKVTNGGPHGVINVSVSPAAISQSCQYVRTLGKVVLVGL
PAGAVCESPVFEHVVKSIQIKGSYVGNRQDTAEAVDFFTRGLVRSPFQIAGLSELPEVFKKMEEGKILGRYVLDTS
K]

Figure 1 (continued):

SEQ ID NO:61: *ADH* gene sequence of *Ogataea polymorpha,* NCYC 495 leu1.1
ATGTCTATTTCGAGAGTTGCTGCATTGAGAAACCAATTTGCTCGTCTAGCCAAGCCGGCTGTAGTCCAGCAGGTCT
TCAGACACTCCACTGCCTCTGCTCCAACCATCCCAAAGACCCAGATGGGATGTGTTTTTGAAACCAACGGCGGTCC
AATTGAGTACAAGGAGATCCCAGTTCCAAAGCCAAAGCCAAACGAGATTCTGGTCCACGTCAAGTACTCTGGTGTG
TGCCACACCGACTTGCACGCCTGGAAGGGTGACTGGCCACTGCCTGTCAAACTCCCACTTGTGGGTGGTCACGAGG
GTGCCGGTGTTGTCGTTGCCAAGGGTGAGAACGTTAAAAACTTCGAGATCGGCGACTTGGCCGGTATCAAATGGCT
GAACGGCTCGTGTATGGGTTGTGAGTTCTGTCAACAGGGTGCCGAACCAAACTGTCCTGACGCCGACCTTTCCGGT
TACACACACGACGGTTCTTTCCAACAATACGCCACTGCTGACGCTGTCCAGGCCGCTAAGCTGCCTCCAGGAACTG
ACCTCGCTGCTGTTGCTCCAATTTTGTGTGCTGGTGTGACTGTTTACAAGGCCTTGAAGACTGCTGCTTTGCGTCC
AGGTCAGATTGTTGCTATTTCCGGTGCCGCCGGTGGATTGGGTTCTCTTGCCGTTCAATACGCTGTCGCCATGGGT
CTGAGAGTTCTGGGTATTGACGGTGGTGAGCAGAAGGGCGAGTTCATCAAGAAGCTCGGTGCCGAATTCTACGTCG
ACTTCACCAAGGAGAAGGACATTGTGTCTGCCATCCAGAAGGTCACCAATGGCGGTCCACACGGTGTCATCAACGT
GTCTGTGTCTCCAGCTGCTATCTCCCAGTCTTGTCAATACGTGAGAACCCTCGGTAAGTTGTTCTGGTTGGTCTT
CCAGCCGGCGCTGTTTGCGAATCTCCTGTCTTTGAGCACGTCGTCAAGTCCATCCAGATCAAGGGATCTTATGTTG
GTAACAGACAAGACACTGCCGAGGCCGTGGACTTCTTCACCAGAGGCCTTGTCCGTTCTCCATTCCAAATTGCCGG
TCTTTCCGAGCTGCCTGAGGTCTTCAAGAAGATGGAGGAGGGCAAGATCTTGGGTAGATATGTCCTTGACACTTCT
AAATAA SEQ ID NO:62: ADH2 amino acid sequence of *Saccharomyces cerevisiae,* YJM627
MSIPETQKAIIFYESNGKLEYKDIPVPKPKANELLINVKYSGVCHTDLHAWHGDWPLPVKLPLVGGHEGAGVVVGM
GENVKGWKIGDYAGIKWLNGSCMACEYCELGNESNCPHADLSGYTHDGSFQQYATADAVQAAHIPQGTDLAEVAPV
LCAGITVYKALKSANLRAGHWVAISGAAGGLGSLAVQYAKAMGYRVLGIDGGPGKEELFTSLGGEVFIDFTKEKDI
VSAVVKATNGGAHGIINVSVSEAAIEASTRYCRANGTVVLVGLPAGAKCSSDVFNHVVKSISIVGSYVGNRADTRE
ALDFFARGLVKSPIKVVGLSSLPEIYEKMEKGQIAGRYVVDTSK SEQ ID NO:63: *ADH2* gene sequence of *Saccharomyces cerevisiae,* YJM627
ATGTCTATTCCAGAAACTCAAAAAGCCATTATCTTCTACGAGTCCAACGGTAAGTTGGAATACAAAGATATTCCAG
TTCCAAAGCCAAAGGCCAACGAATTGTTGATCAACGTTAAATACTCTGGTGTCTGTCACACTGACTTGCACGCTTG
GCACGGTGACTGGCCATTGCCAGTTAAGCTACCATTAGTCGGTGGTCACGAAGGTGCCGGTGTCGTTGTCGGCATG
GGTGAAAACGTTAAGGGCTGGAAGATCGGTGACTACGCCGGTATCAAATGGTTGAACGGTTCTTGTATGGCCTGTG
AATACTGTGAATTGGGTAACGAATCCAACTGTCCTCACGCTGACTTGTCTGGTTACACCCACGACGGTTCTTTCCA
ACAATACGCTACCGCTGACGCTGTTCAAGCCGCTCACATTCCTCAAGGTACTGACTTGGCTGAAGTCGCCCCAGTT
TTGTGTGCTGGTATCACCGTCTACAAGGCTTTGAAGTCTGCCAACTTGAGAGCAGGCCACTGGGTGGCCATTTCTG
GTGCTGCTGGTGGTCTAGGTTCTTTGGCTGTTCAATATGCTAAGGCGATGGGTTACAGAGTCTTAGGTATTGATGG
TGGTCCAGGAAAGGAAGAATTGTTTACCTCGCTCGGTGGTGAAGTATTCATCGACTTCACCAAAGAGAAGGACATT
GTTAGCGCAGTCGTTAAGGCTACCAACGGCGGTGCCCACGGTATCATCAATGTTTCCGTTTCCGAAGCCGCTATCG
AAGCTTCTACCAGATACTGTAGGGCGAACGGTACTGTTGTCTTGGTTGGTTTGCCAGCCGGTGCAAAGTGCTCCTC
TGATGTCTTCAACCACGTTGTCAAGTCTATCTCCATTGTCGGCTCTTACGTGGGAACAGAGCTGATACCAGAGAA
GCCTTAGATTTCTTTGCCAGAGGTCTAGTCAAGTCTCCAATAAAGGTAGTTGGCTTATCCAGTTTACCAGAAATTT
ACGAAAAGATGGAGAAGGGCCAAATTGCTGGTAGATACGTTGTTGACACTTCTAAATAA SEQ ID NO:64: ADH2 amino acid sequence of *Candida maltosa,* Xu316
MSSIPTTQKAIIFETNGGKLEYKDIPVPKPKPNELLINVKYSGVCHTDLHAWKGDWPLATKLPLVGGHEGAGVVVA
IGDNVKNWKVGDFAGVKWLNGSCLNCEYCQQGAEPNCAQADLSGYTHDGSFQQYATADAVQAARIPAGTDLATVAP
ILCAGVTVYKALKTANLQPGQWVAISGAAGGLGSLAVQYAKAMGYRVLAIDGGEDKGQFVKSLGAETFIDFTKEKD
VVGAVQKATNGGPHGVINVSVSDRAINQSVEYVRTLGKVVLVGLPAGAKVTAPVFDSVVKSIEIKGSYVGNRKDTA
EAVDFFSRGLIKCPIKIVGLSELPEVYKLMEEGKILGRYVLDTSK Figure 1 (continued):

SEQ ID NO:65: *ADH2* gene sequence of *Candida maltosa,* Xu316
ATGTCTTCTATTCCAACTACTCAAAAAGCTATTATCTTCGAAACCAACGGCGGTAAATTAGAATACAAAGATATCC
CAGTCCCAAAACCAAAACCAAATGAATTGTTGATCAATGTTAAATACTCCGGTGTTTGTCACACTGATTTGCACGC
TTGGAAAGGTGATTGGCCATTAGCCACCAAATTACCATTGGTCGGTGGTCACGAAGGTGCTGGTGTTGTCGTTGCT
ATTGGTGACAATGTCAAGAACTGGAAAGTTGGTGATTTCGCCGGTGTCAAATGTTGAATGGTTCTTGTTTGAACT
GTGAATACTGTCAACAAGGTGCTGAACCAAACTGTGCTCAAGCTGACTTGTCCGGTTACACCCACGATGGTTCTTT
CCAACAATACGCCACTGCCGATGCAGTTCAAGCGGCTAGAATTCCAGCTGGTACTGATTTAGCCACCGTTGCTCCA
ATCTTGTGTGCTGGTGTTACCGTTTACAAGGCTTTGAAGACTGCCAACTTACAACCAGGTCAATGGGTTGCCATTT
CCGGTGCCGCTGGTGGTTTAGGTTCTTTGGCTGTTCAATACGCTAAAGCTATGGGTTACAGAGTCTTGGCCATTGA
CGGTGGTGAAGATAAAGGTCAATTTGTTAAATCTTTGGGTGCTGAAACTTTTATCGATTTTACCAAAGAAAAGGAT
GTTGTTGGTGCTGTCCAAAAAGCTACCAACGGTGGTCCACATGGTGTCATTAACGTCTCTGTTTCCGACAGAGCTA
TCAACCAATCCGTTGAATACGTTAGAACTTTAGGTAAAGTTGTTTTGGTTGGTTTACCAGCTGGTGCTAAAGTCAC
TGCTCCAGTCTTTGACTCCGTCGTTAAATCCATTGAAATTAAAGGTTCTTATGTTGGTAACAGAAAAGACACTGCC
GAAGCCGTTGATTTCTTCTCTAGAGGTTTGATTAAATGTCCAATCAAGATTGTTGGTTTATCTGAATTACCAGAAG
TTTACAAATTGATGGAAGAAGGTAAAATCTTGGGTAGATACGTTTTGGACACCTCCAAATAA SEQ ID NO:66: ADH4 amino acid sequence of *Kluyveromyces marxianus,* DMKU3-1042
MFRLARAQTSITTTSKALGGSRRLFVRLNSSFAIPESQKGVIFYENGGKLEYKDLPVPKPKPNEILINVKYSGVCH
TDLHAWKGDWPLPVKLPLVGGHEGAGVVVAKGENVTNFEIGDYAGIKWLNGSCMSCELCEQGYESNCLQADLSGYT
HDGSFQQYATADAVQAAQIPKGTDLAEIAPILCAGVTVYKALKTADLQPGQWIAISGAAGGLGSLAVQYAKAMGLR
VLGIDGGPGKEELFKSLGGEVFIDFTKSKDMVADIQEATNGGPHGVINVSVSEAAISMSTEYVRPTGVVVLVGLPA
HAYVKSEVFSHVVKSISIKGSYVGNRADTREAIDFFTRGLVKSPIKVVGLSELPKVYELMEAGKILGRYVVDTSK SEQ ID NO:67: *ADH4* gene sequence of *Kluyveromyces marxianus,* DMKU3-1042
ATGTTCAGACTAGCACGCGCTCAGACCAGCATTACCACCACTAGCAAGGCTCTAGGTGGCTCCAGAAGACTATTCG
TCAGACTAAACTCCTCTTTCGCCATCCCAGAATCCCAAAAGGGTGTGATTTTCTACGAAAACGGCGGTAAGTTGGA
ATACAAGGACCTTCCAGTTCCAAAGCCAAAGCCAAATGAAATCTTGATCAACGTCAAGTACTCCGGTGTGTGTCAC
ACTGATTTGCACGCCTGGAAGGGTGACTGGCCATTGCCAGTTAAGTTGCCTTTGGTCGGTGGTCACGAAGGTGCCG
GTGTCGTCGTTGCCAAGGGTGAAAACGTTACCAACTTCGAGATCGGTGACTACGCAGGTATCAAGTGGTTGAACGG
TTCTTGTATGTCTTGTGAACTCTGTGAACAAGGTTACGAATCCAACTGTTTGCAAGCTGACTTGTCTGGTTACACC
CACGACGGTTCCTTCCAACAATATGCCACTGCTGACGCTGTTCAAGCTGCCCAAATTCCAAAGGGTACCGATTTGG
CTGAAATCGCCCCAATCTTGTGTGCCGGTGTCACCGTCTACAAGGCTCTAAAGACCGCTGACTTGCAACCAGGTCA
ATGGATCGCTATCTCCGGTGCTGCCGGTGGTCTTGGTTCCCTAGCCGTGCAATACGCCAAGGCAATGGGTCTAAGA
GTTCTAGGTATCGACGGTGGTCCAGGTAAGGAAGAATTGTTCAAGAGCTTGGGTGGTGAAGTCTTCATTGACTTCA
CAAAGTCCAAGGACATGGTCGCAGACATCCAGGAAGCCACCAACGGTGGTCCTCACGGTGTGATCAACGTCTCCGT
CTCCGAGGCCGCTATCTCCATGTCCACCGAGTACGTCAGACCAACCGGTGTGGTCGTTCTAGTCGGTTTGCCAGCC
CACGCTTACGTCAAGTCCGAAGTCTTCTCCCACGTCGTCAAGTCTATCTCTATTAAGGGTTCTTACGTCGGTAACA
GAGCAGACACCAGAGAAGCTATTGACTTCTTCACCAGAGGTTTGGTCAAGTCTCCAATCAAGGTTGTTGGTTTGTC
TGAATTGCCAAAGGTTTATGAATTGATGGAAGCTGGTAAGATCTTGGGTAGATACGTCGTTGACACTTCCAAATAA SEQ ID NO:68: ADH1 amino acid sequence of *Escherichia coli,* 7.1982
MSEQIPKTQKAVVFDTNGGQLVYKDYPVPTPKPNELLINVKYSGVCHTDLHAWKGDWPLATKLPLVGGHEGAGVVV
GMGENVKGWKIGDFAGIKWLNGSCMSCEFCQQGAEPNCGEADLSGYTHDGSFEQYATADAVQAAKIPAGTDLANVA
PILCAGVTVYKALKTADLAAGQWVAISGAGGGLGSLAVQYARAMGLRVVAIDGGDEKGEFVKSLGAEAYVDFTKDK
DIVEAVKKATDGGPHGAINVSVSEKAIDQSVEYVRPLGKVVLVGLPAHAKVTAPVFDAVVKSIEIKGSYVGNRKDT
AEAIDFFSRGLIKCPIKIVGLSDLPEVFKLMEEGKILGRYVLDTSK Figure 1 (continued):

SEQ ID NO:69: *ADH1* gene sequence of *Escherichia coli*, 7.1982
ATGTCTGAACAAATCCCAAAAACTCAAAAAGCCGTTGTCTTTGATACCAATGGTGGTCAATTAGTCTACAAGGATT
ACCCAGTTCCAACTCCAAAGCCAAATGAATTGTTAATCAACGTCAAATACTCTGGTGTCTGTCACACTGATTTACA
CGCTTGGAAAGGTGACTGGCCATTGGCTACTAAATTGCCATTAGTTGGTGGTCACGAAGGTGCCGGTGTCGTTGTC
GGTATGGGTGAAAACGTCAAAGGATGGAAAATCGGTGACTTTGCCGGTATCAAATGGTTGAACGGTTCTTGTATGA
GTTGTGAATTCTGTCAACAAGGTGCTGAACCAAACTGTGGTGAAGCTGACTTGTCTGGTTACACTCACGATGGTTC
ATTCGAACAATACGCTACTGCTGATGCTGTCCAAGCCGCTAAAATTCCAGCTGGTACTGATTTAGCCAATGTCGCA
CCAATCTTATGTGCTGGTGTTACTGTTTACAAAGCCTTAAAGACTGCTGACTTAGCAGCTGGCCAATGGGTTGCTA
TCTCCGGTGCTGGTGGTGGTTTAGGTTCTTTGGCCGTTCAATACGCCAGAGCCATGGGTTTGAGAGTTGTTGCTAT
TGACGGTGGTGACGAAAAAGGTGAATTTGTTAAATCATTGGGTGCTGAAGCTTACGTTGATTTCACCAAAGATAAA
GATATTGTTGAAGCTGTTAAGAAGGCTACTGATGGTGGTCCACACGGTGCTATCAATGTCTCTGTTTCTGAAAAAG
CCATTGACCAATCTGTTGAATATGTTAGACCATTAGGTAAAGTTGTTTTGGTTGGTTTACCAGCTCACGCTAAAGT
CACTGCTCCAGTTTTCGATGCTGTTGTCAAATCCATTGAAATCAAAGGTTCTTACGTTGGTAACAGAAAAGATACT
GCTGAAGCTATTGACTTCTTCTCCAGAGGTTTAATCAAATGCCCAATCAAGATTGTCGGTTTATCTGACTTGCCAG
AAGTCTTCAAATTGATGGAAGAAGGTAAAATCTTGGGTAGATACGTCTTGGACACCAGTAAATAA SEQ ID NO:70: ADH1 amino acid sequence of *Fusarium graminearum*, PH-1
MAAPQIPSQQWAQIFEKTAGPIEYKQIPVQKPGPDEVLVNVKFSGVCHTDLHAWQGDWPLDTKLPLVGGHEGAGVV
VARGELVKDVKIGEKVGIKWLNGSCLSCSYCQNADESLCAEALLSGYTVDGSFQQYAIAKAIHVARIPEECDLEAI
SPILCAGITVYKGIKESGVKAGQSLAIVGAGGGLGSIAVQYAKAMGIHAIAIDGGEEKEKMCMSLGAQTFIDFTKT
KNIVADVKATTNDGLGPHAALLVAAAEKPFQQATQYIRSKGTVVCIGLPAGAQFSAPVFDTVVRMIQIKGSYVGNR
ADTAEAIDFFRRGLIKVPFKTVGLSELNEVFKLMKAGQVAGRYVVDTSR SEQ ID NO:71: *ADH1* gene sequence of *Fusarium graminearum*, PH-1
ATGGCCGCTCCCCAGATTCCTTCCCAGCAGTGGGCTCAGATCTTCGAGAAGACCGCCGGTCCCATCGAGTACAAGC
AGATTCCCGTCCAGAAGCCTGGCCCCGATGAGGTTCTCGTCAACGTCAAGTTCTCCGGTGTCTGCCACACTGACCT
CCACGCCTGGCAGGGTGACTGGCCCCTCGACACCAAGCTGCCCCTTGTCGGTGGCCACGAGGGTGCCGGTGTTGTC
GTTGCCCGCGGCGAGCTTGTCAAGGATGTCAAGATTGGCGAGAAGGTCGGTATCAAGTGGCTCAACGGTTCTTGCT
TGAGCTGCTCTTACTGCCAAAACGCCGATGAGTCTCTCTGCGCTGAGGCTCTTCTCCGGTTACACCGTCGATGG
ATCTTTCCAGCAATACGCCATCGCCAAGGCTATCCACGTTGCTCGCATCCCTGAGGAGTGTGACCTTGAGGCCATC
TCCCCCATTCTCTGCGCCGGTATCACCGTCTACAAGGGTATCAAGGAGTCCGGTGTCAAGGCCGGCCAGTCTCTTG
CTATCGTCGGTGCTGGTGGTGGTCTCGGTTCCATCGCTGTTCAGTACGCCAAGGCTATGGGTATCCATGCCATTGC
CATTGATGGTGGTGAGGAGAAGGAGAAGATGTGCATGTCTCTCGGTGCCCAAACCTTCATCGACTTCACAAAGACT
AAGAACATCGTCGCTGATGTCAAGGCTACTACCAACGATGGCCTTGGCCCTCACGCTGCTCTCCTCGTCGCTGCTG
CCGAGAAGCCCTTCCAACAGGCTACCCAATACATCCGATCCAAGGGTACCGTCGTCTGCATCGGTCTCCCCGCTGG
TGCTCAGTTCTCTGCCCCCGTCTTCGACACTGTCGTTCGCATGATTCAGATCAAGGGATCTTATGTCGGTAACCGT
GCCGATACTGCTGAGGCCATCGACTTCTTCCGCCGTGGTCTCATCAAGGTTCCCTTCAAGACTGTTGGTCTCTCTG
AGCTCAACGAGGTCTTCAAGCTCATGAAGGCTGGCCAAGTTGCTGGTCGCTATGTCGTTGACACCAGCCGATAA

MUT- METHYLOTROPHIC YEAST

CROSS-REFERENCE TO RELATED APPLICATIONS

This application is the U.S. national stage of International Patent Application No. PCT/EP2020/059284, filed on Apr. 1, 2020 and entitled MUT-METHYLOTROPHIC YEAST, which claims the benefit of priority under 35 U.S.C. § 120 from International Patent Application No. PCT/EP2019/058190, filed Apr. 1, 2019, and from International Patent Application No. PCT/EP2019/058191, filed Apr. 1, 2019. The disclosures of the foregoing applications are incorporated herein by reference in their entirety.

SEQUENCE LISTING

The entire content of a Sequence Listing titled "Sequence_Listing.txt," created on Sep. 29, 2021 and having a size of 172 kilobytes, which has been submitted in electronic form in connection with the present application, is hereby incorporated by reference herein in its entirety.

TECHNICAL FIELD

The invention refers to production of a protein of interest (POI) in a recombinant methylotrophic yeast which is deficient in alcohol oxidase 1 (AOX1) and alcohol oxidase 2 (AOX2).

BACKGROUND

Proteins produced in recombinant host cell culture have become increasingly important as diagnostic and therapeutic agents. For this purpose, cells are engineered and/or selected to produce unusually high levels of a recombinant or heterologous protein of interest. Optimization of cell culture conditions is important for successful commercial production of recombinant or heterologous proteins.

Successful production of proteins of interest (POI) has been accomplished both with prokaryotic and eukaryotic host cells in cell culture. Eukaryotic host cells, in particular mammalian host cells, yeasts or filamentous fungi, or bacteria are commonly used as production hosts for biopharmaceutical proteins as well as for bulk chemicals. The most prominent examples are methylotrophic yeasts like such as Pichia pastoris, which is well reputed for efficient secretion of heterologous proteins. P. pastoris has been reclassified into a new genus, Komagataella, and split into three species, K. pastoris, K. phaffii, and K. pseudopastoris. Strains commonly used for biotechnological applications belong to two proposed species, K. pastoris and K. phaffii. The strains GS115, X-33, CBS2612, and CBS7435 are K. phaffii, while the strain DSMZ70382 is classified into the type species, K. pastoris, which is the reference strain for all the available P. pastoris strains (Kurtzman 2009, J Ind Microbiol Biotechnol. 36(11):1435-8). Mattanovich et al. (Microbial Cell Factories 2009, 8:29 doi:10.1186/1475-2859-8-29) describe the genome sequencing of the type strain DSMZ 70382 of K. pastoris, and analyzed its secretome and sugar transporters.

P. pastoris strains have been used which are deficient in both AOX genes, AOX1 and AOX2 (referred to as Mut-), or deficient in only AOX2 (referred to as $Mut^S$), or not deficient in any of the AOX genes (referred to as Mut+).

Promoters used for protein production in recombinant host cells are either regulated (e.g., induced upon addition of methanol to the medium, methanol-controlled), or constantly active (constitutive). The methanol inducible promoter pAOX1 has been described to control protein expression in Mut-, Mut+ or $Mut^S$ strains.

Chiruvolu et al. (Enzyme Microb. Technol. 1997, 21:277-283) describe the construction of a Mut- strain used for recombinant protein production. It was determined that the Mut- strain did not grow on methanol, which necessitated the use of another carbon source to provide for growth, maintenance and protein production. A POI has been expressed under the control of pAOX1, which has been induced by injection of methanol into the fermentor to maintain a concentration of about 0.5% (v/v).

Chauhan et al. (Process Biochemistry 1999, 34:139-145) describe utilization of a AOX1 deleted host (designated as Mut-, however, understood to be $Mut^S$) carrying a gene for expressing HBsAg under the pAOX1 promoter. Protein expression was inducted by methanol, but a high methanol concentration in the broth was found to be toxic to the cells, because the $Mut^S$ cells were found to be sensitive to the methanol concentration.

Karaoglan et al. (Biotechnol. Lett. 1995, DOI 10.1007/s10529-015-1993-z) describe the functional analysis of alcohol dehydrogenase (ADH) genes in P. pastoris. ADH3 (XM_002491337) and ADH (FN392323) genes were disrupted. The double knockout strain also produced ethanol. It is concluded that the ADH gene does not play a role in ethanol metabolism; and PpADH3 was the only gene responsible for consumption of ethanol in P. pastoris.

Singh and Narang (bioRxiv, DOI:10.1101/573519, preprint) describe β-galactosidase expression in Mut+, a Mute (AOX1-) and Mut- (AOX1- AOX2-) strains of Komagataella phaffii (Pichia pastoris). It was concluded that formate or/and formaldehyde are probably true inducers since both induce $P_{AOX1}$ expression in Mut- which cannot synthesize intracellular methanol from formate or formaldehyde, and propose formate as a promising substitute for methanol since it does not appear to suffer from the deficiencies that afflict methanol.

Wei Shen et al. (Microbial Cell Factories 2016, 15(1):1-11) describe a methanol-free Pichia pastoris protein expression system. Two kinase mutants, Δgut1 and Δdak, showed strong alcohol oxidase activity under non-methanol carbon sources and were used to construct methanol-free expression systems.

Ia Pla et al. (Biotechnol Prog, 2006, pp 881-888) describe $Mut^S$ and Mut+ P. pastoris strains for expressing scFv using AOX promoters and induction by methanol.

EP1905836A1 discloses P. pastoris strains for producing recombinant human interferon alpha, and suggests using an AOX1-disturbed clone which comprises a mutated AOX1 gene, yet no complete deletion of the AOX1 locus.

Ching-Hsiang Chang et al. (BMC Biotechnology 2018, 18(1):81) suggest a flexible pAOX1 induction system in P. pastoris using methanol expression regulator 1 (Mxr1)-reprogrammed cells.

Russmayer H. et al. (BMC Biology 2015, 13(1):80) describe the importance of AOX in regulating P. pastoris expression systems.

Tomas-Gamisans M. et al. (Microbial Biotechnology 2018, 11(1):224-237) describe a P. pastoris genome-scale metabolic model for improved prediction on methanol or glycerol as sole carbon sources.

Moser et al. (Microbial Cell Factories 2017, 16(1):49) describe adaptive laboratory evolution to improve growth and recombinant protein production in P. pastoris.

Recombinant protein production in P. pastoris requires an intense process scheme, leading to high oxygen demand, and heat production, demanding a high biomass concentration and methanol consumption. Oxygen transfer, cooling and biomass separation in downstream processing is expensive. It is thus desirable to develop processes of low oxygen demand and heat production. It is further desirable to increase the yield of protein production, in particular by efficient use of a carbon source.

SUMMARY OF THE INVENTION

It is the objective of the invention to improve recombinant protein production in methylotrophic yeast.

The objective is solved by the subject of the claims and as further described herein.

The invention provides for a recombinant methanol utilization pathway deficient methylotrophic yeast (Mut−) host cell which is engineered:
  a) by one or more genetic modifications to reduce expression of a first and a second endogenous gene compared to the host cell prior to said one or more genetic modifications, wherein
    i. the first endogenous gene encodes alcohol oxidase 1 (AOX1) comprising the amino acid sequence identified as SEQ ID NO:1 or a homologue thereof, and
    ii. the second endogenous gene encodes alcohol oxidase 2 (AOX2) comprising the amino acid sequence identified as SEQ ID NO:3 or a homologue thereof, and
  b) by one or more genetic modifications to increase expression of an alcohol dehydrogenase (ADH2) gene compared to the host cell prior to said one or more genetic modifications, wherein the ADH2 gene encodes an alcohol dehydrogenase (ADH2).

Specifically, the ADH2 protein is an alcohol dehydrogenase classified as EC 1.1.1.1.

As described herein, the term "ADH2" shall refer to either a native alcohol dehydrogenase, such as *P. pastoris* alcohol dehydrogenase comprising or consisting of the amino acid sequence identified as SEQ ID NO:50 (UniProtKB—F2QSX6_KOMPC; FR839629 Genomic DNA Translation: CCA38504.1; gene: PP7435_Chr2-0821), or a sequence which has a certain homology (or sequence identity) to SEQ ID NO:50.

Specifically, the ADH2 may originate from a *P. pastoris* strain or may be a homologue or ortholog thereof which is naturally-occurring originating from or endogenous to a wild-type cell of an organism, such as eukaryotes, including e.g. yeast, in particular of a methylotrophic yeast strain, species, or genus, or which is a mutant of such naturally-occurring ADH2.

Specifically, the ADH2 protein is naturally-occurring in or endogenous to the species of the host cell, or a mutant thereof.

Specifically, the gene encoding the *P. pastoris* alcohol dehydrogenase, herein referred to as ADH2 gene, comprises or consists of the nucleotide sequence identified as SEQ ID NO:51, or a homologous polynucleotide (gene) encoding ADH2, which ADH2 has a certain homology (or sequence identity) to SEQ ID NO:50.

Specifically, the ADH2 gene is endogenous or heterologous to the Mut− host cell. Specifically, the Mut− host cell comprises one or more copies of said ADH2 gene.

Specifically, the ADH2 is any one of:
  a) an ADH2, which is *P. pastoris* ADH2 comprising the amino acid sequence identified as SEQ ID NO:50, or a homologue thereof that is endogenous to a yeast species, in particular methylotrophic yeast; or
  b) a mutant of the ADH2 of a), which is at least 60% identical to SEQ ID NO:50.

The homologous sequences are also referred to as ADH2 homologue or ADH2 homologue.

Exemplary homologues are described in FIG. 1:
  SEQ ID NO:52: ADH2 amino acid sequence of *Komagataella pastoris*, ATCC 28485
  SEQ ID NO:53: ADH2 gene sequence of *Komagataella pastoris*, ATCC 28485
  SEQ ID NO:54: ADH2 amino acid sequence of *Ogataea parapolymorpha*, DL-1
  SEQ ID NO:55: ADH2 gene sequence of *Ogataea parapolymorpha*, DL-1
  SEQ ID NO:56: ADH2 amino acid sequence of *Ogataea parapolymorpha*, DL-1
  SEQ ID NO:57: ADH2 gene sequence of *Ogataea parapolymorpha*, DL-1
  SEQ ID NO:58: ADH amino acid sequence of *Ogataea polymorpha*, NCYC 495 leu1.1
  SEQ ID NO:59: ADH gene sequence of *Ogataea polymorpha*, NCYC 495 leu1.1
  SEQ ID NO:60: ADH amino acid sequence *Ogataea polymorpha*, NCYC 495 leu1.1
  SEQ ID NO:61: ADH gene sequence of *Ogataea polymorpha*, NCYC 495 leu1.1
  SEQ ID NO:62: ADH2 amino acid sequence of *Saccharomyces cerevisiae*, YJM627
  SEQ ID NO:63: ADH2 gene sequence of *Saccharomyces cerevisiae*, YJM627
  SEQ ID NO:64: ADH2 amino acid sequence of *Candida maltosa*, Xu316
  SEQ ID NO:65: ADH2 gene sequence of *Candida maltosa*, Xu316
  SEQ ID NO:66: ADH4 amino acid sequence of *Kluyveromyces marxianus*, DMKU3-1042
  SEQ ID NO:67: ADH4 gene sequence of *Kluyveromyces marxianus*, DMKU3-1042
  SEQ ID NO:68: ADH1 amino acid sequence of *Escherichia coli*, 7.1982
  SEQ ID NO:69: ADH1 gene sequence of *Escherichia coli*, 7.1982
  SEQ ID NO:70: ADH1 amino acid sequence of *Fusarium graminearum*, PH-1
  SEQ ID NO:71: ADH1 gene sequence of *Fusarium graminearum*, PH-1

Specifically, the ADH2 homologue has at least any one of 60%, 70%, 80%, 85%, 90%, or 95% sequence identity to SEQ ID NO:50. An ADH2 homologue is herein understood to encode an ADH2 homologue. Specifically, sequence identity is determined as further disclosed herein, for example when comparing the full-length sequence.

Specifically, the homologue or homologous sequence is characterized by the same qualitative function of the ADH2 protein in a wild-type host cell such as in *P. pastoris*, in particular *K. pastoris* or *K. phaffii* e.g., as alcohol dehydrogenase (EC 1.1.1.1).

Specifically, the homologous sequences of SEQ ID NO:50 is of a species other than *P. pastoris*, in particular *K. pastoris* or *K. phaffii* e.g., another yeast of the *Komagataella* or *Pichia* genus, and expression of the respective endogenous coding sequences increased (e.g., knocked in) as described herein.

If the host cell is of *P. pastoris*, in particular *K. pastoris* or *K. phaffii*, the ADH2 protein may comprise or consist of the endogenous sequence e.g., SEQ ID NO:50, or a homologue to SEQ ID NO:50 of a different strain or species, or an artificial sequence of a mutant ADH2 protein, which is not naturally-occurring in a wild-type strain or organism, in particular which is not naturally-occurring in a methylotrophic yeast.

According to a specific example, the homologous sequence has at least any one of 0.2-fold, 0.3-fold, 0.4-fold, 0.5.fold, 0.6-fold, 0.7-fold, 0.8-fold, 0.9-fold, 1-fold, 1.1-fold, 1.2-fold, 1.3-fold, 1.4-fold, 1.5-fold, 1.6-fold, 1.7-fold, 1.8-fold, 1.9-fold, 2-fold, or even higher alcohol dehydrogenase activity as compared to the activity of the endogenous naturally-occurring P. pastoris alcohol dehydrogenase in a wild-type P. pastoris. The alcohol dehydrogenase activity can be measured in a suitable assay e.g., by an alcohol dehydrogenase assay using cell free extracts. Cell free extracts can be obtained by mechanical disruption of the cell culture by zirconia/silica/glass beads as described by Karaoglan et al. (Biotechnol Lett. 2016; 38(3):463-9). The alcohol dehydrogenase activity can be measured following the formation of NADH by measuring the absorption increase at a wavelength of 340 nm as described by Walker (Biochemical Education. 1992 21(1):42-43). $NAD^+$ and alcohol can be used as substrates and are consumed in equimolar concentrations. NADH production is inversely correlated with $NAD^+$ consumption. Alternatively, a commercial colorimetric alcohol dehydrogenase activity assay kit can be used (MAK053, Sigma-Aldrich). An exemplary assay is herein described in the examples section.

As described herein, the term "AOX1" shall refer to either a native alcohol oxidase 1, such as P. pastoris alcohol oxidase 1 comprising or consisting of the amino acid sequence identified as SEQ ID NO:1 (UniProtKB—F2QY27), or a sequence which has a certain homology (or sequence identity) to SEQ ID NO:1, which may be a homologue of the P. pastoris alcohol oxidase 1 that is endogenous to a methylotrophic yeast species, in particular which is endogenous to the methylotrophic yeast herein used as a host cell, prior to said one or more genetic modifications to reduce expression of said endogenous alcohol oxidase 1. In particular, the AOX1 protein is an ortholog that is endogenous to the species of the host cell species.

Specifically, the gene encoding the P. pastoris alcohol oxidase 1, herein referred to as AOX1 gene, comprises or consists of the nucleotide sequence identified as SEQ ID NO:2.

The homologous sequences are also referred to as AOX1 homologue or AOX1 homologue. Specifically, the AOX1 protein or AOX1 homologue is an alcohol oxidase enzyme classified as EC 1.1.3.13.

Specifically, the AOX1 homologue has at least any one of 60%, 70%, 80%, 85%, 90%, or 95% sequence identity to SEQ ID NO:1. An AOX1 homologue is herein understood to encode an AOX1 homologue. Specifically, sequence identity is determined as further disclosed herein, for example when comparing the full-length sequence.

As described herein, the term "AOX2" shall refer to either a native alcohol oxidase 2, such as P. pastoris alcohol oxidase 2 comprising or consisting of the amino acid sequence identified as SEQ ID NO:3 (UniProtKB—F2R038), or a sequence which has a certain homology (or sequence identity) to SEQ ID NO:3, which may be a homologue of the P. pastoris alcohol oxidase 2 that is endogenous to a methylotrophic yeast species, in particular which is endogenous to the methylotrophic yeast herein used as a host cell, prior to said one or more genetic modifications to reduce expression of said endogenous alcohol oxidase 2. In particular, the AOX2 protein is an ortholog that is endogenous to the species of the host cell species.

Specifically, the gene encoding the P. pastoris alcohol oxidase 2, herein referred to as AOX2 gene, comprises or consists of the nucleotide sequence identified as SEQ ID NO:4.

The homologous sequences are also referred to as AOX2 homologue or AOX2 homologue. Specifically, the AOX2 protein or AOX2 homologue is an alcohol oxidase enzyme classified as EC 1.1.3.13.

Specifically, the AOX2 homologue has at least any one of 60%, 70%, 80%, 85%, 90%, or 95% sequence identity to SEQ ID NO:3. An AOX2 homologue is herein understood to encode an AOX2 homologue. Specifically, sequence identity is determined as further disclosed herein, for example when comparing the full-length sequence.

Specifically, the AOX1 and/or AOX2 proteins are of P. pastoris origin, in particular K. pastoris or K. phaffii origin, if the host cell is P. pastoris, in particular K. pastoris and K. phaffii, respectively. Alternatively, each of the AOX1 and AOX2 proteins comprises a homologous (or orthologous) sequence of the respective protein of in P. pastoris, in particular K. pastoris or K. phaffii, origin, which homologous (orthologous) sequence is endogenous to a wild-type host cell, if of another origin or species. For example, if the host cell is K. phaffii, an endogenous AOX1 or AOX2 protein comprises or consists of the amino acid sequence identified as SEQ ID NO:1 and SEQ ID NO:3, respectively.

According to another example, if the host cell is K. pastoris, the endogenous AOX1 protein comprises or consists of the amino acid sequence identified as SEQ ID NO:9 (Komagataella pastoris, ATCC 28485), which is 99.85% identical to SEQ ID NO:1.

According to another example, if the host cell is K. pastoris, the endogenous AOX2 protein comprises or consists of the amino acid sequence identified as SEQ ID NO:11, which is 99.40% identical to SEQ ID NO:3.

Exemplary homologues are described in FIG. 1:
SEQ ID NO:9: AOX1 amino acid sequence of Komagataella pastoris, ATCC 28485
SEQ ID NO:10: AOX1 nucleotide sequence of Komagataella pastoris, ATCC 28485
SEQ ID NO:11: AOX2 amino acid sequence of Komagataella pastoris, ATCC 28485
SEQ ID NO:12: AOX2 nucleotide sequence of Komagataella pastoris, ATCC 28485
SEQ ID NO:13: MOD1 amino acid sequence of Ogataea methanolica JCM 10240
SEQ ID NO:14: MOD1 nucleotide sequence of Ogataea methanolica JCM 10240
SEQ ID NO:15: MOD2 amino acid sequence of Ogataea methanolica JCM 10240
SEQ ID NO:16: MOD2 nucleotide sequence of Ogataea methanolica JCM 10240
SEQ ID NO:17: pMOD1 promoter sequence of Ogataea methanolica JCM 10240
SEQ ID NO:18: pMOD2 promoter sequence of Ogataea methanolica JCM 10240
SEQ ID NO:19: MOX amino acid sequence of Ogataea polymorpha NCYC 495 leu 1.1
SEQ ID NO:20: MOX nucleotide sequence of Ogataea polymorpha NCYC 495 leu 1.1
SEQ ID NO:21: pMOX promoter sequence of Ogataea polymorpha NCYC 495 leu 1.1

Yet, if the host cell is of a different species (other than K. pastoris and/or K. phaffii), the AOX1 or AOX2 protein sequence which is endogenous to the host cell is a homologue to SEQ ID NO:1 and SEQ ID NO:3, respectively, and expression of such homologue in the host cell (the orthologous sequence of SEQ ID NO:1 and SEQ ID NO:3, respectively) is reduced for the purpose described herein.

Specifically, any or each of the homologous sequences is characterized by the same qualitative function of the respective AOX1 and AOX2 protein in a wild-type host cell such as in *P. pastoris*, in particular *K. pastoris* or *K. phaffii* e.g., as alcohol oxidase (EC 1.1.3.13).

Specifically, the respective homologous sequences of SEQ ID NO:1 and SEQ ID NO:3 are of a species other than *P. pastoris*, in particular *K. pastoris* or *K. phaffii* e.g., another yeast of the *Komagataella* or *Pichia* genus, and expression of the respective endogenous coding sequences reduced or abolished (knocked out) as described herein.

Specifically, both, the AOX1 and AOX2 proteins, are endogenous to the host cell, and the expression of the genes encoding AOX1 and AOX2, respectively, is reduced or deleted.

Specifically, both, the AOX1 and AOX2 proteins, are of the same origin, originating from or endogenous to the same host cell (or host cell species) prior to its engineering for reducing expression of said first and second endogenous genes.

Specifically, both, the AOX1 and AOX2 proteins, are of *P. pastoris* origin, in particular proteins encoded by a respective gene that is endogenous to the host cell, wherein the host cell is *P. pastoris*.

Specifically, both, the AOX1 and AOX2 proteins, are of *Komagataella* phaffii origin, in particular proteins encoded by a respective gene that is endogenous to the host cell, wherein the host cell is *Komagataella* phaffii.

Specifically, both, the AOX1 and AOX2 proteins, are of *Komagataella pastoris* origin, in particular proteins encoded by a respective gene that is endogenous to the host cell, wherein the host cell is *Komagataella pastoris*.

According to a specific aspect, said one or more genetic modifications comprises a disruption, substitution, deletion, knockin or knockout of (i) one or more polynucleotides, or a part thereof; or (ii) an expression control sequence.

According to a specific aspect, said one or more genetic modifications are of one or more endogenous polynucleotides of the host cell described herein, such as coding polynucleotides, including e.g., said polynucleotide (or gene) encoding the respective AOX1, AOX2, or ADH2 protein, in particular the wild-type (unmodified or native) protein, which is naturally-occurring in the host cell species, type or strain, or a nucleotide sequence controlling expression of said polynucleotide (or gene).

According to a specific aspect, said one or more genetic modifications are of an expression control sequence, including e.g., a promoter, ribosomal binding site, transcriptional or translational start and stop sequences, or of an enhancer or activator sequence.

A variety of methods of engineering a host cell can be employed to modulate (reduce or increase) expression of an endogenous polynucleotide, such as
  a) to reduce expression of a gene encoding the respective AOX1 or AOX2 protein, including e.g., disrupting the polynucleotide encoding the respective AOX1 or AOX2 protein, disrupting the promoter which is operably linked to such polynucleotide, replacing such promoter with another promoter which has lower promoter activity; or
  b) to increase expression of a gene encoding the ADH2 protein, including e.g., introducing a polynucleotide encoding the ADH2 protein into the host cell genome, disrupting the promoter which is operably linked to such polynucleotide, replacing such promoter with another promoter which has higher promoter activity.

Specific methods of modifying gene expression employ modulating (e.g., activating, up-regulating, inactivating, inhibiting, or down-regulating) regulatory sequences which modulate the expression of a polynucleotide (a gene), such as using respective transcription regulators targeted to the relevant sequences by an RNA guided ribonuclease used in a CRISPR based method of modifying a host cell, e.g., regulatory sequences selected from the group consisting of promoter, ribosomal binding sites, transcriptional start or stop sequences, translational start or stop sequences, enhancer or activator sequences, repressor or inhibitor sequences, signal or leader sequences, in particular those which control the expression and/or secretion of a protein.

According to a specific aspect, said one or more genetic modifications include a gain-of-function alteration in the ADH2 gene resulting in increasing the level or activity of ADH2.

Specifically, said gain-of-function alteration includes a knockin of the ADH2 gene.

Specifically, said gain-of-function alteration up-regulates the ADH2 gene expression in said cell.

Specifically, said gain-of-function alteration includes an insertion of a heterologous expression cassette to overexpress the ADH2 gene in said cell.

Specifically, said heterologous expression cassette comprises a heterologous polynucleotide comprising an ADH2 gene under the control of a promoter sequence. Such promoter can be any of a constitutive, repressible or inducible promoter.

Specifically, said one or more genetic modifications to increase expression of a gene include one or more genomic mutations including insertion or activation of a gene or genomic sequence which increases expression of a gene or part of a gene by at least 50%, 60%, 70%, 80%, 90%, or 95%, or even more e.g., by a knockin of a heterologous gene, or increasing the copy number of the endogenous gene, as compared to the respective host without such genetic modification.

Specifically, the one or more genetic modifications increasing expression comprise genomic mutations which constitutively improve or otherwise increase the expression of one or more endogenous polynucleotides.

Specifically, the one or more genetic modifications increasing expression comprise genomic mutations introducing one or more inducible or repressible regulatory sequences which conditionally improve or otherwise increase the expression of one or more endogenous polynucleotides. Such conditionally active modifications are particularly targeting those regulatory elements and genes which are active and/or expressed dependent on cell culture conditions.

Specifically, the expression of the polynucleotide encoding the ADH2 protein is increased when using the host cell in a method of producing a protein of interest (POI). Specifically, upon genetic modification, expression of the ADH2 protein is increased under conditions of the host cell culture during which the POI is produced.

Specifically, the host cell is genetically modified to increase the amount (e.g., the level, activity or concentration) of the ADH2 protein, by at least any one of 50%, 60%, 70%, 80%, 90%, or 95%, (mol/mol), or even more, compared to the host cell without said modification, e.g., by a knockin of one or more respective ADH2 genes. According to a specific embodiment, the host cell is genetically modified to comprise one or more insertions of (one or more)

genomic sequences, in particular genomic sequences encoding the respective ADH2 protein, which are integrated in the host cell genome. Such host cell is typically provided as a knockin strain.

According to a specific embodiment, once the host cell described herein is cultured in a cell culture, the total amount of the ADH2 protein in the host cell or host cell culture is increased by at least any one of 50%, 60%, 70%, 80%, 90%, or 95%, (activity % or mol/mol), or even by 100% or more, compared to a reference amount expressed or produced by the host cell prior to or without such genetic modification, or compared to a reference amount produced in a respective host cell culture, or compared to the host cell prior to or without said modification.

Specifically, said one or more genetic modifications to reduce expression of a gene, such as the AOX1 and/or AOX2 genes, include one or more genomic mutations including deletion or inactivation of a gene or genomic sequence which reduces expression of a gene or part of a gene by at least 50%, 60%, 70%, 80%, 90%, or 95%, or even completely abolishes its expression, e.g., by a knockout of the gene, as compared to the respective host without such genetic modification.

Specifically, the one or more genetic modifications reducing expression comprise genomic mutations which constitutively impair or otherwise reduce the expression of one or more endogenous polynucleotides.

Specifically, the one or more genetic modifications reducing expression comprise genomic mutations introducing one or more inducible or repressible regulatory sequences which conditionally impair or otherwise reduce the expression of one or more endogenous polynucleotides. Such conditionally active modifications are particularly targeting those regulatory elements and genes which are active and/or expressed dependent on cell culture conditions.

Specifically, the expression of said one or more endogenous polynucleotides is reduced thereby reducing expression of the polynucleotide encoding the respective AOX1 or AOX2 protein when using the host cell in a method of producing a protein of interest (POI). Specifically, upon genetic modification, expression of both, the AOX1 and AOX2 proteins, is reduced under conditions of the host cell culture during which the POI is produced.

Specifically, the host cell is genetically modified to reduce the amount (e.g., the level, activity or concentration) of both, the AOX1 and AOX2 proteins, by at least any one of 50%, 60%, 70%, 80%, 90%, or 95%, (activity %, or mol/mol) compared to the host cell without said modification, or even by 100%, e.g. to a non-detectable amount, thereby completely abolishing production of both, the AOX1 and AOX2 proteins, e.g., by a knockout of the respective AOX1 and AOX2 genes. According to a specific embodiment, the host cell is genetically modified to comprise one or more deletions of (one or more) genomic sequences, in particular genomic sequences encoding the respective AOX1 and/or AOX2 protein. Such host cell is typically provided as a deletion or knockout strain.

According to a specific aspect, said first and/or second endogenous gene is knocked out by said one or more genetic modifications. Specifically, the Mut– host cell is a ΔAOX1/ΔAOX2 knockout strain.

According to a specific aspect, said first and/or second endogenous gene is knocked out by said one or more genetic modifications; and said ADH2 gene is knocked in by said one or more genetic modifications. Specifically, the Mut– host cell is a ΔAOX1/ΔAOX2+ADH2-OE strain.

According to a specific embodiment, once the host cell described herein is cultured in a cell culture, the total amount of the respective AOX1 and/or AOX2 protein in the host cell or host cell culture is reduced by at least any one of 50%, 60%, 70%, 80%, 90%, or 95%, (mol/mol), or even by 100%, e.g. to a non-detectable amount, compared to a reference amount expressed or produced by the host cell prior to or without such genetic modification, or compared to a reference amount produced in a respective host cell culture, or compared to the host cell prior to or without said modification.

When comparing the host cell described herein for the effect of said genetic modification to increase or reduce production of the respective ADH2, AOX1 or AOX2 protein, it is typically compared to the comparable host cell prior to or without such genetic modification. Comparison is typically made with the same host cell species or type without (or prior to) such genetic modification, which is engineered to produce the recombinant or heterologous POI, in particular when cultured under conditions to produce said POI. However, a comparison can also be made with the same host cell species or type which is not further engineered to produce the recombinant or heterologous POI.

According to a specific aspect, the increase or reduction of the respective ADH2, AOX1 or AOX2 protein is determined by the increase or reduction of the amount (e.g., the level, activity or concentration) of the respective protein in the cell. Specifically, the amount of said protein is determined by a suitable method, such as employing a Western Blot, immunofluorescence imaging, flow cytometry or mass spectrometry, in particular wherein mass spectrometry is liquid chromatography-mass spectrometry (LC-MS), or liquid chromatography tandem-mass spectrometry (LC-MS/MS) e.g., as described by Doneanu et al. (MAbs. 2012; 4(1): 24-44). According to a specific example, alcohol dehydrogenase activity can be measured by an activity assay using cell free extracts. Cell free extracts can be obtained by mechanical disruption of the cell culture by zirconia/silica/glass beads as described by Karaoglan et al. (Biotechnol Lett. 2016; 38(3): 463-9). The alcohol dehydrogenase activity is measured by directly following the formation of NADH by measuring the absorption increase at a wavelength of 340 nm as described by Walker (Biochemical Education. 1992 21(1):42-43). $NAD^+$ and an alcohol are used as substrates and are consumed in equimolar concentrations. NADH production is inversely correlated with $NAD^+$ consumption. Alternatively a commercial colorimetric alcohol dehydrogenase activity assay kit can be used (MAK053, Sigma-Aldrich). Alcohol oxidase activity can be measured calorimetrically with the 2,2'-azino-bis-(3-ethylbenzothiazoline-6-sulfonic acid that reacts with hydrogen peroxide as described by Verduyn et al. (Journal of Microbiological Methods. 1984 (2)1: 15-25) or by measuring the amount of formaldehyde formed as described by Couder and Baratti (Agric. Bioi. Chern. 1980; 44(10):2279-2289). A detailed assay is described herein in the examples section.

According to a specific aspect, the Mut– host cell comprises a heterologous gene of interest expression cassette (GOIEC) comprising an expression cassette promoter (ECP) operably linked to a gene of interest (GOI) encoding a protein of interest (POI).

According to a specific aspect, the Mut– host cell is a recombinant host cell comprising at least one heterologous GOIEC, wherein at least one component or combination of components comprised in the GOIEC is heterologous to the host cell. Specifically, an artificial expression cassette is used, in particular wherein the promoter and GOI are heterologous to each other, not occurring in such combination in nature e.g., wherein either one (or only one) of the promoter and GOI is artificial or heterologous to the other and/or to the host cell described herein; the promoter is an endogenous promoter and the GOI is a heterologous GOI; or the promoter is an artificial or heterologous promoter and the GOI is an endogenous GOI; wherein both, the promoter and GOI, are artificial, heterologous or from different origin, such as from a different species or type (strain) of cells compared to the host cell described herein. Specifically, the ECP is not naturally associated with and/or not operably linked to said GOI in the cell which is used as a host cell described herein.

Specifically, the GOIEC comprises a constitutive, inducible or repressible promoter.

Specific examples of constitutive promoter include e.g., the pGAP and functional variants thereof, any of the constitutive promoter such as pCS1, published in WO2014139608.

Specific examples of inducible or repressible promoter include e.g., the native pAOX1 or pAOX2 and functional variants thereof, any of the regulatory promoter, such as pG1-pG8, and fragments thereof, published in WO2013050551; any of the regulatory promoter, such as pG1 and pG1-x, published in WO2017021541 A1.

Suitable promoter sequences for use with yeast host cells are described in Mattanovich et al. (Methods Mol. Biol. (2012) 824:329-58) and include glycolytic enzymes like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPGI), the 3-phosphoglycerate kinase promoter (PPGK), the glycerol aldehyde phosphate dehydrogenase promoter (pGAP), translation elongation factor promoter (PTEF), and the promoters of *P. pastoris* enolase 1 (PEN01), triose phosphate isomerase (PTPI), ribosomal subunit proteins (PRPS2, PRPS7, PRPS31, PRPL1), alcohol oxidase promoter (PAOX1, PAOX2) or variants thereof with modified characteristics, the formaldehyde dehydrogenase promoter (PFLD), isocitrate lyase promoter (PICL), alpha-ketoisocaproate decarboxylase promoter (PTHI), the promoters of heat shock protein family members (PSSA1, PHSP90, PKAR2), 6-Phosphogluconate dehydrogenase (PGND1), phosphoglycerate mutase (PGPM1), transketolase (PTKL1), phosphatidylinositol synthase (PPIS1), ferro-02-oxidoreductase (PFET3), high affinity iron permease (PFTR1), repressible alkaline phosphatase (PPH08), N-myristoyl transferase (PNMT1), pheromone response transcription factor (PMCM1), ubiquitin (PUBI4), single-stranded DNA endonuclease (PRAD2), the promoter of the major ADP/ATP carrier of the mitochondrial inner membrane (PPET9) (WO2008/128701) and the formate dehydrogenase (FMD) promoter.

Further examples of suitable promoters include *Saccharomyces cerevisiae* enolase (ENO1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase (PGK), and the maltase gene promoter (MAL).

The GAP promoter (pGAP), AOX1 (pAOX1) or AOX2 (pAOX2) promoter or a promoter which is a functional variant thereof and derived from any one of pGAP or pAOX1 or pAOX2 is particularly preferred. pAOX promoters can be induced by methanol and are repressed by glucose. Specifically, the functional variant has at least at least any one of 80%, 85%, 90%, 95%, or 100% sequence identity to the promoter from which it is derived, and has about the same promoter activity (e.g. +/- any one of 50%, 40%, 30%, 20%, or 10%; although the promoter activity may be improved) as compared to the promoter from which it is derived.

According to a specific embodiment, the ECP is methanol-inducible. In particular, the ECP is methanol-controlled. Specifically, the ECP can be fully induced in the methanol containing cell culture. In such case, the methanol may be used not only as a source of energy supplied to the cell culture, but also to induce the POI expression upon inducing the ECP.

According to a specific aspect, the ECP is methanol-inducible by the amount of methanol present in the cell culture used as a carbon source to produce the POI. Specifically, the GOI expression by the heterologous expression cassette is inducible by the methanol-inducible ECP.

Specifically, the ECP is methanol-inducible, and e.g., repressed in the absence of a methanol amount which is less than any one of 0.1%, 0.05%, or 0.01% (v/v) in the cell culture medium or supernatant (herein referred to as a promoter-repressing amount).

Specifically, the ECP is methanol-inducible, and e.g., induced in the presence of a methanol amount which is higher than the promoter-repressing amount e.g., by at least any one of 0.1%, 0.5%, 1%, 1.5%, 2.0%, 2.5%, or 3% (v/v) in the cell culture medium or supernatant (herein referred to as a promoter-inducing amount).

Specifically, the ECP is fully induced by the methanol amount as used in the cell culture method described herein. The ECP promoter is considered to be fully induced, if the culture conditions provide for about maximum induction.

Such amounts in the cell culture medium or supernatant are particularly understood as the amount which upon feeding of the host cell and consumption by the host cell may be detectable. Typically, when producing a POI during the production phase of a cell culture, the cell culture is fed by adding a supplemental carbon source, yet in an amount that is immediately consumed by the cells during POI production, thus, leaving no or only a low remaining amount in the cell culture medium or supernatant, e.g. an amount up to 1.0 g/L.

Specifically, the ECP is endogenous or heterologous to the host cell.

Specifically, the ECP is any one of the following:
a) a pAOX1 promoter comprising or consisting of at least any one of 60%, 65%, 70%, 75%, 80%, 85%, 90%, 95%, or 100% sequence identity to SEQ ID NO:5; or
b) a pAOX2 promoter comprising or consisting of at least any one of 60%, 65%, 70%, 75%, 80%, 85%, 90%, 95%, or 100% sequence identity to SEQ ID NO:6; or
c) a promoter comprising or consisting of a nucleotide sequence selected from the group consisting of SEQ ID NO:36-49.

Specifically, any of the methanol-inducible promoters may be used which are listed in Table 38, in particular those comprising or consisting of a nucleotide sequence selected from the group consisting of SEQ ID NO:36-49.

Functional pAOX1 and pAOX2 promoter variants characterized by a sequence identity of at least 60% are exemplified by the exemplary methanol-inducible promoters further described herein. For example, SEQ ID NO:17 (pMOD1 promoter sequence of *Ogataea methanolica* JCM 10240) has a sequence identity of 54.0% compared to SEQ ID NO:5; and SEQ ID NO:18 (pMOD2 promoter sequence of *Ogataea methanolica* JCM 10240) has a sequence identity of 53.7% compared to SEQ ID NO:6. Sequence identity of the pMOD2 promoter compared to the respective pAOX1 and pAOX2 promoter has been determined by alignment using LALIGN version 36.3.8 g December, 2017; results refer to sequences aligned with the same sequence orientation and highest overlap (Parameters: Matrix: +5/−4; GAP OPEN: −5; Gap Extend: −4; E( ) Threshold 10.0; Output format: MARKX 0; Graphics: Yes).

Further exemplary methanol inducible promoter are listed in Table 38, or pSHB17, pALD4, pFDH1, pDAS1, pDAS2, pPMP20, pFBA1-2 pPMP47, pFLD, pFGH1, pTAL1-2, pDAS2, pCAM1, pPP7435_Chr1-0336 as described by Gasser et al. (Gasser, Steiger, & Mattanovich, 2015, Microb Cell Fact. 14: 196).

As described herein, the term "pAOX1" shall refer to both, a promoter comprising the sequence identified as SEQ ID NO:5, or a sequence which has a certain homology (or sequence identity) to SEQ ID NO:5. The homologous sequence is also referred to as pAOX1 homologue. The pAOX1 homologue may be a native, naturally-occurring sequence or a mutant thereof e.g., produced by any suitable method of mutagenesis.

As described herein, the term "pAOX2" shall refer to both, a promoter comprising the sequence identified as SEQ ID NO:6, or a sequence which has a certain homology (or sequence identity) to SEQ ID NO:6. The homologous sequence is also referred to as pAOX2 homologue. The pAOX2 homologue may be a native, naturally-occurring sequence or a mutant thereof e.g., produced by any suitable method of mutagenesis.

A pAOX1 or pAOX2 mutant described herein is specifically characterized by a promoter strength which is about 0.5-fold to at least any one of 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.3-fold, 3.5-fold, 3.8-fold, 4-fold, 4.5-fold, 5-fold, 5.5-fold, or at least 6-fold increased compared to the respective native pAOX1 or pAOX2 promoter when in the induced state, as determined in a comparable expression system or production host cell line.

Specifically, the promoter strength is determined by the expression level of a POI, such as a model protein (e.g., Green Fluorescence Protein, GFP, including e.g., enhanced GFP, eGFP, Gene Bank Accession no. U57607), and/or the transcription strength, as compared to the reference promoter. Preferably, the transcription analysis is quantitative or semi-quantitative, preferably employing qRT-PCR, DNA microarrays, RNA sequencing and transcriptome analysis.

Specifically, the recombinant host cell described herein comprises only one or multiple heterologous GOIEC, e.g. multiple copies of said expression cassettes, such as at least 2, 3, 4, or 5 copies (gene copy number, GCN). For example, the recombinant host cell comprises up to 2, 3, 4, or five copies. Each of the copies may comprise or consist of the same or different sequences, yet includes the ECP operably linked to the GOI.

According to a specific aspect, the heterologous expression cassette is comprised in an autonomously replicating vector or plasmid, or integrated within a chromosome of said host cell.

The expression cassette may be introduced into the host cell and integrated into the host cell genome (or any of its chromosomes) as intrachromosomal element e.g., at a specific site of integration or randomly integrated, whereupon a high producer host cell line is selected. Alternatively, the expression cassette may be integrated within an extrachromosomal genetic element, such as a plasmid or an artificial chromosome e.g., a yeast artificial chromosome (YAC). According to a specific example, the expression cassette is introduced into the host cell by a vector, in particular an expression vector, which is introduced into the host cell by a suitable transformation technique. For this purpose, the GOI may be ligated into an expression vector.

A preferred yeast expression vector (which is preferably used for expression in yeast) is selected from the group consisting of plasmids derived from pPICZ, pGAPZ, pPIC9, pPICZalfa, pGAPZalfa, pPIC9K, pGAPHis, pPUZZLE or GoldenPiCS.

Techniques for transfecting or transforming host cells for introducing a vector or plasmid are well known in the art. These can include electroporation, spheroplasting, lipid vesicle mediated uptake, heat shock mediated uptake, calcium phosphate mediated transfection (calcium phosphate/DNA co-precipitation), viral infection, and particularly using modified viruses such as, for example, modified adenoviruses, microinjection and electroporation.

Transformants as described herein can be obtained by introducing the expression cassette, vector or plasmid DNA into a host and selecting transformants which express the relevant protein or selection marker. Host cells can be treated to introduce heterologous or foreign DNA by methods conventionally used for transformation of host cells, such as the electric pulse method, the protoplast method, the lithium acetate method, and modified methods thereof. *P. pastoris* is preferably transformed by electroporation. Preferred methods of transformation for the uptake of the recombinant DNA fragment by the microorganism include chemical transformation, electroporation or transformation by protoplastation.

According to a specific aspect, the heterologous GOIEC described herein comprises or consists of an artificial fusion of polynucleotides, including the ECP operably linked to the Gal, and optionally further sequences, such as a signal, leader, or a terminator sequence.

Specifically, the expression cassette comprises the ECP operably linked to the Gal, and optionally further comprises signal and leader sequences, as necessary to express and produce the POI as a secreted protein.

According to a specific aspect, the GOIEC comprises a nucleotide sequence encoding a signal peptide enabling the secretion of the POI.

Specifically, the nucleotide sequence encoding the signal peptide is fused adjacent to the 5'-end of the Gal.

Specifically, the signal peptide is selected from the group consisting of signal sequences from *S. cerevisiae* alpha-mating factor prepro-peptide, the signal peptides from the *P. pastoris* acid phosphatase gene (PHO1) and the extracellular protein X (EPX1) (Heiss, S., V. Puxbaum, C. Gruber, F. Altmann, D. Mattanovich & B. Gasser, Microbiology 2015; 161(7): 1356-68).

Specifically, any of the signal and/or leader sequences as described in WO2014067926 A1 can be used, in particular SEQ ID NO:22 or SEQ ID NO:23.

Specifically, signal sequences as described in WO2012152823 A1 can be used, in particular the signal sequence of native alpha mating factor of *S. cerevisiae* identified as SEQ ID NO:24, or mutants thereof.

According to a specific aspect, the host cell described herein may undergo one or more further genetic modifications e.g., for improving protein production.

Specifically, the host cell is further engineered to modify one or more genes influencing proteolytic activity used to generate protease deficient strains, in particular a strain deficient in carboxypeptidase Y activity. Particular examples are described in WO1992017595A1. Further examples of a protease deficient *Pichia* strain with a functional deficiency in a vacuolar protease, such as proteinase A or proteinase B, are described in U.S. Pat. No. 6,153,424A. Further examples are *Pichia* strains which have an ade2 deletion, and/or deletions of one or both of the protease genes, PEP4 and PRB1, are provided by e.g., ThermoFisher Scientific.

Specifically, the host cell is engineered to modify at least one nucleic acid sequence encoding a functional gene product, in particular a protease, selected from the group consisting of PEP4, PRB1, YPS1, YPS2, YMP1, YMP2, YMP1, DAP2, GRHI, PRD1, YSP3, and PRB3, as disclosed in WO2010099195A1.

Overexpression or underexpression of genes encoding helper factors is specifically applied to enhance expression of a GOI, e.g. as described in WO2015158800A1.

The POI can be any one of eukaryotic, prokaryotic or synthetic peptides, polypeptides, proteins, or metabolites of a host cell.

According to a specific aspect, the POI is heterologous to the Mut− host cell or the ECP.

Specifically, the POI is heterologous to the host cell species.

Specifically, the POI is a secreted peptide, polypeptide, or protein, i.e. secreted from the host cell into the cell culture supernatant.

Specifically, the POI is a eukaryotic protein, preferably a mammalian derived or related protein such as a human protein or a protein comprising a human protein sequence, or a bacterial protein or bacterial derived protein Preferably, the POI is a therapeutic protein functioning in mammals.

In specific cases, the POI is a multimeric protein, specifically a dimer or tetramer.

Specifically, the POI is a peptide or protein selected from the group consisting of an antigen-binding protein, a therapeutic protein, an enzyme, a peptide, a protein antibiotic, a toxin fusion protein, a carbohydrate-protein conjugate, a structural protein, a regulatory protein, a vaccine antigen, a growth factor, a hormone, a cytokine, a process enzyme.

Specifically, the antigen-binding protein is selected from the group consisting of
a) antibodies or antibody fragments, such as any of chimeric antibodies, humanized antibodies, bi-specific antibodies, Fab, Fd, scFv, diabodies, triabodies, Fv tetramers, minibodies, single-domain antibodies like VH, VHH, IgNARs, or V-NAR;
b) antibody mimetics, such as Adnectins, Affibodies, Affilins, Affimers, Affitins, Alphabodies, Anticalins, Avimers, DARPins, Fynomers, Kunitz domain peptides, Monobodies, or NanoCLAMPS; or
c) fusion proteins comprising one or more immunoglobulin-fold domains, antibody domains or antibody mimetics.

A specific POI is an antigen-binding molecule such as an antibody, or a fragment thereof, in particular an antibody fragment comprising an antigen-binding domain. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH, VHH, IgNARs, or V-NAR, or any protein comprising an immunoglobulin-fold domain. Further antigen-binding molecules may be selected from antibody mimetics, or (alternative) scaffold proteins such as e.g., engineered Kunitz domains, Adnectins, Affibodies, Affiline, Anticalins, or DARPins.

According to a specific aspect, the POI is e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant Cl esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, P1-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-11, bremelanotide, ATL-104, recombinant human microplasmin, AX-200, SEMAX, ACV-1, Xen-2174, CJC-1008, dynorphin A, S1-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP—HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OSi, AC-162352, PRX-302, LFn-p24 fusion vaccine (Therapore), EP-1043, S. pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, or TP-9201, adalimumab (HUMIRA), infliximab (REMICADE™), rituximab (RITUXAN™/MAB THERA™), etanercept (ENBREL™), bevacizumab (AVASTIN™), trastuzumab (HERCEPTIN™), pegrilgrastim (NEULASTA™), or any other suitable POI including biosimilars and biobetters.

According to a specific aspect, a fermentation product is isolated from the cell culture, which fermentation product comprises the POI or a host cell metabolite obtained from the Mut– host cell.

According to a specific aspect, the Mut– host cell is a yeast cell of the genus Pichia, Komagataella, Hansenula, Ogataea or Candida.

Specifically, the Mut– host cell is originating from a strain which is of a yeast selected from the group consisting of a Pichia species, such as Pichia pastoris, Pichia methanolica, Pichia kluyveri, and Pichia angusta; Komagataella species, such as Komagataella pastoris, Komagataella pseudopastoris or Komagataella phaffii, Hansenula species, such as Hansenula polymorpha, Ogataea species, such as Ogataea polymorpha, or Ogataea parapolymorpha, and Candida species, such as Candida utilis, Candida cacaoi, and Candida boidinii.

Preferred is the species *Pichia pastoris*. Specifically, the host cell is a *Pichia pastoris* strain selected from the group consisting of CBS 704, CBS 2612, CBS 7435, CBS 9173-9189, DSMZ 70877, X-33, GS115, KM71, KM71H and SMD1168.

Sources: CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmelculturen, Utrecht, The Netherlands), and DSMZ 70877 (German Collection of Microorganisms and Cell Cultures); strains from Invitrogen, such as X-33, GS115, KM71, KM71H and SMD1168.

According to a specific aspect, the invention provides for a method of producing a protein of interest (POI) comprising culturing a Mut− host cell described herein using methanol as a carbon source to produce the POI, in particular such methanol amounts for use as a source of energy, not (only) for methanol-induction of an ECP.

According to a specific aspect, the method comprises culturing the Mut− host cell using methanol as a carbon source to produce the POI, which Mut− host cell comprises a heterologous gene of interest expression cassette (GOIEC) comprising an expression cassette promoter (ECP) operably linked to a gene of interest (GOI) encoding a protein of interest (POI), wherein the Mut− host cell is engineered by one or more genetic modifications to reduce expression of a first and a second endogenous gene compared to the host cell prior to said one or more genetic modifications, wherein
 a) the first endogenous gene encodes alcohol oxidase 1 (AOX1) comprising the amino acid sequence identified as SEQ ID NO:1 or a homologue thereof, and
 b) the second endogenous gene encodes alcohol oxidase 2 (AOX2) comprising the amino acid sequence identified as SEQ ID NO:3 or a homologue thereof.

Specifically, the Mut− host cell is cultured using methanol as a sole carbon source or in a mixture with other carbon sources (or carbohydrates), in particular as a source of energy, such as for growth and/or POI production (synthesis).

Specifically, such other carbon source (herein also referred to as "non-methanol carbon source" is a carbohydrate.

Specifically, the non-methanol carbon source is selected from saccharides, polyols, alcohols, or mixtures of any one or more of the foregoing.

Specifically, the saccharides may be any one or more of monosaccharides, such as a hexose, e.g. glucose, fructose, galactose or mannose, or a disaccharides, such as saccharose; or an alcohol or polyol e.g., ethanol, or any diol, or triol, e.g., glycerol, or a mixture of any of the foregoing. In addition to the methanol amount used as a carbon source as described herein, any such non-methanol carbon source may be additionally used in the cell culture in an amount to produce said POI.

According to a specific embodiment, a cell line of the Mut− host cell is cultured.

Specifically, the cell line is cultured under batch, fed-batch or continuous culture conditions. The culture may be performed in microtiter plates, shake-flasks, or a bioreactor, and optionally starting with a batch phase as the first step, followed by a fed-batch phase or a continuous culture phase as the second step.

According to a specific aspect, the method described herein comprises a growing phase and a production phase.

Specifically, the method comprises the steps:
 a) culturing the host cell under growing conditions (growing phase, or "growth phase"); and a further step
 b) culturing the host cell under growth-limiting conditions in the presence of methanol as a carbon source (production phase), during which the GOI is expressed to produce said POI.

Specifically, the second step b) follows the first step a).
Specifically,
 a) a growing phase, during which the Mut− host cell is cultured using a basal carbon source as a source of energy; is followed by
 b) a production phase, during which the Mut− host cell is cultured using a methanol feed thereby producing the POI.

Specifically, the host cell is cultured in the first step under growing conditions in a cell culture medium comprising the first carbon source, e.g. in an amount sufficient to enable growth of the host cell in cell culture, optionally until the amount of the carbon source is consumed, and further culturing can be under growth-limiting conditions.

Specifically, the second carbon source is methanol and optionally one or more further carbon sources (other than methanol), said second carbon source being referred to as supplemental carbon source.

Specifically, said basal carbon source and/or supplemental carbon source (in addition to methanol) can be selected from saccharides, polyols, alcohols, or mixtures of any one or more of the foregoing.

According to a specific embodiment, the basal carbon source is different from the supplemental carbon source, e.g. quantitatively and/or qualitatively different. The quantitative difference typically provides for the different conditions to repress or induce the ECP promoter activity.

According to a further specific embodiment the basal and the supplemental carbon sources comprise the same type of molecules or carbohydrates, preferably in different concentrations. According to a further specific embodiment, the carbon source is a mixture of two or more different carbon sources.

Any type of organic carbon source may be used, in particular those typically used for host cell culture, in particular for eukaryotic host cell culture. According to a specific embodiment, the carbon source is a hexose, such as glucose, fructose, galactose or mannose, a disaccharide, such as saccharose, an alcohol, such as glycerol or ethanol, or a mixture thereof.

According to a specifically preferred embodiment, the basal carbon source is selected from the group consisting of glucose, glycerol, ethanol, or mixtures thereof. According to a preferred embodiment, the basal carbon source is glycerol.

According to a further specific embodiment, the supplemental carbon source comprises (in addition to methanol) a hexose such as glucose, fructose, galactose and mannose, a disaccharide, such as saccharose, an alcohol, such as glycerol or ethanol, or a mixture thereof. According to a preferred embodiment, the supplemental carbon source comprises glucose in addition to methanol.

Both of said culturing steps specifically comprise cultivating the cell line in the presence of said carbon sources.

Specifically, said growth phase (step a)) culturing is performed in a batch phase; and said production phase (step b)) culturing is performed in fed-batch or a continuous cultivation phase.

Specifically, the host cells are grown in a carbon source rich medium comprising a basal carbon source during the phase of high growth rate (under growing conditions), step a) (e.g. at least 50%, or at least 60%, at least 70%, at least 80%, at least 90%, at least 95%, at least 98%, at least 99%, or up to the maximum growth rate) and producing the POI during a phase of low growth rate (under growth-limiting conditions), step b) (e.g. less than 90%, preferably less than 80%, less than 70%, less than 60%, less than 50%, or less than 40%, less than 30%, less than 20%, less than 10%, less than 5%, less than 3%, less than 2%, less than 1%, less than 0.5%, less than 0.4%, less than 0.3%, or less than 0.2% of the maximum growth rate) while limiting the carbon source, in particular by feeding a defined minimal medium comprising only the amount of carbon source which is completely consumed when maintaining the cell culture in the production phase.

Specifically, an average methanol concentration of at least any one of 0.5, 0.55, 0.6, 0.65, 0.7, 0.75, 0.8, 0.85, 0.9, 0.95, or 1.0% (v/v) e.g., up to any one of 3%, 2.5%, 2%, 1.5%, or 1% (v/v) is used in the host cell culture, specifically in the cell culture medium or supernatant, in particular during a production phase.

Specifically, the average methanol concentration is maintained during a production phase of at least 24 hours, preferably, at least any one of 0.1%, 0.5%, 1%, 1.5%, 2%, 2.5% or 3% (v/v).

According to a specific embodiment, the average methanol concentration is 0.5-2% (v/v), during the production phase of at least 24 hours The average amount or concentration can be calculated as the sum of methanol concentrations as measured in the cell culture, in particular in the cell culture medium or supernatant, at least at the start and at the end of an observation period, and during the observation period e.g., at least every 24 h, or per continuous measurement, divided by the number of measurements.

The methanol concentration in the cell culture can be measured using a suitable standard assay like HPLC, e.g. determined as a residual concentration in the culture medium upon consumption by the cell culture.

Specifically, the methanol feed is at an average feed rate of at least any one of 2, 3, 4, 5, 6, 7, 8, 9, 10, 11, 12, 13, 14, or 15 mg methanol/(g dry biomass*h), or higher e.g., 2-20 or 2-15 mg methanol/(g dry biomass*h) during a production phase.

Methanol may be added to the cell culture in one or more instalments e.g., by one or more injections, or may be continuously added during a certain period of time while producing the POI. The average amount can be calculated as the sum of all methanol additions during an observation period divided by the average total dry biomass and by the duration of the observation period. The average total dry biomass is calculated by measuring the dry biomass concentration at least at the start and at the end of an observation period, and optional during the observation period. The dry biomass concentration is then interpolated between start and the end of the observation period. The interpolated dry biomass concentration is multiplied by the reactor volume at each interval, the calculated values for all intervals are summed and divided by the number of intervals. An interval duration is less than or equal to 1 h.

Specifically, the average feed rate is maintained during a production phase of at least 24 hours, preferably, at least any one of 2, 3, 4, 5, 6, 7, 8, 9, 10, 11, 12, 13, 14 or 15 mg methanol/(g dry biomass*h), or higher e.g., 2-20 or 2-15 mg methanol/(g dry biomass*h).

The observation period is herein understood as a certain period of time during which the cell culture is producing the POI, and particularly understood as a production phase, in particular the production phase of a fed-batch or continuous cell cultivation method. Though the actual POI production process or production phase may be longer than the observation period, the average amount is calculated during a defined observation period.

Specifically, the duration of the POI production process is 10 to 500 h.

Specifically, a batch phase is performed for around 10 to 36 h.

The term "around" with respect to cultivation time shall mean+/−5% or +/−10%.

For example, the specific batch performance time of around 10 to 36 h may be 18 to 39.6 h, specifically 19 to 37.8 h.

According to a specific embodiment, a batch phase is performed using 10 to 50 g/L glycerol, specifically 20 to 40 g/L glycerol as a basal carbon source in batch media, and cultivation is performed at 25° C. for around 27 to 30 h, or at 30° C. for around 23 to 36 h, or at any temperature between 25° C. and 30° C. during a cultivation time of 23 to 36 h. Lowering the glycerol concentration in the batch medium would decrease the length of the batch phase, while increasing the glycerol in the batch medium would even prolong the batch phase. As an alternative to glycerol, glucose can be used, e.g. in about the same amounts.

In a typical system of cell culture and POI expression, wherein a batch phase is followed by a fed-batch phase, specifically, the cultivation in the fed-batch phase is performed for any one of around 15 to 100 h, around 15 to 80 h, around 15 to 70 h, around 15 to 60 h, around 15 to 50 h, around 15 to 45 h, around 15 to 40 h, around 15 to 35 h, around 15 to 30 h, around 15 to 35 h, around 15 to 25 h, or around 15 to 20 h; preferably around 20 to 40 h. Specifically, the cultivation in the fed-batch phase is performed for any one of around 100 h, around 80 h, around 70 h, around 60 h, around 55 h, around 50 h, around 45 h, around 40 h, around 35 h, around 33 h, around 30 h, around 25 h, around 20 h, or around 15 h.

Specifically, the volume specific product formation rate (rP) is the amount of product (mg) formed per Unit Volume (L) and Unit time (h) (mg $(L\ h)^{-1}$). Volume specific product formation rate is also called space time yield (STY) or volumetric productivity.

Specifically, a fed-batch cultivation of the method described herein is performed such that a space time yield of around 30 mg $(L\ h)^{-1}$ (meaning 30 mg $(L\ h)^{-1}$+/−5% or +/−10%). Specifically a space time yield of around 30 mg $(L\ h)^{-1}$ is achieved within around 30 h fed batch, specifically at least any of 27, 28, 29, 30, 31, 32, or 33 mg $(L\ h)^{-1}$ within less than any one of 33 h, 32 h, 31 h, 30 h, 29 h, 28 h, 27 h, 26 h, or 25 h fed batch time can be achieved.

Specifically, the POI is expressed in the production phase under growth-limiting conditions, e.g. by cultivating the cell line at a growth rate of less than the maximal growth rate, typically less than 90%, preferably less than 80%, less than 70%, less than 60%, less than 50%, less than 40%, less than 30%, less than 20%, less than 10%, less than 5%, less than 3%, less than 2%, less than 1%, less than 0.5%, less than 0.4%, less than 0.3%, or less than 0.2% of the maximum growth rate of the cells. Typically the maximum growth rate is individually determined for each type of host cell.

According to a specific aspect, the Mut– host cell is cultured during a production phase under conditions limiting the host cell growth to less than any one of 10%, 9%, 8%, 7%, 6%, 5%, 4%, 3%, 2%, or 1% (w/w biomass).

Specifically, the production phase employs a feed medium that provides for a supplemental carbon source in a growth limiting amount to keep the specific growth rate within the range of 0.0001 $h^{-1}$ to 0.2 $h^{-1}$, preferably 0.005 $h^{-1}$ to 0.15 $h^{-1}$.

According to a specific aspect, the invention provides for the use of a recombinant methanol utilization pathway deficient methylotrophic yeast (Mut–) host cell in a method of producing a fermentation product which method comprises culturing said Mut– host cell under conditions that permit the Mut– host cell to use methanol as a substrate for alcohol dehydrogenase (ADH2), and to produce the fermentation product.

Specifically, said Mut– host cell is deficient of alcohol oxidase 1 (AOX1) and alcohol oxidase 2 (AOX2).

Specifically, in said Mut– host cell, the genes encoding alcohol oxidase 1 (AOX1) and alcohol oxidase 2 (AOX2) are knocked out or deleted.

According to a specific aspect, the invention provides for the use of a recombinant methanol utilization pathway deficient methylotrophic yeast (Mut–) host cell in a method of producing a fermentation product which method comprises culturing said Mut– host cell under conditions that permit the Mut– host cell to produce the fermentation product using methanol as a carbon source, which Mut– host cell is engineered by one or more genetic modifications
a) to reduce expression of a first and a second endogenous gene compared to the host cell prior to said one or more genetic modifications, wherein
 i. the first endogenous gene encodes alcohol oxidase 1 (AOX1) comprising the amino acid sequence identified as SEQ ID NO:1 or a homologue thereof, and
 ii. the second endogenous gene encodes alcohol oxidase 2 (AOX2) comprising the amino acid sequence identified as SEQ ID NO:3 or a homologue thereof, and
b) to increase expression of an alcohol dehydrogenase (ADH2) gene, wherein the ADH2 gene encodes an alcohol dehydrogenase (ADH2).

According to a specific aspect, the invention provides for a method for producing a protein of interest (POI) in a host cell, comprising the steps:
a) genetically engineering the host cell to reduce expression (underexpress) of said first and second genes encoding the AOX1 and AOX2, respectively;
b) genetically engineering the host cell to increase expression (overexpress) of a gene encoding ADH2;
c) introducing into the host cell a heterologous expression cassette comprising a gene of interest (GOI) encoding said POI under the control of an expression cassette promoter (ECP);
d) culturing said host cell under conditions to produce said POI using methanol as a carbon source, thereby particularly providing energy for growth and/or POI production;
e) optionally isolating said POI from the cell culture; and
f) optionally purifying said POI.

Specifically, step a) of the method described herein is carried out before, or after, or concomitantly with step b).

Specifically, steps a) and b) of the method described herein is carried out before, or after, or concomitantly with step c).

According to a specific aspect, the host cell is first genetically modified to reduce expression of said first and second genes encoding the AOX1 and AOX2, respectively, and to increase expression of a gene encoding ADH2, before being engineered for producing the POI. According to a specific example, a wild-type host cell is genetically modified according to steps a) and b) of the method described herein. Specifically, the host cell is provided upon introducing said one or more genetic modifications into a wild-type host cell strain for reduction of said first and second genes encoding the AOX1 and AOX2, respectively, and for increasing expression of the gene encoding ADH2.

According to a further aspect, the host cell is first engineered for producing the heterologous or recombinant POI, before being further genetically modified to reduce said first and second genes encoding the AOX1 and AOX2, respectively, and to increase expression of the gene encoding ADH2. According to a specific example, a wild-type host cell may first be engineered to comprise the expression cassette for POI production. Such engineered host cell may then be further modified to reduce said first and second genes encoding the AOX1 and AOX2, respectively, and to increase expression of the gene encoding ADH2.

According to a further aspect, the host cell is undergoing the engineering steps, including the engineering for POI production and genetically modifying for reduction of said first and second genes encoding the AOX1 and AOX2, respectively, and for increasing expression of the gene encoding ADH2, concomitantly i.e. in one method step, e.g., employing the respective expression cassette, reagents and tools in one or more reaction mixtures.

Specifically, the method employs method steps to produce the recombinant Mut– host cell as further described herein.

Specifically, the heterologous expression cassette comprises the ECP as further described herein.

Specifically, the POI can be produced by culturing the Mut– host cell in an appropriate medium, producing the POI during a culturing step using a cell culture production medium comprising methanol, and isolating the expressed POI from the cell culture, in particular from the cell culture supernatant or medium upon separating the cells, and optionally purifying it by a method appropriate for the expressed product. Thereby, a purified POI preparation can be produced.

It has surprisingly turned out that the Mut– host cell was insensitive to methanol and could effectively uptake and use significant amounts of methanol as necessary to provide energy for POI production. This was surprising because in the prior art, methanol was found to be toxic to a $Mut^S$ strain.

According to a specific example of the cell culture as described herein, the growth of the Mut– host cells was advantageously limited during the production phase, which reduced the necessity of oxygen supply and cooling.

It was even more surprising that the yield of POI production was increased by a heretofore underestimated mechanism of alcohol dehydrogenase and the activity of ADH2 in methylotrophic yeast, which turned out to result in methanol uptake and effective methanol consumption despite of knocking out AOX1 and AOX2 genes in the methanol utilization pathway deficient methylotrophic yeast.

According to a specific example, a methanol-inducible ECP has been advantageously used in a GOIEC. The methanol amounts as used in the cell culture as a carbon source were sufficient to induce expression of the GOI.

FIGURES

FIG. 1: Sequences referred to herein

DETAILED DESCRIPTION OF THE INVENTION

Specific terms as used throughout the specification have the following meaning.

The term "carbon source" as used herein shall mean a fermentable carbon substrate, typically a source carbohydrate, suitable as an energy source for microorganisms, such as those capable of being metabolized by host organisms or production cell lines, in particular sources selected from the group consisting of monosaccharides, oligosaccharides, polysaccharides, alcohols including glycerol, in the purified form, in minimal media or provided in raw materials, such as a complex nutrient material. The carbon source may be used as described herein as a single carbon source or as a mixture of different carbon sources.

As described herein, methanol is used as a carbon source, e.g., as a sole carbon source during a production phase, or in a mixture with a non-methanol carbon source. Specifically, methanol is co-fed to the cell culture with any non-methanol carbon source.

A non-methanol carbon source is herein understood as a carbon source which is any other than methanol, in particular a methanol-free carbon source.

A "basal carbon source" such as described herein typically is a carbon source suitable for cell growth, such as a nutrient for host cells, in particular for eukaryotic cells. The basal carbon source may be provided in a medium, such as a basal medium or complex medium, but also in a chemically defined medium containing a purified carbon source. The basal carbon source typically is provided in an amount to provide for cell growth, in particular during the growth phase in a cultivation process, for example to obtain cell densities of at least 5 g/L cell dry mass, preferably at least 10 g/L cell dry mass, or at least 15 g/L cell dry mass, e.g. exhibiting viabilities of more than 90% during standard sub-culture steps, preferably more than 95%.

The basal carbon source is typically used in an excess or surplus amount, which is understood as an excess providing energy to increase the biomass, e.g. during the cultivation of a cell line with a high specific growth rate, such as during the growth phase of a cell line in a batch or fed-batch cultivation process. This surplus amount is particularly in excess of the limited amount of a supplemental carbon source (as used under growth-limited conditions) to achieve a residual concentration in the fermentation broth that is measurable and typically at least 10 fold higher, preferably at least 50 fold or at least 100 fold higher than during feeding the limited amount of the supplemental carbon source.

A "supplemental carbon source" such as described herein typically is a supplemental substrate facilitating the production of fermentation products by production cell lines, in particular in the production phase of a cultivation process. The production phase specifically follows a growth phase, e.g. in batch, fed-batch and continuous cultivation process. The supplemental carbon source specifically may be contained in the feed of a fed-batch process. The supplemental carbon source is typically employed in a cell culture under carbon substrate limited conditions, i.e. using the carbon source in a limited amount.

Specifically, in a method described herein methanol is used as a supplemental carbon source.

A "limited amount" of a carbon source or a "limited carbon source" is herein understood to specifically refer to the type and amount of a carbon substrate facilitating the production of fermentation products by production cell lines, in particular in a cultivation process with controlled growth rates of less than the maximum growth rate. The production phase specifically follows a growth phase, e.g. in batch, fed-batch and continuous cultivation process. Cell culture processes may employ batch culture, continuous culture, and fed-batch culture. Batch culture is a culture process by which a small amount of a seed culture solution is added to a medium and cells are grown without adding an additional medium or discharging a culture solution during culture.

Continuous culture is a culture process by which a medium is continuously added and discharged during culture. The continuous culture also includes perfusion culture. Fed-batch culture, which is an intermediate between the batch culture and the continuous culture and also referred to as semi-batch culture, is a culture process by which a medium is continuously or sequentially added during culture but, unlike the continuous culture, a culture solution is not continuously discharged.

Specifically preferred is a fed-batch process which is based on feeding of a growth limiting nutrient substrate to a culture. The fed-batch strategy, including single fed-batch or repeated fed-batch fermentation, is typically used in bio-industrial processes to reach a high cell density in the bioreactor. The controlled addition of the carbon substrate directly affects the growth rate of the culture and helps to avoid overflow metabolism or the formation of unwanted metabolic byproducts. Under carbon source limited conditions, the carbon source specifically may be contained in the feed of a fed-batch process. Thereby, the carbon substrate is provided in a limited amount.

Also in chemostat or continuous culture as described herein, the growth rate can be tightly controlled.

The limited amount of a carbon source is herein particularly understood as the amount of a carbon source necessary to keep a production cell line under growth-limited conditions, e.g. in a production phase or production mode. Such a limited amount may be employed in a fed-batch process, where the carbon source is contained in a feed medium and supplied to the culture at low feed rates for sustained energy delivery, e.g. to produce a POI, while keeping the biomass at low specific growth rates. A feed medium is typically added to a fermentation broth during the production phase of a cell culture.

The limited amount of a carbon source may, for example, be determined by the residual amount of the carbon source in the cell culture broth, which is below a predetermined threshold or even below the detection limit as measured in a standard (carbohydrate) assay. The residual amount typically would be determined in the fermentation broth upon harvesting a fermentation product.

The limited amount of a carbon source may as well be determined by defining the average feed rate of the carbon source to the fermenter, e.g. as determined by the amount added over the full cultivation process, e.g. the fed-batch phase, per cultivation time, to determine a calculated average amount per time. This average feed rate is kept low to ensure complete usage of the supplemental carbon source by the cell culture, e.g. between 0.6 g $L^{-1}$ $h^{-1}$ (g carbon source per L initial fermentation volume and h time) and 25 g $L^{-1}$ $h^{-1}$, preferably between 1.6 g $L^{-1}$ $h^{-1}$ and 20 g $L^{-1}$ $h^{-1}$.

The limited amount of a carbon source may also be determined by measuring the specific growth rate, which specific growth rate is kept low, e.g. lower than the maximum specific growth rate, during the production phase, e.g. within a predetermined range, such as in the range of 0.001 $h^{-1}$ to 0.20 $h^{-1}$, or 0.005 $h^{-1}$ to 0.20 $h^{-1}$, preferably between 0.01 $h^{-1}$ and 0.15 $h^{-1}$.

Specifically, a feed medium is used which is chemically defined and comprising methanol.

The term "chemically defined" with respect to cell culture medium, such as a minimal medium or feed medium in a fed-batch process, shall mean a cultivation medium suitable for the in vitro cell culture of a production cell line, in which all of the chemical components and (poly)peptides are known. Typically, a chemically defined medium is entirely free of animal-derived components and represents a pure and consistent cell culture environment.

The term "cell" or "host cell" as used herein shall refer to a single cell, a single cell clone, or a cell line of a host cell. The term "host cell" shall particularly apply to a cell of methylotrophic yeast, which is suitably used for recombination purposes to produce a POI or a host cell metabolite. It is well understood that the term "host cell" does not include human beings. Specifically, host cells as described herein are artificial organisms and derivatives of native (wild-type) host cells. It is well understood that the host cells, methods and uses described herein, e.g., specifically referring to those comprising one or more genetic modifications, said heterologous expression cassettes or constructs, said transfected or transformed host cells and recombinant proteins, are non-naturally-occurring, "man-made" or synthetic, and are therefore not considered as a result of "law of nature".

The term "cell line" as used herein refers to an established clone of a particular cell type that has acquired the ability to proliferate over a prolonged period of time. A cell line is typically used for expressing an endogenous or recombinant gene, or products of a metabolic pathway to produce polypeptides or cell metabolites mediated by such polypeptides.

The host cell producing the POI as described herein is also referred to as "production host cell", and a respective cell line a "production cell line". A "production cell line" is commonly understood to be a cell line ready-to-use for cell culture in a bioreactor to obtain the product of a production process, such as a POI.

Specific embodiments described herein refer to a Mut– production host cell, which can effectively use ADH2 to enzymatically process methanol thereby providing energy to the cell.

Specific embodiments described herein refer to a production cell line which is engineered to underexpress endogenous genes encoding the AOX1 and AOX2 proteins, and to overexpress a gene encoding ADH2, and is characterized by a high yield of POI production under the control of an ECP described herein, using methanol as a carbon source.

The term "cell culture" or "culturing" or "cultivation" as used herein with respect to a host cell refers to the maintenance of cells in an artificial, e.g., an in vitro environment, under conditions favoring growth, differentiation or continued viability, in an active or quiescent state, of the cells, specifically in a controlled bioreactor according to methods known in the industry.

When culturing a cell culture using appropriate culture media, the cells are brought into contact with the media in a culture vessel or with substrate under conditions suitable to support culturing the cells in the cell culture. As described herein, a culture medium is provided that can be used for the growth of host cells e.g., methylotrophic yeast. Standard cell culture techniques are well-known in the art.

The cell cultures as described herein particularly employ techniques which provide for the production of a secreted POI, such as to obtain the POI in the cell culture medium, which is separable from the cellular biomass, herein referred to as "cell culture supernatant", and may be purified to obtain the POI at a higher degree of purity. When a protein (such as e.g., a POI) is produced and secreted by the host cell in a cell culture, it is herein understood that such proteins are secreted into the cell culture supernatant, and can be obtained by separating the cell culture supernatant from the host cell biomass, and optionally further purifying the protein to produce a purified protein preparation.

Cell culture media provide the nutrients necessary to maintain and grow cells in a controlled, artificial and in vitro environment. Characteristics and compositions of the cell culture media vary depending on the particular cellular requirements. Important parameters include osmolality, pH, and nutrient formulations. Feeding of nutrients may be done in a continuous or discontinuous mode according to methods known in the art.

Whereas a batch process is a cell culture mode in which all the nutrients necessary for culturing the cells are contained in the initial culture medium, without additional supply of further nutrients during fermentation, in a fed-batch process, after a batch phase, a feeding phase takes place in which one or more nutrients are supplied to the culture by feeding. Although in most processes the mode of feeding is critical and important, the host cell and methods described herein are not restricted with regard to a certain mode of cell culture.

A recombinant POI can be produced using the host cell and the respective cell line described herein, by culturing in an appropriate medium, isolating the expressed product or metabolite from the culture, and optionally purifying it by a suitable method.

Several different approaches for the production of the POI as described herein are preferred. A POI may be expressed, processed and optionally secreted by transfecting or transforming a host cell with an expression vector harboring recombinant DNA encoding the relevant protein, preparing a culture of the transfected or transformed cell, growing the culture, inducing transcription and POI production, and recovering the POI.

In certain embodiments, the cell culture process is a fed-batch process. Specifically, a host cell transformed with a nucleic acid construct encoding a desired recombinant POI, is cultured in a growth phase and transitioned to a production phase in order to produce a desired recombinant POI.

In another embodiment, host cells described herein are cultured in a continuous mode, e.g., employing a chemostat. A continuous fermentation process is characterized by a defined, constant and continuous rate of feeding of fresh culture medium into a bioreactor, whereby culture broth is at the same time removed from the bioreactor at the same defined, constant and continuous removal rate. By keeping culture medium, feeding rate and removal rate at the same constant level, the cell culture parameters and conditions in the bioreactor remain constant.

A stable cell culture as described herein is specifically understood to refer to a cell culture maintaining the genetic properties, specifically keeping the POI production level high, e.g. at least at a µg level, even after about 20 generations of cultivation, preferably at least 30 generations, more preferably at least 40 generations, most preferred of at least 50 generations. Specifically, a stable recombinant host cell line is provided which is considered a great advantage when used for industrial scale production.

The cell culture described herein is particularly advantageous for methods on an industrial manufacturing scale, e.g. with respect to both the volume and the technical system, in combination with a cultivation mode that is based on feeding of nutrients, in particular a fed-batch or batch process, or a continuous or semi-continuous process (e.g. chemostat).

The host cell described herein is typically tested for its capacity to express the GOI for POI production, tested for the POI yield by any of the following tests: ELISA, activity assay, HPLC, or other suitable tests, such as SDS-PAGE and Western Blotting techniques, or mass spectrometry.

To determine the effect of one or more genetic modifications on the underexpression or reduction of expression of the genes encoding the AOX1 and/or AOX2 protein(s) in the respective cell culture and e.g., on their effect on POI production, the host cell line may be cultured in microtiter plates, shake flask, or bioreactor using fed-batch or chemostat fermentations in comparison with strains without such genetic modification(s) in the respective cell.

The production method described herein specifically allows for the fermentation on a pilot or industrial scale. The industrial process scale would preferably employ volumes of at least 10 L, specifically at least 50 L, preferably at least 1 $m^3$, preferably at least 10 $m^3$, most preferably at least 100 $m^3$.

Production conditions in industrial scale are preferred, which refer to e.g., fed batch culture in reactor volumes of 100 L to 10 $m^3$ or larger, employing typical process times of several days, or continuous processes in fermenter volumes of approximately 50-1000 L or larger, with dilution rates of approximately 0.02-0.15 $h^{-1}$.

The devices, facilities and methods used for the purpose described herein are specifically suitable for use in and with culturing any desired cell line including prokaryotic and/or eukaryotic cell lines. Further, in embodiments, the devices, facilities and methods are suitable for culturing any cell type including suspension cells or anchorage-dependent (adherent) cells and are suitable for production operations configured for production of pharmaceutical and biopharmaceutical products—such as polypeptide products (POI), nucleic acid products (for example DNA or RNA), or cells and/or viruses such as those used in cellular and/or viral therapies.

In certain embodiments, the cells express or produce a product, such as a recombinant therapeutic or diagnostic product. As described in more detail herein, examples of products produced by cells include, but are not limited to, POIs such as exemplified herein including antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), or viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in certain embodiments, devices, facilities and methods allow for the production of eukaryotic cells, such as for example yeast cells, e.g., POIs including proteins, peptides, or antibiotics, amino acids, nucleic acids (such as DNA or RNA), synthesized by said cells in a large-scale manner. Unless stated otherwise herein, the devices, facilities, and methods can include any desired volume or production capacity including but not limited to bench-scale, pilot-scale, and full production scale capacities.

Moreover, and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally, and unless otherwise stated, the devices, systems, and methods described herein can be housed and/or performed in a single location or facility or alternatively be housed and/or performed at separate or multiple locations and/or facilities.

Suitable techniques may encompass culturing in a bioreactor starting with a batch phase, followed by a short exponential fed batch phase at high specific growth rate, further followed by a fed batch phase at a low specific growth rate. Another suitable culture technique may encompass a batch phase followed by a fed-batch phase at any suitable specific growth rate or combinations of specific growth rate such as going from high to low growth rate over POI production time, or from low to high growth rate over POI production time. Another suitable culture technique may encompass a batch phase followed by a continuous culturing phase at a low dilution rate.

A preferred embodiment includes a batch culture to provide biomass followed by a fed-batch culture for high yields POI production.

It is preferred to culture a host cell as described herein in a bioreactor under growth conditions to obtain a cell density of at least 1 g/L cell dry weight, more preferably at least 10 g/L cell dry weight, preferably at least 20 g/L cell dry weight, preferably at least any one of 30, 40, 50, 60, 70, or 80 g/L cell dry weight. It is advantageous to provide for such yields of biomass production on a pilot or industrial scale.

A growth medium allowing the accumulation of biomass, specifically a basal growth medium, typically comprises a carbon source, a nitrogen source, a source for sulphur and a source for phosphate. Typically, such a medium comprises furthermore trace elements and vitamins, and may further comprise amino acids, peptone or yeast extract.

Preferred nitrogen sources include $NH_4H_2PO_4$, or $NH_3$ or $(NH_4)_2SO_4$,

Preferred sulphur sources include $MgSO_4$, or $(NH_4)_2SO_4$ or $K_2SO_4$,

Preferred phosphate sources include $NH_4H_2PO_4$, or $H_3PO_4$, or $NaH_2PO_4$, $KH_2PO_4$, $Na_2HPO_4$ or $K_2HPO_4$;

Further typical medium components include KCl, $CaCl_2$), and Trace elements such as: Fe, Co, Cu, Ni, Zn, Mo, Mn, I, B;

Preferably the medium is supplemented with vitamin $B_7$; A typical growth medium for *P. pastoris* comprises glycerol, sorbitol or glucose, $NH_4H_2PO_4$, $MgSO_4$, KCl, $CaCl_2$), biotin, and trace elements.

In the production phase a production medium is specifically used with only a limited amount of a supplemental carbon source.

Preferably the host cell line is cultured in a mineral medium with a suitable carbon source, thereby further simplifying the isolation process significantly. An example of a preferred mineral medium is one containing an utilizable carbon source (in particular methanol as described herein optionally in combination with e.g., glucose, glycerol, or sorbitol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g., to complement auxotrophies.

Specifically, the cells are cultured under conditions suitable to effect expression of the desired POI, which can be purified from the cells or culture medium, depending on the nature of the expression system and the expressed protein, e.g., whether the protein is fused to a signal peptide and whether the protein is soluble or membrane-bound. As will be understood by the skilled artisan, culture conditions will vary according to factors that include the type of host cell and particular expression vector employed.

A typical production medium comprises a supplemental carbon source, and further $NH_4H_2PO_4$, $MgSO_4$, KCl, $CaCl_2$), biotin, and trace elements.

For example the feed of the supplemental carbon source added to the fermentation may comprise a carbon source with up to 50 wt % utilizable sugars.

The fermentation preferably is carried out at a pH ranging from 3 to 8. Typical fermentation times are about 24 to 120 hours with temperatures in the range of 20° C. to 35° C., preferably 22-30° C.

The POI is preferably expressed employing conditions to produce titers of at least 1 mg/L, preferably at least 10 mg/L, preferably at least 100 mg/L, most preferred at least 1 g/L.

The term "expression" or "expression cassette" as used herein refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into a host cell chromosome. Expression may refer to secreted or non-secreted expression products, including polypeptides or metabolites.

Expression cassettes are conveniently provided as expression constructs e.g., in the form of "vectors" or "plasmids", which are typically DNA sequences that are required for the transcription of cloned recombinant nucleotide sequences, i.e. of recombinant genes and the translation of their mRNA in a suitable host organism. Expression vectors or plasmids usually comprise an origin for autonomous replication or a locus for genome integration in the host cells, selectable markers (e.g., an amino acid synthesis gene or a gene conferring resistance to antibiotics such as zeocin, kanamycin, G418 or hygromycin, nourseothricin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences, such as artificial chromosomes e.g., a yeast artificial chromosome (YAC).

Expression vectors may include but are not limited to cloning vectors, modified cloning vectors and specifically designed plasmids. Preferred expression vectors described herein are expression vectors suitable for expressing of a recombinant gene in a eukaryotic host cell and are selected depending on the host organism. Appropriate expression vectors typically comprise regulatory sequences suitable for expressing DNA encoding a POI in a eukaryotic host cell. Examples of regulatory sequences include promoter, operators, enhancers, ribosomal binding sites, and sequences that control transcription and translation initiation and termination. The regulatory sequences are typically operably linked to the DNA sequence to be expressed.

Specific expression constructs described herein comprise a promoter operably linked to a nucleotide sequence encoding a POI under the transcriptional control of said promoter. Specifically, the promoter is not natively associated with the coding sequence of the POI.

To allow expression of a recombinant nucleotide sequence in a host cell, the expression cassette or vector described herein as GOIEC comprises an ECP, typically a promoter nucleotide sequence which is adjacent to the 5' end of the coding sequence, e.g., upstream from and adjacent to a gene of interest (GOI), or if a signal or leader sequence is used, upstream from and adjacent to said signal and leader sequence, respectively, to facilitate expression and secretion of the POI. The promoter sequence is typically regulating and initiating transcription of the downstream nucleotide sequence, with which it is operably linked, including in particular the Gal.

Specific expression constructs described herein comprise a polynucleotide encoding the POI linked with a leader sequence which causes secretion of the POI from the host cell. The presence of such a secretion leader sequence in the expression vector is typically required when the POI intended for recombinant expression and secretion is a protein which is not naturally secreted and therefore lacks a natural secretion leader sequence, or its nucleotide sequence has been cloned without its natural secretion leader sequence. In general, any secretion leader sequence effective to cause secretion of the POI from the host cell may be used. The secretion leader sequence may originate from yeast source, e.g. from yeast α-factor such as MFa of *Saccharomyces cerevisiae*, or yeast phosphatase, from mammalian or plant source, or others.

In specific embodiments, multicloning vectors may be used, which are vectors having a multicloning site. Specifically, a desired heterologous gene can be integrated or incorporated at a multicloning site to prepare an expression vector. In the case of multicloning vectors, a promoter is typically placed upstream of the multicloning site.

The term "gene expression", or "expressing a polynucleotide" as used herein, is meant to encompass at least one step selected from the group consisting of DNA transcription into mRNA, mRNA processing, mRNA maturation, mRNA export, translation, protein folding and/or protein transport.

The term "increase expression" herein also referred to as "overexpression" refers to any amount higher than an expression level exhibited by a reference standard, which may be the host cell prior to the genetic alteration to increase expression of a certain polynucleotide, or which is otherwise expressed in a host cell of the same type or species which is not engineered to increase expression of said polynucleotide.

If a host cell does not comprise a given gene product, it is possible to introduce the gene product into the host cell for expression; in this case, any detectable expression is encompassed by the term "overexpression."

Overexpression of a gene encoding a protein (such as ADH2), is also referred to as overexpression of a protein (such as ADH2). Overexpression can be achieved in any ways known to a skilled person in the art. In general, it can be achieved by increasing transcription/translation of the gene, e.g. by increasing the copy number of the gene or altering or modifying regulatory sequences or sites associated with expression of a gene. For example, the gene can be operably linked to a strong promoter in order to reach high expression levels. Such promoters can be endogenous promoters or heterologous, in particular recombinant promoters. One can substitute a promoter with a heterologous promoter which increases expression of the gene. Using inducible promoters additionally makes it possible to increase the expression in the course of cultivation. Furthermore, overexpression can also be achieved by, for example, modifying the chromosomal location of a particular gene, altering nucleic acid sequences adjacent to a particular gene such as a ribosome binding site or transcription terminator, introducing a frame-shift in the open reading frame, modifying proteins (e.g., regulatory proteins, suppressors, enhancers, transcriptional activators and the like) involved in transcription of the gene and/or translation of the gene product, or any other conventional means of deregulating expression of a particular gene routine in the art (including but not limited to use of antisense nucleic acid molecules, for example, to block expression of repressor proteins or deleting or mutating the gene for a transcriptional factor which normally represses expression of the gene desired to be overexpressed. Prolonging the life of the mRNA may also improve the level of expression. For example, certain terminator regions may be used to extend the half-lives of mRNA. If multiple copies of genes are included, the genes can either be located in plasmids of variable copy number or integrated and amplified in the chromosome. It is possible to introduce one or more genes or genomic sequences into the host cell for expression.

According to a specific embodiment, a polynucleotide encoding the ADH2 protein can be presented in a single copy or in multiple copies per cell. The copies may be adjacent to or distant from each other. According to another specific embodiment, overexpression of the ADH2 protein employs recombinant nucleotide sequences encoding the ADH2 protein provided on one or more plasmids suitable for integration into the genome (i.e., knockin) of the host cell, in a single copy or in multiple copies per cell. The copies may be adjacent to or distant from each other. Overexpression can be achieved by expressing multiple copies of the polynucleotide, such as 2, 3, 4, 5, 6 or more copies of said polynucleotide per host cell.

A recombinant nucleotide sequence comprising a GOI and a polynucleotide (gene) encoding the ADH2 protein may be provided on one or more autonomously replicating plasmids, and introduced in a single copy or in multiple copies per cell.

Alternatively, the recombinant nucleotide sequence comprising a GOI and a polynucleotide (gene) encoding the ADH2 protein may be present on the same plasmid, and introduced in a single copy or multiple copies per cell.

A heterologous polynucleotide (gene) encoding the ADH2 protein or a heterologous recombinant expression construct comprising the polynucleotide (gene) encoding the ADH2 protein is preferably integrated into the genome of the host cell.

The term "genome" generally refers to the whole hereditary information of an organism that is encoded in the DNA (or RNA). It may be present in the chromosome, on a plasmid or vector, or both. Preferably, polynucleotide (gene) encoding the ADH2 protein is integrated into the chromosome of said cell.

The polynucleotide (gene) encoding the ADH2 protein may be integrated in its natural locus. "Natural locus" means the location on a specific chromosome, where the polynucleotide (gene) encoding the ADH2 protein is located in a naturally-occurring wild-type cell. However, in another embodiment, the polynucleotide (gene) encoding the ADH2 protein is present in the genome of the host cell not at their natural locus, but integrated ectopically. The term "ectopic integration" means the insertion of a nucleic acid into the genome of a microorganism at a site other than its usual chromosomal locus, i.e., predetermined or random integration. In another embodiment, the polynucleotide (gene) encoding the ADH2 protein is integrated into the natural locus and ectopically. Heterologous recombination can be used to achieve random or non-targeted integration. Heterologous recombination refers to recombination between DNA molecules with significantly different sequences.

For yeast cells, the polynucleotide (gene) encoding the ADH2 protein and/or the GOI may be inserted into a desired locus, such as AOX1, GAP, ENO1, TEF, HIS4 (Zamir et al., Proc. NatL Acad. Sci. USA (1981) 78(6):3496-3500), HO (Voth et al. Nucleic Acids Res. 2001 Jun. 15; 29(12): e59), TYR1 (Mirisola et al., Yeast 2007; 24: 761-766), His3, Leu2, Ura3 (Taxis et al., BioTechniques (2006) 40:73-78), Lys2, ADE2, TRP1, GAL1, ADH1 or on the integration of 5S ribosomal RNA gene.

In other embodiments, the polynucleotide (gene) encoding the ADH2 protein and/or the GOI can be integrated in a plasmid or vector. Preferably, the plasmid is a eukaryotic expression vector, preferably a yeast expression vector. Suitable plasmids or vectors are further described herein.

Overexpression of an endogenous or heterologous polynucleotide in a recombinant host cell can be achieved by modifying expression control sequences. Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription. Exemplary expression control sequences are described in, for example, Goeddel, Gene Expression Technology: Methods in Enzymology, Vol. 185, Academic Press, San Diego, Calif. (1990).

In a preferred embodiment, the overexpression is achieved by using an enhancer to express the polynucleotide. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter. Most yeast genes contain only one UAS, which generally lies within a few hundred base pairs of the cap site and most yeast enhancers (UASs) cannot function when located 3' of the promoter, but enhancers in higher eukaryotes can function both 5' and 3' of the promoter.

Many enhancer sequences are known from mammalian genes (globin, RSV, SV40, EMC, elastase, albumin, a-fetoprotein and insulin). One may also use an enhancer from a eukaryotic cell virus, such as the SV40 late enhancer, the cytomegalovirus early promoter enhancer, the polyoma enhancer on the late side of the replication origin, and adenovirus enhancers.

Specifically, the GOI and/or the ADH2 encoding polynucleotide (gene) as described herein, are operably linked to transcriptional and translational regulatory sequences that provide for expression in the host cells. The term "translational regulatory sequences" as used herein refers to nucleotide sequences that are associated with a gene nucleic acid sequence and which regulate the translation of the gene. Transcriptional and/or translational regulatory sequences can either be located in plasmids or vectors or integrated in the chromosome of the host cell. Transcriptional and/or translational regulatory sequences are located in the same nucleic acid molecule of the gene which it regulates.

Specifically, the overexpression of the ADH2 protein can be achieved by methods known in the art, for example by genetically modifying their endogenous regulatory regions, as described by Marx et al., 2008 (Marx, H., Mattanovich, D. and Sauer, M. Microb Cell Fact 7 (2008): 23), such methods include, for example, integration of a recombinant promoter that increases expression of a gene.

For example, overexpression of an endogenous or heterologous polynucleotide in a recombinant host cell can be achieved by modifying the promoters controlling such expression, for example, by replacing a promoter (e.g., an endogenous promoter or a promoter which is natively linked to said polynucleotide in a wild-type organism) which is operably linked to said polynucleotide with another, stronger promoter in order to reach high expression levels. Such promoter may be inductive or constitutive. Modification of a promoter may also be performed by mutagenesis methods known in the art.

In a preferred embodiment, expression of both, the polynucleotide encoding the ADH2 protein and the polynucleotide encoding the POI, is driven by an inducible promoter. In another preferred embodiment, expression of both, the polynucleotide encoding the ADH2 protein and the polynucleotide encoding the POI, is driven by a constitutive promoter. In yet another preferred embodiment, expression of the polynucleotide encoding the ADH2 protein is driven by a constitutive promoter and expression of the polynucleotide encoding the POI is driven by an inducible promoter. In yet another preferred embodiment, expression of the polynucleotide encoding the ADH2 protein is driven by an inducible promoter and expression of the polynucleotide encoding the POI is driven by a constitutive promoter.

Specifically, a methanol-inducible promoter may be employed in expression constructs used to overexpress the gene encoding ADH2 and/or to express a Gal, as further described herein.

As an example, expression of the polynucleotide encoding the ADH2 protein may be driven by a constitutive GAP promoter and expression of the polynucleotide encoding the POI may be driven by the methanol-inducible AOX1 or AOX2 promoter.

In one embodiment, expression of the polynucleotides encoding the ADH2 protein and the POI is driven by the same promoter or same type of promoters in terms of promoter activity (e.g., the promoter strength) and/or expression behaviour (e.g., inducible or constitutive).

The term "reduce expression" herein also referred to as "underexpression" refers to any amount or level (e.g., the activity or concentration) less than an expressed amount or level (e.g., the activity or concentration) exhibited by a reference standard, which may be the host cell prior to the genetic alteration to reduce expression of a certain polynucleotide, or which is otherwise expressed in a host cell of the same type or species which is not engineered to lower expression of said polynucleotide. Reduction of expression as described herein specifically refers to a polynucleotide or gene encoding a defined AOX1 protein or AOX2 protein, in particular a gene that is endogenous to the host cell prior to engineering. In particular, the respective gene product is the defined AOX1 protein or AOX2 protein as described herein. Upon engineering the host cell by genetic modification to reduce expression of said gene the expression of said gene product or polypeptide is at a level which is less than the expression of the same gene product or polypeptide prior to a genetic modification of the host cell or in a comparable host which has not been genetically modified. "Less than" includes, e.g., 10%, 20%, 30%, 40%, 50%, 60%, 70%, 80, 90% or more. No expression of the gene product or a polypeptide is also encompassed by the term "reduction of expression" or "underexpression."

According to specific embodiments described herein, the host cell is engineered to knock-down or knockout (for inactivation or deletion of a gene or a part thereof) the endogenous host cell gene encoding the AOX1 protein or AOX2 protein (as defined herein, including e.g. homologues or orthologues of the sequences naturally-occurring in wild-type P. pastoris), or other (coding or non-coding) nucleotide sequences which confer the host cell's ability to express or produce said AOX1 protein or AOX2 protein.

Specifically, a deletion strain is provided, wherein a nucleotide sequence is disrupted.

The term "disrupt" as used herein refers to the significant reduction to complete removal of the expression or activity of one or more endogenous proteins in a host cell, such as by knock-down or knockout. This may be measured as presence of this one or more endogenous proteins in a cell culture or culture medium of the host cell, such as by mass spectrometry wherein the total content of an endogenous protein may be less than a threshold or non-detectable. Alternatively it may be measured as the enzymatic activity of the endogenous protein.

The term "disrupted" specifically refers to a result of genetic engineering by at least one step selected from the group consisting of gene silencing, gene knock-down, gene knockout, delivery of a dominant negative construct, conditional gene knockout, and/or by gene alteration with respect to a specific gene.

The term "knock-down", "reduction" or "deletion" in the context of gene expression as used herein refers to experimental approaches leading to reduced expression of a given gene compared to expression in a control cell. Knock-down of a gene can be achieved by various experimental means such as introducing nucleic acid molecules into the cell which hybridize with parts of the gene's mRNA leading to its degradation (e.g., shRNAs, RNAi, miRNAs) or altering the sequence of the gene in a way that leads to reduced transcription, reduced mRNA stability, diminished mRNA translation, or reduced activity of the encoded protein.

A complete inhibition of expression of a given gene is referred to as "knockout". Knockout of a gene means that no functional transcripts are synthesized from said gene leading to a loss of function normally provided by this gene. Gene knockout is achieved by altering the DNA sequence leading to disruption or deletion of the gene or its regulatory sequences, or part of such gene or regulatory sequences. Knockout technologies include the use of homologous recombination techniques to replace, interrupt or delete crucial parts or the entire gene sequence or the use of DNA-modifying enzymes such as zinc-finger or meganucleases to introduce double strand breaks into DNA of the target gene e.g., described by Gaj et al. (Trends Biotechnol. 2013; 31(7):397-405).

Specific embodiments employ one or more knockout plasmids or cassettes which are transformed or transfected into the host cells. By homologous recombination the target gene in the host cells can be disrupted. This procedure is typically repeated until all alleles of the target gene are stably removed.

One specific method for knocking out a specific gene as described herein is the CRISPR-Cas9 methods as described in e.g., Weninger et al. (J. Biotechnol. 2016, 235:139-49). Another method includes the split marker approach as described by e.g. Heiss et al. 2013 (Appl Microbiol Biotechnol. 97(3):1241-9.)

Another embodiment refers to target mRNA degradation by using small interfering RNA (siRNA) to transfect the host cell and targeting a mRNA encoding the target protein expressed endogenously by said host cell.

Expression of a gene may be inhibited or reduced by methods which directly interfere with gene expression, encompassing, but not restricted to, inhibition or reduction of DNA transcription, e.g., by use of specific promoter-related repressors, by site specific mutagenesis of a given promoter, by promoter exchange, or inhibition or reduction of translation, e.g., by RNAi or non-coding RNA induced post-transcriptional gene silencing. The expression of a dysfunctional, or inactive gene product with reduced activity, can, for example, be achieved by site specific or random mutagenesis, insertions or deletions within the coding gene.

The inhibition or reduction of the activity of gene product can, for example, be achieved by administration of, or incubation with, an inhibitor to the respective enzyme, prior to or simultaneously with protein expression. Examples for such inhibitors include, but are not limited to, an inhibitory peptide, an antibody, an aptamer, a fusion protein or an antibody mimetic against said enzyme, or a ligand or receptor thereof, or an inhibitory peptide or nucleic acid, or a small molecule with similar binding activity.

Gene silencing, gene knock-down and gene knockout refers to techniques by which the expression of a gene is reduced, either through genetic modification or by treatment with an oligonucleotide with a sequence complementary to either an mRNA transcript or a gene. If genetic modification of DNA is done, the result is a knock-down or knockout organism. If the change in gene expression is caused by an oligonucleotide binding to an mRNA or temporarily binding to a gene, this results in a temporary change in gene expression without modification of the chromosomal DNA and is referred to as a transient knock-down.

In a transient knock-down, which is also encompassed by the above term, the binding of this oligonucleotide to the active gene or its transcripts causes decreased expression through blocking of transcription (in the case of gene-binding), degradation of the mRNA transcript (e.g., by small interfering RNA (siRNA) or antisense RNA) or blocking mRNA translation.

Other approaches to carry out gene silencing, knock-down or knockout are known to the skilled person from the respective literature, and their application in the context of the present invention is considered as routine. Gene knockout refers to techniques by which the expression of a gene is fully blocked, i.e. the respective gene is inoperative, or even removed. Methodological approaches to achieve this goal are manifold and known to the skilled person. Examples are the production of a mutant which is dominantly negative for the given gene. Such mutant can be produced by site directed mutagenesis (e.g., deletion, partial deletion, insertion or nucleic acid substitution), by use of suitable transposons, or by other approaches which are known to the skilled person from the respective literature, the application of which in the context of the present invention is thus considered as routine. One example is knockout by use of targeted Zinc Finger Nucleases. A respective Kit is provided by Sigma Aldrich as "CompoZR knockout ZFN". Another approach encompasses the use of Transcription activator-like effector nucleases (TALENs).

The delivery of a dominant negative construct involves the introduction of a sequence coding for a dysfunctional gene expression product, e.g., by transfection. Said coding sequence is functionally coupled to a strong promoter, in such way that the gene expression of the dysfunctional enzyme overrules the natural expression of the gene expression product, which, in turn, leads to an effective physiological defect of the respective activity of said gene expression product.

A conditional gene knockout allows blocking gene expression in a tissue- or time-specific manner. This is done, for example, by introducing short sequences called loxP sites around the gene of interest. Again, other approaches are known to the skilled person from the respective literature, and their application in the context of the present invention is considered as routine.

One other approach is gene alteration which may lead to a dysfunctional gene product or to a gene product with reduced activity. This approach involves the introduction of frame shift mutations, nonsense mutations (i.e., introduction of a premature stop codon) or mutations which lead to an amino acid substitution which renders the whole gene product dysfunctional, or causing a reduced activity. Such gene alteration can for example be produced by mutagenesis (e.g., deletion, partial deletion, insertion or nucleic acid substitution), either unspecific (random) mutagenesis or site directed mutagenesis. Protocols describing the practical application of gene silencing, gene knock-down, gene knockout, delivery of a dominant negative construct, conditional gene knockout, and/or gene alteration are commonly available to the skilled artisan, and are within his routine. The technical teaching provided herein is thus entirely enabled with respect to all conceivable methods leading to an inhibition or reduction of gene expression of a gene product, or to the expression of a dysfunctional, or inactive gene product, or with reduced activity.

Genetic modifications described herein may employ tools, methods and techniques known in the art, such as described by J. Sambrook et al., Molecular Cloning: A Laboratory Manual (3rd edition), Cold Spring Harbor Laboratory, Cold Spring Harbor Laboratory Press, New York (2001).

The term "endogenous" as used herein is meant to include those molecules and sequences, in particular endogenous genes or proteins, which are present in the wild-type (native) host cell, prior to its modification to reduce expression of the respective endogenous genes and/or reduce the production of the endogenous proteins. In particular, an endogenous nucleic acid molecule (e.g., a gene) or protein that does occur in (and can be obtained from) a particular host cell as it is found in nature, is understood to be "host cell endogenous" or "endogenous to the host cell". Moreover, a cell "endogenously expressing" a nucleic acid or protein expresses that nucleic acid or protein as does a host of the same particular type as it is found in nature. Moreover, a host cell "endogenously producing" or that "endogenously produces" a nucleic acid, protein, or other compound produces that nucleic acid, protein, or compound as does a host cell of the same particular type as it is found in nature.

Thus, even if an endogenous protein is no more produced by a host cell, such as in a knockout mutant of the host cell, where the protein encoding gene is inactivated or deleted, the protein is herein still referred to as "endogenous".

The term "heterologous" as used herein with respect to a nucleotide sequence, construct such as an expression cassette, amino acid sequence or protein, refers to a compound which is either foreign to a given host cell, i.e. "exogenous", such as not found in nature in said host cell; or that is naturally found in a given host cell, e.g., is "endogenous", however, in the context of a heterologous construct or integrated in such heterologous construct, e.g., employing a heterologous nucleic acid fused or in conjunction with an endogenous nucleic acid, thereby rendering the construct heterologous. The heterologous nucleotide sequence as found endogenously may also be produced in an unnatural, e.g., greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence not natively associated with a promoter, e.g., to obtain a hybrid promoter, or operably linked to a coding sequence, as described herein. As a result, a hybrid or chimeric polynucleotide may be obtained. A further example of a heterologous compound is a POI encoding polynucleotide operably linked to a transcriptional control element, e.g., a promoter, to which an endogenous, naturally-occurring POI coding sequence is not normally operably linked.

The term "operably linked" as used herein refers to the association of nucleotide sequences on a single nucleic acid molecule, e.g., a vector, or an expression cassette, in a way such that the function of one or more nucleotide sequences is affected by at least one other nucleotide sequence present on said nucleic acid molecule. By operably linking, a nucleic acid sequence is placed into a functional relationship with another nucleic acid sequence on the same nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically, such nucleic acids operably linked to each other may be immediately linked, i.e. without further elements or nucleic acid sequences in between the nucleic acid encoding the signal peptide and the nucleic acid sequence encoding a POI.

The term "methylotrophic yeast" as used herein refers to of yeast genera and species which share a common metabolic pathway that enables them to use methanol as a sole carbon source for their growth. In a transcriptionally regulated response to methanol induction, several of the enzymes are rapidly synthesized at high levels. Since the promoters controlling the expression of these genes are among the strongest and most strictly regulated yeast promoters, methylotrophic yeast are attractive as hosts for the large scale production of recombinant proteins.

The methylotrophic yeast as described herein is mutated by one or more genetic modifications to render it deficient in the methanol utilization pathway, in particular by underexpressing one or both of the genes encoding the endogenous AOX1 and AOX2 proteins, respectively. A methylotrophic yeast which is underexpressing or otherwise deficient in expressing both, the gene encoding the AOX1 protein and the gene encoding the AOX2 protein is herein understood as "Mut–". For the purpose describe herein, such Mut– yeast is still referred to as "methylotrophic yeast", because comprising a functional methanol utilization pathway prior to such genetic modification(s).

A "promoter" sequence is typically understood to be operably linked to a coding sequence, if the promoter controls the transcription of the coding sequence. If a promoter sequence is not natively associated with the coding sequence, its transcription is either not controlled by the promoter in native (wild-type) cells or the sequences are recombined with different contiguous sequences.

The promoter which is used for the purpose described herein, is herein referred to as "ECP". The ECP may be a constitutive, inducible or repressible promoter. In a specific embodiment, the ECP is a promoter which is inducible by methanol and a methanol carbon source, respectively.

The ECP as described herein in particular initiates, regulates, or otherwise mediates or controls the expression of a POI coding DNA. Promoter DNA and coding DNA may be from the same gene or from different genes, and may be from the same or different organisms.

An inducible ECP as described herein is specifically understood as being a regulatable promoter, which has different promoter strength in the repressed and induced state. The term "regulatable" with respect to an inducible or repressible regulatory element, such as a promoter described herein shall refer to an element that is repressed in a host cell in the presence of an excess amount of a substance (such as a nutrient in the cell culture medium) e.g., in the growth phase of a batch culture, and de-repressed to induce strong activity e.g., in the production phase (such as upon upon feeding of a supplemental substrate, or adding methanol for methanol-induction), according to a fed-batch strategy. A regulatory element can as well be designed to be regulatable, such that the element is inactive without addition of a cell culture additive, and active in the presence of such additive. Thus, expression of a POI under the control of such regulatory element can be induced upon addition of such additive.

The strength of the ECP specifically refers to its transcription strength, represented by the efficiency of initiation of transcription occurring at that promoter with high or low frequency. The higher transcription strength, the more frequently transcription will occur at that promoter. Promoter strength is a typical feature of a promoter, because it determines how often a given mRNA sequence is transcribed, effectively giving higher priority for transcription to some genes over others, leading to a higher concentration of the transcript. A gene that codes for a protein that is required in large quantities, for example, typically has a relatively strong promoter. The RNA polymerase can only perform one transcription task at a time and so must prioritize its work to be efficient. Differences in promoter strength are selected to allow for this prioritization.

A strong ECP is herein preferred, in particular an ECP which is relatively strong in the fully induced state, which is typically understood as the state of about maximal activity. The relative strength is commonly determined with respect to a comparable promoter, herein referred to as a reference promoter, which can be a standard promoter, such as the respective pGAP promoter of the cell as used as the host cell.

The frequency of transcription is commonly understood as the transcription rate, e.g. as determined by the amount of a transcript in a suitable assay, e.g. RT-PCR or Northern blotting. For example, the transcription strength of a promoter according to the invention is determined in the host cell which is *P. pastoris* and compared to the native pGAP promoter of *P. pastoris*.

The strength of a promoter to express a gene of interest is commonly understood as the expression strength or the capability of support a high expression level/rate. For example, the expression and/or transcription strength of a promoter of the invention is determined in the host cell which is *P. pastoris* and compared to the native pGAP promoter of *P. pastoris*.

The comparative transcription strength compared to a reference promoter may be determined by standard methods, such as by measuring the quantity of transcripts, e.g. employing a microarray, or else in a cell culture, such as by measuring the quantity of respective gene expression products in recombinant cells. In particular, the transcription rate may be determined by the transcription strength on a microarray, Northern blot or with quantitative real time PCR (qRT-PCR) or with RNA sequencing (RNA-seq) where the data show the difference of expression level between conditions with high growth rate and conditions with low growth rate, or conditions employing different media composition, and a high signal intensity as compared to the reference promoter.

The expression rate may, for example, be determined by the amount of expression of a reporter gene, such as eGFP.

ECP as described herein exerts a relatively high transcription strength, e.g., reflected by a transcription rate or transcription strength of at least 15% as compared to the native pGAP promoter in the host cell, also called "homologous pGAP promoter". Preferably the transcription rate or strength is at least any one of 20%, 30%, 40%, 50%, 60%, 70%, 80%, 90% or 100%, or even higher, such as at least any one of 110%, 120%, 130%, 140%, 150%, 160%, 170%, 180%, 190%, or 200%, or even higher, as compared to the native pGAP promoter, such as determined in the (e.g. eukaryotic) host cell selected as a host cell for recombination purpose to produce the POI.

The native pGAP promoter typically initiates expression of the gap gene encoding glyceraldehyde-3-phosphate dehydrogenase (GAPDH), which is a constitutive promoter present in most living organisms. GAPDH (EC 1.2.1.12), a key enzyme of glycolysis and gluconeogenesis, plays a crucial role in catabolic and anabolic carbohydrate metabolism.

The native pGAP promoter specifically is active in a recombinant eukaryotic cell in a similar way as in a native eukaryotic cell of the same species or strain, including the unmodified (non-recombinant) or recombinant eukaryotic cell. Such native pGAP promoter is commonly understood to be an endogenous promoter, thus, homologous to the host cell, and may serve as a standard or reference promoter for comparison purposes. The relative expression or transcription strength of a promoter as described herein is usually compared to the native pGAP promoter of a cell of the same species or strain that is used as a host for producing a POI.

The term "mutagenesis" as used herein shall refer to a method of providing mutants of a nucleotide sequence, e.g. through insertion, deletion and/or substitution of one or more nucleotides, so to obtain variants thereof with at least one change in the non-coding or coding region. Mutagenesis may be through random, semi-random or site directed mutation. Variants can be produced by a suitable mutagenesis method using a parent sequence as a reference. Certain mutagenesis methods encompass those methods of engineering the nucleic acid or de novo synthesizing a nucleotide sequence using the respective parent sequence information as a template. Specific mutagenesis methods apply rational engineering of a mutant.

The term "nucleotide sequence" or "nucleic acid sequence" used herein refers to either DNA or RNA. "Nucleic acid sequence" or "polynucleotide sequence" or simply "polynucleotide" refers to a single or double-stranded polymer of deoxyribonucleotide or ribonucleotide bases read from the 5' to the 3' end. It includes expression cassettes, self-replicating plasmids, infectious polymers of DNA or RNA, and non-functional DNA or RNA.

The term "protein of interest (POI)" as used herein refers to a polypeptide or a protein that is produced by means of recombinant technology in a host cell. More specifically, the protein may either be a polypeptide not naturally-occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g., of a promoter sequence. In some cases the term POI as used herein also refers to any metabolite product by the host cell as mediated by the recombinantly expressed protein.

The term "sequence identity" of a variant, homologue or orthologue as compared to a parent nucleotide or amino acid sequence indicates the degree of identity of two or more sequences. Two or more amino acid sequences may have the same or conserved amino acid residues at a corresponding position, to a certain degree, up to 100%. Two or more nucleotide sequences may have the same or conserved base pairs at a corresponding position, to a certain degree, up to 100%.

Sequence similarity searching is an effective and reliable strategy for identifying homologs with excess (e.g., at least 50%) sequence identity. Sequence similarity search tools frequently used are e.g., BLAST, FASTA, and HMMER.

Sequence similarity searches can identify such homologous proteins or genes by detecting excess similarity, and statistically significant similarity that reflects common ancestry. Homologues may encompass orthologues, which are herein understood as the same protein in different organisms, e.g., variants of such protein in different different organisms or species.

An orthologous sequence of the same protein in different organisms or species is typically homologous to the protein sequence, specifically of orthologs originating from the same genus. Typically, orthologs have at least about any one of 25%, 30%, 35%, 40%, 50%, 60%, 70%, 80%, 85%, 90%, or 95% identity, up to 100% sequence identity.

Specifically, orthologs of a protein can be determined upon replacement of said protein or the gene encoding said protein by the orthologous sequences in a knock-out host cell, which host cell has been modified to knockout the respective gene or protein prior to such replacement.

For example, if a putative ADH2, AOX1 or AOX2 protein is functional in a *P. pastoris* host cell replacing the respective endogenous protein in a *P. pastoris* host cell in which the gene encoding such endogenous protein has been knocked out, such putative ADH2, AOX1 or AOX2 protein can be considered a respective homologue for the purpose described herein.

The AOX1 protein comprising or consisting of the amino acid sequence identified as SEQ ID NO:1 is of *K. phaffii* origin. It is well understood that there are homologous sequences present in other methylotrophic yeast host cells. For example, yeast of *Pichia pastoris* comprise the respective homologous sequences. *Pichia pastoris* has been reclassified into a new genus, *Komagataella*, and split into three species, *K. pastoris, K. phaffii*, and *K. pseudopastoris*.

Specific homologous sequences of SEQ ID NO:1 are e.g., found in *K. pastoris* (e.g., SEQ ID NO:9, such as encoded by the nucleotide sequence comprising or consisting of SEQ ID NO:10), *Ogataea polymorpha* (e.g., SEQ ID NO:19 such as encoded by the nucleotide sequence comprising or consisting of SEQ ID NO:20) or *Ogataea methanolica* (e.g., SEQ ID NO:13 such as encoded by the nucleotide sequence comprising or consisting of SEQ ID NO:14).

The AOX2 protein comprising or consisting of the amino acid sequence identified as SEQ ID NO:3 is of *K. phaffii* origin. It is well understood that there are homologous sequences present in other methylotrophic yeast host cells. For example, yeast of *Pichia pastoris* comprise the respective homologous sequences. *Pichia pastoris* has been reclassified into a new genus, *Komagataella*, and split into three species, *K. pastoris, K. phaffii*, and *K. pseudopastoris*.

Specific homologous sequences of SEQ ID NO:3 are e.g., found in *K. pastoris* (e.g., SEQ ID NO:11, such as encoded by the nucleotide sequence comprising or consisting of SEQ ID NO:12), *Ogataea polymorpha* (e.g., SEQ ID NO:19, such as encoded by the nucleotide sequence comprising or consisting of SEQ ID NO:20), or *Ogataea methanolica* (e.g., SEQ ID NO:15, such as encoded by the nucleotide sequence comprising or consisting of SEQ ID NO:16).

*Ogataea polymorpha* has only one alcohol oxidase, herein exemplified by SEQ ID NO:19. Thus, reducing expression of AOX1 and AOX2 in *Ogataea polymorpha* as described herein is effectively carried out by reducing expression of the endogenous alcohol oxidase of *Ogataea polymorpha*.

Any homologous sequence of an AOX1 or AOX2 protein with a certain sequence identity described herein, in particular any such protein which is an ortholog of the *P. pastoris* AOX1 or AOX2 protein, is included in the definition of the respective AOX1 protein or AOX2 protein, as described herein.

The ADH2 protein comprising or consisting of the amino acid sequence identified as SEQ ID NO:50 is of *K. phaffii* origin. It is well understood that there are homologous sequences present in other methylotrophic yeast host cells. For example, yeast of *Pichia pastoris* comprise the respective homologous sequences. *Pichia pastoris* has been reclassified into a new genus, *Komagataella*, and split into three species, *K. pastoris, K. phaffii*, and *K. pseudopastoris*.

Specific homologous sequences of SEQ ID NO:50 are e.g., any one of SEQ ID NO:52, 54, 56, 58, 60, 62, 64, 66, 68, or 70.

Any homologous sequence of an ADH2 protein with a certain sequence identity described herein, in particular any such protein which is an ortholog of the *P. pastoris* ADH2 protein, as described herein.

"Percent (%) amino acid sequence identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

For purposes described herein, the sequence identity between two amino acid sequences is determined using the NCBI BLAST program version BLASTP 2.8.1 with the following exemplary parameters: Program: blastp, Word size: 6, Expect value: 10, Hitlist size: 100, Gapcosts: 11.1, Matrix: BLOSUM62, Filter string: F, Compositional adjustment: Conditional compositional score matrix adjustment.

"Percent (%) identity" with respect to a nucleotide sequence e.g., of a promoter or a gene, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

For purposes described herein (unless indicated otherwise), the sequence identity between two amino acid sequences is determined using the NCBI BLAST program version BLASTN 2.8.1 with the following exemplary parameters: Program: blastn, Word size: 11, Expect threshold: 10, Hitlist size: 100, Gap Costs: 5.2, Match/Mismatch Scores: 2,-3, Filter string: Low complexity regions, Mark for lookup table only.

The term "isolated" or "isolation" as used herein with respect to a POI shall refer to such compound that has been sufficiently separated from the environment with which it would naturally be associated, in particular a cell culture supernatant, so as to exist in "purified" or "substantially pure" form. Yet, "isolated" does not necessarily mean the exclusion of artificial or synthetic mixtures with other compounds or materials, or the presence of impurities that do not interfere with the fundamental activity, and that may be present, for example, due to incomplete purification. Isolated compounds can be further formulated to produce preparations thereof, and still for practical purposes be isolated—for example, a POI can be mixed with pharmaceutically acceptable carriers or excipients when used in diagnosis or therapy.

The term "purified" as used herein shall refer to a preparation comprising at least 50% (mol/mol), preferably at least 60%, 70%, 80%, 90% or 95% of a compound (e.g., a POD. Purity is measured by methods appropriate for the compound (e.g., chromatographic methods, polyacrylamide gel electrophoresis, HPLC analysis, and the like). An isolated, purified POI as described herein may be obtained by purifying the cell culture supernatants to reduce impurities.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The following standard methods are preferred: cell (debris) separation and wash by Microfiltration or Tangential Flow Filter (TFF) or centrifugation, POI purification by precipitation or heat treatment, POI activation by enzymatic digest, POI purification by chromatography, such as ion exchange (IEX), hydrophobic interaction chromatography (HIC), Affinity chromatography, size exclusion (SEC) or HPLC Chromatography, POI precipitation of concentration and washing by ultrafiltration steps.

A highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

An isolated and purified POI can be identified by conventional methods such as Western blot, HPLC, activity assay, or ELISA.

The term "recombinant" as used herein shall mean "being prepared by or the result of genetic engineering. A recombinant host may be engineered to delete and/or inactivate one or more nucleotides or nucleotide sequences, and may specifically comprise an expression vector or cloning vector containing a recombinant nucleic acid sequence, in particular employing nucleotide sequence foreign to the host. A recombinant protein is produced by expressing a respective recombinant nucleic acid in a host. The term "recombinant" with respect to a POI as used herein, includes a POI that is prepared, expressed, created or isolated by recombinant means, such as a POI isolated from a host cell transformed to express the POI. In accordance with the present invention conventional molecular biology, microbiology, and recombinant DNA techniques within the skill of the art may be employed. Such techniques are explained fully in the literature. See, e.g., Maniatis, Fritsch & Sambrook, "Molecular Cloning: A Laboratory Manual, Cold Spring Harbor, (1982).

Certain recombinant host cells are "engineered" host cells which are understood as host cells which have been manipulated using genetic engineering, i.e. by human intervention. When a host cell is engineered to reduce expression or to underexpress a given gene or the respective protein, the host cell is manipulated such that the host cell has no longer the capability to express such gene and protein, respectively, compared to the host cell under the same condition prior to manipulation, or compared to the host cells which are not engineered such that said gene or protein is underexpressed.

The foregoing description will be more fully understood with reference to the following examples. Such examples are, however, merely representative of methods of practicing one or more embodiments of the present invention and should not be read as limiting the scope of invention.

EXAMPLES

Example 1: Generation of Methanol Utilization Negative Strains of *Pichia pastoris*

In order to generate the methanol utilization negative strains (Mut⁻) two genes responsible for the methanol utilization named AOX1 and AOX2 were deleted from the genome of *Pichia pastoris* (syn. *Komagataella phaffii*).

a) For this purpose the *P. pastoris* strain (CBS2612, CBS-KNAW Fungal Biodiversity Centre, Centraalbureau voor Schimmelcultures, Utrecht, The Netherlands) was made electrocompetent. The strain was inoculated into 100 mL YPD media (main culture) for 16-20 hours (25° C.; 180 rpm) and harvested at an optical density ($OD_{600}$) from 1.8-3 by centrifugation (5 min, 1500 g, 4° C.) in two 50 mL falcon tubes. The cell pellet was resuspended in 10 mL YPD+20 mM HEPES+25 mM DTT and incubated (30 min; 25° C.; 180 rpm). After the incubation period the falcon tubes were filled with 40 mL ice cold sterile distilled water and centrifuged (5 min, 1500 g; 4° C.) (Eppendorf AG, Germany). The cell pellet was resuspended in ice cold sterile 1 mM HEPES buffer, pH 8 and centrifuged (5 min, 1500 g, 4° C.). The cell pellet was resuspended in 45 mL ice cold 1 M sorbitol and centrifuged (5 min, 1500 g, 4° C.). The pellet was resuspended in 500 μL ice cold 1M sorbitol and 80 μL aliquoted into ice cold 1.5 mL Eppendorf tubes. The aliquoted electro competent cells were kept at −80° C. till used.

b) Cultivation of yeast strains was done in YPD media (10 g/L yeast extract, 20 g/L peptone, 20 g/L glucose) or YPD agar plates (10 g/L yeast extract, 20 g/L peptone, 20 g/L glucose, 20 g/L agar-agar) containing 500 μg/mL Geneticin or 200 μg/mL Hygromycin when necessary for selection.

c) For generating the deletion strains of AOX1 and AOX2 the split marker cassette approach was used (Gasser et al., 2013). The DNA fragments for generating the gene deletions are found in Table 1. The split marker cassette was carrying an antibiotic resistance cassette for Geneticin flanked by LoxP sites.

d) The deletions were done by adding 0.5 μg AOX1 split marker cassette 1 and 0.5 μg AOX1 split marker cassette 2 to the aliquoted electro competent cells and incubated for 5 min on ice. The electroporation was performed at 2 kV for 4 milliseconds (Gene Pulser, Bio-Rad Laboratories, Inc, USA). After transformation the electroporated cells were suspended in 1 mL YPD media and regenerated for 1.5 h to 3 h on 30° C. shaking at 700 rpm on a thermoshaker (Eppendorf AG, Germany). Later 20 µL and 150 µL of the cell suspension was plated on YPD plates containing 500 µg/mL Geneticin for selection and incubated on 28° C. for 48 hours. The colonies that appeared were re-streaked onto fresh YPD plates containing 500 µg/mL Geneticin. The correct disruption of AOX1 locus was verified by PCR on genomic DNA using the primers AOX1_ctrl_Fwd and AOX1_ctrl_Rev (Table 2) binding outside of the deletion cassette. One clone was selected based on PCR amplification and sequencing of the PCR amplicon confirming correct deletion of the desired gene creating a *P. pastoris* aox1Δ::KanMX strain. A liquid culture was incubated from a single positive colony and made electrocompetent as explained in Example 1a), except for the addition of 500 µg/mL Geneticin to the liquid medium for generating the main culture. The strains were electroporated with 500 µg pTAC_Cre_Hph_Mx4 plasmid carrying a Cre recombinase needed for deletion of the Geneticin antibiotic resistance cassette between the LoxP regions and a Hygromycin resistance cassette for selection (Marx, Mattanovich, & Sauer, 2008). The electroporation was done as described and selected for loss of Geneticin resistance by restreaking the transformants in parallel on YPD with 500 µg/mL Geneticin and 200 µg/mL Hygromycin and YPD plates with only 200 µg/mL Hygromycin. Clones were selected which were unable to grow on YPD plates with 500 µg/mL Geneticin and 200 µg/mL Hygromycin, but could grow on YPD plates with only 200 µg/mL Hygromycin. The successful deletion of the AOX1 coding region and antibiotic marker was verified by PCR amplification with the primers AOX1_ctrl_Fwd and AOX1_ctrl_Rev (Table 2) and sequencing of the PCR amplicon (Microsynth AG, Swiss). The generated strain is called *P. pastoris* CBS2612 Δaox1 and has a Mut$^S$ phenotype. It was selected for further genetic manipulation.

e) The *P. pastoris* CBS2612 Δaox1 was used to generate electro competent cells with the protocol described in a) and was electroporated with 0.5 µg AOX2 split marker cassette 1 and 0.5 µg AOX2 split marker cassette 2 (Table 1) with the procedure described in d). The antibiotic marker was removed with the same procedure as described in d). The successful deletion of the AOX2 coding region and antibiotic marker was verified by PCR amplification with the primers AOX2_ctrl_fwd & AOX2_ctrl_rev (Table 2) and sequencing of the PCR amplicon (Microsynth AG, Swiss). The generated strain is called *P. pastoris* CBS2612 Δaox1Δaox2 and has a methanol utilization negative (Mut$^-$) phenotype.

f) Genomic DNA for PCR amplifications was isolated with the Wizard® Genomic DNA Purification Kit (Promega Corporation, USA) as per the manufacturer's recommendation. The PCR amplification reactions were done with the Q5 polymerase (New England Biolabs, Inc., USA) as per the manufacturer's recommendations.

TABLE 1

Split marker cassette DNA sequence used for generating the AOX1 and AOX2 deletion strains.

| DNA fragment | DNA sequence 5' to 3' |
| --- | --- |
| AOX1 split marker cassette 1 | (SEQ ID NO: 25)<br>AGGGGTCCAAGTAAGAAGCTTCTTGCTGTAGAATTTGGGCATATGTGCTGGTGACAAAG<br>GCATCTCTGCCTTGAGTTTCTGACGGCGGGACAGCATTCTTACCGGATATATAACACCA<br>ATTGCCAGCACCACCAATCTCAGAGGTACCCCTAACAAACTTAATAAAATCTTGGGTAT<br>CAACTTCATTAAGCTTTGTAGTTTGCAAGTACTTATAAACAAAATTCCGTAAGGTGTCG<br>TCTTGAGGCTGGGACTTGACAAACTGCCAAAATGGCAACAAATCTACTGGCTTGGCCAT<br>AATTTTGACATTCGAGTCATCAAAGGTAAATTCAACCGGAGACTTGTATTCTTTATTGA<br>TAACTTTCTCATATAGGACATTGTCAGGAACACGATGAAACCAGGATGCCCCCAAATCC<br>AATGAGACTGAGGTTTCATGAGTCGCAACCAACCTACCTCCAATACGGTCCCTACCCTC<br>TAAAATCAACGCATTCACGCCATTGCTTTTGAGATCGACTGCAGCTTTGATGCCTGAAA<br>TCCCAGCGCCTACAATGATGACATTTGGATTTGGTTGACTCATGTTGGTATTGTGAAAT<br>AGACGCAGATCGGGAACACTGAAAAATAACAGTTATTATTCGAGATCTAACATCCAAAG<br>ACGAAAGGTTGAATGAAACCTTTTTGCCATCCGACATCCACAGGTCCATTCTCACACAT<br>AAGTGCCAAACGCAACAGGAGGGGATACACTAGCAGCAGACCGTTGCAAACGCAGGACC<br>TCCACTCCTCTTCTCCTCAACACCCACTTTTGCCATCGAAAAACCAGCCCAGTTATTGG<br>GCTTGATTGGAGCTCGCTCATTCCAATTCCTTCTATTAGGCTACTAACACCATGACTTT<br>ATTAGCCTGTCTATCCTGGCCCCCCTGGCGAGGTTCATGTTTGTTTATTTCCGAATGCA<br>ACAAGCTCCGCATTACACCCGAACATCACTCCAGATGAGGGCTTTCTGAGTGTGGGGTC<br>AGTACGCTGCAGGTCGACAACCCTTAATATAACTTCGTATAATGTATGCTATACGAAGT<br>TATTAGGTCTAGATCGGTACCGACATGGAGGCCCAGAATACCCTCCTTGACAGTCTTGA<br>CGTGCGCAGCTCAGGGGCATGATGTGACTGTCGCCCGTACATTTAGCCCATACATCCCC<br>ATGTATAATCATTTGCATCCATACATTTTGATGGCCGCACGGCGCGAAGCAAAAATTAC<br>GGCTCCTCGCTGCAGACCTGCGAGCAGGGAAACGCTCCCCTCACAGACGCGTTGAATTG<br>TCCCCACGCCGCGCCCCTGTAGAGAAATATAAAAGGTTAGGATTTGCCACTGAGGTTCT<br>TCTTTCATATACTTCCTTTTAAAATCTTGCTAGGATACAGTTCTCACATCACATCCGAA<br>CATAAACAACCATGGGTAAGGAAAAGACTCACGTTTCGAGGCCGCGATTAAATTCCAAC<br>ATGGATGCTGATTTATATGGGTATAAATGGGCTCGCGATAATGTCGGGCAATCAGGTGC<br>GACAATCTATCGATTGTATGGGAAGCCCGATGCGCCAGAGTTGTTTCTGAAACATGGCA<br>AAGGTAGCGTTGCCAATGATGTTACAGATGAGATGGTCAGACTAAACTGGCTGACGGAA<br>TTTATGCCTCTTCCGACCATCAAGCATTTTATCCGTACTCCTGATGATGCATGGTTACT<br>CACCACTGCGATCCCCGGCAAAACAGCATTCCAGGTATTAGAAGAATATCCTGATTCAG<br>GTGAAAATATTGTTGATGCGCTGGCAGTGTTCCTGCGCCGGTTGCATTCGATTCCTGTT<br>TGTAATTGTCCTTTTAACAGCGATCGCGTATTTCGTCTCGCTCAGGCGCAATCACGAAT |

TABLE 1-continued

Split marker cassette DNA sequence used for generating the AOX1 and AOX2 deletion strains.

| DNA fragment | DNA sequence 5' to 3' |
|---|---|
| | GAATAACGGTTTGGTTGATGCGAGTGATTTTGATGACGAGCGTAATGGCTGGCCTGTTG<br>AACAAGTCTGGAAAGAAATGCATAAGCTTTTGCCATTCTCACCG |
| AoX1<br>split marker<br>cassette 2 | (SEQ ID NO: 26)<br>AAGCCCGATGCGCCAGAGTTGTTTCTGAAACATGGCAAAGGTAGCGTTGCCAATGATGT<br>TACAGATGAGATGGTCAGACTAAACTGGCTGACGGAATTTATGCCTCTTCCGACCATCA<br>AGCATTTTATCCGTACTCCTGATGATGCATGGTTACTCACCACTGCGATCCCCGGCAAA<br>ACAGCATTCCAGGTATTAGAAGAATATCCTGATTCAGGTGAAAATATTGTTGATGCGCT<br>GGCAGTGTTCCTGCGCCGGTTGCATTCGATTCCTGTTTGTAATTGTCCTTTTAACAGCG<br>ATCGCGTATTTCGTCTCGCTCAGGCGCAATCACGAATGAATAACGGTTTGGTTGATGCG<br>AGTGATTTTGATGACGAGCGTAATGGCTGGCCTGTTGAACAAGTCTGGAAAGAAATGCA<br>TAAGCTTTTGCCATTCTCACCGGATTCAGTCGTCACTCATGGTGATTTCTCACTTGATA<br>ACCTTATTTTTGACGAGGGGAAATTAATAGGTTGTATTGATGTTGGACGAGTCGGAATC<br>GCAGACCGATACCAGGATCTTGCCATCCTATGGAACTGCCTCGGTGAGTTTTCTCCTTC<br>ATTACAGAAACGGCTTTTTCAAAAATATGGTATTGATAATCCTGATATGAATAAATTGC<br>AGTTTCATTTGATGCTCGATGAGTTTTTCTAATCAGTACTGACAATAAAAAGATTCTTG<br>TTTTCAAGAACTTGTCATTTGTATAGTTTTTTTATATTGTAGTTGTTCTATTTTAATCA<br>AATGTTAGCGTGATTTATATTTTTTTTCGCCTCGACATCATCTGCCCAGATGCGAAGTT<br>AAGTGCGCAGAAAGTAATATCATGCGTCAATCGTATGTGAATGCTGGTCGCTATACTGG<br>TACCATTCGAGAACCCTTAATATAACTTCGTATAATGTATGCTATACGAAGTTATTAGG<br>TGATATCAGATCCACTGCCATTTGCCTGAGAGATGCAGGCTTCATTTTTGATACTTTTT<br>TATTTGTAACCTATATAGTATAGGATTTTTTTTGTCATTTTGTTTCTTCTCGTACGAGC<br>TTGCTCCTGATCAGCCTATCTCGCAGCTGATGAATATCTTGTGGTAGGGGTTTGGGAAA<br>ATCATTCGAGTTTGATGTTTTTCTTGGTATTTCCCACTCCTCTTCAGAGTACAGAAGAT<br>TAAGTGAGACGTTCGTTTGTGCAAGCTTCAACGATGCCAAAAGGGTATAATAAGCGTCA<br>TTTGCAGCATTGTGAAGAAAACTATGTGGCAAGCCAAGCCTGCGAAGAATGTATTTTAA<br>GTTTGACTTTGATGTATTCACTTGATTAAGCCATAATTCTCGAGTATCTATGATTGGAA<br>GTATGGGAATGGTGATACCCGCATTCTTCAGTGTCTTGAGGTCTCCTATCAGATTATGC<br>CCAACTAAAGCAACCGGAGGAGGAGATTTCATGGTAAATTTCTCTGACTTTTGGTCATC<br>AGTAGACTCGAACTGTGAGACTATCTCGGTTATGACAGCAGAAATGTCCTTCTTGGAGA<br>CAGTAAATGAAGTCCCACCAATAAAGAAATCCTTGTTATCAGGAACAAACTTCTTGTTT<br>CGAACTTTTTCGGTGCCTTGAACTATAAAATGTAGAGTGGATATGTCGGGTAGGAATGG<br>AGCGGGCAAATGCTTACCTTCTGGACCTTCAAGAGGTATGTAGGGTTTGTAGATACTGA<br>TGCCAACTTCAGTGACAACGTTGCTATTTCGTTCAAACCATTCCGAATCCAGAGAAATC<br>AAAGTTGTTTGTCTACTATTGATCCAAGCCAGTGCGGTCTTGAAACTGACAATAGTGTG<br>CTCGTGTTTTGAGGTCATCTTTGT |
| AOX2<br>split marker<br>cassette 1 | (SEQ ID NO: 27)<br>GTACGGGTTTACTGATTTGACATATCTTGGTACTAACGTTACCAATGGTGTTCCAAATA<br>ACGCAGATGATGAGCGTGGTTGCATTGCTGGATTTGACAACACTGGTTTCGTGCTGGGA<br>ACTTCATCCTCGTTGTTTAATCAGTTTATTCTGCAACTGAATACGAGTGATCTTTCAGG<br>AGCAATTTACCAAATCATTGAGCATTTTCTGACTGGACTTAGCGAAGACGAAGACGACA<br>TTGCTATCTATTCCCCCAACCCTTTCTACAAAAGTACGTATGCAGGAGTAGGTGCCATT<br>GCGGAAAATGACACCCTTTACTTGGTTGATGGTGGAGAGGATAACCAAAACGTCCCTCT<br>GCAGCCTCTACTTCAAAAGGAGCGTGACGTTGATATCATCTTTGCGTTTGACAACAGTG<br>CAGACACTGACCTCTCTTGGCCAAACGGTTCATCATTAGTCAACACCTACATGAGACAG<br>TTTTCTTCTCAAGCAAATGGAACAACGTTCCCTTATGTACCTGATACCACCACTTTCCT<br>AAACTTGAATCTTTCGAGTAAGCCAACCTTCTTTGGTTGTGATGCTAGAAATTTGACAG<br>ACATTGTTGAAGGCACGGATCACATTCCTCCCCTGGTTGTTTATCTGGCCAATAGACCT<br>TTCTCGTATTGGAGTAACACTTCAACTTTCAAGTTAGACTACTCTGAATCCGAGAAGAG<br>AGGAATGATCCAAAACGGTTTTGAAGTGTCGTCTCGTTTGAACATGACTATTGATGAAG<br>AATGGCGTACTTGTGTTGGATGTGCAATCATTCGTAGACAGCAGGAGAGATCCAATGCA<br>ACACAAACAGAGCAATGTAGAAGATGTTTTGAGAATTATTGTTGGAACGGTGATATTGA<br>CACTTCCACCGAAGATATCCCCGTTAATTTTACCACTACTGGAGCAACCAATGAGGAGA<br>ATGACAACTCCACTTCAATATCATCGGCCAATTCGGTAGCACCTTCCAAACTTTGGTAC<br>CAAGCACCATTGCTGTTGGTCGGCCTTGTCGCATTCTTCATCTAGTACGTACGCTGCAG<br>GTCGACAACCCTTAATATAACTTCGTATAATGTATGCTATACGAAGTTATTAGGTCTAG<br>ATCGGTACCGACATGGAGGCCCAGAATACCCTCCTTGACAGTCTTGACGTGCGCAGCTC<br>AGGGGCATGATGTGACTGTCGCCCGTACATTTAGCCCATACATCCCCATGTATAATCAT<br>TTGCATCCATACATTTTGATGGCCGCACGGCGCGAAGCAAAAATTACGGCTCCTCGCTG<br>CAGACCTGCGAGCAGGGAAAGCTCCCCTCACAGACGCGTTGAATTGTCCCCACGCCGC<br>GCCCCTGTAGAGAAATATAAAAGGTTAGGATTTGCCACTGAGGTTCTTCTTTCATATAC<br>TTCCTTTTAAAATCTTGCTAGGATACAGTTCTCACATCACATCCGAACATAAACAACCA<br>TGGGTAAGGAAAAGACTCACGTTTCGAGGCCGCGATTAAATTCCAACATGGATGCTGAT<br>TTATATGGGTATAAATGGGCTCGCGATAATGTCGGGCAATCAGGTGCGACAATCTATCG<br>ATTGTATGGGAAGCCCGATGCGCCAGAGTTGTTTCTGAAACATGGCAAAGGTAGCGTTG<br>CCAATGATGTTACAGATGAGATGGTCAGACTAAACTGGCTGACGGAATTTATGCCTCTT<br>CCGACCATCAAGCATTTTATCCGTACTCCTGATGATGCATGGTTACTCACCACTGCGAT<br>CCCCGGCAAAACAGCATTCCAGGTATTAGAAGAATATCCTGATTCAGGTGAAAATATTG<br>TTGATGCGCTGGCAGTGTTCCTGCGCCGGTTGCATTCGATTCCTGTTTGTAATTGTCCT<br>TTTAACAGCGATCGCGTATTTCGTCTCGCTCAGGCGCAATCACGAATGAATAACGGTTT<br>GGTTGATGCGAGTGATTTTGATGACGAGCGTAATGGCTGGCCTGTTGAACAAGTCTGGA<br>AAGAAATGCATAAGCTTTTGCCATTCTCACCG |

TABLE 1-continued

Split marker cassette DNA sequence used for generating the AOX1 and AOX2 deletion strains.

| DNA fragment | DNA sequence 5' to 3' |
|---|---|
| AoX2 split marker cassette 2 | (SEQ ID NO: 28)<br>AAGCCCGATGCGCCAGAGTTGTTTCTGAAACATGGCAAAGGTAGCGTTGCCAATGATGT<br>TACAGATGAGATGGTCAGACTAAACTGGCTGACGGAATTTATGCCTCTTCCGACCATCA<br>AGCATTTTATCCGTACTCCTGATGATGCATGGTTACTCACCACTGCGATCCCCGGCAAA<br>ACAGCATTCCAGGTATTAGAAGAATATCCTGATTCAGGTGAAAATATTGTTGATGCGCT<br>GGCAGTGTTCCTGCGCCGGTTGCATTCGATTCCTGTTTGTAATTGTCCTTTTAACAGCG<br>ATCGCGTATTTCGTCTCGCTCAGGCGCAATCACGAATGAATAACGGTTTGGTTGATGCG<br>AGTGATTTTGATGACGAGCGTAATGGCTGGCCTGTTGAACAAGTCTGGAAAGAAATGCA<br>TAAGCTTTTGCCATTCTCACCGGATTCAGTCGTCACTCATGGTGATTTCTCACTTGATA<br>ACCTTATTTTTGACGAGGGGAAATTAATAGGTTGTATTGATGTTGGACGAGTCGGAATC<br>GCAGACCGATACCAGGATCTTGCCATCCTATGGAACTGCCTCGGTGAGTTTTCTCCTTC<br>ATTACAGAAACGGCTTTTTCAAAAATATGGTATTGATAATCCTGATATGAATAAATTGC<br>AGTTTCATTTGATGCTCGATGAGTTTTTCTAATCAGTACTGACAATAAAAAGATTCTTG<br>TTTTCAAGAACTTGTCATTTGTATAGTTTTTTTATATTGTAGTTGTTCTATTTTAATCA<br>AATGTTAGCGTGATTTATATTTTTTTTCGCCTCGACATCATCTGCCCAGATGCGAAGTT<br>AAGTGCGCAGAAAGTAATATCATGCGTCAATCGTATGTGAATGCTGGTCGCTATACTGG<br>TACCATTCGAGAACCCTTAATATAACTTCGTATAATGTATGCTATACGAAGTTATTAGG<br>TGATATCAGATCCACTTCCTCTTACGGCTTTCTTTCCCAAAAAATCATTGGGGAAATGT<br>GCCCCTCATCAGAGTCCAATGACCCATGAATAAAGTTTCTTGTACTGTTTAAGACGATG<br>AATTGCAACGATAATCCGAGCAGTTTACGGGGTACATCACGTGCTTTGCATATGATCTC<br>GGAGTCGGATCAGTTCCGGATGTGATGTATTACCCCATAGTTTCAAACTCTAATGCAGC<br>CGCCAAGTGCCATACACCCTCCATCAATCTATGCTTAAAGTTTTTCACCATCGTTGGGT<br>GGTGATGATGACTCGCTTAGTCTCTGCTGTTCGATATTAACTTTGTAAGGATCGCCCTT<br>GGATGGAAAATTGAGGGGTTGTAACCTGAATTTGCAGGCTACTTACATTGGACTTTTGA<br>GAAGGCTGGACGGTTGATGAAGAGGGCTGGGTGCAGAGGAATGGAAAAAAATTTAGTTG<br>AGAGGACTGCTTGAAATTTTAGGAAATGGAGTCCTTTAAGCTGACAAAACTTCAAGGAT<br>GGGGATTTTCATGTAGCTTTTTCATGCCTTCGACAAGCTAAAGGAAGGTAATTGATTCT<br>GGATAAATGGATATTTGATCTGCTTTAGCAGATGTCAAAGTTCTACTAGTGATAGTCTG<br>GTATCTCGTAGCCTTCAATTGGGCGTATCTTACTCGAAGTGTTATATTTTTAGCTGACG<br>AGACGAAGAACGAGAGAGTATTGACACATTCAGAGGTAAGACAATATGTCGTATTATCA<br>AAATAAGTATCGAACCTCTATTAGGAGCCTACTGGCTCAAATGTGCAACCTTAGTGGTG<br>ATTGTCTCTGCTTCTTGATCACAATCTGTCGTGTTTGAGAGTGCCGATGTATGATTTTT<br>AGTAAATGTTTTTCAGAAAAGGCGCTAAGTAAATAACCAGTAAGTAATAAATAACGTAA<br>AAGTGATTTGAATCATAAAAGAATCAAGATAGAGGTCAAAGCATAGATAATCCCCC |

TABLE 2

Polymerase chain reaction primers

| Primer Name | DNA sequence 5' to 3' |
|---|---|
| AOX1_ctrl_Fwd | GGCTGGAAATAGATGTAGGGAG<br>(SEQ ID NO: 29) |
| AOX1_ctrl_Rev | TCGCATCTCCGCAAATTTCTC<br>(SEQ ID NO: 30) |
| AOX2_ctrl_fwd | GATCCCATTCCCTATCCATGT<br>(SEQ ID NO: 31) |
| AOX2_ctrl_rev | CTCTCCCCCCTCGTAATCTT<br>(SEQ ID NO: 32) |

Example 2: Production of Intracellular eGFP with P. pastoris ΔAox1 and P. pastoris ΔAox1ΔAox2 Under the Methanol Inducible AOX1 Promoter To test the protein producing ability and promoter activity the P. pastoris Δaox1Δaox2 and P. pastoris Δaox1 strains were transformed with an expression constructs for enhanced green fluorescent protein (eGFP) (Table 4). The eGFP coding sequence was under the expression control of the PAOX$_1$: PP7435_chr4 (237941 . . . 238898).

a) The expression construct BB3aN_pAOX1_GFP_ScCYCtt was assembled using the Golden Gate assembly procedure as described (Prielhofer et al., 2017) from the plasmids BB1_12_pAOX1, BB1_23_eGFP, BB1_34_ScCYC1tt and BB3aN_14*. The plasmids and sequences are available in the Golden PiCS kit #1000000133 (Addgene, Inc., USA). Before electroporation the plasmids were linearized with the restriction enzyme AscI (New England Biolabs, Inc., USA) as per the manufacturer's protocol and purified with the Hi Yield® Gel/PCR DNA Fragment Extraction Kits (Süd-Laborbedarf GmbH, Germany). 500 ng of the linearized plasmid was transformed into electrocompetent P. pastoris Δaox1Δaox2 and P. pastoris Δaox1 as previously described in Example 1a) and 1d). Positive transformants were selected on YPD with 100 μg/L Nourseothricin and used for later screening experiments.

b) Small scale screening experiments of intracellular eGFP expression in the P. pastoris Δaox1Δaox2 and P. pastoris Δaox1. Ten transformants from Example 2a) were picked and inoculated into an overnight culture in 24 deep well plates containing 2 mL YPD and 100 μg/L Nourseothricin per well. All transformants were tested in duplicates. The 24 well plates were sealed with an air permissible membrane and incubated at 25° C. and 280 rpm. For screening of the intracellular expression level of eGFP the overnight cultures were transferred to 24 deep well plates with 2.5 mL minimal ASMv6 media with 25 g/L polysaccharide and 0.3% amylase (m2p-labs GmbH, Germany) for slow glucose release and incubated for two hours followed by an addition of either 0.2% (v/v) or 1% (v/v) methanol for induction of eGFP production. eGFP measurements were done 4 and 20 hours after induction using a Gallios flow cytometer (Beckman Coulter, Inc., USA). For this purpose the cells were diluted to an $OD_{600}$ of 0.5 in phosphate buffered saline containing 0.24 g/L $KH_2PO_4$, 1.8 g/L $Na_2HPO_4*2H_2O$, 0.2 g/L KCl, 8 g/L NaCl. 20,000 events were measured. FX values were calculated with the software FACS Express version 3 (De Novo Software, USA) using the equation:

$$FX = \left(\frac{FL1}{FSC^{1.5}}\right) * 8000$$

FX = Dimensionless value

FL1 = Fluorescence measured with a 505-545 nm filter

FSC = Forward scatter

The method was already described (Ata, Prielhofer, Gasser, Mattanovich, & Çalik, 2017; Hohenblum, Borth, & Mattanovich, 2003; Prielhofer et al., 2013).

c) Minimal media ASMv6: 6.3 g/L $(NH_4)_2HPO_4$, 0.8 g/L $(NH_4)_2SO_4$, 0.49 g/L $MgSO_4*7H_2O$, 2.64 g/L KCl, 0.054 g/L $CaCl_2*2H_2O$, 22 g/L citric acid monohydrate, 1.47 mL/L PTM0 trace metals, 0.8 mg/L biotin 20 mL/L $NH_4OH$ (25%); pH set to 6.5 with KOH.

d) The results are displayed in Table 3. Fluorescence was a proxy to determine the intracellular eGFP levels and the intracellular eGFP levels were a proxy for determining the activity of the $P_{AOX1}$. The results show that at 20 hours under 1% methanol induction the promoter is active in the *P. pastoris* Δaox1Δaox2 strain and eGFP is produced. The induction of the *P. pastoris* Δaox1 Δaox2 BB3aN_pAOX1_GFP_ScCYCtt strain is better at 1% than at 0.2% methanol after 20 h, no difference between methanol concentrations is observed in the *P. pastoris* Δaox1 strain.

TABLE 3

Results (FX values) with standard deviation from experiment described in Example 2b)

| | *P. pastoris* Δaox1Δaox2 | *P. pastoris* Δaox1 | negative control | |
| --- | --- | --- | --- | --- |
| | BB3aN_pAOX1_ GFP_ScCYCtt | BB3aN_pAOX1_ GFP_ScCYCtt | *P. pastoris* Δaox1Δaox2 | *P. pastoris* Δaox1 |
| 0.2% MeOH at 4h | 4.39 ± 0.90 | 6.26 ± 1.74 | | 2.92 |
| 1% MeOH at 4h | 5.59 ± 1.09 | 7.39 ± 1.57 | 2.95 | 2.89 |
| 0.2% MeOH at 20h | 37.81 ± 12.71 | 84.18 ± 4.57 | 2.37 | 2.70 |
| 1% MeOH at 20h | 62.89 ± 8.81 | 89.85 ± 3.90 | 2.35 | 2.42 |

TABLE 4

Coding sequences of the Genes of interest expressed in *P. pastoris* Δaox1Δaox2 and *P. pastoris* Δaox1.

| Gene of interest name | DNA sequence 5' to 3' |
| --- | --- |
| enhanced green fluorescent protein (eGFP) | (SEQ ID NO: 33)<br>ATGGTGAGCAAGGGCGAGGAGCTGTTCACCGGGGTGGTGCCCATCCTGGTCG<br>AGCTGGACGGCGACGTAAACGGCCACAAGTTCAGCGTGTCCGGCGAGGGCGA<br>GGGCGATGCCACCTACGGCAAGCTGACCCTGAAGTTCATCTGCACCACCGGC<br>AAGCTGCCCGTGCCCTGGCCCACCCTCGTGACCACCCTGACCTACGGCGTGC<br>AGTGCTTCAGCCGCTACCCCGACCACATGAAGCAGCACGACTTCTTCAAGTC<br>CGCCATGCCCGAAGGCTACGTCCAGGAGCGCACCATCTTCTTCAAGGACGAC<br>GGCAACTACAAGACCCGCGCCGAGGTGAAGTTCGAGGGCGACACCCTGGTGA<br>ACCGCATCGAGCTGAAGGGCATCGACTTCAAGGAGGACGGCAACATCCTGGG<br>GCACAAGCTGGAGTACAACTACAACAGCCACAACGTCTATATCATGGCCGAC<br>AAGCAGAAGAACGGCATCAAGGTGAACTTCAAGATCCGCCACAACATCGAGG<br>ACGGCAGCGTGCAGCTCGCCGACCACTACCAGCAGAACACCCCCATCGGCGA<br>CGGCCCCGTGCTGCTGCCCGACAACCACTACCTGAGCACCCAGTCCGCCCTG<br>AGCAAAGACCCCAACGAGAAGCGCGATCACATGGTCCTGCTGGAGTTCGTGA<br>CCGCCGCCGGGATCACTCTCGGCATGGACGAGCTGTACAAGTAA |
| Human serum albumin (HSA) with its native secretion leader | (SEQ ID NO: 34)<br>ATGAAGTGGGTTACTTTCATCTCCTTGTTGTTCTTGTTCTCCTCAGCTTACT<br>CCAGAGGTGTTTTCAGAAGAGATGCTCACAAGTCCGAGGTTGCTCACAGATT<br>CAAGGACTTGGGTGAAGAGAACTTCAAGGCTTTGGTTTTGATCGCTTTCGCT<br>CAGTACTTGCAGCAGTGTCCATTCGAGGACCACGTTAAGTTGGTTAACGAGG<br>TTACTGAGTTCGCTAAGACTTGTGTTGCTGACGAATCCGCTGAGAACTGTGA<br>TAAGTCCTTGCACACTTTGTTCGGTGACAAGTTGTGTACTGTTGCTACTTTG<br>AGAGAAACTTACGGTGAGATGGCTGACTGTTGTGCTAAGCAAGAGCCTGAGA<br>GAAACGAGTGTTTCTTGCAACACAAGGACGACAACCCAAACTTGCCAAGATT<br>GGTTAGACCAGAGGTTGACGTTATGTGTACTGCTTTCCACGACAACGAAGAG<br>ACTTTCTTGAAGAAGTACTTGTACGAGATCGCTAGAAGACACCCATACTTCT<br>ACGCTCCAGAGTTGTTGTTCTTCGCTAAGAGATACAAGGCTGCTTTCACTGA |

TABLE 4-continued

Coding sequences of the Genes of interest expressed in P. pastoris Δaox1Δaox2 and P. pastoris Δaox1.

| Gene of interest name | DNA sequence 5' to 3' |
|---|---|
| | GTGTTGTCAGGCTGCTGATAAGGCTGCTTGTTTGTTGCCAAAGTTGGACGAG<br>TTGAGAGATGAGGGTAAGGCTTCTTCCGCTAAGCAGAGATTGAAGTGTGCTT<br>CCTTGCAGAAGTTCGGAGAGAGAGCTTTTAAGGCTTGGGCTGTTGCTAGATT<br>GTCCCAGAGATTCCCAAAGGCTGAGTTCGCTGAGGTTTCCAAGTTGGTTACT<br>GACTTGACTAAGGTTCACACAGAGTGTTGTCACGGTGACTTGTTGGAATGTG<br>CTGATGACAGAGCTGACTTGGCTAAGTACATCTGTGAGAACCAGGATTCCAT<br>CTCCTCCAAGTTGAAAGAATGTTGTGAGAAGCCTTTGTTGGAGAAGTCCCAC<br>TGTATCGCTGAGGTTGAAAACGACGAAATGCCAGCTGACTTGCCATCTTTGG<br>CTGCTGACTTCGTTGAATCCAAGGACGTCTGCAAGAACTACGCTGAGGCTAA<br>GGACGTTTTCTTGGGTATGTTCTTGTATGAGTACGCTAGAAGACATCCAGAC<br>TACTCCGTTGTTTTGTTGTTGAGATTGGCTAAGACTTACGAGACTACTTTGG<br>AGAAGTGTTGTGCTGCTGCTGACCCACATGAGTGTTACGCTAAGGTTTTCGA<br>CGAGTTCAAGCCATTGGTTGAGGAACCACAGAACTTGATCAAGCAGAACTGT<br>GAGTTGTTCGAGCAGTTGGGTGAGTACAAGTTCCAGAACGCTTTGTTGGTTA<br>GATACACTAAGAAGGTTCCACAGGTTTCCACTCCAACTTTGGTTGAGGTTTC<br>CAGAAACTTGGGTAAGGTTGGTTCCAAGTGTTGTAAGCACCCAGAGGCTAAG<br>AGAATGCCATGTGCTGAGGACTACTTGTCTGTTGTTTTGAACCAGTTGTGTG<br>TCTTGCACGAAAAGACACCAGTTTCCGACAGAGTTACTAAGTGTTGTACTGA<br>ATCCTTGGTTAACAGAAGACCTTGTTTCTCCGCTTTGGAGGTTGACGAGACT<br>TACGTTCCAAAAGAGTTCAACGCTGAGACTTTCACTTTCCACGCTGACATCT<br>GTACTTTGTCCGAGAAAGAGAGACAGATCAAGAAGCAGACTGCTTTGGTTGA<br>GTTGGTTAAGCACAAGCCAAAGGCTACAAAAGAGCAGTTGAAGGCTGTTATG<br>GACGACTTCGCTGCTTTCGTTGAGAAATGTTGTAAGGCTGACGACAAAGAGA<br>CTTGTTTCGCTGAAGAGGGTAAGAAGTTGGTTGCTGCTTCCCAAGCTGCTTT<br>GGGTCTGTAA |
| variable region of a camelid antibody (VHH) with the S. cerevisiae a-mating factor leader | (SEQ ID NO: 35)<br>ATGAGATTCCCATCTATTTTCACCGCTGTCTTGTTCGCTGCCTCCTCTGCAT<br>TGGCTGCCCCTGTTAACACTACCACTGAAGACGAGACTGCTCAAATTCCAGC<br>TGAAGCAGTTATCGGTTACTCTGACCTTGAGGGTGATTTCGACGTCGCTGTT<br>TTGCCTTTCTCTAACTCCACTAACAACGGTTTGTTGTTCATTAACACCACTA<br>TCGCTTCCATTGCTGCTAAGGAAGAGGGTGTCTCTCTCGAGAAGAGACAAGC<br>CGGTGGTTCATTAAGATTGTCCTGTGCTGCCTCTGGTAGAACTTTCACTTCT<br>TTCGCAATGGGTTGGTTTAGACAAGCACCTGGAAAAGAGAGAGAGTTTGTTG<br>CTTCTATCTCCAGATCCGGTACTTTAACTAGATACGCTGACTCTGCCAAGGG<br>TAGATTCACTATTTCTGTTGACAACGCCAAGAACACTGTTTCTTTGCAAATG<br>GACAACCTTAACCCAGATGACACCGCAGTCTATTACTGTGCCGCTGACTTGC<br>ACAGACCATACGGTCCAGGAACCCAAAGATCCGATGAGTACGATTCTTGGGG<br>TCAGGGAACTCAAGTCACTGTCTCTTCAGGTGGTGGATCTGGTGGTGGAGGT<br>TCAGGTGGTGGAGGATCCGGTGGTGGTGGTTCTGGTGGTGGTGGATCTGGTG<br>GAGGTGAAGTTCAACTTGTCGAATCCGGTGGTGCACTTGTCCAACCTGGTGG<br>ATCTCTTAGACTTTCTTGTGCCGCCTCCGGTTTTCCTGTTAACCGTTACTCT<br>ATGCGTTGGTACAGACAAGCCCCTGGAAAAGAACGTGAATGGGTTGCCGGAA<br>TGTCCTCAGCTGGTGACAGATCCTCCTACGAAGATTCTGTGAAGGGACGTTT<br>CACCATCTCCAGAGATGACGCCCGTAACACCGTTTACCTTCAAATGAACTCC<br>CTTAAGCCTGAGGATACTGCCGTCTACTATTGTAACGTGAATGTCGGATTTG<br>AATACTGGGGACAGGGAACCCAAGTTACTGTCTCTTCCGGTGGACATCACCA<br>CCACCATCACTAATAG |

Example 3: Generation of P. pastoris ΔAox1 and P. pastoris ΔAox1ΔAox2 Strains Producing Secreted HSA and VHH Under the Methanol Inducible AOX1 Promoter To test the ability to produce secreted recombinant proteins in the P. pastoris Δaox1 Δaox2 strain and compare it with the P. pastoris Δaox1 strains, the strains were transformed with expression constructs for two secreted model proteins: (1) Human serum albumin with its native secretion leader (HSA) or (2) variable region of a camelid antibody with the S. cerevisiae α-mating factor secretion leader (VHH). The coding sequence of these genes of interest (codon-optimized and synthesized by external providers) can be found in Table 4.

a) The pPM2pN21_pAOX1_HSAopt_CycTT and pPM2pZ30_pAOX1_αMF-vHH_CycTT expression constructs used for HSA and VHH production are derivatives of the pPuzzle ZeoR vector described in WO2008128701A2, consisting of the E. coli pUC19 on and the Zeocin antibiotic resistance cassette. In this case of pPM2pN21_pAOX1_HSAopt_CycTT the Zeocin resistance is exchanged for Nourseothricin resistance via restriction and ligation. Additionally the vectors are carrying an integration sequence that is homologous to the PGI locus PP7435_Chr3 (1366329 . . . 1367193) for efficient integration. The expression vector is described in more details elsewhere (Gasser et al., 2013; Stadlmayr et al., 2010). Expression of the gene of interest (GOI) was mediated by the $P_{AOX1}$ PP7435_chr4 (237941 . . . 238898) and the Saccharomyces cerevisiae CYC1 transcription terminator. The gene for human serum albumin (HSA) (GenBank NP_000468) was codon optimized for P. pastoris and synthesized. It has a native secretion leader and is therefore secreted into the supernatant. The gene for VHH is codon optimized for P. pastoris and synthetized (Table 4), it has an N-terminal S.

cerevisiae α-mating type leader for secretion into the supernatant. For the purpose of transformation of the expression constructs the circular vectors were linearized by restriction in the PGI1 homologous sequence with XmnI (New England Biolabs, Inc., USA) and purified with the Hi Yield® Gel/PCR DNA Fragment Extraction Kits (Süd-Laborbedarf GmbH, Germany).

b) Electroporation of electrocompetent P. pastoris Δaox1 Δaox2 and P. pastoris Δaox1 with 500 ng linearized pPM2pN21_pAOX1_HSAopt_CycTT and pPM2pZ30_pAOX1_αMF-vHH_CycTT plasmid and selection were carried out as previously described in Example 1a) and Example 1d). The selection was carried out on YPD plates with 100 µg/mL Nourseothricin or 25 µg/mL Zeocin, respectively.

Example 4: Small Scale Screening of the HSA and VHH Producing P. pastoris ΔAox1 ΔAox2 and P. pastoris ΔAox1 a) For the pre-culture the transformants were inoculated in 2 mL YPD with 100 µg/mL Nourseothricin or 25 µg/mL Zeocin based on the antibiotic resistance used for selection. For each expression construct twelve transformants were picked for screening. Pre-culture and screening cultures were cultivated in 24 well plates sealed with an air permeable membrane and incubated on 25° C. on 280 rpm. The screening culture was inoculated with a start optical density ($OD_{600}$) of 8 into 2 mL of minimal media (ASMv6) with a slow glucose release system based on 6 mm feedbeads (Kuhner Shaker GmbH, Germany) to keep the cultures in glucose limit. The strains were compared with different methanol feed procedures differing in total methanol received and duration (Table 5).

b) After the incubation period 1 mL of the each culture was removed and centrifuged in a pre-weighted Eppendorf tube. The supernatant was removed and the protein concentration was measured with the Caliper LabChip GXII Touch (Perkin Elmer, inc., USA) as per the manufacturer's instructions. The wet cell weight was determined by weighting the Eppendorf tube with the cell pellet and calculated as follows: Weight (full)−Weight (empty)=Wet cell weight (WCW) (g/L). Out of this data the yield was calculated: Yield (µg/g)=Protein concentration/Wet cell weight. Data of transformants that had double the concentration or had no detectible protein in the supernatant were removed from analysis as outliers. The outliers are considered as transformants that have either two copies of the expression construct or no copy at all (Aw & Polizzi, 2013; Schwarzhans et al., 2016).

TABLE 5

Overview of the screening strategies used for testing the secreted protein production yield of the transformed strains.

| Protocol | Incubation period | Feedbeads | Start $OD_{600}$ | Methanol pulse | Total methanol | Methanol shot time points |
|---|---|---|---|---|---|---|
| Standard | 48 h | 12 mm | 8 | 4× | 3.5% (v/v) | 4 h*, 19 h, 27 h, 43 h |
| One shot | 48 h | 3 × 6 mm | 8 | 1× | 1% (v/v) | 3 h |
| Two shot | 48 h | 3 × 6 mm | 8 | 2× | 2% (v/v) | 3 h, 23 h |
| One shot - extended | 72 h | 3 × 6 mm | 8 | 1× | 1% (v/v) | 3 h |
| Two shot - extended | 72 h | 3 × 6 mm | 8 | 2× | 2% (v/v) | 3 h, 43 h |

*The first shot was 0.5% methanol.

c) The results show that the P. pastoris Δaox1Δaox2 can produce secreted proteins under the induction of the $P_{AOX1}$ and that the yield is comparable to the P. pastoris Δaox1 used as industry standard (Table 6). In the "Two shot—extended" strategy the P. pastoris Δaox1Δaox2 shows a better yield indicating that under longer cultivation times with less methanol the P. pastoris Δaox1Δaox2 has an yield advantage. Furthermore this shows that it is possible to use limited glucose conditions to screen P. pastoris Δaox1Δaox2 strains producing secreted proteins controlled by the $P_{AOX1}$ and methanol induction.

TABLE 6

Average secreted product yield with standard deviation in pg product / g WCW of the tested strains in different screening conditions.

| | Standard | One shot | Two shot | One shot extended | Two shot extended |
|---|---|---|---|---|---|
| P. pastoris Δaox1Δaox2 pPM2pZ30_pAOX1_αMF-vHH_CycTT | 733 ± 59 | 219 ± 32 | 379 ± 38 | 0 | 410 ± 16 |
| P. pastoris Δaox1 pPM2pZ30_pAOX1_αMF-vHH_CycTT | 1465 ± 239 | 195 ± 66 | 413 ± 114 | 0 | 239 ± 77 |
| P. pastoris Δaox1Δaox2 pPM2pN21_pAOX1_HSAopt_CycTT | 443 ± 111 | 138 ± 24 | 251 ± 110 | 228 ± 33 | 363 ± 55 |
| P. pastoris Δaox1 pPM2pN21_pAOX1_HSAopt_CycTT | 840 ± 36 | 79 ± 9 | 388 ± 61 | 83 ± 18 | 277 ± 23 |

Example 5: Bioreactor Cultivations

To determine the behavior and process parameters of P. pastoris Δaox1Δaox2 in fed-batch mode in a recombinant protein production setting, bioreactor cultivations were performed. The cultivations were performed as follows.

a) DASGIP bioreactors were used with a working volume of 0.7 L (Eppendorf AG, Germany). One Bioreactor system consists of four reactors that are arranged in one bio-block for controlling the temperature. Each reactor was connected to 4 peristaltic pumps that were software controlled. Additionally each reactor had 2 balances available that were connected to the DASGIP control software (Eppendorf AG, Germany) for adjusting the pump speed gravimetrically. Each reactor was connected with a controllable gas supply (pressured air, $N_2$, $O_2$ could be mixed in any desired amount) and a gas analyzer for $O_2$ and $CO_2$ concentration measurement in the reactor off gas. The reactors had a pH probe and Dissolved Oxygen (DO) probe connected to the DASGIP control software. The DASGIP control software was recording all parameters in one minute intervals.
b) The bioreactor cultivation media consisted of BSM medium (Mellitzer et al., 2014): 11.48 g/L $H_3PO_4$, 0.5 g/L $CaCl_2*2H_2O$, 7.5 g/L $MgSO_4*7H_2O$, 9 g/L $K_2SO_4$, 2 g/L KOH, 40 g/L Glycerol, 0.25 g/L NaCl, 4.35 mL/L PTM0, 0.87 mg/L Biotin, 0.1 mL/L Glanapon 2000, pH set to 5.5 with 25% $NH_3$.
c) PTM0 consisted of: 6.0 g $CuSO_4*5H_2O$, 0.08 g NaI, 3.36 g $MnSO_4*H_2O$, 0.2 g $Na_2MoO_4*2H_2O$, 0.02 g $H_3BO_3$, 0.82 g $CoCl_2$, 20.0 g $ZnCl_2$, 65.0 g $FeSO_4*7H_2O$, 5 mL/L $H_2SO_4$ (95%-98%).
d) The Glucose feed media consisted of: 50% (w/w) glucose, 2.08 mg/kg Biotin, 10.4 mL/kg PTM0. The methanol feed media was: 50% (v/v) or 100% (v/v) methanol. The glycerol feed media consisted of: 60% (w/w) glycerol, 2.08 mg/kg Biotin, 10.4 mL/kg PTM0.
e) The Dissolved Oxygen (DO) set point was 20%. In certain cases the DO control was deactivated and the agitation and aeration were manually set to a constant 750 rpm and 9.5 sL/h. The pH was set to 5.0 or 5.5 with either 12.5% or 25% $NH_3$ controlled by the DASGIP control software. Acid control was achieved with 10% $H_3PO_4$ by manual addition when necessary. The temperature was set at 25° C. The start $OD_{600}$ was 2 and the start volume was 300 mL plus 15 mL of inoculation culture.
f) Sampling was done on a daily basis (approximately every 24 hours). First a 3 mL aspirate was taken from the reactor to remove the dead volume of the sampling port. Then 9 mL of sample were taken. 3×2 mL were pipetted into reweighted 2 mL Eppendorf tubes and 1×1.5 mL into one 1.5 mL Eppendorf tube. The samples were centrifuged (16,000 g, 10 min, 4° C.). The supernatant was collected for protein and HPLC analysis and stored at –20° C. The pellet was washed by resuspension in 1 mL 0.1 M HCl to remove trace salts and centrifuged again (16,000 g, 10 min, 4° C.). The pellet was then dried for 24 hours at 105° C. to determine the dry cell weight. The dry cell weight was calculated as follows: (Weight (full)–Weight (empty))/2=Dry cell weight (g/L) and calculated as the average of three replicates. If only a HPLC sample was need only 2 mL of sample were taken.
g) Cell viability was measured by staining the cell suspension with propidium iodide. For this the cell suspension from the reactor sample was diluted with phosphate buffered saline to on $OD_{600}$ of 0.5 and mixed with a stock solution of propidium iodide to a final concentration of 10 µM prior to measurement with the Gallios flow cytometer (Beckman coulter, Inc., USA) with a filter of 590-650 nm. 50,000 events were measured per sample.

Example 6: Determining the Evaporation Rate of Methanol from the Bioreactors without Cells To assess the evaporation rate of methanol from the reactors by aeration and agitation the reactors were filled with sterile media and pulsed with methanol, samples were taken to determine the methanol concentration.
a) For this example two reactors were filled with 310 mL of BSM media without glycerol and two reactors were filled with 500 mL BSM media without glycerol to simulate the media at the end of the batch phase where the glycerol is consumed by the growing culture.
b) The reactor stirrer speed was set to 760 rpm and gassing to 9.5 sL/h as would be the case in a cultivation of the P. pastoris Δaox1Δaox2. The parameters can be found in Table 7.
c) A 50% (v/v) methanol pulse was added manually to increase the methanol concentration to 1% (v/v) and a sample was taken to determine the actual achieved concentration. Samples were taken at 3.4, 6.5, 22.4, 31.0, 47.9 hours by first removing 3 mL of dead volume from the sample port and discarding the aspirate. Immediately after that a 4 mL sample was taken.
d) HPLC measurement of methanol concentration were done as described previously (Blumhoff, Steiger, Marx, Mattanovich, & Sauer, 2013). For identification and quantification pure standards were used. The column was an Aminex HPX-87H (Bio-Rad Laboratories, Inc, USA) run at 60° C. with a 4 mM $H_2SO_4$ mobile phase at 0.6 mL/min. The detector was a refraction index detector RID-10 A (Shimadzu, Corp., Japan) and the calculations were done with the LabSolutions v5.85 software (Shimadzu, Corp., Japan).
e) The evaporation rate was calculated only from the first and last sample with the biggest time and concentration difference. The changes in concentration between the adjacent samples were marginal and measurement error could have a significant impact on the calculation. The data can be found in Table 8. R1 and R2 filled with 500 mL media had a mean value of 0.063 $g*L^{-1}*h^{-1}$.

TABLE 7

Reactor parameters and methanol pulse volume.

| Reactor | Volume (mL) | Agitation (rpm) | Gassing (sL/h) | 50% (v/v) methanol (ml) |
|---|---|---|---|---|
| R1 | 310 | 760 | 9.5 | 6.2 |
| R2 | 310 | 760 | 9.5 | 6.2 |
| R3 | 500 | 760 | 9.5 | 10 |
| R4 | 500 | 760 | 9.5 | 10 |

TABLE 8

Methanol concentration at the sampling timepoints and the calculated evaporation rate.

| Reactor | 0 | 3.4 | 6.5 | 22.4 | 31.0 | 46.9 | dc/dt (g $L^{-1}$ $h^{-1}$) |
|---|---|---|---|---|---|---|---|
| | | | Methanol (g/L) | | | | |
| R1 | 7.91 | 6.13 | 7.53 | 6.76 | 6.10 | 5.49 | 0.052 |
| R2 | 7.80 | 7.14 | 7.49 | 6.72 | 6.28 | 4.29 | 0.075 |
| R3 | 7.47 | 7.73 | 5.07* | 7.05 | 6.93 | 6.43 | 0.022 |
| R4 | 7.54 | 7.80 | 6.33* | 6.97 | 4.39* | 6.49 | 0.022 |

*are too low and are considered as outliers.

Example 7: Determining the Methanol Uptake Rate of P. pastoris ΔAox1ΔAox2

To determine the methanol uptake rate the P. pastoris Δaox1Δaox2 pPM2pN21_pAOX1_HSAopt_CycTT strain was cultivated in a bioreactor. The culture was grown till a certain biomass concentration. Then a methanol pulse was applied and samples were taken immediately after the pulse and approximately 20 hours later. The goal was to determine the methanol uptake rate of the Mut⁻ strain and compare it to the methanol evaporation rate measured in Example 6.

tracted evaporation an evaporation rate of 22 mg L⁻¹ h⁻¹ was estimated based on the results in Example 6e), Table 8. This outcome was completely new and unexpected. Till now it was reported and accepted in published literature that the Mut⁻ is unable to metabolise methanol and that the decrease of methanol is due to evaporation loss (Looser et al., 2015).

TABLE 9

Data overview specific methanol uptake rate ($q_{methanol}$) and apparent methanol loss (dc/dt).

| Reactor | Volume (mL) | CDW (g/L) | Methanol at 0 h (g/L) | Methanol at 19.5 h (g/L) | dc/dt (g L⁻¹ h⁻¹) | $q_{methanol}$ (mg g⁻¹ h⁻¹) | $q_{methanol}$-evaporated (subtracted evaporation) (mg g⁻¹ h⁻¹) |
|---|---|---|---|---|---|---|---|
| R1 | 378 | 73.4 | 10.71 | 3.67 | 0.361 | 4.92 | 4.61 |
| R2 | 372 | 72.6 | 10.74 | 3.35 | 0.379 | 5.22 | 4.90 | a) Pre-culture: 24 hours prior to reactor inoculation 50 mL YPD containing 100 µg/L Nourseothricin were inoculated with P. pastoris Δaox1Δaox2 pPM2pN21_pAOX1_HSAopt_CycTT. 3 hours prior to inoculation of the reactors the pre-culture was diluted by another 50 mL YPD containing 100 µg/L Nourseothricin. Before inoculation the appropriate amount of culture was centrifuged (1500 g, 5 min, 20° C.) and resuspended in 15 mL of BSM media with an OD₆₀₀ of 42.

b) The reactors filled with 300 mL BSM media were inoculated with 15 mL of P. pastoris Δaox1Δaox2 pPM2pN21_pAOX1_HSAopt_CycTT culture. The target inoculation OD₆₀₀ in the reactor was 2. At the end of the batch phase as indicated by a dissolved oxygen spike, a 50% (w/w) glucose feed was started at 2.4 mL/h for 24 hours to increase the biomass. Two hours after the glucose feed start a 9.5 mL 50% (v/v) methanol shot was given to increase the methanol concentration to 1.5% (measured concentration was R1=1.47% and R2=1.48%). This was done to induce methanol consumption. At the end of the glucose feed phase samples for cell dry weight and HPLC were taken.

c) After the glucose phase the agitation and gassing was set to a constant 750 rpm and 9.5 sL/h. An additional 50% methanol pulse was added to increase the concentration to 1.5% and immediately a sample was taken (measured concentration was R1=1.36% and R2=1.36%). The concentration was measured again after 19.5 hours and used to determine the specific methanol uptake rate ($q_{methanol}$).

d) The methanol concentration decrease (dc/dt) for this experiment was substantially higher at 0.37 g L⁻¹ h⁻¹ on average compared to the values obtained for the evaporation rate in Example 6e), Table 8 that ranges from 0.022 to 0.063 g L⁻¹ h⁻¹.

The specific methanol uptake rate was calculated based on the data represented in Table 9 as follows.

$$q_{methanol} = ((C_{methanol}^{t_0} - C_{methanol}^{t_{19.5}})/C_{biomass})/(t_0 - t_{19.5})$$

The volume was constant over the measured time period. The average specific methanol uptake rate ($q_{methanol}$) without subtracted evaporation was 5.07 mg g⁻¹ h⁻¹. For the calculations of the specific methanol uptake rate with sub- Example 8: Cultivation Strategy 1—Applying a Constant Glucose/Methanol Co-Feed to the P. pastoris ΔAox1 ΔAox2

The P. pastoris Δaox1 Δaox2 pPM2pN21_pAOX1_HSAopt_CycTT strain was cultivated in a recombinant protein production scenario. The strain was fed with a constant limited glucose feed and induced with methanol for protein production.

a) The inoculation was done as described in Example 7a) b). The cultivation was separated into two phases. (1) Phase one: The batch was started at OD₆₀₀ of 2 in BSM medium. The batch phase end was indicated by a dissolved oxygen spike at 22.27 h for reactor R1 and 21.52 h for reactor R2.

b) (2) Phase two: A fed-batch phase with a 50% (w/w) glucose feed was started after phase one at a feed rate of 2.4 mL/h for 97 hours. At the same time a 50% (v/v) methanol pulse was added with the aim to increase the methanol concertation to 1.5% (v/v). A HPLC sample was taken as described in Example 6d) to measure the exact concentration and an additional pulse was added if necessary. A methanol feed calculated based on the predicted biomass concentration and the specific methanol uptake rate of 5 mg g⁻¹ h⁻¹ as measured in Example 7d) was applied. The methanol concentration was measured daily at line by HPLC.

c) The methanol feed was calculated in hourly intervals as follows:

$$R_{methanol} = q_{methanol} * X_{predicted} * t_{interval}$$

$$T_{methanol} = T_{methanol-previous\ interval} - R_{methanol} + A_{methanol-previous\ interval} - \left(\frac{T_{methanol-previous\ interval}}{V_{reactor-previous\ interval}} * V_{sample-previous\ interval}\right)$$

$$A_{methanol} = V_{reactor} * C_{methanol,target} - T_{methanol}$$

$$F_{methanol} = \left(\frac{A_{methanol}}{\rho_{methanol}}\right) * 0.002$$

$$V_{reactor} = V_{reactor-previous\ interval} + F_{Glucose} + F_{methanol}$$

$$X_{predicted} = X_{predicted-previous} + \left(Y_{(\frac{x}{s})} * (F_{glucose} * \rho_{50\%\ glucose} * 50\%)\right) - \left(V_{sample} * \left(\frac{X_{predicted-previous\ interval}}{V_{reactor-previous\ interval}}\right)\right)$$

-continued $q_{methanol}$ = specific methanol uptake rate (mg g$^{-1}$h$^{-1}$)

$X_{predicted}$ = predicted total biomass in cell dry weight (g)

$t_{interval}$ = time interval (h)

$R_{methanol}$ = methanol consumption at $t_{interval}$ (mg)

$T_{methanol}$ = total methanol (mg)

-continued $m_{end}$ = 50% methanol container weight at feedend (g)

$\rho_{50\% \ methanol}$ = 50% methanol density (g/ml)

$\rho_{methanol}$ = 100% methanol density (g/ml)

$C_{methanol-end}$ = methanol concentration at feedend (g/L)

$V_{reactor-end}$ = reactor volume at feedend (L)

TABLE 10

Bioreactor cultivation process data and specific productivity ($q_P$) for Example 8. The methanol concentration was adjusted 2.22 hours after the sample was taken by an additional 50% (v/v) methanol pulse for R1 = 5.6 mL, R2 = 2.3 mL.

| Time (h) | Volume (mL) | | YDM (g/L) | | Recombinant protein concentration (mg/L) | | Specific productivity ($q_P$) (µg g$^{-1}$ h$^{-1}$) | | Methanol concentration (g/L) | |
|---|---|---|---|---|---|---|---|---|---|---|
| | R1 | R2 | R1 | R2 | R1 | R2 | R1 | R2 | R1 | R2 |
| 22.30 | 318.2 | 318.0 | 25.2 | 25.0 | 0.0 | 0.0 | | | | |
| 24.60 | | | | | | | | | 4.9* | 9.0* |
| 43.22 | 382.9 | 378.3 | 66.4 | 67.0 | 75.4 | 75.2 | 64.50 | 63.63 | 10.3 | 11.9 |
| 68.20 | 458.5 | 453.1 | 99.0 | 101.5 | 164.0 | 142.5 | 31.74 | 23.35 | 9.4 | 10.0 |
| 92.45 | 528.9 | 521.5 | 119.8 | 122.0 | 235.9 | 211.6 | 18.83 | 17.28 | 11.0 | 10.7 |
| 116.37 | 621.6 | 613.5 | 135.1 | 136.9 | 363.6 | 338.4 | 28.30 | 27.17 | 10.3 | 9.9 |
| 120.12 | 625.3 | 617.6 | 136.0 | 137.3 | 390.9 | 378.6 | 28.90 | 30.17 | 10.4 | 10.0 |

*Represents a control sample after the methanol pulse.

-continued $A_{methanol}$ = methanol addition (mg)

$F_{methanol}$ = 50% (v/v) methanol feed (mL)

$C_{methanol \ target}$ = target methanol concentration (mg/mL)

$V_{reactor}$ = reactor volumen (mL)

$F_{glucose}$ = 50% (v/v) glucose feed (mL)

$V_{sample}$ = volume of sample if applicable in the interval, else it is 0

$Y_{(\frac{x}{s})}$ = biomass yield on glucose (g/g)

d) Because of the predicted specific methanol uptake rate based on example 7d) it was possible to keep the methanol concentration at excess during the bioreactor cultivation from 1.19% to 1.5% (v/v) of methanol with only once per day at line methanol concentration measurements and feed adjustment.

e) The process and productivity data can be found in Table 10. The overall average specific productivity was 29.4 µg g$^{-1}$ h$^{-1}$. The methanol concentration at the end of the cultivation was 10.4 and 10.0 g/L (1% (v/v) methanol corresponds to 7.92 g/L) for reactor R1 and R2. The total amount of consumed methanol in phase two by reactor R1 and R2 was 25.03 g and 24.07 g. This was calculated by the following equation:

$$T_{consumed \ methanol} =$$

$$\left( \frac{(m_{start} - m_{end})}{\rho_{50\% \ methanol}} * 50\% * \rho_{methanol} \right) - (C_{methanol-end} * V_{reactor-end})$$

$T_{consumed \ methanol}$ = total consumed methanol (g)

$m_{start}$ = 50% methanol container weight at phase start (g)

Example 9: Cultivation Strategy 2—a Feed Strategy with a Separated Glucose Feed Phase and a Methanol Only Feed Phase The *P. pastoris* Δaox1Δaox2 pPM2pN21_pAOX1_HSAopt_CycTT strain was tested in a recombinant protein production scenario where first a limited glucose feed was applied to increase the biomass followed by a separated phase with a methanol pulse and feed to induce protein production.

a) The bioreactor cultivation was separated into three phases. (1) Phase one consisted of the batch phase on BSM media with a start OD$_{600}$ of 2. The inoculation was done as described in Example 7a) b). The batch phase lasted for 19.68 and 19.50 hours for reactor R3 and R4, respectively. (2) Phase two was a 50% (w/w) glucose feed at 4.8 mL/h for 25 hours to increase the biomass concentration. (3) Phase three was started with a 50% (v/v) methanol pulse to reach a target concentration of 1.5% (v/v) and a methanol feed profile calculated based on the predicted cell dry weigh and specific methanol uptake rate as described in Example 8c) for 72.7 hours. Methanol concentration was measured at line with HPLC every day as described in Example 6d) to measure the exact concentration and an additional compensation pules was added if necessary. In this phase the reactor stirrer speed was set to a constant 760 rpm and gassing to 9.5 sL/h.

b) The process and productivity data can be found in Table 11. The maximal and minimal methanol concentration throughout the cultivations ranged from 4.3 g/L to 12.55 g/L. The overall average specific productivity was 32.9 µg g$^{-1}$ h$^{-1}$. The methanol concentration at the end of the cultivation was 7.10 and 7.47 g/L for reactor R3 and R4. The amount of consumed methanol in Phase three by reactor R3 and R4 was 12.0 g and 12.6 g. This was calculated as in Example 8e). Because the biomass was constant in phase three the methanol uptake rate ($q_{methanol}$) for phase three was calculated as in the following equation.

$$q_{methanol} = \frac{T_{consumed\ methanol}}{X_{biomass-average} * t_{phase\ 3}}$$

$T_{consumed\ methanol}$ = total consumed methanol in phase 3 (mg)

$X_{biomass-average}$ = average biomass in phase 3 (g)

$t_{phase\ 3}$ = duration of phase 3 (h)

In phase three the $q_{methanol}$ for reactor R3 is 3.79 mg g$^{-1}$ h$^{-1}$ and for reactor R4 it is 3.92 mg g$^{-1}$ h$^{-1}$.

c) The total biomass in Table 11 was corrected for the sample withdraw of 12 mL and shows that the biomass was not increasing. Overall the total biomass in phase three decreased by 4.5% and 3.4% for reactor R3 and R4. Astonishingly, the culture was nonetheless producing secreted recombinant proteins. This shows that the *P. pastoris* Δaox1Δaox2 pPM2pN21_pAOX1_HSAopt_CycTT strain can efficiently produce recombinant secreted proteins even when fed only with methanol at no apparent growth. The total average amount of proteins produced in phase three with methanol as the only carbon source is 105 mg.

$T_{biomass} = V_{reactor} * CDW + \Sigma(CDW_{previous} * V_{sample})$ $T_{biomass}$ = total corrected biomass CDW = cell dry weight $V_{sample}$ = volume of sample a) This bioreactor cultivation was separated into three phases. (1) Phase one was the batch phase. For this the reactors were inoculated with the production strain *P. pastoris* Δaox1Δaox2 pPM2pN21_pAOX1_HSAopt_CycTT with a start OD$_{600}$ of 2. The inoculation was done as described in Example 7a) b). The batch phase lasted for 19.35 and 19.37 hours for reactor R1 and R2, respectively. The end of the batch phase was indicated by a dissolved oxygen peak. (2) At this point Phase two was started. Phase two consisted of a 50% (w/w) glucose feed at 4.8 mL/h for 25 hours. At the start of Phase two a 50% (v/v) methanol pulse was applied to increase methanol concentration to the target of 1.5% (v/v) and a subsequent methanol feed was started to counteract methanol consumption, evaporation and dilution by the glucose feed. (3) Phase three consisted of a methanol only feed for 72.9 hours. In this phase the reactor stirrer speed was set to a constant 760 rpm and gassing to 9.5 sL/h. Methanol concentration was measured at line with HPLC every day as described in Example 6d). An additional compensation pulse was added if necessary.

b) The methanol feed was calculated in hourly intervals as in Example 9b):

c) The process and productivity data can be found in Table 12. The maximal and minimal methanol concentration throughout the cultivation of the two repeats ranged from 6.9 g/L to 11.4 g/L. The overall average specific productivity was 45.8 µg g$^{-1}$ h$^{-1}$, the average specific productivity in phase three was 34.0 µg g$^{-1}$ h$^{-1}$. The methanol concentration at the end of the cultivation was 8.0 g/L for reactor R1 and R2. The amount of consumed methanol in phase three by reactor R1 and R2 was 14.4 g and 14.1 g. This was calculated by the

TABLE 11

Bioreactor cultivation process data and productivity ($q_P$) for Example 9.
The total biomass was corrected for 12 mL sampling as in Example 9 b).

| Phase | Time (h) | Volume (mL) R3 | Volume (mL) R4 | YDM (g/L) R3 | YDM (g/L) R4 | Total Biomass (g) R3 | Total Biomass (g) R4 | Recombinant protein concentration (mg/L) R3 | Recombinant protein concentration (mg/L) R4 | Specific productivity ($q_P$) (µg g$^{-1}$ h$^{-1}$) R3 | Specific productivity ($q_P$) (µg g$^{-1}$ h$^{-1}$) R4 | Methanol concentration (g/L) R3 | Methanol concentration (g/L) R4 |
|---|---|---|---|---|---|---|---|---|---|---|---|---|---|
| 1 | 20.13 | 317.9 | 318.5 | 25.5 | 25.5 | 8.1 | 8.1 | | | | | | |
| 2 | 29.92 | 366.5 | 368.0 | 67.2 | 67.0 | 24.9 | 24.9 | 0.0 | 0.0 | 0.0 | 0.0 | | |
|  | 45.02 | 445.8 | 447.8 | 108.0 | 107.7 | 49.2 | 49.3 | 0.0 | 0.0 | 0.0 | 0.0 | | |
| 3 | 47.08 | | | | | | | | | | | 12.1* | 12.5* |
|  | 53.00 | 444.2 | 446.1 | 104.4 | 103.7 | 48.8 | 48.6 | 46.1 | 45.7 | 35.56 | 35.6 | | |
|  | 69.58 | 432.2 | 435.7 | 103.3 | 102.9 | 48.3 | 48.5 | 106.7 | 107.8 | 22.51 | 23.3 | 4.3 | 5.9 |
|  | 93.93 | 434.7 | 437.0 | 98.5 | 99.1 | 47.7 | 48.2 | 244.0 | 251.0 | 38.67 | 39.9 | 6.6 | 7.4 |
|  | 118.12 | 434.4 | 435.9 | 94.2 | 95.3 | 47.0 | 47.6 | 350.9 | 350.2 | 33.07 | 30.0 | 7.1 | 7.5 |

*Represents a control sample after the methanol pulse.

Example 10: Cultivation Strategy 3—a Feed Strategy with a Glucose/Methanol Co-Feed Phase and a Separated Methanol Only Feed Phase The *P. pastoris* Δaox1Δaox2 pPM2pN21_pAOX1_HSAopt_CycTT strain was tested in a recombinant protein production scenario where after the batch phase a limited glucose feed and an additional methanol pulse and feed was applied to achieve a biomass increase and recombinant protein production simultaneously. After the desired biomass was reached the glucose feed was stopped but the methanol feed continued for the rest of the cultivation.

equation as shown in Example 9b). Because the biomass was constant in phase three the methanol uptake rate was calculated ($q_{methanol}$) for phase three as shown in Example 9b). In phase three the $q_{methanol}$ for reactor R1 was 4.61 mg g$^{-1}$ h$^{-1}$ and for reactor R2 it was 4.54 mg g$^{-1}$ h$^{-1}$. Overall the biomass decreased by 5.7% and 5.5% for reactor R1 and R2 in phase three. Again, this shows that with the *P. pastoris* Δaox1Δaox2 strain production at no apparent growth is possible. The average total amount of recombinant protein produced in phase three with methanol as the only carbon source is 106 mg which is similar to the 105 mg of recombinant protein produced in Example 9, phase three. This is also illustrated by the similar specific productivity in phase three from Example 9 at 32.9 µg g$^{-1}$ h$^{-1}$ and at 34.0 µg g$^{-1}$ h$^{-1}$ in this example. In conclusion the productivity in phase three (methanol only feed phase) did not depend whether the cultures were induced in phase two (glucose feed phase) or not. Because recombinant protein production is independent of growth the methanol only feed strategy has several advantages when used with the *P. pastoris* Δaox1Δaox2 strain. In a bioreactor cultivation without a methanol only feed phase as in Example 8 the process is constrained by the maximal reactor volume and the yeast dry mass concentration. After a certain time this constraints stop the cultivation process either by reaching the maximal volume or maximal desired biomass concentration. By using a methanol feed phase in combination with the *P. pastoris* Δaox1Δaox2 as in Example 9 the cultivation time is no longer limited by the biomass concentration or volume as the biomass is not increasing and the volume increase is negligible. As a consequence cultures at high biomass concentrations can be kept in the bioreactor for longer periods of time without reaching these constraints and allow for longer production phases that increase the concentration of the protein of interest. A methanol only feed phase is also applied when using the methanol utilization slow *P. pastoris* Δaox1 strain as shown in the following Example 12 but these advantages are not present there because *P. pastoris* Δaox1 is continuously growing on a methanol only feed and therefore exhibits the same constraints as discussed. Restricting the *P. pastoris* Δaox1 to the same methanol feed rate as the *P. pastoris* Δaox1Δaox2 results in productivity loss. Further process related improvements of the *P. pastoris* Δaox1Δaox2 strain are discussed in Example 12.

a) As in Example 10a), this bioreactor cultivation was separated into three phases. (1) Phase one was the batch phase. For this the reactors were inoculated with the production strain *P. pastoris* Δaox1Δaox2 pPM2pZ30_pAOX1_αMF-vHH_CycTT with a start OD$_{600}$ of 2 as described in Example 7a) b). The batch phase lasted for 18.79 and 19.33 hours for reactor R1 and R2, respectively. The end of the batch phase was indicated by a dissolved oxygen peak. (2) At this point Phase two was started. Phase two consisted of a 50% (w/w) glucose feed at 4.8 mL/h for 33.9 hours to increase the biomass even higher than in Example 10. At the start of Phase two a 50% (v/v) methanol pulse was added to increase the methanol concentration to the target value of 1.5% (v/v) and a subsequent methanol feed was started to counteract methanol consumption, evaporation and dilution by the glucose feed. (3) Phase three consisted of a methanol only feed for 63.9 hours. The stirrer speed was set to a constant 760 rpm and gassing to 9.5 sL/h. Methanol concentration was measured at line with HPLC every day as described in Example 6d). An additional compensation pulse was added if necessary.

b) The methanol feed was calculated as described in Example 9b) The process and productivity data can be found in Table 13. The maximal and minimal methanol concentration throughout the cultivation of the two repeats ranged from 8.7 g/L (R1) to 11.3 g/L (R1). The overall average specific productivity was 118.0 µg g$^{-1}$ h$^{-1}$ and in phase three 88.2 µg g$^{-1}$ h$^{-1}$. The methanol concentration at the end of the cultivation was 10.5 and 10.8 g/L for reactor R1 and R2. The amount of consumed methanol by reactor R1 and R2 was 26.6 g and 26.0 g. This was calculated by the following equation as shown in Example 8e). This amount is higher as in Example 10 due to the higher biomass concentration,

TABLE 12

Bioreactor cultivation process data and specific productivity (q$_P$) for Example 10. The total biomass was corrected for 12 mL sampling as in Example 9 b).

| Phase | Time (h) | Volume (mL) | | YDM (g/L) | | Total Biomass (g) | | Recombinant protein concentration (mg/L) | | Specific productivity (q$_P$) (µg g$^{-1}$ h$^{-1}$) | | Methanol concentration (g/L) | |
|---|---|---|---|---|---|---|---|---|---|---|---|---|---|
| | | R1 | R2 | R1 | R2 | R1 | R2 | R1 | R2 | R1 | R2 | R1 | R2 |
| 1 | 20.13 | 318.0 | 317.7 | 25.0 | 24.9 | 7.9 | 7.9 | 0.0 | 0.0 | 0.0 | 0.0 | | |
| 2 | 21.87 | | | | | | | | | | | 11.0* | 11.4* |
| | 29.92 | 374.5 | 374.2 | 65.3 | 64.6 | 24.7 | 24.5 | 47.7 | 51.9 | 88.6 | 97.3 | | |
| | 45.02 | 464.2 | 461.8 | 104.0 | 103.1 | 49.4 | 48.7 | 203.0 | 243.4 | 87.1 | 108.6 | 7.2 | 6.9 |
| 3³ | 53.00 | 462.7 | 460.9 | 99.7 | 99.5 | 48.4 | 48.2 | 246.1 | 265.5 | 38.6 | 21.5 | | |
| | 69.58 | 457.4 | 455.6 | 95.9 | 96.3 | 47.4 | 47.4 | 357.3 | 371.8 | 47.3 | 44.9 | 7.9 | 7.5 |
| | 93.93 | 459.8 | 458.3 | 91.9 | 91.2 | 46.9 | 46.5 | 459.5 | 515.0 | 33.9 | 47.4 | 8.2 | 7.1 |
| | 118.12 | 462.0 | 460.8 | 88.3 | 87.3 | 46.6 | 46.0 | 494.8 | 568.2 | 14.8 | 21.6 | 8.0 | 8.0 |

*Represents a control sample after the methanol pulse.

Example 11: Cultivation Strategy 3—a Feed Strategy with a Glucose/Methanol Co-Feed Phase and a Separated Methanol Only Feed Phase Applied to *P. pastoris* ΔAox1ΔAox2 Secreting VHH To check secreted recombinant protein production with another secreted protein the bioreactor cultivation described in Example 10a) was repeated with the strain *P. pastoris* Δaox1Δaox2 pPM2pZ30_pAOX1_αMF-vHH_CycTT.

but still significantly (5-times) lower than in a Mut$^S$ strain (as described in Example 12). Because the biomass was constant in phase three the methanol uptake rate (q$_{methanol}$) was calculated for phase three as shown in Example 9b). In phase three the q$_{methanol}$ for reactor R1 was 4.75 mg g$^{-1}$ h$^{-1}$ and for reactor R2 it was 4.68 mg g$^{-1}$ h$^{-1}$.

c) Overall the biomass decreased by 4.4% and 4.9% for reactor R1 and R2 in phase three as in previous Examples. The data in Table 13 clearly show that the *P. pastoris* Δaox1Δaox2 strains can produce secreted recombinant proteins even in gram per liter amounts. In the methanol only feed phase the vHH concentration increased by 815.5 mg/L, meaning that an average total of 323.1 mg of antibody fragment was produced using methanol as the only carbon source.

37.1 mg g$^{-1}$ h$^{-1}$ and 37.6 mg g$^{-1}$ h$^{-1}$ for reactor R2. The q$_{methanol}$ in phase four facilitates an unwanted biomass increase. 53.2% (R1) and 52.4% (R2) of the total biomass at cultivation finish are generated during phase four growth on methanol.

TABLE 13

Bioreactor cultivation process data and productivity (q$_P$) for Example 11. The total biomass was corrected for 12 mL sampling as in Example 9 b)

| Phase | Time (h) | Volume (mL) | | YDM (g/L) | | Total biomass (g) | | Recombinant protein concentration (mg/L) | | Specific productivity (q$_P$) (µg g$^{-1}$ h$^{-1}$) | | Methanol concentration (g/L) | |
|---|---|---|---|---|---|---|---|---|---|---|---|---|---|
| | | R1 | R2 | R1 | R2 | R1 | R2 | R1 | R2 | R1 | R2 | R1 | R2 |
| 1 | 20.00 | 316.7 | 316.7 | 25.1 | 25.2 | 7.9 | 8.0 | 0.0 | 0.0 | 0.0 | 0.0 | | |
| 2 | 21.42 | | | | | | | | | | | 10.9* | 10.9* |
| | 28.22 | 358.4 | 358.7 | 60.2 | 60.1 | 21.9 | 21.9 | 58.2 | 59.7 | 137.8 | 141.5 | | |
| | 44.83 | 449.9 | 449.8 | 105.8 | 105.2 | 48.6 | 48.3 | 494.4 | 464.5 | 222.8 | 208.3 | 7.8 | 7.9 |
| | 53.58 | 499.8 | 499.4 | 124.1 | 122.9 | 64.3 | 63.7 | 776.8 | 854.1 | 176.0 | 246.2 | | |
| 3 | 68.83 | 502.5 | 503.3 | 115.5 | 116.3 | 61.8 | 62.3 | 1156.0 | 1030.0 | 142.5 | 72.2 | 8.7 | 9.5 |
| | 92.00 | 511.3 | 511.1 | 110.8 | 109.4 | 61.8 | 61.1 | 1337.2 | 1374.0 | 55.8 | 97.5 | 11.3 | 9.8 |
| | 117.92 | 525.0 | 527.3 | 104.7 | 102.7 | 61.5 | 60.6 | 1623.2 | 1638.6 | 85.7 | 85.8 | 10.5 | 10.8 |

*Represents a control sample after the methano pulse.

Example 11.1: Process Parameters Obtained with *P. pastoris* ΔAox1ΔAox2 (Mut$^-$) Strains Compared to a Methanol Utilization Slow *P. pastoris* ΔAox1 (Mut$^S$) Cultivated with an Established Bioreactor Cultivation Protocol For comparison the *P. pastoris* Δaox1 pPM2pN21_pAOX1_HSAopt_CycTT was cultivated with an established cultivation protocol for the Mut$^S$ phenotype (Potvin, Ahmad, & Zhang, 2012).

a) This bioreactor cultivation was separated into four phases. (1) Phase one was the batch phase. For this the reactors were inoculated with the production strain *P. pastoris* Δaox1 pPM2pN21_pAOX1_HSAopt_CycTT with a start OD$_{600}$ of 2 as described in Example 7a) b). The batch phase lasted for 20.17 and 20.30 hours for reactors R1 and R2, respectively. The end of the batch phase was indicated by a dissolved oxygen peak. (2) Phase two is a linearly increasing (y=0.225x+1.95) 60% glycerol feed for 8 hours. (3) Phase three was a co-feed phase with a linearly decreasing (y=3.75−0.111x) 60% glycerol feed and a linearly increasing (y=0.028x+0.6) 100% methanol feed for 18 hours (4) Phase four is a methanol only feed phase with a linearly increasing 100% methanol feed (y=0.028x+1.10) for 72 hours. The total run time was 119.25 hours.

b) The glycerol and methanol feed was gravimetrically controlled based on the equations in a) by the DASGIP control software (Eppendorf AG, Germany)

c) The process and productivity data can be found in Table 13.1. The overall average specific productivity from phase three to four (the production phases) was 61.7 µg g$^{-1}$ h$^{-1}$. The average total amount of consumed methanol was 165.8 g over the whole cultivation period and 150.6 g in phase four (methanol only feed phase). The residual methanol concentration in the culture broth was considered to be zero as this was a methanol limited cultivation. Phase four in this example corresponds to phase three in Examples 9, 10 and 11. Based on the average biomass in phase four the methanol uptake rate (q$_{methanol}$) as shown in Example 9b) was calculated. The q$_{methanol}$ in phase four for reactor R1 is d) The comparison of strain related process parameters are depicted in table Table 13.2 and an overview of the specific methanol uptake rates and feed rates from the presented examples can be found in Table 13.3. By using the *P. pastoris* Δaox1Δaox2 Mut$^-$ for recombinant protein production several of the key processes parameters improved considerably compared to a process with the *P. pastoris* Δaox1. The heat of reaction is reduced substantially by more than 80% leading to a reduced need for cooling. The specific oxygen uptake rate and oxygen transfer rate is reduced by more than 80% leading to a reduced need for mixing and aeration, reducing the flow rate of aeration as well as the need to supply pure oxygen to the bioreactor vessels. The lower specific methanol uptake rate reduces the amount of methanol needed in a cultivation. Methanol is toxic and flammable.

Use of the Mut$^-$ strains represents a technical and safety improvement as it reduces the quantities of methanol that need to be handled and stored in a production facility. Another advantage is the lower sensitivity of the *P. pastoris* Δaox1Δaox2 to high methanol concentrations. This is confirmed by cell viability data of the strain *P. pastoris* Δaox1Δaox2 in Example 10 and *P. pastoris* Δaox1 in this example. In Example 10 the viability of the Mut$^-$ cells in reactors R1 and R2 at the end of the process was 99.8% and 99.7%. In contrast the cell viability of the Mut$^S$ cells in reactors R1 and R2 in this example was 95.9% and 96.5%. The lower sensitivity and higher viability of the *P. pastoris* Δaox1Δaox2 strain has an effect on the purity of the recombinant produced secreted protein. Lysed cells release proteases that degrade the protein of interest and add unwanted soluble protein in the supernatant, both effects lead to lower purity and loss of the protein of interest in the supernatant. The purity of the *P. pastoris* Δaox1 in this example was 72% and 77% for reactors R1 and R2, in comparison the purity of the *P. pastoris* Δaox1Δaox2 in Example 10 was 85% for both reactors R1 and R2.

TABLE 13.1

Bioreactor cultivation process data and specific productivity ($q_{product}$) for Example 11.1.

| Phase | Time (h) | Volume (mL) R1 | Volume (mL) R2 | YDM (g/L) R1 | YDM (g/L) R2 | Total biomass (g) R1 | Total biomass (g) R2 | Recombinant protein concentration (mg/L) R1 | Recombinant protein concentration (mg/L) R2 | Specific productivity ($q_P$) (pg g$^{-1}$ h$^{-1}$) R1 | Specific productivity ($q_P$) (pg g$^{-1}$ h$^{-1}$) R2 |
|---|---|---|---|---|---|---|---|---|---|---|---|
| 1 | 20.3 | 318.1 | 316.5 | 26.6 | 25.9 | 8.5 | 8.2 | | | | |
| 2 | 28.5 | 330.4 | 328.6 | 51.6 | 51.4 | 17.0 | 16.9 | 0.0 | 0.0 | 0.00 | 0.0 |
| 3 | 47.1 | 392.5 | 390.3 | 99.6 | 100.4 | 39.1 | 39.2 | 129.6 | 112.9 | 65.57 | 56.6 |
| 4 | 69.8 | 428.4 | 426.5 | 111.5 | 111.4 | 47.7 | 47.5 | 260.9 | 306.7 | 36.89 | 53.9 |
|   | 92.9 | 487.8 | 487.3 | 126.9 | 124.6 | 61.9 | 60.7 | 548.1 | 534.7 | 67.14 | 56.7 |
|   | 119.3 | 581.9 | 584.9 | 143.7 | 140.8 | 83.6 | 82.3 | 893.9 | 927.9 | 61.55 | 72.7 |

TABLE 13.2

Comparison of key bioreactor cultivation parameters overall and on the methanol only feed phases of P. pastoris Δaox1Δaox2 pPM2pN21_pAOX1_HSAopt_CycTT in Example 10 and P. pastoris Δaox1 pPM2pN21_pAOX1_HSAopt_CycTT in Example 11.1.

| | | P. pastoris Δaox1Δaox2 pPM2pN21_ pAOX1_HSAopt_CycTT Example 10 | P. pastoris Δaox1 pPM2pN21_ pAOX1_HSAopt_CycTT Example 11.1 | Change |
|---|---|---|---|---|
| Overall | HSA concentration (mg/L) | 531 | 911 | −42% |
| | $q_{product}$ (μg g$^{-1}$ h$^{-1}$) | 46 | 62 | −26% |
| Methanol only feed phase: Example 10- Phase three; Example 11.1 - Phase four | Duration (h) | 73.1 | 72.2 | |
| | Heat production rate (W/L) | 3 | 19.2 | −84% |
| | OTR (mM/h) | 23 | 149 | −85% |
| | Heat of reaction (kJ) | 359 | 2286 | −84% |
| | Integrated OTR (MA 120 min) | | | |
| | Heat of combustion (kJ) | 324 | 2468 | −87% |
| | qO2 (mmol g$^{-1}$ h$^{-1}$) | | | −81% |
| | $q_{methanol}$ (mg g$^{-1}$ h$^{-1}$) | 4.6 | 37.4 | −88% |
| | Protein (mg) | 106 | 250 | −58% |
| | Protein/methanol (mg g$^{-1}$) | 7 | 1.7 | +311% |
| | Protein/O$_2$ (mg mol$^{-1}$) | 135 | 51 | +164% |
| | Protein/Heat of reaction (mg kJ$^{-1}$) | 0.30 | 0.11 | +172% |

TABLE 13.3

Specific methanol uptake rates and methanol feed rates based on average cell dry weight in the methanol only feed phase.

| | Example 7 R1 | Example 7 R2 | Example 9 R3 | Example 9 R4 | Example 10 R1 | Example 10 R2 | Example 11 R1 | Example 11 R2 | Example 11.1 R1 | Example 11.1 R2 |
|---|---|---|---|---|---|---|---|---|---|---|
| Reactor | | | | | | | | | | |
| $q_{methanol}$ (mg g$^{-1}$ h$^{-1}$) | 4.92 | 5.22 | 3.79 | 3.92 | 4.61 | 4.54 | 4.75 | 4.68 | 37.1* | 37.1* |
| Feed rate (mg g$^{-1}$ h$^{-1}$) | NA | NA | 4.79 | 4.89 | 5.80 | 5.73 | 5.78 | 7.71 | 37.1 | 37.6 |

*As Example 11.1 has a limited methanol feed the $q_{methanol}$ and feed rate are considered equal.

Example 12: Generation of Methanol Utilization Negative and Alcohol Dehydrogenase Defective Strains The methanol consumption of the *P. pastoris* Mut⁻ strain observed in Example 7 was unexpected and new. Based on this knowledge the hypothesis was formed that alcohol dehydrogenases might be responsible for this characteristic. To test the effect of alcohol dehydrogenases on methanol consumption in the *P. pastoris* Δaox1Δaox2 two potential alcohol dehydrogenases were selected ADH2: PP7435_Chr2-0821 and ADH900: PP7435 Chr2-0990 for deletion. Three strains were created, (1) an ADH2 defective strain, (2) an ADH900 defective strain and (3) a double deletion ADH2 & ADH900 strain by exchanging the coding region of the gene with an antibiotic resistance. Effectively the strains (1) *P. pastoris* Δaox1Δaox2 adh2Δ::HphR, (2) *P. pastoris* Δaox1Δaox2 Adh900Δ::KanMX and (3) *P. pastoris* Δaox1Δaox2 adh2Δ::HphR adh900Δ::KanMX were created.

a) *P. pastoris* Δaox1Δaox2 was made electrocompetent as described in Example 1a). For generating the ADH2 deletions the spilt marker approach was used described in example 1b). The electrocompetent cells were transformed with 500 ng of Adh2 split marker cassette 1 and 500 ng Adh2 split marker cassette 2 as described in Example 1d). The cassette sequences can be found in Table 14. The transformants were selected on YPD plates with 200 μg/mL Hygromycin. One clone was selected based on PCR amplification and sequencing of the PCR amplicon. The successful substitution of the ADH2 coding region with the antibiotic marker was verified by PCR amplification with the primers Adh2_KO_ctrl_fwd & Adh2_KO_ctrl_rev (Table 15) and sequencing of the PCR amplicon (Microsynth AG, Swiss). The generated strain is called (1) *P. pastoris* Δaox1Δaox2 adh2Δ::HphR.

b) The *P. pastoris* Δaox1Δaox2 strain was made electrocompetent as described in Example 1a). The electrocompetent cells were transformed with 500 ng of Adh900 split marker cassette 1 and 500 ng Adh900 split marker cassette 2 as described in Example 1d). The cassette sequences can be found in Table 14. The transformants were selected on YPD plates with 500 μg/mL Geneticin. One clone was selected based on PCR amplification and sequencing of the PCR amplicon. The successful substitution of the ADH900 coding region with antibiotic marker was verified by PCR amplification with the primers Adhl1_KO_Ctrl_fwd & Adhl1_KO_Ctrl_rev (Table 15) and sequencing of the PCR amplicon (Microsynth AG, Swiss). The generated strain is called (2) *P. pastoris* Δaox1Δaox2 Adh900Δ::KanMX.

c) The *P. pastoris* Δaox1Δaox2 adh2Δ::HphR strain was made electrocompetent as described in Example 1a) apart from that 200 μg/mL Hygromycin were added to the main culture medium. The electrocompetent cells were transformed with 500 ng of Adh900 split marker cassette 1 and 500 ng Adh900 split marker cassette 2 as described in Example 1d). The cassette sequences can be found in Table 14. The transformants were selected on YPD plates with 200 μg/mL Hygromycin and 500 μg/mL Geneticin. One clone was selected based on PCR amplification and sequencing of the PCR amplicon. The successful substitution of the ADH900 coding region with the antibiotic marker was verified by PCR amplification with the primers Adhl1_KO_Ctrl_fwd & Adhl1_KO_Ctrl_rev (Table 15) and sequencing of the PCR amplicon (Microsynth AG, Swiss). The generated strain is called (3) *P. pastoris* Δaox1Δaox2 Adh2Δ::Hph R Adh900Δ::KanMX.

d) Genomic DNA for PCR amplifications was isolated with the Wizard® Genomic DNA Purification Kit (Promega Corporation, USA) as per manufacturer's recommendations. The PCR amplification reactions were done with the Q5 polymerase (New England Biolabs, Inc., USA) as per manufacturer's recommendations.

TABLE 14

Split marker cassette DNA sequence used for generating the Adh2 and Adh900 deletion strains.

| DNA fragment | DNA sequence 5' to 3' |
| --- | --- |
| Adh2 split marker cassette 1 | (SEQ ID NO: 72)<br>CGTATCTACCGATGATGGCACCAGCCTCCATCTGTTCGTAGACCTTAGCAAGTTCAGACA<br>GACCGATAATCTTGATAGGAGCCTTGACCAAACCTCTGGTGAACAAGTCGATGGCCTCGG<br>CACTGTCCTCTCTGTTTCCAACGTAAGATCCCTTGATCTCGATGGACTTCAGAACGTGCC<br>AGAAAACGTCAGAGTTGACAACGGCACCAGATGGCAGACCAACCAAAACAACCTTACCCA<br>AAGTTCTAACGTATTGGACAGATTGGTTGATAGCATGTGGGGAAACGGAGACGTTAATAA<br>CACCGTGTGGACCACCGTTGGTGAGCTTTTGGACTTCAGCAACGACGTCCTTAGTCTTAG<br>TGAAGTCGACGAAGACCTCAGCACCCAAGGACTTGACAAATTCACCCTTGTCGGCACCAC<br>CATCAATACCCAAAACTCTCAAACCCAGAGCCTTGGCGTATTGAACGGCAAGAGAACCCA<br>GTCCTCCACCAGCACCAGAAATGGCAACCCATTGGCCAATACGCAAGTCAGCGGTCTTAA<br>GAGCCTTGTAAACGGTGATACCAGCACACAGAATTGGGGCAACTTCAGCCAAGTCAGCCT<br>CCTTTGGAATTCTGGCGGCTTGGGTGGCATCAGCAGTAGCATACTGCTGGAAAGATCCGT<br>CGTGGGTGAAACCAGACAGGTCAGCCTTGGCACAACTGGATTCAGCACCTTGGATACAGT<br>ACTCACAGTTCAAACAAGAACCGTTCAACCATTTGATACCAGCGTAGTCACCGATAGTGG<br>ATCTGATATCACCTAATAACTTCGTATAGCATACATTATACGAAGTTATATTAAGGGTTC<br>TCGAATGGTACCTTGCTCACATGTTGATCTCCAGCTTGCAAATTAAAGCCTTCAGCGCTC<br>CCAAAACCTTCTCAAGCAAGGTTTTCAGTATAATGTTACATGCGTACACGCGTCTGTACA<br>GAAAAAAAAGAAAAATTTGAAATATAAATAACGTTCTTAATACTAACATAACTATAAAAA<br>AATAAATAGGGACCTAGACTTCAGGTTGTCTAACTCCTTCCTTTTCGGTTAGAGCGGATG<br>TGGGGGAGGGCGTGAATGTAAGCGTGACATAACTAATTACATGATATCGACAAAGGAAA<br>AGGGGGACGGATCTCCGAGGTAAAATAGAACAACTACAATATAAAAAAACTATACAAATG<br>ACAAGTTCTTGAAAACAAGAATCTTTTTATTGTCAGTACTGATTATTCCTTTGCCCTCGG<br>ACGAGTGCTGGGGCGTCGGTTTCCACTATCGGCGAGTACTTCTACACAGCCATCGGTCCA<br>GACGGCCGCGCTTCTGCGGGCGATTTGTGTACGCCCGACAGTCCCGGCTCCGGATCGGAC<br>GATTGCGTCGCATCGACCCTGCGCCCAAGCTGCATCATCGAAATTGCCGTCAACCAAGCT<br>CTGATAGAGTTGGTCAAGACCAATGCGGAGCATATACGCCCGGAGCCGCGGCGATCCTGC<br>AAGCTCCGGATGCCTCCGCTCGAAGTAGCGCGTCTGCTGCTCCATACAAGCCAACCACGG |

TABLE 14-continued

Split marker cassette DNA sequence used for generating the Adh2 and Adh900 deletion strains.

| DNA fragment | DNA sequence 5' to 3' |
| --- | --- |
| | CCTCCAGAAGAAGATGTTGGCGACCTCGTATTGGGAATCCCCGAACATCGCCTCGCTCCA<br>GTCAATGACCGCTGTTATGCGGCCATTGTCCGTCAGGACATTGTTGGAGCCGAAATCCGC<br>GTGCACGAGGTGCCGGACTTCGGGGCAGTCCTCGGCCCAAAGCATCAGCTCATCGAGAGC<br>CTGCGCGACGGACGCACTGACGGTGTCGTCCATCACAGTTTGCCAGTGATACACATGGGG<br>ATCAGCAATCGCGCATATGAAATCACGCCATGTAGTGTATTGACCGATTCCTTGCGGTCC<br>GAATGGGCCGAACCCGCTCGTCTGGCTAAGATCGGCCGCAGCGATCGCATCCATGGCCTC<br>CGCGACCGGCTGCAGAACAGCGGGCAGTTCGGTTTCAGGCAGGTCT |
| Adh2<br>split marker<br>cassette 2 | (SEQ ID NO: 73)<br>AGATGTTGGCGACCTCGTATTGGGAATCCCCGAACATCGCCTCGCTCCAGTCAATGACCG<br>CTGTTATGCGGCCATTGTCCGTCAGGACATTGTTGGAGCCGAAATCCGCGTGCACGAGGT<br>GCCGGACTTCGGGGCAGTCCTCGGCCCAAAGCATCAGCTCATCGAGAGCCTGCGCGACGG<br>ACGCACTGACGGTGTCGTCCATCACAGTTTGCCAGTGATACACATGGGGATCAGCAATCG<br>CGCATATGAAATCACGCCATGTAGTGTATTGACCGATTCCTTGCGGTCCGAATGGGCCGA<br>ACCCGCTCGTCTGGCTAAGATCGGCCGCAGCGATCGCATCCATGGCCTCCGCGACCGGCT<br>GCAGAACAGCGGGCAGTTCGGTTTCAGGCAGGTCTTGCAACGTGACACCCTGTGCACGGC<br>GGGAGATGCAATAGGTCAGGCTCTCGCTGAATTCCCCAATGTCAAGCACTTCCGGAATCG<br>GGAGCGCGGCCGATGCAAAGTGCCGATAAACATAACGATCTTTGTAGAAACCATCGGCGC<br>AGCTATTTACCCGCAGGACATATCCACGCCCTCCTACATCGAAGCTGAAAGCACGAGATT<br>CTTCGCCCTCCGAGAGCTGCATCAGGTCGGAGACGCTGTCGAACTTTTCGATCAGAAACT<br>TCTCGACAGACGTCGCGGTGAGTTCAGGCTTTTTACCCATGGTTTAGTTCCTCACCTTGT<br>CGTATTATACTATGCCGATATACTATGCCGATGATTAATTGTCAACACCGCCCTTAGATT<br>AGATTGCTATGCTTTCTTTCTAATGAGCAAGAAGTAAAAAAAGTTGTAATAGAACAAGAA<br>AAATGAAACTGAAACTTGAGAAATTGAAGACCGTTTATTAACTTAAATATCAATGGGAGG<br>TCATCGAAAGAGAAAAAAATCAAAAAAAAAAAATTTTCAAGAAAAAGAAACGTGATAAAA<br>ATTTTTATTGCCTTTTTAGACGAAGAAAAAGAAACGAGGCGGTCTCTTTTTTCTTTTCCA<br>AACCTTTAGTACGGGTAATTAACGACACCCTAGAGGAAGAAAGAGGGGAAATTTAGTATG<br>CTGTGCTTGGGGGTTTTGNAAATGGTACGGCGATGCGCGGAATCCGAGAAAATCTGGAAG<br>AGTAAAAAAGGAGTAGAAACATTTTGAAGCTATGGTGTGTGGTACCGATCTAGACCTAAT<br>AACTTCGTATAGCATACATTATACGAAGTTATATTAAGGGTTGTCGACCTGCAGCGTACG<br>GCACGAATTCGCACCCCGGAGAGCGCTCACCCCCGTTTTCAAACAGCGGGGGGAGCACAA<br>AATGTTGAAAACTACACAGATCTTTTCGGACACCGGTCGCTTTATGTAGTCGACATGCAG<br>ATTCTCCCAAATGGAAAACGAGATTGGACAATTTGTGGAGTTGGAAAGGGGGTGGGAAT<br>CAACGAAATTAGCAGATTCATGGGCAATTGGCAGGACTGGGCAGAAGGGGTGAGAATTGC<br>AATCGAATGGAACAGGCACTCCCGTTGCGAAATCAAAAAAGTCTCGCTATCTGAACTGAT<br>TTTTTTTAAGCAGCAACTTACGGTCAATACATCTCCGATGGAGGAATTTTTCACCCCTCG<br>CTAACTAGATGGGCCCCTTCTAAGAAATTTGGGTTTAAGGTTGGGCAGTCAGTCAGTGCA<br>CCAATGCTAACTGCCATTTGTCCAAAGAGGGGTGCAAGGATGAGGGACCGTTGAGAATAA<br>GATTTGGGGTGTTAATCGGTGATACTGATTTGTCAAAGAGTGGGGAGGACTGCTGGGCAT<br>TGTTCACCCCCCTAGTTGTTAGAGTTCGATAGCCGGCCGAATCACCCCCCTCTTCTTACA<br>TAATCATTGTCACTATGTGGGGTCTCTACAGTCTCACCCTGCGATCCGGGACGACGCCGC<br>GAAATTAGGGGGCAAGTCTCCTCCGGGCATGCAATATTGGTAACAGGATCAATTGATGCG<br>AGAAAAGTTGGAGGGGGTGTAAAATTCAAGCCCACAAAGTCACACCCTTATGCCTGTAGA<br>GGGGCAATCGGAGAGCAGCCATGGGGTGT |
| Adh900<br>split marker<br>cassette 1 | (SEQ ID NO: 74)<br>CACTCCAGTTGGGCCATTACCGAACATTTTGCCATTGTAGGCGATTAGTAAGTATTAACA<br>AGACAGCTGACTATACGTTTATTCTCAAACAATATTTCCCTTTTTGGTTTTGACCTCGCT<br>TTAATCAATTTTTCAGACCTGATCCCACCTACTTTTCTTCGGCCTCAACTTCAATCTGAC<br>TCTTCTCTCTCAATTGGTACCAACCAGCCAGAAAATGTCCTTCCGTTACTTGAAACGGCA<br>TTTCTCTACAGCTACAAACGCAATTGCTCTCCTTAGCAGACCTGAATTCAAAATAGGTCG<br>AATTGTGGACGTCGTGAAACATCCAAATGCAGACAAACTTTATGTCTCGTCGATTTCTGT<br>GGGAAACAATTATGCCTCGGGTACATCCAACACCCTAACCGTTTGCAGCGGCTTGGTGGA<br>CTACTTTTCAGTTCCCGAATTGCTTCAGCGACGGGTCGTTGTGGTCACAAACCTCAAGCC<br>ATCGAAGATGAGAGGTGTAACATCGGAGGCAATGCTTTTGGCAGGGGAAAAGTCGGGGAA<br>AGTGGAATTGGTCGAGCCGCCAATGTCCGGGAGAGAGGGCGAATCACTCCACTTCGAAGG<br>TGTAGAAATTACATCAGAGGAGAGCGCCAATCAATTGCATTTGCCTGCTAAGCGATTGAA<br>GAAGTCAGAGTGGAGTCAACTGGCGGAAGGTCTACAGACAAATGACCAGCGTGAAGTGGT<br>CTTCCACAGCCAAATTGGCTCCAAACGAATTTACGCTTTAGTAGGAGCGAGTACTGAAAA<br>ATGCACGTTAGCGACTCTTGCGCAGGCCGTCGTACGATAAGGGCAATATGGTTGAGAACG<br>TTCCTCACCCAAATAAAATCATCGTACGCTGCAGGTCGACAACCCTTAATATAACTTCGT<br>ATAATGTATGCTATACGAAGTTATTAGGTCTAGATCGGTACCGACATGGAGGCCCAGAAT<br>ACCCTCCTTGACAGTCTTGACGTGCGCAGCTCAGGGGCATGATGTGACTGTCGCCCGTAC<br>ATTTAGCCCATACATCCCCATGTATAATCATTTGCATCCATCATTTTGATGGCCGCACG<br>GCGCGAAGCAAAAATTACGGCTCCTCGCTGCAGACCTGCGAGCAGGGAAACGCTCCCCTC<br>ACAGACGCGTTGAATTGTCCCCACGCCGCGCCCTGTAGAGAAATATAAAAGGTTAGGAT<br>TTGCCACTGAGGTTCTTCTTTCATATACTTCCTTTTAAAATCTTGCTAGGATACAGTTCT<br>CACATCACATCCGAACATAAACAACCATGGGTAAGGAAAAGACTCACGTTTCGAGGCCGC<br>GATTAAATTCCAACATGGATGCTGATTTATATGGGTATAAATGGGCTCGCGATAATGTCG<br>GGCAATCAGGTCGCGACAATCTATCGATTGTATGGGAAGCCCGATGCGCCAGAGTTGTTTC<br>TGAAACATGGCAAAGGTAGCGTTGCCAATGATGTTACAGATGAGATGGTCAGACTAAACT<br>GGCTGACGGAATTTATGCCTCTTCCGACCATCAAGCATTTTATCCGTACTCCTGATGATG<br>CATGGTTACTCACCACTGCGATCCCCGGCAAAACAGCATTCCAGGTATTAGAAGAATATC<br>CTGATTCAGGTGAAAATATTGTTGATGCGCTGGCAGTGTTCCTGCGCCGGTTGCATTCGA<br>TTCCTGTTTGTAATTGTCCTTTTAACAGCGATCGCGTATTTCGTCTCGCTCAGGCGCAAT |

TABLE 14-continued

Split marker cassette DNA sequence used for generating the Adh2 and Adh900 deletion strains.

| DNA fragment | DNA sequence 5' to 3' |
|---|---|
| | CACGAATGAATAACGGTTTGGTTGATGCGAGTGATTTTGATGACGAGCGTAATGGCTGGC<br>CTGTTGAACAAGTCTGGAAAGAAATGCATAAGCTTTTGCCATTCTCACCG |
| Adh900<br>split marker<br>cassette 2 | (SEQ ID NO: 75)<br>AAGCCCGATGCGCCAGAGTTGTTTCTGAAACATGGCAAAGGTAGCGTTGCCAATGATGTT<br>ACAGATGAGATGGTCAGACTAAACTGGCTGACGGAATTTATGCCTCTTCCGACCATCAAG<br>CATTTTATCCGTACTCCTGATGATGCATGGTTACTCACCACTGCGATCCCCGGCAAAACA<br>GCATTCCAGGTATTAGAAGAATATCCTGATTCAGGTGAAAATATTGTTGATGCGCTGGCA<br>GTGTTCCTGCGCCGGTTGCATTCGATTCCTGTTTGTAATTGTCCTTTTAACAGCGATCGC<br>GTATTTCGTCTCGCTCAGGCGCAATCACGAATGAATAACGGTTTGGTTGATGCGAGTGAT<br>TTTGATGACGAGCGTAATGGCTGGCCTGTTGAACAAGTCTGGAAAGAAATGCATAAGCTT<br>TTGCCATTCTCACCGGATTCAGTCGTCACTCATGGTGATTTCTCACTTGATAACCTTATT<br>TTTGACGAGGGGAAATTAATAGGTTGTATTGATGTTGGACGAGTCGGAATCGCAGACCGA<br>TACCAGGATCTTGCCATCCTATGGAACTGCCTCGGTGAGTTTTCTCCTTCATTACAGAAA<br>CGGCTTTTTCAAAAATATGGTATTGATAATCCTGATATGAATAAATTGCAGTTTCATTTG<br>ATGCTCGATGAGTTTTTCTAATCAGTACTGACAATAAAAAGATTCTTGTTTTCAAGAACT<br>TGTCATTTGTATAGTTTTTTTATATTGTAGTTGTTCTATTTTAATCAAATGTTAGCGTGA<br>TTTATATTTTTTTTCGCCTCGACATCATCTGCCCAGATGCGAAGTTAAGTGCGCAGAAAG<br>TAATATCATGCGTCAATCGTATGTGAATGCTGGTCGCTATACTGGTACCATTCGAGAACC<br>CTTAATATAACTTCGTATAATGTATGCTATACGAAGTTATTAGGTGATATCAGATCCACT<br>CTGTAGTGAGGGTTGGTGGTCTGACGAACATCCAGCAAGGTGTTCCACCTGAAATTTTTC<br>ACCTTGGAGGGTAATGTGATGACGCCATTTCCTGTGCAAATGCTTTTCGTTTTGAACAGT<br>GCAACTTTTGTATCAGATCTTCATCTACTTGATGCCATCTCAACAAATCCCTCATTTACT<br>AGCGTGTGAAGGAATCTAGATTTTCCACTGATAAGCCAATTTGTCGGAAATCCCCCGCGC<br>GGGAGTTGGCGTTCAGTACGAGCCACACACGTTTCTTTTGGACAACCAAAGCATCCGCCT<br>GAAGGGACAACTTGCATTCAACGGCTTCAGTTGGAAACGTCAGAGCTGACCTATAGTTTG<br>CTAGAACCGTTTTCTCTGTTTACGTTTACGTCTCCTCAAATTTGCGCTCGGTATGTCCTT<br>CCTAATTAGCGGGAAAAGCTGTTCTTAGTTAATACGGAGAAAGTTTCGGGGTTACCGTTC<br>CGGGAAGAGGAGGGGTCATCTCTCTCATCTCATCCAACCATTAAGTTTCTTCCAAAACTT<br>CAGGATAATCAGTTTAACCACCGACAGGAGTCAGATTTGAGATTGACAGAAAGTTTTTCC<br>GTCCATTTCCTCATCTTGTCGCCGTTATCAGTCAATCTCTATGGTTATCTGGAATTTCTT<br>TTTTCTTTTAATTCATCTTCTTTTTATCCCGCGCCTTTGGCGTTCTAGCTCATCTCATGA<br>AAACAAAACCCTCTCATGTTCGGATAATTCCAGCGGCTTTCACTTTCAGATGACACATAG<br>ATTGGACTCAACCATGGCTATCTGGGGTATACGGACGTTGGCAAGGGCGTTAATTTTTCA<br>GGACAAACGGAAATGCCATGGCTCCAGGGAAAGGCATTCCTATTGCAAACCTAGACCGTC<br>GAACCTCTCCTATCGCCTACCAGTCACCCAGCTATCCCTAGGCAACTCATCTCCTTCAAG<br>CGGATTGCAACCTGCTAAGCCAAATTAGATCTGGCCACAGAAATGCCGCAATATTTCTTG<br>GCTCTCCCCTCCC |

TABLE 15

Polymerase chain reaction primers.

| Primer Name | DNA sequence 5' to 3' |
|---|---|
| Adh2_KO_ctrl_fwd | GAATTGAGCCAAAAAAGGAGAGG<br>(SEQ ID NO: 76) |
| Adh2_KO_ctrl_rev | GATGGAATAGGAGACTAGGTGTG<br>(SEQ ID NO: 77) |
| AdhII_KO_Ctrl_fwd | TGGTTGAGACGTTTGTATTG<br>(SEQ ID NO: 78) |
| AdhII_KO_Ctrl_rev | TGGGTTGGGAGTTTAGTG<br>(SEQ ID NO: 79) |

Example 13: Generation of Adh2 and Adh900 Overexpression Methanol Utilization Negative Strains For the purpose of checking the effect of ADH2 and ADH900 overexpression. An expression construct was created being composed of a constitutive promoter PGAP: PP7425_Chr1 (596296 . . . 596790) and the ADH2 coding sequence or the ADH900 coding sequence, respectively. The ADH2 and ADH900 coding sequence (Table 16) were modified to eliminate BbsI and BsaI restriction sites in the coding sequence without affecting the amino acid sequence of the gene product. The generated strains were designated P. pastoris Δaox1 Δaox2 BB3aZ_pGAP_Adh2_CycTT and P. pastoris Δaox1Δaox2 BB3aZ_pGAP_Adh900_CycTT.

a) For the purpose of using the Golden Gate assembly method the restriction sites of restriction enzymes BbsI and BsaI (New England Biolabs, Inc., USA) needed to be removed from the coding sequence without affecting the amino acid sequence of the gene product. This process is called Curing. The coding sequence of ADH2 PP7435_Chr2-0821 was modified at c.45G>A and c.660C>G. The coding sequence of ADH900 PP7435_Chr2-0990 was modified at c.42C>G. The cured coding sequence used for Golden Gate assembly can be found in Table 15. Note that the first 12 base pairs and the last 15 base pairs are not part of the coding sequence and are needed for Golden Gate assembly.

b) Golden Gate assembly as used here was already described (Prielhofer et al., 2017). (1) The expression construct BB3aZ_pGAP_Adh2_CycTT was assembled as follows. The Adh2_GG_cured DNA fragment (Table 15) was cloned into the BB1_23 backbone, creating the BB1_23_Adh2. The expression construct was generated by Golden Gate assembly of BB3aZ_14* (backbone), BB1_23_Adh2 (coding sequence) BB1_12_pGAP (promoter), BB1_34_ScCYC1tt (terminator). (2) The expression construct BB3aZ_pGAP_Adh900_CycTT was assembled as follows. The Adh900_GG_cured DNA fragment (Table 15) was cloned into the BB1_23 backbone, creating the BB1_23_Adh900. The expression construct was generated by Golden Gate assembly of BB3aZ_14* (backbone), BB1_23_Adh900 (coding sequence) BB1_12_pGAP (promoter), BB1_34_ScCYC1tt (terminator). The plasmids and sequences are available in the Golden PiCS kit #1000000133 (Addgene, Inc., USA).

TABLE 16

ADH2 and ADH900 native coding sequence and ADH2 cured coding sequence with mutations in c.45G > A and c.660C > G and ADH900 cured coding sequence with mutations in c.42C > G used for Golden Gate assembly. The first 12 base pairs and the last 15 base pairs are not part of the coding sequence and are used for Golden Gate assembly.

| DNA fragment | DNA sequence 5' to 3' |
| --- | --- |
| ADH2 coding sequence | (SEQ ID NO: 80)<br>ATGTCTCCAACTATCCCAACTACACAAAAGGCTGTTATCTTCGAGACCAACGGCG<br>GTCCCCTAGAGTACAAGGACATTCCAGTCCCAAAGCCAAAGTCAAACGAACTTTT<br>GATCAACGTTAAGTACTCCGGTGTCTGTCACACTGATTTGCACGCCTGGAAGGGT<br>GACTGGCCATTGGACAACAAGCTTCCTTTGGTTGGTGGTCACGAAGGTGCTGGTG<br>TCGTTGTCGCTTACGGTGAGAACGTCACTGGATGGGAGATCGGTGACTACGCTGG<br>TATCAAATGGTTGAACGGTTCTTGTTTGAACTGTGAGTACTGTATCCAAGGTGCT<br>GAATCCAGTTGTGCCAAGGCTGACCTGTCTGGTTTCACCCACGACGGATCTTTCC<br>AGCAGTATGCTACTGCTGATGCCACCCAAGCCGCCAGAATTCCAAAGGAGGCTGA<br>CTTGGCTGAAGTTGCCCCAATTCTGTGTGCTGGTATCACCGTTTACAAGGCTCTT<br>AAGACCGCTGACTTGCGTATTGGCCAATGGGTTGCCATTTCTGGTGCTGGTGGAG<br>GACTGGGTTCTCTTGCCGTTCAATACGCCAAGGCTCTGGGTTTGAGAGTTTTGGG<br>TATTGATGGTGGTGCCGACAAGGGTGAATTTGTCAAGTCCTTGGGTGCTGAGGTC<br>TTCGTCGACTTCACTAAGACTAAGGACGTCGTTGCTGAAGTCCAAAAGCTCACCA<br>ACGGTGGTCCACACGGTGTTATTAACGTCTCCGTTTCCCCACATGCTATCAACCA<br>ATCTGTCCAATACGTTAGAACTTTGGGTAAGGTTGTTTTGGTTGGTCTGCCATCT<br>GGTGCCGTTGTCAACTCTGACGTTTTCTGGCACGTTCTGAAGTCCATCGAGATCA<br>AGGGATCTTACGTTGGAAACAGAGAGGACAGTGCCGAGGCCATCGACTTGTTCAC<br>CAGAGGTTTGGTCAAGGCTCCTATCAAGATTATCGGTCTGTCTGAACTTGCTAAG<br>GTCTACGAACAGATGGAGGCTGGTGCCATCATCGGTAGATACGTTGTGGACACTT<br>CCAAATAA |
| ADH900 coding sequence | (SEQ ID NO: 81)<br>ATGTCTGTGATGAAAGCCCTCGTGTACGGTGGTAAGAACGTCTTCGCCTGGAAAA<br>ACTTCCCTAAACCAACTATCTTGCACCCAACAGATGTCATCGTTAAGACGGTGGC<br>TACTACCATCTGCGGAACAGACTTGCACATCTTGAAAGGTGATGTTCCAGAGGTC<br>AAACCTGAAACCGTCTTGGGTCATGAAGCAATTGGAGTCGTTGCGAATCTATCGGTG<br>ATAACGTCAAAAACTTCAGCATTGGTGATAAGGTGCTGGTTTCATGCATCACCAG<br>TTGTGGAAGCTGTTACTACTGTAAGAGAAACTTGCAGAGTCATTGCAAGACCGGT<br>GGATGGAAATTAGGTCACGATTTGAACGGTACGCAGGCTGAGTTTGTCCGTATCC<br>CATATGGAGACTTCTCATTGCACCGTATTCCTCATGAAGCAGATGAAAAGGCAGT<br>TCTGATGCTGTCTGACATCTTACCTACTGCTTACGAAGTTGGTGTTCTTGCCGGA<br>AATGTCCAAAAGGGAGACTCAGTTGCCATTGTCGGCGCCGGTCCAGTTGGTCTTG<br>CCGCTCTGCTGACTGTCAAAGCCTTTGAGCCTTCTGAAATTATTATGATTGACAC<br>TAACGATGAAAGACTGAGTGCCTCCTTGAAATTGGGAGCCACCAAGGCAGTCAAC<br>CCAACCAAGGTCAGCAGTGTCAAAGATGCTGTTTATGATATTGTCAATGCCACTG<br>TCCGCGTCAAGGAGAACGACCTGGAGCCAGGTGTCGATGTTGCCATTGAGTGTGT<br>TGGTGTTCCTGACACGTTTGCAACTTGTGAAGAGATTATCGCCCCAGGTGGCCGT<br>ATTGCCAATGTTGGTGTTCACGGCACTAAAGTGGATTTACAACTGCAAGACCTAT<br>GGATCAAGAACATTGCTATCACCACCGGTTTGGTAGCCACATACTCCACTAAAGA<br>CCTGTTGAAGCGAGTCTCTGACAAGTCTCTAGACCCTACACCACTGGTTACACAT<br>GAGTTCAAGTTCAGTGAATTTGAGAAGGCCTATGAGACTTCTCAAATGCTGCCA<br>CCACCAAAGCCATCAAGATTTTCTTATCTGCCGATTAA |
| Adh2_GG_cured | (SEQ ID NO: 82)<br>GATAGGTCTCACATGTCTCCAACTATCCCAACTACACAAAAGGCTGTTATCTTCG<br>AAACCAACGGCGGTCCCCTAGAGTACAAGGACATTCCAGTCCCAAAGCCAAAGTC<br>AAACGAACTTTTGATCAACGTTAAGTACTCCGGTGTCTGTCACACTGATTTGCAC<br>GCCTGGAAGGGTGACTGGCCATTGGACAACAAGCTTCCTTTGGTTGGTGGTCACG<br>AAGGTGCTGGTGTCGTTGTCGCTTACGGTGAGAACGTCACTGGATGGGAGATCGG<br>TGACTACGCTGGTATCAAATGGTTGAACGGTTCTTGTTTGAACTGTGAGTACTGT<br>ATCCAAGGTGCTGAATCCAGTTGTGCCAAGGCTGACCTGTCTGGTTTCACCCACG<br>ACGGATCTTTCCAGCAGTATGCTACTGCTGATGCCACCCAAGCCGCCAGAATTCC<br>AAAGGAGGCTGACTTGGCTGAAGTTGCCCCAATTCTGTGTGCTGGTATCACCGTT<br>TACAAGGCTCTTAAGACCGCTGACTTGCGTATTGGCCAATGGGTTGCCATTTCTG<br>GTGCTGGTGGAGGACTGGGTTCTCTTGCCGTTCAATACGCCAAGGCTCTGGGTTT<br>GAGAGTTTTGGGTATTGATGGTGGTGCCGACAAGGGTGAATTTGTCAAGTCCTTG<br>GGTGCTGAGGTGTTCGTCGACTTCACTAAGACTAAGGACGTCGTTGCTGAAGTCC<br>AAAAGCTCACCAACGGTGGTCCACACGGTGTTATTAACGTCTCCGTTTCCCCACA<br>TGCTATCAACCAATCTGTCCAATACGTTAGAACTTTGGGTAAGGTTGTTTTGGTT<br>GGTCTGCCATCTGGTGCCGTTGTCAACTCTGACGTTTTCTGGCACGTTCTGAAGT<br>CCATCGAGATCAAGGGATCTTACGTTGGAAACAGAGAGGACAGTGCCGAGGCCAT<br>CGACTTGTTCACCAGAGGTTTGGTCAAGGCTCCTATCAAGATTATCGGTCTGTCT<br>GAACTTGCTAAGGTCTACGAACAGATGGAGGCTGGTGCCATCATCGGTAGATACG<br>TTGTGGACACTTCCAAATAAGCTTAGAGACCGATC |

TABLE 16-continued

ADH2 and ADH900 native coding sequence and ADH2 cured coding sequence with mutations in c.45G > A and c.660C > G and ADH900 cured coding sequence with mutations in c.42C > G used for Golden Gate assembly. The first 12 base pairs and the last 15 base pairs are not part of the coding sequence and are used for Golden Gate assembly.

| DNA fragment | DNA sequence 5' to 3' |
|---|---|
| Adh900_GG_cured | (SEQ ID NO: 83)<br>GATAGGTCTCACATGTCTGTGATGAAAGCCCTCGTGTACGGTGGTAAGAACGTGT<br>TCGCCTGGAAAAACTTCCCTAAACCAACTATCTTGCACCCAACAGATGTCATCGT<br>TAAGACGGTGGCTACTACCATCTGCGGAACAGACTTGCACATCTTGAAAGGTGAT<br>GTTCCAGAGGTCAAACCTGAAACCGTCTTGGGTCATGAAGCAATTGGAGTCGTCG<br>AATCTATCGGTGATAACGTCAAAAACTTCAGCATTGGTGATAAGGTGCTGGTTTC<br>ATGCATCACCAGTTGTGGAAGCTGTTACTACTGTAAGAGAAACTTGCAGAGTCAT<br>TGCAAGACCGGTGGATGGAAATTAGGTCACGATTTGAACGGTACGCAGGCTGAGT<br>TTGTCCGTATCCCATATGGAGCTTCTCATTGCACCGTATTCCTCATGAAGCAGA<br>TGAAAAGGCAGTTCTGATGCTGTCTGACATCTTACCTACTGCTTACGAAGTTGGT<br>GTTCTTGCCGGAAATGTCCAAAAGGGAGACTCAGTTGCCATTGTCGGCGCCGGTC<br>CAGTTGGTCTTGCCGCTCTGCTGACTGTCAAAGCCTTTGAGCCTTCTGAAATTAT<br>TATGATTGACACTAACGATGAAAGACTGAGTGCCTCCTTGAAATTGGGAGCCACC<br>AAGGCAGTCAACCCAACCAAGGTCAGCAGTGTCAAAGATGCTGTTTATGATATTG<br>TCAATGCCACTGTCCGCGTCAAGGAGAACGACCTGGAGCCAGGTGTCGATGTTGC<br>CATTGAGTGTGTTGGTGTTCCTGACACGTTTGCAACTTGTGAAGAGATTATCGCC<br>CCAGGTGGCCGTATTGCCAATGTTGGTGTTCACGGCACTAAAGTGGATTTACAAC<br>TGCAAGACCTATGGATCAAGAACATTGCTATCACCACCGGTTTGGTAGCCACATA<br>CTCCACTAAAGACCTGTTGAAGCGAGTCTCTGACAAGTCTCTAGACCCTACACCA<br>CTGGTTACACATGAGTTCAAGTTCAGTGAATTTGAGAAGGCCTATGAGACTTCTC<br>AAAATGCTGCCACCACCAAAGCCATCAAGATTTTCTTATCTGCCGATTAAGCTTA<br>GAGACCGATC | c) The *P. pastoris* Δaox1Δaox2 strain was made electrocompetent as described in Example 1a). The BB3aZ_pGAP_Adh2_CycTT expression construct and the BB3aZ_pGAP_Adh900_CycTT expression construct was linearized with AscI (New England Biolabs, Inc., USA) as per the manufacturer's protocol and purified with the Hi Yield® Gel/PCR DNA Fragment Extraction Kits (Süd-Laborbedarf GmbH, Germany). 500 ng of the linearized plasmid was transformed into electrocompetent *P. pastoris* Δaox1Δaox2 as previously described in Example 1a) and 1d). Positive transformants were selected on YPD plates with 25 µg/mL Zeocin. The successful integration of the expression construct was verified by PCR amplification with primers 109_BB3aN_ctrl_fwd and pGAP_goi_rev_v2 (Table 17) with genomic DNA as template. The created strains are called *P. pastoris* Δaox1Δaox2 BB3aZ_pGAP_Adh2_CycTT and *P. pastoris* Δaox1Δaox2 BB3aZ_pGAP_Adh900_CycTT.

d) Genomic DNA for PCR amplifications was isolated with the Wizard® Genomic DNA Purification Kit (Promega Corporation, USA) as per manufacturer's recommendations. The PCR amplification reactions were done with the Q5 polymerase (New England Biolabs, Inc., USA) as per manufacturer's recommendations.

TABLE 17

Polymerase chain reaction primers.

| Primer Name | DNA sequence 5' to 3' |
|---|---|
| 109_BB3aN_ctrl_fwd | TTGATCTTTTCTACGGGGTGG<br>(SEQ ID NO: 84) |
| pGAP_goi_rev_v2 | GGTGTTTTGAAGTGGTACGG<br>(SEQ ID NO: 85) |

Example 14: Measurement of Alcohol Dehydrogenase Activity in Cell Free Extract of Methanol Utilization Negative Alcohol Dehydrogenase Defective Strains To check for the successful deletion of the alcohol dehydrogenases on the phenotype level the alcohol dehydrogenase activity in cell free extracts with ethanol as a substrate was measured. Ethanol is generally regarded as the primary substrate for Adh2.

a) An overnight culture was done in 2 mL of YPD media in 24 well plates sealed by an air permeable membrane at 25° C. and 280 rpm. The strains used, were from Example 12a) *P. pastoris* Δaox1Δaox2 Adh2Δ::HphR, Example 12b) *P. pastoris* Δaox1Δaox2 Adh2Δ::HphR Adh900Δ::KanMX and Example 1e) *P. pastoris* Δaox1Δaox2. As an additional control the *P. pastoris* X33 (Thermo Fisher Scientific Inc., USA) and the *P. pastoris* X33 ΔAdh2 (Nocon et al., 2014) was used.

b) The cell free extracts were prepared by centrifuging (16.000 g, 5 min, 4° C.) the overnight culture and resuspending it in 1 mL phosphate buffered saline. After a second centrifuge step (16.000 g, 5 min, 4° C.) the cells were resuspended in 0.5 mL of cell lysis buffer with glass beats. The cultures were lysed in a ribolyser (MP Biomedicals, Inc., USA) by bead beating for 3×20 seconds at 6 m/s with 1 minute cooling on ice in-between steps. After the lysis step the cultures were centrifuged (16.000 g, 5 min, 4° C.) and the supernatant was transferred to a fresh Eppendorf tube and centrifuged again (16.000 g, 30 min, 4° C.) to remove any carried over cell debris. After the second centrifugation step the supernatant was stored at −20° C. till use.

c) The cell lysis buffer consisted of 20 mM HEPES, 420 mM NaCl, 1.5 mM $MgCl_2$, 10% Glycerol, 1 SIGMA-FAST™ Protease Inhibitor Cocktail Tablets (Sigma-Aldrich GmbH) per 50 mL. The assay buffer consisted of 100 mM MOPS, 5 mM $MgSO_4$, 2 mM $NAD^+$ at pH 8.9.

d) The protein concertation of the cell free extracts was measured by Pierce™ BCA Protein Assay (Thermo Scientific, Inc., USA) as per manufacturer's recommendations and uniformly adjusted to a common concentration of 3.8 mg/mL for all samples.

e) The alcohol dehydrogenase activity assays were done in a 96 well plate. The measurements were done in a microplate reader (Tecan Group Ltd., Swiss) by measuring the absorbance of NADH at 340 nm. Temperature was set at 42° C. To start the assay 20 μL cell free extracts were added to the assay buffer and equilibrated for 10 to 15 minutes before the addition of 1 M of ethanol as a substrate. The total end volume was 300 μL. The activity in mU/mg was calculated from the maximal linear absorption increase after addition of the substrate ethanol. One activity unit corresponds to 1 μmol substrate (NAD$^+$) consumed per minute. This was calculated from the absorption data using the Lambert-Beer law and the coefficient $\varepsilon_{NADH}$=6220 M$^{-1}$ cm$^{-1}$.

f) The results show clearly the effect of AHD gene deletion on the Alcohol dehydrogenase activity of the cell free extracts (Table 18). By deleting the ADH2 gene an activity reduction of 94% is achieved. This is additionally confirmed by the P. pastoris X33 strains. By deleting also the second alcohol dehydrogenase gene ADH900 a combined activity reduction by 99% is observed.

TABLE 18

Alcohol dehydrogenase activity of cell free extracts on ethanol as a substrate.

| | Alcohol dehydrogenase activity (mU/mg) | | |
|---|---|---|---|
| | Mean | Standard Error | Clones tested |
| P. pastoris CBS2612 Δaox1Δaox2 | 1293.8 | 244.9 | 3 |
| P. pastoris CB52612 Δaox1Δaox2 Adh2Δ::HphR | 80.8 | 7.9 | 6 |
| P. pastoris CBS2612 Δaox1Δaox2 Adh2Δ::HphR Adh900Δ::KanMX | 8.0 | 0.4 | 6 |
| P. pastoris X33 | 1196.5 | 28.3 | 3 |
| P. pastoris X33 Adh2Δ::HphR | 88.5 | 2.1 | 7 |

Example 15: Measurement of Methanol Uptake Rates of Methanol Utilization Negative and Alcohol Dehydrogenase Deficient Strains To determine the methanol uptake rate the Mut$^-$ and alcohol dehydrogenase deficient strains were cultivated in a bioreactor. The strains tested were the P. pastoris Δaox1Δaox2 Adh2Δ::HphR, P. pastoris Δaox1Δaox2 Adh900Δ::KanMX and P. pastoris Δaox1Δaox2 Adh2Δ::HphR Adh900Δ::KanMX. The cultures was grown till a certain biomass concentration. Then a methanol pulse was applied and the methanol concentration was measured immediately after the pulse and approximately 20 hours later. The experimental setup is already described in detail in Example 7. The goal was to determine the specific methanol uptake rate of the alcohol dehydrogenase deficient strains and compare it to the methanol uptake rate measured in Example 7.

a) The reactors filled with 300 mL BSM media were inoculated with 15 mL of P. pastoris Δaox1Δaox2 adh2Δ::HphR (reactor aR2 and aR4) and P. pastoris Δaox1Δaox2 adh900Δ::KanMX (reactor aR1 and aR3). The target start OD$_{600}$ was 2. At the end of the batch phase as indicated by a dissolved oxygen spike, a 50% (w/w) glucose feed was started at 2.8 mL/h for 24 hours to increase the biomass. Two hours after the glucose feed start a 50% (v/v) methanol shot was given to increase the methanol concentration to 1.5% (measured concentration was aR1=1.64%, aR2=1.66%, aR3=1.59% and aR4=1.67%). This was done to induce methanol consumption. At the end of the glucose feed phase samples for cell dry weight and HPLC were taken.

b) After the glucose feed phase the agitation and gassing was set to a constant 750 rpm and 9.5 sL/h. An additional 50% methanol pulse was added to increase the concentration to 1.5% and immediately a HPLC sample was taken (measured concentration was aR1=1.36%, aR2=1.44%, aR3=1.34% and aR4=1.45%). The concentration was measured again after 18.4 hours and used to determine the specific methanol uptake rate (q$_{methanol}$).

c) A separate bioreactor cultivation was started to measure the uptake rate of the double ADH deletion strain P. pastoris Δaox1Δaox2 adh2Δ::HphR adh900Δ::KanMX. The cultivation was carried as explained in this example and Example 7. The P. pastoris Δaox1Δaox2 Adh2Δ::HphR Adh900Δ::KanMX was inoculated into reactor cR3 and cR4. The target start OD$_{600}$ was 2. At the end of the batch phase as indicated by a dissolved oxygen spike, a 50% (w/w) glucose feed was started at 2.4 mL/h for 24 hours to increase the biomass. Two hours after the glucose feed start a 50% (v/v) methanol shot was given to increase the methanol concentration to 1.5% (measured concentration was cR3=1.50% and cR4=1.47%). This was done to induce methanol consumption. At the end of the glucose feed phase samples for cell dry weight and HPLC were taken.

d) After the glucose feed phase the agitation and gassing was set to a constant 750 rpm and 9.5 sL/h. An additional 50% methanol pulse was added to increase the concentration to 1.5% and immediately a HPLC sample was taken (measured concentration was cR3=1.37% and cR4=1.49%). The concentration was measured again after 19.5 hours and used to determine the specific methanol uptake rate (q$_{methanol}$).

e) The specific methanol uptake rate was calculated as in Example 7d). By deleting the ADH2 a surprising and substantial reduction in methanol uptake rate was achieved (Table 19). The dc/dt of methanol is at 0.07 to 0.06 g L$^{-1}$ h$^{-1}$ for aR2 and aR4 which is only slightly higher that the evaporation observed in Example 6. In contrast the methanol uptake rate of the ADH900 deletion strain is not reduced and was in fact slightly higher than the measured uptake rate of the P. pastoris Δaox1Δaox2 in Example 7. This difference can be attributed to slightly different conditions between Example 7 and this example, the difference being a slightly higher reactor volume and methanol concentration after the methanol pulse. The double ADH deletion strain does not show an observable reduction of the methanol uptake rate compared to the already low uptake rate of the ADH2 deletion strain. These results unexpectedly confirmed that the ADH2 gene and its product, the enzyme Adh2, are to the biggest extend responsible for the characteristics observed for P. pastoris Δaox1Δaox2 and that the observations in Example 7 are not the consequence of spontaneous methanol oxidation or the promiscuous activity of any other enzyme.

Therefore, it was concluded that the main responsible gene and enzyme for methanol uptake in the *P. pastoris* Δaox1Δaox2 is the ADH2 gene and its product the enzyme Adh2.

TABLE 19

Overview specific methanol uptake rates ($q_{methanol}$) and apparent methanol loss (dc/dt) for the ADH deletion strains.

| Reactor | ADH gene | Volume (mL) | CDW (g/L) | Methanol at 0 h (g/L) | Methanol at 18.4 h (g/L) | dc/dt (g L$^{-1}$ h$^{-1}$) | $q_{methanol}$ (mg g$^{-1}$ h$^{-1}$) |
|---|---|---|---|---|---|---|---|
| aR1 | Adh900Δ::KanMX | 392 | 73.4 | 10.75 | 3.49 | 0.40 | 5.38 |
| aR2 | Adh2Δ::HphR | 385 | 74.1 | 11.40 | 10.20 | 0.07 | 0.89 |
| aR3 | Adh900Δ::KanMX | 395 | 71.2 | 10.61 | 3.24 | 0.40 | 5.63 |
| aR4 | Adh2Δ::HphR | 382 | 74.7 | 11.47 | 10.34 | 0.06 | 0.82 |
| cR3 | Adh2Δ::HphR Adh900Δ::KanMX | 373 | 73.9 | 10.8 | 10.0* | 0.04 | 0.55 |
| cR4 | Adh2Δ::HphR Adh900Δ::KanMX | 369 | 73.9 | 11.8 | 10.6* | 0.06 | 0.85 |

*The methanol concentration is measured at 19.5 h.

Example 16: Measurement of Methanol Uptake Rates of Methanol Utilization Negative and Alcohol Dehydrogenase Overexpression Strains To confirm that Adh2 is the responsible enzyme for the consumption of methanol in the *P. pastoris* Δaox1Δaox2 and to investigate if it is possible to increase the methanol uptake rate with overexpression of the ADH2 or ADH900 genes the specific methanol uptake rate of *P. pastoris* Δaox1Δaox2 BB3aZ_pGAP_Adh2_CycTT and *P. pastoris* Δaox1Δaox2 BB3aZ_pGAP_Adh900_CycTT strain was measured in a bioreactor cultivation. The experiment was done as described in Example 7 and 15.

a) The reactors filled with 300 mL BSM media were inoculated with 15 mL of *P. pastoris* Δaox1Δaox2 BB3aZ_pGAP_Adh2_CycTT (reactor R1 and R3) and *P. pastoris* Δaox1Δaox2 BB3aZ_pGAP_Adh900_CycTT (R2 and R4). The target start OD$_{600}$ was 2. At the end of the batch phase as indicated by a dissolved oxygen spike, a 50% (w/w) glucose feed was started at 2.8 mL/h for 24 hours to increase the biomass. Two hours after the glucose feed start a 50% (v/v) methanol shot was given to increase the methanol concentration to 1.5% (measured concentration was R1=1.56%, R2=1.53%, R3=1.52% and R4=1.54%). This was done to induce methanol consumption. At the end of the glucose feed phase samples for cell dry weight and HPLC were taken.

b) After the glucose feed phase the agitation and gassing was set to a constant 750 rpm and 9.5 sL/h. An additional 50% methanol pulse was added to increase the concentration to 1.5% and immediately a HPLC sample was taken (measured concentration was R1=1.30%, R2=1.30%, R3=1.35% and R4=1.30%). The concentration was measured again after 4.1, 20.1 hours and used to determine the specific methanol uptake rate ($q_{methanol}$).

c) An additional sampling time point at 4.1 hours was chosen because a higher methanol uptake rate was expected. The average methanol uptake rate at 4.1 hours was 7.72 mg g$^{-1}$ h$^{-1}$ for the ADH2 overexpressing strain *P. pastoris* Δaox1Δaox2 BB3aZ_pGAP_Adh2_CycTT and 5.61 mg g$^{-1}$ h$^{-1}$ for the ADH900 overexpressing strain *P. pastoris* Δaox1Δaox2 BB3aZ_pGAP_Adh900_CycTT. After 20.1 hours the average uptake rate decreases to 6.35 mg g$^{-1}$ h$^{-1}$ for the ADH2 overexpressing strain and to 5.16 mg g$^{-1}$ h$^{-1}$ for the ADH900 overexpressing strain (Table 20). As previously discussed in Example 15e) no significant difference to the parent *P. pastoris* Δaox1Δaox2 can be observed when deleting the ADH900 gene and the same is true when overexpressing the ADH900 gene. On the other hand, the ADH2 overexpressing strain had a 37% and 23% higher uptake rate at 4.1 and 21.7 hours compared to the ADH900 overexpressing strain. Further underlining the unexpected finding that Adh2 is the responsible enzyme for the consumption of methanol and that it is possible to increase the methanol consumption with overexpression of the ADH2 gene.

TABLE 20

Overview specific methanol uptake rates ($q_{methanol}$) and apparent methanol loss (dc/dt) for the ADH overexpressing strains.

| Reactor | ADH gene | Volume (mL) | CDW (g/L) | Methanol at 0 h (g/L) | Methanol at 4.1 h (g/L) | Methanol at 20.1 h (g/L) | $q_{methanol}$ (mg g$^{-1}$ h$^{-1}$) At 4.1 h | $q_{methanol}$ (mg g$^{-1}$ h$^{-1}$) At 20.1 h |
|---|---|---|---|---|---|---|---|---|
| R1 | P$_{GAP}$ADH2 | 398 | 72.9 | 10.3 | 8.0 | 1.2 | 7.65 | 6.18 |
| R2 | P$_{GAP}$ADH900 | 400 | 71.7 | 10.3 | 8.7 | 2.9 | 5.30 | 5.09 |
| R3 | P$_{GAP}$ADH2 | 406 | 70.7 | 10.7 | 8.4 | 1.3 | 7.80 | 6.51 |
| R4 | P$_{GAP}$ADH900 | 399 | 71.3 | 10.3 | 8.6 | 2.8 | 5.91 | 5.23 |

Example 17: Strain Generation with Methanol-Inducible Promoters for ADH2 Overexpression For the purpose of investigating the effect of methanol inducible ADH2 overexpression, two overexpression constructs were created being composed of methanol inducible promoters $P_{AOX1}$ PP7435_chr4 (237941 . . . 238898) and $P_{FLD1}$ PP7435_Chr3 (262922 . . . 263518) controlling the expression of the ADH2 coding sequence. The ADH2 coding sequence was modified to eliminate BbsI and BsaI restriction sites in the coding sequence without affecting the amino acid sequence of the gene product (Table 16). The generated strains were designated P. pastoris Δaox1Δaox2 BB3aZ_pAOX1_Adh2_CycTT and P. pastoris Δaox1Δaox2 BB3aZ_pFLD1_Adh2_CycTT.

a) The expression constructs were created using Golden Gate assembly as already described (Prielhofer et al., 2017). (1) The expression construct BB3aZ_pAOX1_Adh2_CycTT was assembled as follows. The Adh2_GG_cured DNA fragment (Table 16) was cloned into the BB1_23 backbone, creating the BB1_23_Adh2. The expression construct was generated by Golden Gate assembly of BB3aZ_14* (backbone), BB1_23_Adh2 (coding sequence) BB1_12_pAOX1 (promoter), BB1_34_ScCYC1tt (terminator). (2) The expression construct BB3aZ_pFLD1_Adh2_CycTT was generated by Golden Gate assembly of BB3aZ_14* (backbone), BB1_23_Adh2 (coding sequence) BB1_12_pFLD1 (promoter), BB1_34_ScCYC1tt (terminator). The plasmids and sequences are available in the Golden PiCS kit #1000000133 (Addgene, Inc., USA).

b) The P. pastoris Δaox1Δaox2 strain was made electrocompetent as described in Example 1a). The BB3aZ_pAOX1_Adh2_CycTT expression construct and the BB3aZ_pFLD1_Adh2_CycTT expression construct was linearized with AscI (New England Biolabs, Inc., USA) as per the manufacturer's protocol and purified with the Hi Yield® Gel/PCR DNA Fragment Extraction Kits (Süd-Laborbedarf GmbH, Germany). 500 ng of the linearized plasmid was transformed into electrocompetent P. pastoris Δaox1Δaox2 as previously described in Example 1a) and 1d). Positive transformants were selected on YPD plates with 25 µg/mL Zeocin. The successful integration of the expression construct was verified by PCR amplification with primers 109_BB3aN_ctrl_fwd and pGAP_goi_rev_v2 (Table 17) with genomic DNA as template. The created strains are called P. pastoris Δaox1Δaox2 BB3aZ_pAOX1_Adh2_CycTT and P. pastoris Δaox1Δaox2 BB3aZ_pFLD1_Adh2_CycTT.

c) Genomic DNA for PCR amplifications was isolated with the Wizard® Genomic DNA Purification Kit (Promega Corporation, USA) as per manufacturer's recommendations. The PCR amplification reactions were done with the Q5 polymerase (New England Biolabs, Inc., USA) as per manufacturer's recommendations.

Example 18: Measurement of Specific Methanol Uptake Rates of Methanol Utilization Negative Strains with Methanol Inducible Promoters for PH2 Overexpression To investigate the effect of ADH2 overexpression with methanol inducible promotors on the specific methanol uptake rate, a bioreactor cultivation was set up as described in Example 7 and Example 16. For this purpose, the strains P. pastoris Δaox1Δaox2 BB3aZ_pAOX1_Adh2_CycTT and P. pastoris Δaox1Δaox2 BB3aZ_pFLD1_Adh2_CycTT generated in Example 17 were used.

a) The reactors filled with 300 mL BSM media were inoculated with 15 mL of P. pastoris Δaox1Δaox2 BB3aZ_pAOX1_Adh2_CycTT (reactor R1 and R2) and P. pastoris Δaox1Δaox2 BB3aZ_pFLD1_Adh2_CycTT (R3 and R4). The target start $OD_{600}$ was 2. At the end of the batch phase as indicated by a dissolved oxygen spike, a 50% (w/w) glucose feed was started at 2.8 mL/h for 24 hours to increase the biomass. Two hours after the glucose feed start a 50% (v/v) methanol shot was given to increase the methanol concentration to 1.5% (measured concentration was R1=1.57%, R2=1.57%, R3=1.57% and R4=1.70%). This was done to induce methanol consumption and the methanol inducible promotors. At the end of the glucose feed phase samples for cell dry weight and HPLC were taken.

b) After the glucose feed phase the agitation and gassing was set to a constant 750 rpm and 9.5 sL/h. An additional 50% methanol pulse was added to increase the concentration to 1.5% and immediately a HPLC sample was taken (measured concentration was R1=1.42%, R2=1.39%, R3=1.39% and R4=1.42%). The concentration was measured again after 4.2 hours and used to determine the specific methanol uptake rate ($q_{methanol}$). After the initial pulse was nearly consumed a second methanol pulse was applied and immediately a HPLC sample was taken (measured concentration was R1=1.61%, R2=1.65%, R3=1.50% and R4=1.47%). The concentration was measured again after 6.2 hours and used to determine the specific methanol uptake rate ($q_{methanol}$) a second time.

c) The specific methanol uptake rate ($q_{methanol}$) was determined using two methanol pulses. The time between the first pulse and the sampling time point was 4.2 hours. The time between the second methanol pulse and the sampling point was 6.2 hours. The average methanol uptake rate after 4.2 hours after the first pulse was 8.3 mg $g^{-1}$ $h^{-1}$ for the $P_{FLD1}$ADH2 overexpressing strain P. pastoris Δaox1Δaox2 BB3aZ_pFLD1_Adh2_CycTT and 11.6 mg $g^{-1}$ $h^{-1}$ for the $P_{AOX1}$ADH2 overexpressing strain P. pastoris Δaox1Δaox2 BB3aZ_pAOX1_Adh2_CycTT (Table 21). 6.2 hours after the second methanol pulse the average uptake rate increased to 10.1 mg $g^{-1}$ $h^{-1}$ for the $P_{FLD1}$ADH2 overexpressing strain and to 13.8 mg $g^{-1}$ $h^{-1}$ for the $P_{AOX1}$ADH2 overexpressing strain (Table 22). This data shows that longer methanol induction times lead to an increased expression of Adh2 and specific methanol uptake rate when methanol inducible promotors are used. The strains can therefore sustain and even increase the specific methanol uptake rate over time in a medium with methanol as the only energy and carbon source. Compared to the P. pastoris Δaox1Δaox2 pPM2pN21_pAOX1_HSAopt_CycTT strain described in Example 7 the specific methanol uptake rate was increased on average by 1.6 fold for the P. pastoris Δaox1Δaox2 BB3aZ_pFLD1_Adh2_CycTT and by 2.3 fold for the P. pastoris Δaox1 Δaox2 BB3aZ_pAOX1_Adh2_CycTT.

TABLE 21

Overview of the specific methanol uptake rates ($q_{methanol}$) with the methanol inducible ADH2 overexpression after the first methanol pulse.

| Reactor | ADH gene | Volume (mL) | CDW (g/L) | Methanol $1^{st}$ pulse (g/L) | Methanol 4.2 h after $1^{st}$ methanol pulse (g/L) | $q_{methanol}$ (mg g$^{-1}$ h$^{-1}$) |
|---|---|---|---|---|---|---|
| R1 | $P_{AOX1}$ADH2 | 400 | 77.7 | 11.2 | 7.6 | 11.2 |
| R2 | $P_{AOX1}$ADH2 | 401 | 76.4 | 11.0 | 7.2 | 11.9 |
| R3 | $P_{FLD1}$ADH2 | 400 | 75.1 | 11.0 | 8.5 | 8.0 |
| R4 | $P_{FLD1}$ADH2 | 401 | 75.8 | 11.3 | 8.6 | 8.5 |

TABLE 22

Overview of the specific methanol uptake rates ($q_{methanol}$) with the methanol inducible ADH2 overexpression after the second methanol pulse.

| Reactor | ADH gene | Volume (mL) | CDW (g/L) | Methanol $2^{nd}$ pulse (g/L) | Methanol 6.2 h after $2^{nd}$ methanol pulse (g/L) | $q_{methanol}$ (mg g$^{-1}$ h$^{-1}$) |
|---|---|---|---|---|---|---|
| R1 | $P_{AOX1}$ADH2 | 394 | 72.7 | 12.7 | 6.3 | 14.4 |
| R2 | $P_{AOX1}$ADH2 | 393 | 72.6 | 13.1 | 7.1 | 13.3 |
| R3 | $P_{FLD1}$ADH2 | 393 | 71.1 | 11.9 | 7.4 | 10.2 |
| R4 | $P_{FLD1}$ADH2 | 394 | 73.0 | 11.7 | 7.1 | 10.1 |

Example 19: Generation of ADH2 Overexpressing Strains Producing a Secreted Recombinant Protein To investigate if the ADH2 overexpression and the consequential increase in specific methanol uptake rate have an impact on the recombinant protein production the P. pastoris Δaox1 Δaox2 producing HSA and vHH from Example 3 were transformed with the $P_{AOX1}$ADH2 and $P_{FLD1}$ADH2 overexpression constructs and screened in small scale with an adapted protocol described in Example 4.

a) The overexpression constructs were done using Golden Gate assembly as already described (Prielhofer et al., 2017). (1) The expression construct BB3aK_pAOX1_Adh2_CycTT was generated by Golden Gate assembly of BB3aK_14* (backbone), BB1_23_Adh2 (coding sequence) from Example 17, BB1_12_pAOX1 (promoter), BB1_34_ScCYC1tt (terminator). (2) The expression construct BB3aK_pFLD1_Adh2_CycTT was generated by Golden Gate assembly of BB3aK_14* (backbone), BB1_23_Adh2 (coding sequence) from Example 17, BB1_12_pFLD1 (promoter), BB1_34_ScCYC1tt (terminator). The plasmids and sequences are available in the Golden PiCS kit #1000000133 (Addgene, Inc., USA).

b) The P. pastoris Δaox1 Δaox2 pPM2pN21_pAOX1_HSAopt_CycTT and P. pastoris Δaox1Δaox2 pPM2pZ30_pAOX1_αMF-vHH_CycTT strain were made electrocompetent as described in Example 1a). The BB3aK_pAOX1_Adh2_CycTT expression construct and the BB3aK_pFLD1_Adh2_CycTT expression construct was linearized with AscI (New England Biolabs, Inc., USA) as per the manufacturer's protocol and purified with the Hi Yield® Gel/PCR DNA Fragment Extraction Kits (Süd-Laborbedarf GmbH, Germany). 500 ng of the linearized plasmid was transformed into electrocompetent P. pastoris Δaox1 Δaox2 pPM2pN21_pAOX1_HSAopt_CycTT and P. pastoris Δaox1Δaox2 pPM2pZ30_pAOX1_αMF-vHH_CycTT as previously described in Example 1a) and 1d). Positive transformants were selected on YPD plates with 500 μg/mL geneticin and 25 μg/mL zeocin for the P. pastoris Δaox1 Δaox2 pPM2pZ30_pAOX1_αMF-vHH_CycTT_BB3aK_pAOX1_Adh2_CycTT and the P. pastoris Δaox1 Δaox2 pPM2pZ30_pAOX1_αMF-vHH_CycTT_BB3aK_pFLD1_Adh2_CycTT transformants. The P. pastoris Δaox1Δaox2 pPM2pN21_pAOX1_HSAopt_CycTT_BB3aK_pAOX1_Adh2_CycTT and P. pastoris Δaox1Δaox2 pPM2pN21_pAOX1_HSAopt_CycTT_BB3aK_pFLD1_Adh2_CycTT transformants were selected on YPD plates with 500 μg/mL geneticin and 100 μg/L nourseothricin. Multiple clones per transformation were selected for further screening (Example 20). The created strains are named: P. pastoris Δaox1 Δaox2 $P_{AOX1}$FISA $P_{AOX1}$ADH2, P. pastoris Δaox1 Δaox2 $P_{AOX1}$HSA, $P_{FLD1}$ADH2, P. pastoris Δaox1 Δaox2 $P_{AOX1}$vHH $P_{AOX1}$ADH2 and P. pastoris Δaox1 Δaox2 $P_{AOX1}$vHH $P_{FLD1}$ADH2.

Example 20: Small Scale Screening of ADH2 Overexpressing Strains Producing a Secreted Recombinant Protein Multiple clones from the transformants described in Example 19 were tested in small scale screening to investigate the impact of the ADH2 overexpression on recombinant protein production. The screening procedure was adapted from the two shot-extended protocol and the standard protocol described in Example 4.

a) For the pre-culture of the *P. pastoris* Δaox1 Δaox2 $P_{AOX1}$HSA $P_{AOX1}$ADH2 and *P. pastoris* Δaox1 Δaox2 $P_{AOX1}$HSA $P_{FLD1}$ADH2 clones were inoculated in 2 mL YPD with 500 µg/mL geneticin and 100 µg/mL nourseothricin, the *P. pastoris* Δaox1 Δaox2 $P_{AOX1}$vHH $P_{AOX1}$ADH2 and *P. pastoris* Δaox1 Δaox2 $P_{AOX1}$vHH $P_{FLD1}$ADH2 clones were inoculated on 500 µg/mL Geneticin and 25 µg/mL Zeocin. The parental strains were inoculated in two replicates on YPD with 100 µg/mL Nourseothricin or 25 µg/mL Zeocin based on the antibiotic resistance used for selection. For each expression construct eleven clones were picked for screening. Pre-culture and screening cultures were cultivated in 24 well plates sealed with an air permeable membrane and incubated on 25° C. on 280 rpm. The screening culture was inoculated with a start optical density ($OD_{600}$) of 8 into 2 mL of minimal media (ASMv6) with a slow glucose release system EnPump200 (Enpresso GmbH, Germany) based on a polysaccharide solution and an enzyme to keep the cultures in glucose limit. The strains were compared with two different methanol feed procedures differing in total methanol received and incubation time (Table 23).

b) After the incubation period 1 mL of each culture was removed and centrifuged in a pre-weighted Eppendorf tube. The supernatant was removed and the protein concentration was measured with the Caliper LabChip GXII Touch (Perkin Elmer, inc., USA) as per the manufacturer's instructions. The wet cell weight was determined by weighting the Eppendorf tubes with the cell pellet and calculated as follows: Weight (full)–weight (empty)=wet cell weight (WCW) (g/L). Out of this data the yield was calculated: Yield (µg/g)=protein concentration/wet cell weight.

TABLE 23

Overview of the screening strategies used for testing the secreted protein production yield of the transformed strains in Example 20.

| Protocol | Incubation period | Polysaccharide (g/L) | Enzyme (%) | Methanol shot | Total methanol (v/v) | Methanol shot time points (h) |
|---|---|---|---|---|---|---|
| Standard | 48 h | 25 | 0.35 | 4 x | 3.5% | 4*, 19, 27, 43 |
| Two shot-extended | 72 h | 25 | 0.20 | 2 x | 2% | 3, 43 |

*The first shot was 0.5% (v/v) methanol.

c) The results are summed up in Table 24. Surprisingly, the overexpression increased the protein yield (µg/g) by up to 1.7 fold for vHH and 2.3 fold for HSA when compared to the parental Mut⁻ strains. Indeed, proving that the overexpression of the ADH2 improves recombinant protein production of the *P. pastoris* Δaox1 Δaox2.

d) Average performing strains were selected for bioreactor cultivation. The successful integration of the expression construct was verified by PCR amplification with primers 109_BB3aN_ctrl_fwd and pGAP_goi_rev_v2 (Table 17) with genomic DNA as template. Genomic DNA for PCR amplifications was isolated with the Wizard® Genomic DNA Purification Kit (Promega Corporation, USA) as per manufacturer's recommendations. The PCR amplification reactions were done with the Q5 polymerase (New England Biolabs, Inc., USA) as per manufacturer's recommendations.

TABLE 24

Average secreted product yield in µg product / g WCW with standard deviation in different screening conditions. *t-test statistically significant difference ($p<0.05$) from the parent strain.

| | | Screening protocol | |
|---|---|---|---|
| Descriptive name | Name | Two shot - extended | Standard Mut$^S$ |
| Parent strain: Δaox1Δaox2 $P_{AOX1}$vHH | *P. pastoris* Δaox1Δa0x2 pPM2pZ30_pAOX1_αMF-vHH_CycTT | 1766 | 1428 |
| Δaox1Δaox2 $P_{AOX1}$vHH $P_{AOX1}$ADH2 | *P. pastoris* Δaox1Δaox2 pPM2pZ30_pAOX1_αMF-vHH_CycTT BB3aK_pAOX1_Adh2_CycTT | 2394* ± 640 | 2441* ± 211 |
| Δaox1Δaox2 $P_{AOX1}$vHH $P_{FLD1}$ADH2 | *P. pastoris* Δaox1Δaox2 pPM2pZ30_pAOX1_αMF-vHH_CycTT BB3aK_pFLD1_Adh2_CycTT | 1907± 381 | 1810* ± 175 |

TABLE 24-continued

Average secreted product yield in μg product / g WCW with standard deviation in different screening conditions. *t-test statistically significant difference (p<0.05) from the parent strain.

| Descriptive name | Name | Screening protocol | |
|---|---|---|---|
| | | Two shot - extended | Standard Mut$^S$ |
| Parent strain: Δaox1Δaox2 P$_{AOX1}$HSA | P. pastoris Δaox1Δaox2 pPM2pN21_pAOX1_HSAopt_CycTT | 635 | 459 |
| Δaox1Δaox2 P$_{AOX1}$HSA P$_{AOX1}$ADH2 | P. pastoris Δaox1Δaox2 pPM2pN21_pAOX1_HSAopt_CycTT BB3aK_pAOX1_Adh2_CycTT | 1485* ± 183 | 711* ± 135 |
| Δaox1Δaox2 P$_{AOX1}$HSA P$_{FLD1}$ADH2 | P. pastoris Δaox1Δaox2 pPM2pN21_pAOX1_HSAopt_CycTT BB3aK_pFLD1_Adh2_CycTT | 1198 ± 96 | 621* ± 85 |

Example 21: The Methanol Utilization Negative Strain with ADH2 Overexpression Producing HSA as a Model Protein. Cultivated with Strategy 3—a Feed Strategy with a Glucose/Methanol Co-Feed Phase and a Separated Methanol Only Feed Phase A bioreactor cultivation was performed to evaluate the recombinant protein producing ability of the methanol utilization negative ADH2 overexpressing strain generated in Example 19 and selected in Example 20. For this purpose, P. pastoris Δaox1Δaox2 pPM2pN21_pAOX1_HSAopt_CycTT BB3aK_pAOX1_Adh2_CycTT (Δaox1Δaox2 P$_{AOX1}$HSA P$_{AOX1}$ADH2) and P. pastoris Δaox1Δaox2 pPM2pN21_pAOX1_HSAopt_CycTT BB3aK_pFLD1_Adh2_CycTT (Δaox1Δaox2 P$_{AOX1}$HSA P$_{FLD1}$ADH2) strains were cultivated with the strategy 3 as described in Example 10 and Example 11.
  a) This bioreactor cultivation was separated into three phases. (1) Phase one was the batch phase. The reactors were inoculated with the production strains with a start OD$_{600}$ of 2. The inoculation was done as described in Example 7a) b). The end of the batch phase was indicated by a dissolved oxygen spike. (2) At this point Phase two was started. Phase two consisted of a 50% (w/w) glucose feed at 4.8 mL/h for 25 hours. At the start of Phase two a 50% (v/v) methanol pulse was applied to increase methanol concentration to the target of 1.5% (v/v) and a subsequent methanol feed was started to counteract methanol consumption, evaporation and dilution by the glucose feed. (3) Phase three consisted of a methanol only feed for 19.6 (R1, R2) and 21.6 (R5, R6) hours. Methanol concentration was measured at line with HPLC as described in Example 6d). An additional compensation pulse was added if necessary. The methanol feed was calculated in hourly intervals as in Example 8 and 9b). The strains used in each of the reactors R1, R2, R5 and R6 are identified in Table 25.
  b) The process and productivity data can be found in Table 26 and Table 27. The maximal and minimal methanol concentration throughout the cultivation of reactors R1, R2, R5 and R6 ranged from 8.0 g/L to 13.6 g/L. Reactors R1, R2 and R5, R6 were producing HSA as a model protein. The specific productivity (q$_P$) at 68.7 hours in phase 3 shows a positive impact of the ADH2 overexpression with either the P$_{AOX1}$ or P$_{FLD1}$ compared to Example 10 (Table 28, Table 29). A weighted average of the q$_P$ was calculated for Example 10, timepoints 45.02 to 69.58 hours for easier comparison. The q$_P$ in Example 10 from timepoint 45.02 to 69.58 h is on average 40.9 μg g$^{-1}$ h$^{-1}$. The q$_P$ in the present example for reactor the P$_{AOX1}$ADH2 overexpression (R1, R2) from timepoint 49.1 to 68.7 hours is on average 84.3 μg g$^{-1}$ h$^{-1}$. This is a 2 fold increase compared to Example 10 (Table 28). The P$_{FLD1}$ADH2 overexpression (R5, R6) in the similar timeframe (47.1 to 68.7 hours) show an average q$_P$ of 71 μg g$^{-1}$ h$^{-1}$. This represents a 1.7 fold increase in q$_P$ (Table 29). Volumetric productivity at timepoint 68.7 hours is increased by 1.21 fold for P$_{AOX1}$ADH2 overexpression (Table 30) and 1.13 for the P$_{FLD1}$ADH2 overexpression (Table 31). The increased q$_P$ and volumetric productivity in this example is demonstrating the benefits of the ADH2 overexpression in the P. pastoris Δaox1 Δaox2 strain for recombinant protein production.

TABLE 25

Overview of the strains used in Example 21 and Example 22.

| Reactor | Descriptive name | Name |
|---|---|---|
| R1 | P. pastoris Δaox1Δaox2 P$_{AOX1}$HSA P$_{AOX1}$ADH2 | P. pastoris Δaox1Δaox2 pPM2pN21_pAOX1_HSAopt_CycTT BB3aK_pAOX1_Adh2_CycTT |
| R2 | P. pastoris Δaox1Δaox2 P$_{AOX1}$HSA P$_{AOX1}$ADH2 | P. pastoris Δaox1Δaox2 pPM2pN21_pAOX1_HSAopt_CycTT BB3aK_pAOX1_Adh2_CycTT |
| R3 | P. pastoris Δaox1Δaox2 P$_{AOX1}$vHH P$_{AOX1}$ADH2 | P. pastoris Δaox1Δaox2 pPM2pZ30_pAOX1_αMF-vHH_CycTT BB3aK_pAOX1_Adh2_CycTT |
| R4 | P. pastoris Δaox1Δaox2 P$_{AOX1}$vHH P$_{AOX1}$ADH2 | P. pastoris Δaox1Δaox2 pPM2pZ30_pAOX1_αMF-vHH_CycTT BB3aK_pAOX1_Adh2_CycTT |
| R5 | P. pastoris Δaox1Δaox2 P$_{AOX1}$HSA P$_{FLD1}$ADH2 | P. pastoris Δaox1Δaox2 pPM2pN21_pAOX1_HSAopt_CycTT BB3aK_pFLD1_Adh2_CycTT |
| R6 | P. pastoris Δaox1Δaox2 P$_{AOX1}$HSA P$_{FLD1}$ADH2 | P. pastoris Δaox1Δaox2 pPM2pN21_pAOX1_HSAopt_CycTT BB3aK_pFLD1_Adh2_CycTT |
| R7 | P. pastoris Δaox1Δaox2 P$_{AOX1}$vHH P$_{FLD1}$ADH2 | P. pastoris Δaox1Δaox2 pPM2pZ30_pAOX1_αMF-vHH_CycTT BB3aK_pFLD1_Adh2_CycTT |
| R8 | P. pastoris Δaox1Δaox2 P$_{AOX1}$vHH P$_{FLD1}$ADH2 | P. pastoris Δaox1Δaox2 pPM2pZ30_pAOX1_αMF-vHH_CycTT BB3aK_pFLD1_Adh2_CycTT |

TABLE 26

Bioreactor cultivation process data and specific productivity ($q_P$) for HSA with the $P_{AOX1}$ADH2 overexpression from Example 21.

| $P_{AOX1}$ HSA $P_{AOX1}$ ADH2 Phase | Time (h) | Volume (mL) R1 | Volume (mL) R2 | YDM (g/L) R1 | YDM (g/L) R2 | Recombinant protein concentration (mg/L) R1 | Recombinant protein concentration (mg/L) R2 | Specific productivity ($q_P$) (µg g$^{-1}$ h$^{-1}$) R1 | Specific productivity ($q_P$) (µg g$^{-1}$ h$^{-1}$) R2 | Methanol concentration (g/L) R1 | Methanol concentration (g/L) R2 |
|---|---|---|---|---|---|---|---|---|---|---|---|
| 1 | 24.0 | 318 | 317 | 24.8 | 24.0 | | | | | 0.0 | 0.0 |
| 2 | 26.2 | | | | | | | | | *9.4 | *9.9 |
|   | 49.1 | 502 | 501 | 100.4 | 100.2 | 208.9 | 218.6 | 96.0 | 101.1 | 13.8 | 13.6 |
| 3 | 68.7 | 517 | 517 | 95.2 | 95.8 | 445.6 | 423.8 | 90.2 | 78.3 | 8.0 | 8.7 |

*Represents a control sample after the methanol pulse.

TABLE 27

Bioreactor cultivation process data and specific productivity ($q_P$) for HSA with the $P_{FLD1}$ADH2 overexpression from Example 21.

| $P_{AOX1}$ HSA $P_{FLD1}$ ADH2 Phase | Time (h) | Volume (mL) R5 | Volume (mL) R6 | YDM (g/L) R5 | YDM (g/L) R6 | Recombinant protein concentration (mg/L) R5 | Recombinant protein concentration (mg/L) R6 | Specific productivity ($q_P$) (µg g$^{-1}$ h$^{-1}$) R5 | Specific productivity ($q_P$) (µg g$^{-1}$ h$^{-1}$) R6 | Methanol concentration (g/L) R5 | Methanol concentration (g/L) R6 |
|---|---|---|---|---|---|---|---|---|---|---|---|
| 1 | 21.9 | 308 | 306 | 25.2 | 25.2 | | | | | | |
| 2 | 23.8 | | | | | | | | | *10.6 | *11.0 |
|   | 47.1 | 488 | 486 | 101.2 | 100.5 | 208.5 | 203.9 | 94.2 | 93.1 | 11.6 | 11.0 |
| 3 | 68.7 | 515 | 513 | 95.4 | 95.2 | 412.5 | 395.6 | 73.0 | 69.0 | 10.8 | 10.4 |

*Represents a control sample after the methanol pulse.

TABLE 28

Comparison of specific productivity ($q_P$) of methanol utilization negative strain producing HSA from Example 10 to the $P_{AOX1}$ADH2 overexpressing strain from Example 21 in phase 3.

| Example 10 Δaox1Δaox2 $P_{AOX1}$HSA | | | Example 21 Δaox1Δaox2 $P_{AOX1}$HSA $P_{AOX1}$ADH2 | | | Example 10 Δaox1Δaox2 $P_{AOX1}$HSA | | Example 21 Δaox1Δaox2 $P_{AOX1}$HSA $P_{AOX1}$ADH2 | | Fold increase |
|---|---|---|---|---|---|---|---|---|---|---|
| $q_P$ (µg g$^{-1}$ h$^{-1}$) | | | $q_P$ (µg g$^{-1}$ h$^{-1}$) | | | $q_P$ (µg g$^{-1}$ h$^{-1}$) | | | | |
| Time (h) | R1 | R2 | Time (h) | R1 | R2 | Time (h) | Average | Time (h) | Average | |
| 45.02 | | | 49.1 | | | 45.02 | | 49.1 | | |
| 53.00 | 38.6 | 21.5 | | | | 53.00 | Weighted average | | | |
| 69.58 | 47.3 | 44.9 | 68.7 | 90.2 | 78.3 | 69.58 | 40.9 | 68.7 | 84.3 | 2.06 |

TABLE 29

Comparison of specific productivity ($q_P$) of methanol utilization negative strain producing HSA from Example 10 to the $P_{FLD1}$ADH2 overexpressing strain from Example 21 in phase 3.

| Example 10 Δaox1Δaox2 $P_{AOX1}$HSA | | | Example 21 Δaox1Δaox2 $P_{AOX1}$HSA $P_{FLD1}$ADH2 | | | Example 10 Δaox1Δaox2 $P_{AOX1}$HSA | | Example 21 Δaox1Δaox2 $P_{AOX1}$HSA $P_{FLD1}$ADH2 | | Fold increase |
|---|---|---|---|---|---|---|---|---|---|---|
| $q_P$ (µg g$^{-1}$ h$^{-1}$) | | | $q_P$ (µg g$^{-1}$ h$^{-1}$) | | | $q_P$ (µg g$^{-1}$ h$^{-1}$) | | | | |
| Time (h) | R1 | R2 | Time (h) | R5 | R6 | Time (h) | Average | Time (h) | Average | |
| 45.02 | | | 47.1 | | | 45.02 | | 47.1 | | |
| 53.00 | 38.6 | 21.5 | | | | 53.00 | Weighted average | | | |
| 69.58 | 47.3 | 44.9 | 68.7 | 73.0 | 69.0 | 69.58 | 40.9 | 68.7 | 71.0 | 1.74 |

TABEL 30

Comparison of volumetric productivity of methanol utilization negative strain producing HSA from Example 10 to the $P_{AOX1}$ADH2 overexpressing strain from Example 21.

| | Example 10 ΔaoxlΔaox2 $P_{AOX1}$HSA | | Example 21 ΔaoxlΔaox2 $P_{AOX1}$HSA $P_{AOX1}$ADH2 | | Example 10 ΔaoxlΔaox2 $P_{AOX1}$HSA | Example 21 ΔaoxlΔaox2 $P_{AOX1}$HSA $P_{AOX1}$ADH2 | Fold |
|---|---|---|---|---|---|---|---|
| | R1 | R2 | R1 | R2 | Average | Average | increase |
| Recombinant protein (mg/L) | 357.3 | 371.8 | 445.6 | 423.8 | 364.6 | 434.7 | |
| Biomass (g/L) | 95.9 | 96.3 | 95.2 | 95.8 | 96.1 | 95.5 | |
| *Corrected recombinant protein (mg/L) | 244.2 | 253.6 | 305.6 | 289.8 | 248.9 | 297.7 | |
| Time (h) | | | | | 69.58 | 68.7 | |
| Volumetric productivity (mg $L^{-1}h^{-1}$) | | | | | 3.58 | 4.33 | 1.21 |

*Corrected recombinant concentration ($C_{cP}$) for the biomass volume, $C_{cP} = C_p*(1-C_x*F_c)$, $F_c = 0.0033$.

TABLE 31

Comparison of volumetric productivity of methanol utilization negative strain producing HSA from Example 10 to the $P_{FLD1}$ADH2 overexpressing strain from Example 21.

| | Example 10 ΔaoxlΔaox2 $P_{AOX1}$HSA | | Example 21 ΔaoxlΔaox2 $P_{AOX1}$HSA $P_{FLD1}$ADH2 | | Example 10 ΔaoxlΔaox2 $P_{AOX1}$HSA | Example 21 ΔaoxlΔaox2 $P_{AOX1}$HSA $P_{FLD1}$ADH2 | Fold |
|---|---|---|---|---|---|---|---|
| | R1 | R2 | R5 | R6 | Average | Average | increase |
| Recombinant protein (mg/L) | 357.3 | 371.8 | 412.5 | 395.6 | 364.6 | 404.1 | |
| Biomass (g/L) | 95.9 | 96.3 | 95.4 | 95.2 | 96.1 | 95.3 | |
| *Corrected recombinant protein (mg/L) | 244.2 | 253.6 | 282.6 | 271.3 | 248.9 | 277.0 | |
| Time (h) | | | | | 69.58 | 68.7 | |
| Volumetric productivity (mg $L^{-1}h^{-1}$) | | | | | 3.58 | 4.03 | 1.13 |

*Corrected recombinant concentration ($C_{cP}$) for the biomass volume, $C_{cP} = C_p*(1-C_x*F_c)$, $F_c = 0.0033$.

Example 22: The Methanol Utilization Negative Strain with ADH2 Overexpression Producing vHH as a Model Protein. Cultivated with Strategy 3—A Feed Strategy with a Glucose/Methanol Co-Feed Phase and a Separated Methanol Only Feed Phase A bioreactor cultivation was performed to evaluate the recombinant protein producing ability of the methanol utilization negative ADH2 overexpressing strain generated in Example 19 and selected in Example 20. For this purpose, *P. pastoris* Δaox1Δaox2 pPM2pZ30_pAOX1_vHH_CycTT BB3aK_pAOX1_Adh2_CycTT (Δaox1Δaox2 $P_{AOX1}$vHH $P_{AOX1}$ADH2) and *P. pastoris* Δaox1Δaox2 pPM2pZ30_pAOX1_vHH_CycTT BB3aK_pFLD1_Adh2_CycTT (Δaox1Δaox2 $P_{AOX1}$vHH $P_{FLD1}$ADH2) strains were cultivated with the strategy 3 as described in Example 10 and Example 11.

a) This bioreactor cultivation was separated into three phases. (1) Phase one was the batch phase. The reactors were inoculated with the production strains with a start $OD_{600}$ of 2. The inoculation was done as described in Example 7a) b). The end of the batch phase was indicated by a dissolved oxygen spike. (2) At this point Phase two was started. Phase two consisted of a 50% (w/w) glucose feed at 4.8 mL/h for 25 hours. At the start of Phase two a 50% (v/v) methanol pulse was applied to increase methanol concentration to the target of 1.5% (v/v) and a subsequent methanol feed was started to counteract methanol consumption, evaporation and dilution by the glucose feed. (3) Phase three consisted of a methanol only feed for 43.6 (R3, R4) and 44.6 (R7, R8) hours. Methanol concentration was measured at line with HPLC as described in Example 6d). An additional compensation pulse was added if necessary. The methanol feed was calculated in hourly intervals as in Example 8 and 9b). The strains used in each reactors R3, R4, R7 and R8 can be found in Table 25.

b) The process and productivity data can be found in Table 32 and Table 33. The maximal and minimal methanol concentration throughout the cultivation of reactors R3, R4, R7 and R8 ranged from 8.6 g/L to 14.4 g/L. Reactors R3, R4 and R7 were producing vHH as a model protein. The ADH2 overexpression had a positive impact on specific productivity ($q_P$) compared to Example 11. For easier comparison a weighted average of the $q_P$ was calculated for phase two (timepoints 20.0 to 53.6 hours) of Example 11. The comparison shows that $P_{AOX1}$ADH2 overexpression (R3, R4) has a 1.71 fold and the $P_{FLD1}$ADH2 overexpression (R7, R8) a 1.78 fold increase on $q_P$ in phase two (Table 34, Table 35). At later timepoints in phase three the improvements are even larger. At timepoints 92.7 and 91.7 the $q_P$ is the increase by 3.76 fold ($P_{AOX1}$ADH2 overexpression) and 3.86 fold ($P_{FLD1}$ADH2 overexpression) (Table 34, Table 35). Additionally, volumetric productivity was improved at least 1.9 fold compared to the parental strain in Example 11 in both cases (Table 35, Table 36). The increased $q_P$ and volumetric productivity in this example is demonstrating the benefits of the ADH2 overexpression in the *P. pastoris* Δaox1Δaox2 strain for recombinant protein production.

TABLE 32

Bioreactor cultivation process data and specific productivity ($q_P$) for vHH with the $P_{AOX1}$ADH2 overexpression from Example 22.

| $P_{AOX1}$ vHH $P_{AOX1}$ ADH2 Phase | Time (h) | Volume (mL) | | YDM (g/L) | | Recombinant protein concentration (mg/L) | | Specific productivity ($q_P$) ($\mu g\ g^{-1}\ h^{-1}$) | | Methanol concentration (g/L) | |
|---|---|---|---|---|---|---|---|---|---|---|---|
| | | R3 | R4 | R3 | R4 | R3 | R4 | R3 | R4 | R3 | R4 |
| 1 | 24.0 | 318 | 318 | 24.9 | 24.3 | | | | | | |
| 2 | 26.2 | | | | | | | | | *9.8 | *10.3 |
| | 49.1 | 501 | 502 | 102.6 | 100.6 | 696.1 | 783.0 | 310.3 | 359.4 | 13.9 | 14.4 |
| 3 | 68.7 | 518 | 518 | 94.9 | 94.6 | 1688.5 | 1724.9 | 376.1 | 362.0 | 9.4 | 9.7 |
| | 92.7 | 544 | 543 | 86.7 | 85.2 | 2466.5 | 2364.8 | 307.4 | 268.3 | 8.6 | 8.9 |

*Represents a control sample after the methanol pulse.

TABLE 33

Bioreactor cultivation process data and specific productivity ($q_P$) for vHH with the $P_{FLD1}$ADH2 overexpression from Example 22.

| $P_{AOX1}$ vHH $P_{FLD1}$ ADH2 Phase | Time (h) | Volume (mL) | | YDM (g/L) | | Recombinant protein concentration (mg/L) | | Specific productivity ($q_P$) ($\mu g\ g^{-1}\ h^{-1}$) | | Methanol concentration (g/L) | |
|---|---|---|---|---|---|---|---|---|---|---|---|
| | | R7 | R8 | R7 | R8 | R7 | R8 | R7 | R8 | R7 | R8 |
| 1 | 21.9 | 306 | 307 | 24.5 | 24.3 | | | | | | |
| | 23.8 | | | | | | | | | *10.8 | *10.7 |
| 2 | 47.1 | 485 | 484 | 100.3 | 98.6 | 738.1 | 761.1 | 339.0 | 358.0 | 10.8 | 11.5 |
| | 68.7 | 514 | 513 | 93.3 | 92.3 | 1511.7 | 1555.3 | 284.7 | 297.8 | 11.2 | 11.7 |
| 3 | 91.7 | 516 | 514 | 85.8 | 85.2 | 2270.9 | 2364.4 | 285.7 | 305.6 | 10.5 | 10.5 |

*Represents a control sample after the methanol pulse.

TABLE 34

Comparison of specific productivity ($q_P$) of methanol utilization negative strain producing vHH from Example 11 to the $P_{AOX1}$ADH2 overexpressing strain from Example 22.

| | Example 11 Δaox1Δaox2 $P_{AOX1}$vHH | | | Example 22 Δaox1Δaox2 $P_{AOX1}$vHH $P_{AOX1}$ADH2 | | | Example 11 Δaox1Δaox2 $P_{AOX1}$vHH | | Example 22 Δaox1Δaox2 $P_{AOX1}$vHH $P_{AOX1}$ADH2 | | |
|---|---|---|---|---|---|---|---|---|---|---|---|
| | $q_P$($\mu g\ g^{-1}\ h^{-1}$) | | Time | $q_P$($\mu g\ g^{-1}\ h^{-1}$) | | Time | $q_P$($\mu g\ g^{-1}\ h^{-1}$) | Time | $q_P$($\mu g\ g^{-1}\ h^{-1}$) | Fold |
| Time (h) | R1 | R2 | (h) | R3 | R4 | (h) | Average | (h) | Average | increase |
| 20.00 | | | 24.0 | | | 20.00 | Weighted | 24.0 | | |
| 28.22 | 137.8 | 141.5 | | | | 28.22 | average | | | |
| 44.83 | 222.8 | 208.3 | | | | 44.83 | 195.8 | | | |
| 53.58 | 176.0 | 246.2 | 49.1 | 310.3 | 359.4 | 53.58 | | 49.1 | 335 | 1.71 |
| 68.83 | 142.5 | 72.2 | 68.7 | 376.1 | 362 | 68.83 | 107.4 | 68.7 | 369 | 3.44 |
| 92.00 | 55.8 | 97.5 | 92.7 | 307.4 | 268.3 | 92.00 | 76.7 | 92.7 | 288 | 3.76 |

TABLE 35

Comparison of specific productivity (qP) of methanol utilization negative strain producing vHH from Example 11 to the PFLD1ADH2 overexpressing strain from Example 22.

| | Example 11 ΔaoxlΔaox2 $P_{AOX1}$vHH | | Example 22 ΔaoxlΔaox2 $P_{AOX1}$vHH $P_{FLD1}$ADH2 | | Example 11 ΔaoxlΔaox2 $P_{AOX1}$vHH | Example 22 ΔaoxlΔaox2 $P_{AOX1}$vHH $P_{FLD1}$ADH2 | | Fold increase |
|---|---|---|---|---|---|---|---|---|
| | $q_P$(µg g$^{-1}$ h$^{-1}$) | | $q_P$(µg g$^{-1}$ h$^{-1}$) | | $q_P$(µg g$^{-1}$ h$^{-1}$) | $q_P$(µg g$^{-1}$ h$^{-1}$) | | |
| Time (h) | R1 | R2 | Time (h) | R7 | R8 | Time (h) | Average | Time (h) | Average |
| 20.00 | | | 21.9 | | | 20.00 | Weighted | 21.9 | |
| 28.22 | 137.8 | 141.5 | | | | 28.22 | average | | |
| 44.83 | 222.8 | 208.3 | | | | 44.83 | 195.8 | | |
| 53.58 | 176.0 | 246.2 | 47.1 | 339.0 | 358.0 | 53.58 | | 47.1 | 349 | 1.78 |
| 68.83 | 142.5 | 72.2 | 68.7 | 284.7 | 297.8 | 68.83 | 107.4 | 68.7 | 291 | 2.71 |
| 92.00 | 55.8 | 97.5 | 91.7 | 285.7 | 305.6 | 92.00 | 76.7 | 91.7 | 296 | 3.86 |

TABLE 36

Comparison of volumetric productivity of methanol utilization negative strain producing vHH from Example 11 to the $P_{AOX1}$ADH2 overexpressing strain from Example 22.

| | Example 11 ΔaoxlΔaox2 $P_{AOX1}$vHH | | Example 22 ΔaoxlΔaox2 $P_{AOX1}$vHH $P_{AOX1}$ADH2 | | Example 11 ΔaoxlΔaox2 $P_{AOX1}$vHH | Example 22 ΔaoxlΔaox2 $P_{AOX1}$vHH $P_{AOX1}$ADH2 | Fold increase |
|---|---|---|---|---|---|---|---|
| | R1 | R2 | R3 | R4 | Average | Average | |
| Recombinant protein (mg/L) | 1337.2 | 1374.0 | 2466.5 | 2364.8 | 1355.6 | 2415.7 | |
| Biomass (g/L) | 110.8 | 109.4 | 86.7 | 85.2 | 110.1 | 86.0 | |
| *Corrected recombinant protein (mg/L) | 848.3 | 878.0 | 1760.8 | 1699.9 | 863.1 | 1730.4 | |
| Time (h) | 92.0 | 92.0 | 92.7 | 92.7 | 92.0 | 92.7 | |
| Volumetric productivity (mg L$^{-1}$ h$^{-1}$) | | | | | 9.38 | 18.67 | 1.99 |

*Corrected recombinant concentration ($C_{cP}$) for the biomass volume, $C_{cP} = C_p*(1-C_x*F_c)$, $F_c = 0.0033$.

TABLE 37

Comparison of volumetric productivity of methanol utilization negative strain producing vHH from Example 11 to the $P_{FLD1}$ADH2 overexpressing strain from Example 22.

| | Example 11 ΔaoxlΔaox2 $P_{AOX1}$vHH | | Example 22 ΔaoxlΔaox2 $P_{AOX1}$vHH $P_{FLD1}$ADH2 | | Example 11 ΔaoxlΔaox2 $P_{AOX1}$vHH | Example 22 ΔaoxlΔaox2 $P_{AOX1}$vHH $P_{FLD1}$ADH2 | Fold increase |
|---|---|---|---|---|---|---|---|
| | R1 | R2 | R7 | R8 | Average | Average | |
| Recombinant protein (mg/L) | 1337.2 | 1374.0 | 2270.9 | 2364.4 | 1355.6 | 2317.7 | |
| Biomass (g/L) | 110.8 | 109.4 | 85.8 | 85.2 | 110.1 | 85.5 | |
| *Corrected recombinant protein (mg/L) | 848.3 | 878.0 | 1627.9 | 1699.9 | 863.1 | 1663.8 | |
| Time (h) | 92.0 | 92.0 | 91.7 | 91.7 | 92.00 | 91.7 | |
| Volumetric productivity (mg L$^{-1}$ h$^{-1}$) | | | | | 9.38 | 18.14 | 1.93 |

*Corrected recombinant concentration ($C_{cP}$) for the biomass volume, $C_{cP} = C_p*(1-C_x*F_c)$, $F_c = 0.0033$.

TABLE 38

Methanol inducible promoters and their respective chromosomal positions in the strain *P. pastoris* CBS7435 (Gasser, Steiger, & Mattanovich, 2015)

| | | |
|---|---|---|
| P$_{SHB17}$ | PP7435_chr2 (340616...341606) | (SEQ ID NO: 36) GCAAGGCAACTGAGAAATTGAATAGTGGTTTCAAGCCCGCTGACTTTTT GTATTATCTCAATGTCGGTGTTTCACAGTCCCCAGAAGGGGCTTTGCC TTCAAGGGAGACGGAAGAGACATCGTCAACCCTGGGGAGAAGTATTTCA AATGGCGCAAGTTCGCTAATTTTTACGATTAAGCAGTGCTGTATGGGGT AGTTAATAAATCGGGAATATCCTTCTGACGTGACTGTAACAAATCTCTT TTTACGTGGTGCGCATACTGGACAGAGGCAGAGTCTCAATTTCTTCTTT TGAGACAGGCTACTACAGCCTGTGATTCCTCTTGGTACTTGGATTTGCT TTTATCTGGCTCCGTTGGGAACTGTGCCTGGGTTTTGAAGTATCTTGTG GATGTGTTTCTAACACTTTTTCAATCTTCTTGGAGTGAGAATGCAGGAC TTTGAACATCGTCTAGCTCGTTGGTAGGTGAACCGTTTTACCTTGCATG TGGTTAGGAGTTTTCTGGAGTAACCAAGACCGTCTTATCATCGCCGTAA AATCGCTCTTACTGTCGCTAATAATCCCGCTGGAAGAGAAGTTCGAACA GAAGTAGCACGCAAAGCTCTTGTCAAATGAGAATTGTTAATCGTTTGAC AGGTCACACTCGTGGGCTATGTACGATCAACTTGCCGGCTGTTGCTGGA GAGATGACACCAGTTGTGGCATGGCCAATTGGTATTCAGCCGTACCACT GTATGGAAAATGAGATTATCTTGTTCTTGATCTAGTTTCTTGCCATTTT AGAGTTGCCACATTCGTAGGTTTCAGTACCAATAATGGTAACTTCCAAA CTTCCAACGCAGATACCAGAGATCTGCCGATCCTTCCCCAACAATAGGA GCTTACTACGCCATACATATAGCCTATCTATTTTCACTTTCGCGTGGGT GCTTCTATATAAACGGTTCCCCATCTTCCGTTTCATACTACTTGAATTT TAAGCACTAAA |
| P$_{ALD4}$ | PP7435_chr2 (1466285...1467148) | (SEQ ID NO: 37) CTTTTCTTTGGGCAAGGAAAAATCAAGAAAAAGCAGAGGTTAAAGTTTT CAGGGGAATGGCAATTGCTTTATATATGGGAGAAAGTTAACTACGTCGG TGCTGTAGGCGTAGAGAGCGACTGGAGAATGCGTGATGAGGTCGTCTCT TTTCGCCCCCCCTTGGCGGGGTAAAAATTGCACTACTGCAGAATTACTA CACCCCTATTCCGAGGAGACGGAGTGCGACAAAAATGGTAAAGTTCACC CTAGTCTGCGACTTTTAATTGACGGACACCGGCGTTTACATGCGAAAAA AACTAAAGTGCGCGCATTTCACGGCCGAGGGGGGTCCCACTTGGGACTG AGAGGGGGTGGGATCTGAAATCGAGGAGGTATCAAGACCCCCCGTTTCT CAACTCCCTAATCAAAAATTACGAAGTCCTCGTTGGAAAGGAGTTAAAA TAATTAAGCGGGGTCGGACGCCATACCGAGGTTATCTTGCAGGCATTTT ACTAATATTGGAATTCGGAGCTCAACTTGCAACCAGGCAGGGTTTAGCT ATGTAATCAATGTAATCAATATAATAAAGCACTACCACATCGAAGGTTT GGGAGGGAGGCCAATAGTGTCCCCCACAGGGTGCTGATATCGCGATTCT TGGGTGAGGAGACACATATTTCACTCCTCTCACCAACCAACCAAGCGGC TCCTCGCAAGATGATTTATCCGATTATCCGGACACTATACTCCCATCCA GTTTGATGCCGATTTCATCGATTGTCCTAAATAATCCTTAAATATGTAT AGAACGGTACCCTGGGGTTACATAATCCTTATTTAATAATCCCTCCCCC ACCGCTTTTCTTTTTTTTCTTCTTATTGTC |
| P$_{FDH1}$ | PP7435_chr3 (423504...424503) | (SEQ ID NO: 38) AAATGGCAGAAGGATCAGCCTGGACGAAGCAACCAGTTCCAACTGCTAA GTAAAGAAGATGCTAGACGAAGGAGACTTCAGAGGTGAAAAGTTTGCAA GAAGAGAGCTGCGGGAAATAAATTTTCAATTTAAGGACTTGAGTGCGTC CATATTCGTGTACGTGTCCAACTGTTTTCCATTACCTAAGAAAAACATA AAGATTAAAAAGATAAACCCAATCGGGAAACTTTAGCGTGCCGTTTCGG ATTCCGAAAAACTTTTGGAGCGCCAGATGACTATGGAAAGAGGAGTGTA CCAAAATGGCAAGTCGGGGGCTACTCACCGGATAGCCAATACATTCTCT AGGAACCAGGGATGAATCCAGGTTTTTGTTGTCACGGTAGGTCAAGCAT TCACTTCTTAGGAATATCTCGTTGAAAGCTACTTGAAATCCCATTGGGT GCGGAACCAGCTTCTAATTAAATAGTTCGATGATGTTCTCTAAGTGGGA CTCTACGGCTCAAACTTCTACACAGCATCATCTTAGTAGTCCCTTCCCA AAACACCATTCTAGGTTTCGGAACGTAACGAAACAATGTTCCTCTCTTC ACATTGGGCCGTTACTCTAGCCTTCCGAAGAACCAATAAAAGGGACCGG CTGAAACGGGTGTGGAAACTCCTGTCCAGTTTATGGCAAAGGCTACAGA AATCCCAATCTTGTCGGGATGTTGCTCCTCCCAAACGCCATATTGTACT GCAGTTGGTGCGCATTTTAGGGAAAATTTACCCCAGATGTCCTGATTTT CGAGGGCTACCCCCAACTCCCTGTGCTTATACTTAGTCTAATTCTATTC AGTGTGCTGACCTACACGTAATGATGTCGTAACCCAGTTAAATGGCCGA AAAACTATTTAAGTAAGTTTATTTCTCCTCCAGATGAGACTCTCCTTCT TTTCTCCGCTAGTTATCAAACTATAAACCTATTTTACCTCAAATACCTC CAACATCACCCACTTAAACA |
| P$_{DAS1}$ | PP7435_chr3 (634140...634688) | (SEQ ID NO: 39) AATGATATAAACAACAATTGAGTGACAGGTCTACTTTGTTCTCAAAAGG CCATAACCATCTGTTTGCATCTCTTATCACCACACCATCCTCCTCATCT GGCCTTCAATTGTGGGGAACAACTAGCATCCCAACACCAGACTAACTCC ACCCAGATGAAACCAGTTGTCGCTTACCAGTCAATGAATGTTGAGCTAA CGTTCCTTGAAACTCGAATGATCCCAGCCTTGCTGCGTATCATCCCTCC GCTATTCCGCCGCTTGCTCCAACCATGTTTCCGCCTTTTTCGAACAAGT TCAAATACCTATCTTTGGCAGGACTTTTCCTCCTGCCTTTTTTAGCCTC AGGTCTCGGTTAGCCTCTAGGCAAATTCTGGTCTTCATACCTATATCAA CTTTTCATCAGATAGCCTTTGGGTTCAAAAAAGAACTAAAGCAGGATGC |

TABLE 38-continued

Methanol inducible promoters and their respective chromosomal positions in the strain P. pastoris CBS7435 (Gasser, Steiger, & Mattanovich, 2015)

| | | |
|---|---|---|
| | | CTGATATATAAATCCCAGATGATCTGCTTTTGAAACTATTTTCAGTATC<br>TTGATTCGTTTACTTACAAACAACTATTGTTGATTTTATCTGGAGAATA<br>ATCGAACAAA |
| P<sub>DAS2</sub> | PP7435_chr3<br>(632201...633200) | (SEQ ID NO: 40)<br>ATTACTGTTTTGGGCAATCCTGTTGATAAGACGCATTCTAGAGTTGTTT<br>CATGAAAGGGTTACGGGTGTTGATTGGTTTGAGATATGCCAGAGGACAG<br>ATCAATCTGTGGTTTGCTAAACTGGAAGTCTGGTAAGGACTCTAGCAAG<br>TCCGTTACTCAAAAAGTCATACCAAGTAAGATTACGTAACACCTGGGCA<br>TGACTTTCTAAGTTAGCAAGTCACCAAGAGGGTCCTATTTAACGTTTGG<br>CGGTATCTGAAACACAAGACTTGCCTATCCCATAGTACATCATATTACC<br>TGTCAAGCTATGCTACCCCACAGAAATACCCCAAAAGTTGAAGTGAAAA<br>AATGAAAATTACTGGTAACTTCACCCCATAACAAACTTAATAATTTCTG<br>TAGCCAATGAAAGTAAACCCCATTCAATGTTCCGAGATTTAGTATACTT<br>GCCCCTATAAGAAACGAAGGATTTCAGCTTCCTTACCCCATGAACAGAA<br>ATCTTCCATTTACCCCCCACTGGAGAGATCCGCCCAAACGAACAGATAA<br>TAGAAAAAAGAAATTCGGACAAATAGAACACTTTCTCAGCCAATTAAAG<br>TCATTCCATGCACTCCCTTTAGCTGCCGTTCCATCCCTTTGTTGAGCAA<br>CACCATCGTTAGCCAGTACGAAAGAGGAAACTTAACCGATACCTTGGAG<br>AAATCTAAGGCGCGAATGAGTTTAGCCTAGATATCCTTAGTGAAGGGTT<br>GTTCCGATACTTCTCCACATTCAGTCATAGATGGGCAGCTTTGTTATCA<br>TGAAGAGACGGAAACGGGCATTAAGGGTTAACCGCCAAATTATATAAAG<br>ACAACATGTCCCCAGTTTAAAGTTTTTCTTTCCTATTCTTGTATCCTGA<br>GTGACCGTTGTGTTTAATATAACAAGTTCGTTTTAACTTAAGACCAAAA<br>CCAGTTACAACAAATTATAACCCCTCTAAACACTAAAGTTCACTCTTAT<br>CAAACTATCAAACATCAAAA |
| P<sub>PMP20</sub> | PP7435_Chr1<br>(2418090...2419089) | (SEQ ID NO: 41)<br>GTCAACTGCGTACTCTTTTGTCGAATGGACTACTGAATCTGCCTCGATA<br>GCCACTATAGGAAGGTCCATAGAGGCCAGTTTTTCAACTAGTCTTGGTG<br>GAAAGAAACCGACAAAGCCTTTCATGGAGTCACCGATACTGAAAGGTTC<br>AAACAAAGAATGCTTGGGTAGTCTCTTAATACCCATGGCAACGAAAAAG<br>GGGTCTTCATTGTTCAACATGAATTCGTATCCACCTTTAATGTAGTCAT<br>AAAGCTGCTGAAGTTCCGAATCAGTGATGGAACTGTCTACAGTGACAAT<br>ATAGGAGTTCTCAATCACCTTATATCCAGTCGAATATATCTGGATAGGG<br>TCGGGTCTCACTGTGGAAGATTCAAATGGGTTAGATCCCTGTAATTTCA<br>GCGATGGAGACTCAGTATGATGGGCAAGGAAAACGGCAATTGGATATT<br>CAATTGGTCAAGAGATGGTATCAAAAGCGAGTGTGCCAGGGTAGCCACG<br>GTAGCCACTGATGCTAATCTGATAATTTTCATTTCTGGAGTGTCAAAAC<br>AGTAGTGATAAAAGGCTATGAAGGAGGTTGTCTAGGGGCTCGCGGAGGA<br>AAGTGATTCAAACAGACCTGCCAAAAAGAGAAAAAAGAGGGAATCCCTG<br>TTCTTTCCAATGGAAATGACGTAACTTTAACTTGAAAAATACCCCAACC<br>AGAAGGGTTCAAACTCAACAAGGATTGCGTAATTCCTACAAGTAGCTTA<br>GAGCTGGGGGAGAGACAACTGAAGGCAGCTTAACGATAACGCGGGGGGA<br>TTGGTGCACGACTCGAAAGGAGGTATCTTAGTCTTGTAACCTCTTTTTT<br>CCAGAGGCTATTCAAGATTCATAGGCGATATCGATGTGGAGAAGGGTGA<br>ACAATATAAAAGGCTGGAGAGATGTCAATGAAGCAGCTGGATAGATTTC<br>AAATTTTCTAGATTTCAGAGTAATCGCACAAAACGAAGGAATCCCACCA<br>AGCAAAAAAAAAAATCTAAG |
| P<sub>FBA1-2</sub> | PP7435_Chr1<br>(1162918_1163621) | (SEQ ID NO: 42)<br>AAATTAATCCATAAGATAAGGCAAATGTGCTTAAGTAATTGAAAACAGT<br>GTTGTGATTATATAAGCATGGTATTTGAATAGAACTACTGGGGTTAACT<br>TATCTAGTAGGATGGAAGTTGAGGGAGATCAAGATGCTTAAAGAAAAGG<br>ATTGGCCAATATGAAAGCCATAATTAGCAATACTTATTTAATCAGATAA<br>TTGTGGGGCATTGTGACTTGACTTTTACCAGGACTTCAAACCTCAACCA<br>TTTAAACAGTTATAGAAGACGTACCGTCACTTTTGCTTTTAATGTGATC<br>TAAATGTGATCACATGAACTCAAACTAAAATGATATCTTTTACTGGACA<br>AAAATGTTATCCTGCAAACAGAAAGCTTTCTTCTATTCTAAGAAGAACA<br>TTTACATTGGTGGGAAACCTGAAAACAGAAAATAAATACTCCCCAGTGA<br>CCCTATGAGCAGGATTTTTGCATCCCTATTGTAGGCCTTTCAAACTCAC<br>ACCTAATATTTCCCGCCACTCACACTATCAATGATCACTTCCCAGTTCT<br>CTTCTTCCCCTATTCGTACCATGCAACCCTTACACGCCTTTTCCATTTC<br>GGTTCGGATGCGACTTCCAGTCTGTGGGGTACGTAGCCTATTCTCTTAG<br>CCGGTATTTAAACATACAAATTCACCCAAATTCTACCTTGATAAGGTAA<br>TTGATTAATTTCATAAAT |
| P<sub>PMP47</sub> | PP7435_Chr3<br>(2033196...2034195) | (SEQ ID NO: 43)<br>AGCTCAGATTGGAAATGATTTTTGATCCTACCAAGAAGCCTTTGATTTC<br>CAGAATCTCCGCTAAGTAAGTAACCCCCGCAAACGCATGCATCCATGCA<br>AACAAAATACTAACAATTTTAGCCCCGTTGTTGAGAAACCCAGAAAATT<br>GAATGTTCAACCAATCCAGACGATCAATAAGAAAAAAGGCCCAAAGGCT<br>ACTTCCAAACCTGCTGCCGCCAAACCTGCTCCTTCAAAAGCCGGTCCCA<br>AGGGAGGTAAGAAGGTGAGAAAGCCAAAGAAGACAGTTGAAGAATTGGA<br>TCAGGGAAATGGCTGACTACTTTGAAAATAAGAATTAGCCCAACAAATA<br>TGTACAAGTATTATATAAATGAATCTACATGGTGTGTTTTATTTAGATC |

TABLE 38-continued

Methanol inducible promoters and their respective chromosomal
positions in the strain P. pastoris CBS7435 (Gasser, Steiger, &
Mattanovich, 2015)

| | | |
|---|---|---|
| | | CTCCAAACCAAGGAAAGAAACTAAACTTATCTCCGGACTTACGAGTCAA<br>ATAACTATCCGCAGTTCCTTGGAACTCAGACTTTCTTCCATAAGCGGTC<br>ATATCATCTTTGGACTGTGGGAATCCTGGACGAATCTTTGAAATGTCAT<br>AATCTTGCTCTCTATCTCCAAGCACAGCGTCCGGTAAATGCTGGTTCTT<br>CTTTCTCAGATGAATCTTGGATTTAACAAATAAAGCCGTGCCTATGGCT<br>AATGTACTCAAAAACAAAGTCTGCTTCCAGAATTTCGCAAACGATGGAA<br>TGCCATTTCCTGTAAATGTACTCATTGAACCTATGTTTGATTAAAGTTG<br>GTGTGAAGTCATCAAACGAGAGTAAAATCAGATACTCGTGCACCGGCCA<br>AAATTGACTGAGCTAATCTCTGCAGGCTTGACATCCGAACACAACAAAT<br>AGGCGACAAATCTTAACTATCTAATCGTAGGCTATGGTAGAACTTTGTG<br>GGGGTAGAGGAAGACTACAACAGCAAGACAAAACAAAAGAGTCATAGTT<br>TGACTCTCTGCTTTTTCTTCTTTCTCTTCTTTTTCTTCCTCCATATTC<br>GTTATTTATTTCGAACTGGA |
| $P_{FLD}$ | PP7435_Chr3<br>(262519...263518) | (SEQ ID NO: 44)<br>CAGCCATTAATCTCACCTCAGTTTTTGAATCAGTAGAATTTTTAATGAA<br>ACAAACGGTTGGTATATTATTTGATAGAGTTGCCAAATTTCCAAAGATA<br>AATTTTTCATCAGGTAATATCCTGAATACCGTAACATAGTGACTATTGG<br>AAGACACTGCTATCATATTATATTTCGGATAAAAATCCAAACCCCAGAC<br>CGACCTCTTGAGTCTCAACTCCAAGTCAGCCGCAACTTTAATTATCCGT<br>GGATTGGGAGCTAGTTTGGACAACGCATCAGTATAATATAACTTTACGG<br>TTCCATTATCAGACGCTATTGCAAGAACTTCCTTTCCATTGATCTCGCC<br>AATGCGGCAGTAATTGATATCGTAGGGTAGGTCTGGAAAGACGCTGGCG<br>CTTGTGTCCCATTCTGCAGGAATCTCTGGCACGGTGCTAATGGTAGTTA<br>TCCAACGGAGCTGAGGTAGTCGATATATCTGGATATGCCGCCTATAGGA<br>TAAAAACAGGAGAGGGTGAACCTTGCTTATGGCTACTAGATTGTTCTTG<br>TACTCTGAATTCTCATTATGGGAAACTAAACTAATCTCATCTGTGTGTT<br>GCAGTACTATTGAATCGTTGTAGTATCTACCTGGAGGGCATTCCATGAA<br>TTAGTGAGATAACAGAGTTGGGTAACTAGAGAGAATAATAGACGTATGC<br>ATGATTACTACACAACGGATGTCGCACTCTTTCCTTAGTTAAAACTATC<br>ATCCAATCACAAGATGCGGGCTGGAAAGACTTGCTCCCGAAGGATAATC<br>TTCTGCTTCTATCTCCCTTCCTCATATGGTTTCGCAGGGCTCATGCCCC<br>TTCTTCCTTCGAACTGCCCGATGAGGAAGTCCTTAGCCTATCAAAGAAT<br>TCGGGACCATCATCGATTTTTAGAGCCTTACCTGATCGCAATCAGGATT<br>TCACTACTCATATAAATACATCGCTCAAAGCTCCAACTTTGCTTGTTCA<br>TACAATTCTTGATATTCACA |
| $P_{FGH1}$ | PP7435_Chr3<br>(555587...556586) | (SEQ ID NO: 45)<br>TGGTTCCCTCTCGGTCCAATACCAAAAATATTATCACCATACAGGTCTC<br>CCTTCGATACCAGTGCAAAGTTGAACCGTGGGATTACCTTGGAATCTAC<br>AAAAATAGTGTCACTCACAAGTTTGTCATCAACCACGCTGCCGCTTGCA<br>AAGGAGAACTGAACATGAAGGTTGTTAGGGTTTGTTATATTGGAATAAG<br>TGGTGGATTTGTTGAAGGCGAACGCACCAAAGCTACATCCGTCCTGAGC<br>ACACTGTGAATTTGTCACGGAATTGACCAAGAGGTCAGACGATCCTGTA<br>TCCCATTGAGCCGTTATGCTTTGTGGGGGAAACCCTATTTCTATCGTAC<br>TAAGAAAACCAATGGTGAACTCATATTCGGTATCAATGGCGACGATTCC<br>AGCATAGCCTGTAGACAGTAACAACACTAGGGCAACAGCAACTAACATA<br>TCTTCATTGATGAAACGTTGTGATCGGTGTGACTTTTATAGTAAAAGCT<br>ACAACTGTTTGAAATACCAAGATATCATTGTGAATGGCTCAAAAGGGTA<br>ATACATCTGAAAAACCTGAAGTGTGGAAAATTCCGATGGAGCCAACTCA<br>TGATAACGCAGAAGTCCCATTTTGCCATCTTCTCTTGGTATGAAACGGT<br>AGAAAATGATCCGAGTATGCCAATTGATACTCTTGATTCATGCCCTATA<br>GTTTGCGTAGGGTTTAATTGATCTCCTGGTCTATCGATCTGGGACGCAA<br>TGTAGACCCCATTAGTGGAAACACTGAAAGGGATCCAACACTCTAGGCG<br>GACCCGCTCACAGTCATTTCAGGACAATCACCACAGGAATCAACTACTT<br>CTCCCAGTCTTCCTTGCGTGAAGCTTCAAGCCTACAACATAACACTTCT<br>TACTTAATCTTTGATTCTCGAATTGTTTACCCAATCTTGACAACTTAGC<br>CTAAGCAATACTCTGGGGTTATATATAGCAATTGCTCTTCCTCGCTGTA<br>GCGTTCATTCCATCTTTCTA |
| $P_{TAL1-2}$ | PP7435_Chr2<br>(644082...645082) | (SEQ ID NO: 46)<br>GATATCGATCTACACTTAATAGTAGATGACGAGGCATCTCTCCAATAGG<br>TACCATATCTGGTGTTTCTTGTAATTTAAGAATCTGTTGGTCTATGAAT<br>GTAGATTTGTCATGAACAATGATATATGGGTCAGGAGGACAAGATGGTT<br>TCTCTGAGTTGGGTTGTTGAGGTGCCTGGCAAGACTTCGGAGCGTTGAT<br>ATCCCCAAGACTTGTAGTGACCGATAGTTGAAGCGTGTGTTTGCAGGAA<br>CGGCACATCAATGCAACTTTCGTAACTTTGGAATTGAGAGTTGATGCAC<br>TGATGACGATACCCGAAATTTTGACGATTTTACCAATATGACTTGAAGA<br>CAAGTCTCTCATTGAAACCTTATTATCGTTACTAAGCAAAACGAGCTGA<br>CAAGAAGGGAAGGTGGTCGGTATTTCCTCGTTGTTCAAATATATGATTC<br>TCCTGGCAATATCTGTGATGGCCTGTTCAAAAAGTGGAATCATTTCTGC<br>AGGATCATCTACCAACTTTTTATTGAGCTCCTCATTGAATACGATTAAG<br>TGGTCATTTTGAATCGTCAGTAAGTACTTGTTTACAAGTAAATTCTGTC<br>TGAGTTGTTCTCTGTAGATGTACTGATTTTCCATACGAAACTCCAAAAT<br>GAACGAACGGAATGCCTTAATGACCTCACTGAACTGGTCATCGTTCTGT<br>TCTCCGGGAAGGACACTTGTGTTAAAGACTGATGCTCTATCAAAGGACA |

TABLE 38-continued

Methanol inducible promoters and their respective chromosomal positions in the strain *P. pastoris* CBS7435 (Gasser, Steiger, & Mattanovich, 2015)

| | | |
|---|---|---|
| | | TTGCAACAAAGTATAAACGGTTGTGAGCGGGAAAAAGATGTGTAGGTAA<br>TTGTCGTAGATGAGACTGATTCAGTAGAAAACGCGTCCTGCACTATTTT<br>TTTCTTTCTTCATTACATTTCCTAATCGGGACAAAATGAATCTAAAGAC<br>GTGGTTATGTAGTACACGCATCGATAGGCTATCCCCATACCAAAACACT<br>ATTTTACCCCATCCTTGACAGGTTATAAATATGCGATAGTATGAGTATC<br>TTCAAATTCAGCTGAAATATC |
| P*DAS2* | PP7435_Chr3<br>(633689-634688) | SEQ ID NO: 47)<br>AATAAAAAAACGTTATAGAAAGAAATTGGACTACGATATGCTCCAATCC<br>AAATTGTCAAAATTGACCACCGAAAAAGAACAATTGGAATTTGACAAGA<br>GGAACAACTCACTAGATTCTCAAACGGAGCGTCACCTAGAGTCAGTTTC<br>CAAGTCAATTACAGAAAGTTTGGAAACAGAAGAGGAGTATCTACAATTG<br>AATTCCAAACTTAAAGTCGAGCTGTCCGAATTCATGTCGCTAAGGCTTT<br>CTTACTTGGACCCCATTTTTGAAAGTTTCATTAAAGTTCAGTCAAAAAT<br>TTTCATGGACATTTATGACACATTAAAGAGCGGACTACCTTATGTTGAT<br>TCTCTATCCAAAGAGGATTATCAGTCCAAGATCTTGGACTCTAGAATAG<br>ATAACATTCTGTCGAAAATGGAAGCGCTGAACCTTCAAGCTTACATTGA<br>TGATTAGAGCAATGATATAAACAACAATTGAGTGACAGGTCTACTTTGT<br>TCTCAAAAGGCCATAACCATCTGTTTGCATCTCTTATCACCACACCATC<br>CTCCTCATCTGGCCTTCAATTGTGGGGAACAACTAGCATCCCAACACCA<br>GACTAACTCCACCCAGATGAAACCAGTTGTCGCTTACCAGTCAATGAAT<br>GTTGAGCTAACGTTCCTTGAAACTCGAATGATCCCAGCCTTGCTGCGTA<br>TCATCCCTCCGCTATTCCGCCGCTTGCTCCAACCATGTTTCCGCCTTTT<br>TCGAACAAGTTCAAATACCTATCTTTGGCAGGACTTTTCCTCCTGCCTT<br>TTTTAGCCTCAGGTCTCGGTTAGCCTCTAGGCAAATTCTGGTCTTCATA<br>CCTATATCAACTTTTCATCAGATAGCCTTTGGGTTCAAAAAAGAACTAA<br>AGCAGGATGCCTGATATATAAATCCCAGATGATCTGCTTTTGAAACTAT<br>TTTCAGTATCTTGATTCGTTTACTTACAAACAACTATTGTTGATTTTAT<br>CTGGAGAATAATCGAACAAA |
| P*CAM1* | PP7435_Chr3<br>(178828-179827) | SEQ ID NO: 48)<br>ATTGTTGTGAATACTCTCCTTCATTTGGATTTCTTGGACTTCGGACTCT<br>CTTGATCTCTCTTCGAAAGTTTTAACTCTGTTCATGTATAATTTTACCC<br>GCTGTAGGTCGCTCATAATACCATGAGTATGCACATCTTTTACTCCATT<br>AACTTTCAGGTATGCAAAATACAATGAAGATAGTATATAGCTCAAAGAA<br>TTTAGCATTTTGCATTGATCTAATTGTGACATTTTCTCTATGATATCAT<br>CTAGCTTCTTAAACTCGAGAATCTCGTCCAACGAGGCAGAAACATTGTC<br>CAGTCTTACGTCAAGATTATTCACGAGTTTCTGGACCGTATCAACGTTT<br>TCCATCTTAAGATTACAGTAAGTATCGTCCTTTTGAACTGCAAAGGTAG<br>AAAAGTTAATTTTTGATTGGTAGTACACTATGAAACTTGCTCACCCCA<br>ATCTTTCCTCCTGACAGGTTGATCTTTATCCCTCTACTAAATTGCCCCA<br>AGTGTATCAAGTAGACTAGATCTCGCGAAAGAACAGCCTAATAAACTCC<br>GAAGCATGATGGCCTCTATCCGGAAAACGTTAAGAGATGTGGCAACAGG<br>AGGGCACATAGAATTTTTAAAGCAGCTGAAGAATGCTATCATAGTCCGT<br>AAAAATGTGATAGTACTTTGTTTAGTGCGTACGCCACTTATTCGGGGCC<br>AATAGCTAAACCCAGGTTTGCTGGCAGCAAATTCAACTGTAGATTGAAT<br>CTCTCTAACAATAATGGTGTTCAATCCCCTGGCTGGTCACGGGGAGGAC<br>TATCTTGCGTGATCCGCTTGGAAAATGTTGTGTATCCCTTTCTCAATTG<br>CGGAAAGCATCTGCTACTTCCCATAGGCACCAGTTACCCAATTGATATT<br>TCCAAAAAAGATTACCATATGTTCATCTAGAAGTATAAATACAAGTGGA<br>CATTCAATGAATATTTCATTCAATTAGTCATTGACACTTTCATCAACTT<br>ACTACGTCTTATTCAACAAT |
| P*PP7435_<br>Chr1-0336* | PP7435_Ch1<br>(615194-615193) | SEQ ID NO: 49)<br>TATACGGTCTATCCACTTTGGAAACGATGTAGTTGAAACGGGGAAGTAA<br>TAGTGGTTCCCAAACGACATGAAGAGGTTATATAAGTTTGCAAGAGGGT<br>GACACCATTTTAGTTGTGGTTCCCGGGTATTTTTTAATCTTTTTAGTC<br>TAAGATAGCCTCCCCAGATATTACCGAGTTGGGCCATTTGGGGCGGTAT<br>CGGTGGTATCTGATGGTAGCGCGTTTTTACATGCCTGTGCATTGAACTG<br>GCAAAGAGTATACTATCGTGGGGCCCTGAAGGAGGCAGCAAATGGACCG<br>TCAATTGGTTGATCAGGGACTCAAGACAGGTATTGAGCTTTTCAAACAA<br>AAAGAGTATAGGCGCTGCTACAAGGCATTTACTTCTACTATCAATTTCA<br>TTGAGAATGATCCCGAGTTGGCCGCCAGCTGTGTATCTCAACTGATATC<br>TCTGTTAGATTGTAGGGCAGCCTGTTTGGAAAAGCTAGATCAATTGAAT<br>ATGGCCTTGAAAGATGGTCTTAAAATGATCAAGAGAGAGTGCCACAACT<br>GCAAGGGTTATTTGAGAACTTGCAAAATTTTAGACCTACAAGGGAAGAT<br>CAGTGAGGCTTTGTCTACAGCAAGAGAAGGGATCTCCATAATAGAAACT<br>AGAAGAGATCAGGATAATCAATTTAGATATTCCAAGGTTCTTTTGGAAC<br>AATTAAAGGAACTGAAAATGCACTGAAAATCAAATTGGACAAGAAAAA<br>TCAGCTACACTTCAAAGTTTTAAAGTTTGACGCACCAGTGCCTTGTACA<br>AAGAAACTAAGATTAGTCACTCCAAGAACAATAGATCCTTCCATTTTTT<br>TGCCGATAGAGCTAGTGAAGCTGATCTTTCGCCTGTTGAATTTCTCAGA<br>CATGTATGCCTGTTTATTGGTCTCAACAAATGGAACTCAATTATATCC<br>TCATCACCGGAACTGTTTCGAAAACTTCAGTTGAAATCCCAACTGTCCA<br>ACAAGGCGTTAAACAATTGT |

REFERENCES

Ata, Ö., Prielhofer, R., Gasser, B., Mattanovich, D., & çalik, P. (2017). Transcriptional engineering of the glyceraldehyde-3-phosphate dehydrogenase promoter for improved heterologous protein production in *Pichia pastoris*: Transcriptional Engineering of the P GAP for Gene Overexpression in *P. pastoris*. Biotechnology and Bioengineering, 114 (10), 2319-2327.

Aw, R., & Polizzi, K. M. (2013). Can too many copies spoil the broth? Microbial Cell Factories, 12, 128.

Blumhoff, M., Steiger, M. G., Marx, H., Mattanovich, D., & Sauer, M. (2013). Six novel constitutive promoters for metabolic engineering of *Aspergillus niger*. Applied Microbiology and Biotechnology, 97 (1), 259-267.

Gasser, B., Prielhofer, R., Marx, H., Maurer, M., Nocon, J., Steiger, M., . . . . Mattanovich, D. (2013). *Pichia pastoris*: protein production host and model organism for biomedical research. Future Microbiology, 8 (2), 191-208.

Gasser, B., Steiger, M. G., & Mattanovich, D. (2015). Methanol regulated yeast promoters: production vehicles and toolbox for synthetic biology. Microbial Cell Factories, 14 (1).

Hohenblum, H., Borth, N., & Mattanovich, D. (2003). Assessing viability and cell-associated product of recombinant protein producing *Pichia pastoris* with flow cytometry. Journal of Biotechnology, 102 (3), 281-290.

Looser, V., Bruhlmann, B., Bumbak, F., Stenger, C., Costa, M., Camattari, A., . . . . Kovar, K. (2015). Cultivation strategies to enhance productivity of *Pichia pastoris*: A review. Biotechnology Advances, 33 (6), 1177-1193.

Marx, H., Mattanovich, D., & Sauer, M. (2008). Overexpression of the riboflavin biosynthetic pathway in *Pichia pastoris*. Microbial Cell Factories, 7 (1), 23.

Mellitzer, A., Ruth, C., Gustafsson, C., Welch, M., Birner-Grünberger, R., Weis, R., . . . . Glieder, A. (2014). Synergistic modular promoter and gene optimization to push cellulase secretion by *Pichia pastoris* beyond existing benchmarks. Journal of Biotechnology, 191, 187-195.

Nocon, J., Steiger, M. G., Pfeffer, M., Sohn, S. B., Kim, T. Y., Maurer, M., . . . . Mattanovich, D. (2014). Model based engineering of *Pichia pastoris* central metabolism enhances recombinant protein production. Metabolic Engineering, 24, 129-138.

Prielhofer, R., Barrero, J. J., Steuer, S., Gassler, T., Zahrl, R., Baumann, K., . . . . Marx, H. (2017). GoldenPiCS: a Golden Gate-derived modular cloning system for applied synthetic biology in the yeast *Pichia pastoris*. BMC Systems Biology, 11 (1).

Prielhofer, R., Maurer, M., Klein, J., Wenger, J., Kiziak, C., Gasser, B., & Mattanovich, D. (2013). Induction without methanol: novel regulated promoters enable high-level expression in *Pichia pastoris*. Microbial Cell Factories, 12 (1), 5.

Schwarzhans, J.-P., Wibberg, D., Winkler, A., Luttermann, T., Kalinowski, J., & Friehs, K. (2016). Integration event induced changes in recombinant protein productivity in *Pichia pastoris* discovered by whole genome sequencing and derived vector optimization. Microbial Cell Factories, 15, 84.

Stadlmayr, G., Mecklenbräuker, A., Rothmüller, M., Maurer, M., Sauer, M., Mattanovich, D., & Gasser, B. (2010). Identification and characterisation of novel *Pichia pastoris* promoters for heterologous protein production. Journal of Biotechnology, 150 (4), 519-529.

The invention claimed is:

1. A recombinant methanol utilization pathway deficient methylotrophic yeast (Mut⁻) host cell which is engineered:
   a) by one or more genetic modifications to reduce expression of a first and a second endogenous gene compared to the host cell prior to said one or more genetic modifications, wherein
      i. the first endogenous gene encodes alcohol oxidase 1 (Aox1) comprising the amino acid sequence identified as SEQ ID NO:1 or a homologue thereof, and
      ii. the second endogenous gene encodes alcohol oxidase 2 (Aox2) comprising the amino acid sequence identified as SEQ ID NO:3 or a homologue thereof, and
   b) by one or more genetic modifications that increases expression of an alcohol dehydrogenase 2 (Adh2) gene compared to the host cell prior to said one or more genetic modifications, wherein the Adh2 gene encodes an alcohol dehydrogenase 2 (ADH2), and wherein the methylotrophic yeast is a *P. pastoris* strain.

2. The Mut⁻ host cell of claim 1, wherein said one or more genetic modifications to reduce expression of the first and second endogenous gene or said one or more genetic modifications that increases expression of the Adh2 gene comprises a disruption, substitution, or deletion of (i) one or more polynucleotides, or a part thereof; or (ii) an expression control sequence.

3. The Mut⁻ host cell of claim 2, wherein said expression control sequence is selected from the group consisting of a promoter, a ribosomal binding site, transcriptional or translational start and stop sequences, an enhancer and an activator sequence.

4. The Mut⁻ host cell of claim 1, wherein said first and/or second endogenous gene is knocked out by said one or more genetic modifications.

5. The Mut⁻ host cell of claim 1, wherein the Adh2 gene is endogenous or heterologous to the Mut– host cell.

6. The Mut⁻ host cell of claim 1, wherein the ADH2 is any one of:
  a) a *P. pastoris* ADH2 comprising the amino acid sequence of SEQ ID NO:50, or a homologue thereof that is endogenous to a yeast species; or
  b) a mutant of the ADH2 of a), which is at least 60% identical to SEQ ID NO:50.

7. The Mut⁻ host cell of claim 1, wherein said one or more genetic modifications include a gain-of-function alteration in the Adh2 gene resulting in an increase in the level or activity of ADH2.

8. The Mut⁻ host cell of claim 7, wherein said gain-of-function alteration includes a knockin of the Adh2 gene.

9. The Mut⁻ host cell of claim 7, wherein said gain-of-function alteration up-regulates Adh2 gene expression in said cell.

10. The Mut⁻ host cell of claim 7, wherein said gain-of-function alteration includes an insertion of a heterologous expression cassette to overexpress the Adh2 gene in said cell.

11. The Mut⁻ host cell of claim 10, wherein said heterologous expression cassette comprises a heterologous polynucleotide comprising an Adh2 gene under the control of a promoter sequence.

12. The Mut⁻ host cell of claim 1, wherein the Mut⁻ host cell comprises a heterologous gene of interest expression cassette (GOIEC) comprising an expression cassette promoter (ECP) operably linked to a gene of interest (GOI) encoding a protein of interest (POI).

13. The Mut⁻ host cell of claim 12, wherein the ECP is a methanol-inducible promoter.

14. The Mut⁻ host cell of claim 13, wherein the ECP is any one of the following:
  a) a pAOX1 promoter comprising at least 60% sequence identity to SEQ ID NO: 5;
  b) a pAOX2 promoter comprising at least 60% sequence identity to SEQ ID NO: 6; or
  c) a promoter comprising a nucleotide sequence selected from the group consisting of SEQ ID NO:36-49.

15. The Mut⁻ host cell of claim 12, wherein the GOIEC further comprises a nucleotide sequence encoding a signal peptide enabling the secretion of the POI.

16. The Mut⁻ host cell of claim 15, wherein the nucleotide sequence encoding the signal peptide is fused adjacent to the 5'-end of the GOI.

17. The Mut⁻ host cell of claim 12, wherein the POI is heterologous to the Mut⁻ host cell or the ECP.

18. The Mut⁻ host cell of claim 12, wherein the POI is a peptide or protein selected from the group consisting of an antigen-binding protein, a therapeutic protein, an enzyme, a peptide, a protein antibiotic, a toxin fusion protein, a carbohydrate-protein conjugate, a structural protein, a regulatory protein, a vaccine antigen, a growth factor, a hormone, a cytokine, and a process enzyme.

19. A method of producing a protein of interest (POI), comprising culturing the Mut⁻ host cell of claim 1 using methanol as a carbon source to produce the POI.

20. The method of claim 19, further comprising isolating a fermentation product from the cell culture, wherein the fermentation product comprises the POI or a host cell metabolite obtained from the Mut⁻ host cell.

21. The method of claim 19, wherein:
  a) a growing phase of the culturing step, during which the Mut⁻ host cell is cultured using a basal carbon source as a source of energy, is followed by
  b) a production phase of the culturing step, during which the Mut⁻ host cell is cultured using a methanol feed, thereby producing the POI.

22. The method of claim 21, wherein an average methanol concentration of 0.5-2.0% (v/v) is used in the host cell culture during the production phase, wherein the production phase is at least 24 hours in length.

23. The method of claim 22, wherein the methanol feed is at an average feed rate of at least 2 mg methanol/(g dry biomass*h) during the production phase of at least 24 hours.

24. The method of claim 21, wherein the Mut⁻ host cell is cultured during the production phase under conditions limiting the host cell growth to less than 10% (w/w biomass).

25. The Mut⁻ host cell of claim 1, wherein the one or more genetic modifications to reduce expression of the first and second endogenous genes comprises a knockout, or the one or more genetic modifications that increases expression of the Adh2 gene comprises a knockin, of (i) one or more polynucleotides or a part thereof; or (ii) an expression control sequence.

\* \* \* \* \*

SEQUENCE LISTING

```
<160> NUMBER OF SEQ ID NOS: 85

<210> SEQ ID NO 1
<211> LENGTH: 663
<212> TYPE: PRT
<213> ORGANISM: Komagataella phaffii

<400> SEQUENCE: 1
```

Met Ala Ile Pro Glu Glu Phe Asp Ile Leu Val Leu Gly Gly Gly Ser
1               5                   10                  15

Ser Gly Ser Cys Ile Ala Gly Arg Leu Ala Asn Leu Asp His Ser Leu
            20                  25                  30

Lys Val Gly Leu Ile Glu Ala Gly Glu Asn Asn Leu Asn Asn Pro Trp
        35                  40                  45

Val Tyr Leu Pro Gly Ile Tyr Pro Arg Asn Met Lys Leu Asp Ser Lys
    50                  55                  60

Thr Ala Ser Phe Tyr Thr Ser Asn Pro Ser Pro His Leu Asn Gly Arg
65                  70                  75                  80

Arg Ala Ile Val Pro Cys Ala Asn Ile Leu Gly Gly Gly Ser Ser Ile
                85                  90                  95

Asn Phe Met Met Tyr Thr Arg Gly Ser Ala Ser Asp Tyr Asp Asp Phe
            100                 105                 110

Glu Ala Glu Gly Trp Lys Thr Lys Asp Leu Leu Pro Leu Met Lys Lys
        115                 120                 125

Thr Glu Thr Tyr Gln Arg Ala Cys Asn Asn Pro Glu Ile His Gly Phe
    130                 135                 140

-continued

```
Glu Gly Pro Ile Lys Val Ser Phe Gly Asn Tyr Thr Tyr Pro Val Cys
145                 150                 155                 160

Gln Asp Phe Leu Arg Ala Thr Glu Ser Gln Gly Ile Pro Tyr Val Asp
                165                 170                 175

Asp Leu Glu Asp Leu Val Thr Ala His Gly Ala Glu His Trp Leu Lys
            180                 185                 190

Trp Ile Asn Arg Asp Thr Gly Arg Arg Ser Asp Ser Ala His Ala Phe
        195                 200                 205

Val His Ser Thr Met Arg Asn His Asp Asn Leu Tyr Leu Ile Cys Asn
    210                 215                 220

Thr Lys Val Asp Lys Ile Ile Val Glu Asp Gly Arg Ala Ala Ala Val
225                 230                 235                 240

Arg Thr Val Pro Ser Lys Pro Leu Asn Ala Lys Lys Pro Thr His Lys
                245                 250                 255

Val Tyr Arg Ala Arg Lys Gln Ile Val Leu Ser Cys Gly Thr Ile Ser
                260                 265                 270

Ser Pro Leu Val Leu Gln Arg Ser Gly Phe Gly Asp Pro Ile Lys Leu
            275                 280                 285

Arg Ala Ala Gly Val Lys Pro Leu Val Asn Leu Pro Gly Val Gly Arg
        290                 295                 300

Asn Phe Gln Asp His Tyr Cys Phe Phe Ser Pro Tyr Arg Ile Lys Pro
305                 310                 315                 320

Gln Tyr Glu Ser Phe Asp Asp Phe Val Arg Gly Asp Ala Asn Ile Gln
                325                 330                 335

Lys Lys Val Phe Asp Gln Trp Tyr Ala Asn Gly Thr Gly Pro Leu Ala
                340                 345                 350

Thr Asn Gly Ile Glu Ala Gly Val Lys Ile Arg Pro Thr Pro Glu Glu
            355                 360                 365

Leu Ser Gln Met Asp Glu Ser Phe Gln Glu Gly Tyr Arg Glu Tyr Phe
        370                 375                 380

Glu Asp Lys Pro Asp Lys Pro Val Met His Tyr Ser Ile Ile Ala Gly
385                 390                 395                 400

Phe Phe Gly Asp His Thr Lys Ile Pro Pro Gly Lys Tyr Met Thr Met
                405                 410                 415

Phe His Phe Leu Glu Tyr Pro Phe Ser Arg Gly Ser Ile His Ile Thr
                420                 425                 430

Ser Pro Asp Pro Tyr Ala Thr Pro Asp Phe Asp Pro Gly Phe Met Asn
            435                 440                 445

Asp Glu Arg Asp Met Ala Pro Met Val Trp Ser Tyr Lys Lys Ser Arg
450                 455                 460

Glu Thr Ala Arg Lys Met Asp His Phe Ala Gly Glu Val Thr Ser His
465                 470                 475                 480

His Pro Leu Phe Pro Tyr Ser Ser Glu Ala Arg Ala Tyr Glu Met Asp
                485                 490                 495

Leu Glu Thr Ser Asn Ala Tyr Gly Gly Pro Leu Asn Leu Thr Ala Gly
            500                 505                 510

Leu Ala His Gly Ser Trp Thr Gln Pro Leu Lys Lys Pro Ala Gly Arg
        515                 520                 525

Asn Glu Gly His Val Thr Ser Asn Gln Val Glu Leu His Pro Asp Ile
    530                 535                 540

Glu Tyr Asp Glu Glu Asp Asp Lys Ala Ile Glu Asn Tyr Ile Arg Glu
545                 550                 555                 560
```

| His | Thr | Glu | Thr | Thr | Trp | His | Cys | Leu | Gly | Thr | Cys | Ser | Ile | Gly | Pro |
|-----|-----|-----|-----|-----|-----|-----|-----|-----|-----|-----|-----|-----|-----|-----|-----|
|     |     |     |     | 565 |     |     |     |     | 570 |     |     |     |     | 575 |     |

Arg Glu Gly Ser Lys Ile Val Lys Trp Gly Gly Val Leu Asp His Arg
                580                 585                 590

Ser Asn Val Tyr Gly Val Lys Gly Leu Lys Val Gly Asp Leu Ser Val
            595                 600                 605

Cys Pro Asp Asn Val Gly Cys Asn Thr Tyr Thr Thr Ala Leu Leu Ile
        610                 615                 620

Gly Glu Lys Thr Ala Thr Leu Val Gly Glu Asp Leu Gly Tyr Thr Gly
625                 630                 635                 640

Glu Ala Leu Asp Met Thr Val Pro Gln Phe Lys Leu Gly Thr Tyr Glu
                645                 650                 655

Lys Thr Gly Leu Ala Arg Phe
            660

<210> SEQ ID NO 2
<211> LENGTH: 1992
<212> TYPE: DNA
<213> ORGANISM: Komagataella phaffii

<400> SEQUENCE: 2

```
atggctatcc ccgaagagtt tgatatccta gttctaggtg gtggatccag tggatcctgt      60
attgccggaa gattggcaaa cttggaccac tccttgaaag ttggtcttat cgaagcaggt     120
gagaacaacc tcaacaaccc atgggtctac cttccaggta tttacccaag aaacatgaag     180
ttggactcca agactgcttc cttctacact tctaacccat ctcctcactt gaatggtaga     240
agagccattg ttccatgtgc taacgtcttg ggtggtggtt cttctatcaa cttcatgatg     300
tacaccagag gttctgcttc tgattacgat gacttccaag ccgagggctg gaaaaccaag     360
gacttgcttc cattgatgaa aaagactgag acctaccaaa gagcttgcaa caaccctgac     420
attcacggtt cgaaggtcc aatcaaggtt tctttcggta actacaccta cccagtttgc     480
caggacttct tgagggcttc tgagtcccaa ggtattccat acgttgacga cttggaagac     540
ttggttactg ctcacggtgc tgaacactgg ttgaagtgga tcaacagaga cactggtcgt     600
cgttccgact ctgctcatgc atttgtccac tctactatga aaaccacga caacttgtac     660
ttgatctgta acacgaaggt cgacaaaatt attgtcgaag acggaagagc tgctgctgtt     720
agaaccgttc caagcaagcc tttgaaccca agaagccaa gtcacaagat ctaccgtgct     780
agaaagcaaa tcgttttgtc ttgtggtacc atctcctctc cattggtttt gcaaagatcc     840
ggttttggtg acccaatcaa gttgagagcc gctggtgtta agcctttggt caacttgcca     900
ggtgtcggaa gaaacttcca agaccactac tgtttcttca gtccttacag aatcaagcct     960
cagtacgagt ctttcgatga cttcgtccgt ggtgatgctg agattcaaaa gagagtcttt    1020
gaccaatggt acgccaatgg tactggtcct cttgccacta cggtatcga agctggtgtc    1080
aagatcagac aacaccaga gaactctct caaatggacg aatccttcca ggagggttac    1140
agagaatact tcgaagacaa gccagacaag ccagttatgc actactccat cattgctggt    1200
ttcttcggtg accacaccaa gattcctcct ggaaagtaca tgactatgtt ccacttcttg    1260
gaatacccat tctccagagg ttccattcac attacctccc cagacccata cgcagctcca    1320
gacttcgacc aggtttcat gaacgatgaa agagacatgg ctcctatggt ttgggcttac    1380
aagaagtcta gagaaaccgc tagaagaatg gaccactttg ccggtgaggt cacttctcac    1440
caccctctgt tcccatactc atccgaggcc agagccttgg aaatggattt ggagaccctct    1500
```

```
aatgcctacg gtggaccttt gaacttgtct gctggtcttg ctcacggttc ttggactcaa    1560
cctttgaaga agccaactgc aaagaacgaa ggccacgtta cttcgaacca ggtcgagctt    1620
catccagaca tcgagtacga tgaggaggat gacaaggcca ttgagaacta cattcgtgag    1680
cacactgaga ccacatggca ctgtctggga acctgttcca tcggtccaag agaaggttcc    1740
aagatcgtca atggggtgg tgttttggac cacagatcca acgtttacgg agtcaagggc    1800
ttgaaggttg gtgacttgtc cgtgtgccca gacaatgttg ttgtaacac ctacaccacc    1860 gctcttttga tcggtgaaaa gactgccact ttggttggag aagatttagg atactctggt    1920
gaggccttag acatgactgt tcctcagttc aagttgggca cttacgagaa gaccggtctt    1980
gctagattct aa                                                        1992
```

<210> SEQ ID NO 3
<211> LENGTH: 663
<212> TYPE: PRT
<213> ORGANISM: Komagataella phaffii

<400> SEQUENCE: 3

```
Met Ala Ile Pro Glu Glu Phe Asp Ile Leu Val Leu Gly Gly Gly Ser
1               5                   10                  15

Ser Gly Ser Cys Ile Ala Gly Arg Leu Ala Asn Leu Asp His Ser Leu
            20                  25                  30

Lys Val Gly Leu Ile Glu Ala Gly Glu Asn Asn Leu Asn Asn Pro Trp
        35                  40                  45

Val Tyr Leu Pro Gly Ile Tyr Pro Arg Asn Met Lys Leu Asp Ser Lys
    50                  55                  60

Thr Ala Ser Phe Tyr Thr Ser Asn Pro Ser Pro His Leu Asn Gly Arg
65                  70                  75                  80

Arg Ala Ile Val Pro Cys Ala Asn Ile Leu Gly Gly Gly Ser Ser Ile
                85                  90                  95

Asn Phe Met Met Tyr Thr Arg Gly Ser Ala Ser Asp Tyr Asp Asp Phe
            100                 105                 110

Glu Ala Glu Gly Trp Lys Thr Lys Asp Leu Leu Pro Leu Met Lys Lys
        115                 120                 125

Thr Glu Thr Tyr Gln Arg Ala Cys Asn Asn Pro Glu Ile His Gly Phe
    130                 135                 140

Glu Gly Pro Ile Lys Val Ser Phe Gly Asn Tyr Thr Tyr Pro Val Cys
145                 150                 155                 160

Gln Asp Phe Leu Arg Ala Thr Glu Ser Gln Gly Ile Pro Tyr Val Asp
                165                 170                 175

Asp Leu Glu Asp Leu Val Thr Ala His Gly Ala Glu His Trp Leu Lys
            180                 185                 190

Trp Ile Asn Arg Asp Thr Gly Arg Arg Ser Asp Ser Ala His Ala Phe
        195                 200                 205

Val His Ser Thr Met Arg Asn His Asp Asn Leu Tyr Leu Ile Cys Asn
    210                 215                 220

Thr Lys Val Asp Lys Ile Ile Val Glu Asp Gly Arg Ala Ala Ala Val
225                 230                 235                 240

Arg Thr Val Pro Ser Lys Pro Leu Asn Ala Lys Lys Pro Thr His Lys
                245                 250                 255

Val Tyr Arg Ala Arg Lys Gln Ile Val Leu Ser Cys Gly Thr Ile Ser
            260                 265                 270
```

-continued

Ser Pro Leu Val Leu Gln Arg Ser Gly Phe Gly Asp Pro Ile Lys Leu
        275                 280                 285

Arg Ala Ala Gly Val Lys Pro Leu Val Asn Leu Pro Gly Val Gly Arg
    290                 295                 300

Asn Phe Gln Asp His Tyr Cys Phe Phe Ser Pro Tyr Arg Ile Lys Pro
305                 310                 315                 320

Gln Tyr Glu Ser Phe Asp Asp Phe Val Arg Gly Asp Ala Asn Ile Gln
                325                 330                 335

Lys Lys Val Phe Asp Gln Trp Tyr Ala Asn Gly Thr Gly Pro Leu Ala
                340                 345                 350

Thr Asn Gly Ile Glu Ala Gly Val Lys Ile Arg Pro Thr Pro Glu Glu
                355                 360                 365

Leu Ser Gln Met Asp Glu Ser Phe Gln Glu Gly Tyr Arg Glu Tyr Phe
            370                 375                 380

Glu Asp Lys Pro Asp Lys Pro Val Met His Tyr Ser Ile Ile Ala Gly
385                 390                 395                 400

Phe Phe Gly Asp His Thr Lys Ile Pro Pro Gly Lys Tyr Met Thr Met
                    405                 410                 415

Phe His Phe Leu Glu Tyr Pro Phe Ser Arg Gly Ser Ile His Ile Thr
                420                 425                 430

Ser Pro Asp Pro Tyr Ala Thr Pro Asp Phe Asp Pro Gly Phe Met Asn
        435                 440                 445

Asp Glu Arg Asp Met Ala Pro Met Val Trp Ser Tyr Lys Lys Ser Arg
450                 455                 460

Glu Thr Ala Arg Lys Met Asp His Phe Ala Gly Glu Val Thr Ser His
465                 470                 475                 480

His Pro Leu Phe Pro Tyr Ser Ser Glu Ala Arg Ala Tyr Glu Met Asp
                485                 490                 495

Leu Glu Thr Ser Asn Ala Tyr Gly Gly Pro Leu Asn Leu Thr Ala Gly
                500                 505                 510

Leu Ala His Gly Ser Trp Thr Gln Pro Leu Lys Lys Pro Ala Gly Arg
            515                 520                 525

Asn Glu Gly His Val Thr Ser Asn Gln Val Glu Leu His Pro Asp Ile
530                 535                 540

Glu Tyr Asp Glu Glu Asp Asp Lys Ala Ile Glu Asn Tyr Ile Arg Glu
545                 550                 555                 560

His Thr Glu Thr Thr Trp His Cys Leu Gly Thr Cys Ser Ile Gly Pro
                    565                 570                 575

Arg Glu Gly Ser Lys Ile Val Lys Trp Gly Gly Val Leu Asp His Arg
                580                 585                 590

Ser Asn Val Tyr Gly Val Lys Gly Leu Lys Val Gly Asp Leu Ser Val
                595                 600                 605

Cys Pro Asp Asn Val Gly Cys Asn Thr Tyr Thr Thr Ala Leu Leu Ile
610                 615                 620

Gly Glu Lys Thr Ala Thr Leu Val Gly Glu Asp Leu Gly Tyr Thr Gly
625                 630                 635                 640

Glu Ala Leu Asp Met Thr Val Pro Gln Phe Lys Leu Gly Thr Tyr Glu
                645                 650                 655

Lys Thr Gly Leu Ala Arg Phe
            660

<210> SEQ ID NO 4
<211> LENGTH: 1992

<212> TYPE: DNA
<213> ORGANISM: Komagataella phaffii

<400> SEQUENCE: 4

```
atggccattc ctgaagaatt cgatattctt gtcctgggtg gtggatccag tggatcctgt      60
attgccggaa gattggccaa cttgaccac tccttgaaag ttggtcttat cgaggctggt     120
gagaacaatc ttaacaaccc atgggtctac cttccaggta tttacccaag aaacatgaag    180
ttggactcca aaactgcttc tttctacacc tccaacccct tctctcattt gaatggtaga    240
agagctattg tcccatgtgc caacatcttg ggtggtggtt cttcgatcaa cttcatgatg    300
tacaccagag gttccgcttc tgattacgat gactttgaag ctgagggatg gaagaccaag    360
gatttgcttc cttttgatgaa gaagactgag acttaccaaa gagcttgcaa caaccctgaa    420
attcacggtt ttgaaggtcc aatcaaggtt tctttcggta actacactta cccagtttgt    480
caagacttct tgagagcaac tgaatcccaa ggtattccat acgttgacga cttggaagac    540
ttggtgactg ctcatggtgc tgaacactgg ctgaaatgga tcaacagaga cactggtcgt    600
cgttccgact tgctcatgc cttcgttcat tctacgatga aaaccacga caatctgtac      660
ttgatctgca acaccaaagt tgacaagatt attgttgaag acggaagagc tgctgctgtc    720
agaaccgttc caagtaaacc tttgaacgca agaagccaa ctcacaaggt ttatcgtgct     780
agaaagcaaa tcgttttgtc ttgtggtacc atctcttctc ctctggttct gcaaagatcc    840
ggttttggtg acccaatcaa attgagagcc gctggtgtta agcctttggt caacttgcca    900
ggtgttggaa gaaacttcca agaccactac tgcttcttct ctccttacag aattaagccc    960
caatacgagt ctttcgatga cttcgtacgt ggtgacgcta acattcaaaa gaaggtattc   1020
gaccaatggt acgctaacgg tactggtcca ttggccacca acggtattga agccggtgtc   1080
aagattagac caactccaga agaattatct cagatggacg agtccttcca agagggttac   1140
agagagtact tcgaagacaa accagacaag ccagttatgc actattccat cattgctggt   1200
ttcttcggtg accacaccaa gattccacct ggaaagtaca tgaccatgtt ccacttcttg   1260
gagtacccat tctccagagg ttctatccac atcacctctc cagacccata cgcaactcca   1320
gactttgacc caggtttcat gaacgatgaa agagacatgg ctcctatggt ctggtcttac   1380
aagaagtcca gagagactgc cagaaaaatg gaccactttg ctggtgaggt tacttcccac   1440
caccctctgt tcccatactc atccgaggcc agagcttacg agatggattt ggagacctcc   1500
aacgcctacg gtggaccact gaacttgact gctggtcttg ctcacggttc ttggactcag   1560
cctttgaaga agcctgctgg aagaaacgaa ggacatgtta cttccaacca agtcgagctt   1620
catccagaca ttgagtacga tgaggaggat gataaggcca ttgagaacta cattcgtgag   1680
cacactgaga ccacatggca ctgtctggga acctgttcca ttggtccaag agagggttcc   1740
aagatcgtca atggggtgg tgttttggat cacagatcta acgtttacgg agtcaagggc   1800
ctgaaggttg gtgacttgtc cgtctgtcca gacaatgttg ttgtaacac ctacaccacc    1860
gctctttga tcggtgaaaa gactgccacc ttggttggtg aagacttagg atacacaggt   1920
gaggccttag acatgactgt acctcagttc aagttgggca cttacgagaa gactggtctt   1980
gctagattct ag                                                        1992
```

<210> SEQ ID NO 5
<211> LENGTH: 1000
<212> TYPE: DNA
<213> ORGANISM: Komagataella phaffii

<400> SEQUENCE: 5

```
catgttggta ttgtgaaata gacgcagatc gggaacactg aaaaataaca gttattattc      60
gagatctaac atccaaagac gaaaggttga atgaaacctt tttgccatcc gacatccaca     120
ggtccattct cacacataag tgccaaacgc aacaggaggg gatacactag cagcagaccg     180
ttgcaaacgc aggacctcca ctcctcttct cctcaacacc cacttttgcc atcgaaaaac     240
cagcccagtt attgggcttg attggagctc gctcattcca attccttcta ttaggctact     300
aacaccatga ctttattagc ctgtctatcc tggccccct ggcgaggttc atgtttgttt      360
atttccgaat gcaacaagct ccgcattaca cccgaacatc actccagatg agggctttct     420
gagtgtgggg tcaaatagtt tcatgttccc caaatggccc aaaactgaca gtttaaacgc     480
tgtcttggaa cctaatatga caaaagcgtg atctcatcca agatgaacta agtttggttc     540
gttgaaatgc taacggccag ttggtcaaaa agaaacttcc aaaagtcggc ataccgtttg     600
tcttgtttgg tattgattga cgaatgctca aaaataatct cattaatgct tagcgcagtc     660
tctctatcgc ttctgaaccc cggtgcacct gtgccgaaac gcaaatgggg aaacacccgc     720
tttttggatg attatgcatt gtctccacat tgtatgcttc caagattctg gtgggaatac     780
tgctgatagc ctaacgttca tgatcaaaat ttaactgttc taaccoctac ttgacagcaa     840
tatataaaca gaaggaagct gccctgtctt aaaccttttt tttatcatca ttattagctt     900
actttcataa ttgcgactgg ttccaattga caagcttttg attttaacga cttttaacga     960
caacttgaga agatcaaaaa acaactaatt attcgaaacg                          1000
```

<210> SEQ ID NO 6
<211> LENGTH: 1000
<212> TYPE: DNA
<213> ORGANISM: Komagataella phaffii

<400> SEQUENCE: 6

```
gcttaaagga ctccatttcc taaaatttca agcagtcctc tcaactaaat ttttttccat      60
tcctctgcac ccagccctct tcatcaaccg tccagcctc tcaaaagtcc aatgtaagta     120
gcctgcaaat tcaggttaca acccctcaat tttccatcca agggcgatcc ttacaaagtt     180
aatatcgaac agcagagact aagcgagtca tcatcaccac ccaacgatgg tgaaaaactt     240
taagcataga ttgatggagg gtgtatgca cttggcggct gcattagagt ttgaaactat     300
ggggtaatac atcacatccg gaactgatcc gactccgaga tcatatgcaa agcacgtgat     360
gtaccccgta aactgctcgg attatcgttg caattcatcg tcttaaacag tacaagaaac     420
tttattcatg ggtcattgga ctctgatgag gggcacattt ccccaatgat ttttgggaa      480
agaaagccgt aagaggacag ttaagcgaaa gagacaagac aacgaacagc aaaagtgaca     540
gctgtcagct acctagtgga cagttgggag tttccaattg gttggttttg aattttacc      600
catgttgagt tgtccttgct ctccttgca acaatgcaa gttgataaga catcaccttc       660
caagataggc tatttttgtc gcataaattt ttgtctcgga gtgaaaccc cttttatgtg      720
aacagattac agaagcgtcc tacccttcac cggttgagat ggggagaaaa ttaagcgatg     780
aggagacgat tattggtata aaagaagcaa ccaaaatccc ttattgtcct tttctgatca     840
gcatcaaaga atattgtctt aaaacgggct tttaactaca ttgttcttac acattgcaaa     900
cctcttcctt ctatttcgga tcaactgtat tgactacatt gatctttttt aacgaagttt     960
acgacttact aaatccccac aaacaaatca actgagaaaa                          1000
```

<210> SEQ ID NO 7
<211> LENGTH: 1000
<212> TYPE: DNA
<213> ORGANISM: Komagataella pastoris

<400> SEQUENCE: 7

```
atatcgtgaa atagacccaa atccggacac tgtgaaataa acagttagt atgcgaaatc      60
taacatccaa gaacgagaaa ctaaataaga cattttgcca tccgacatct acaaaccaca    120
tcaccctcac acataagtgc caaaacgcag caggagggac acccagcagc agaagccgtg    180
tcgaacgcag gacctccact tctcttctcc tcaacatcca ctttcgttat tgaaaaccag    240
cctgcttaaa aaaactgatt ggagctcgct cattccagtc cccttttgtta ggctactaag    300
accacgactt tattagcctg tccattctgg ttcctggcga gacttattct tgtttgttta    360
ttttcgaatg caacaaagct ccgcattaca tccgaacatc actttagatg agggctttct    420
gagtgtgggg tcgaatagtt tcatgttccc ccaatggccc aaaactgaca ctttaaacgc    480
tgtcttcgaa cttaatatgg caaaagcgtg atctcatcca agacgaacta agtttggttc    540
gttgaaatgc taacggccag ttggtcaaaa agaaacttcc aaaagtcggc atatcgtttg    600
tcttgtttgg tattcataga cgaatgctca agaatattct cattaatgct tagcgcagtc    660
tctgtatcgc ttctggaccc cggtgcagtt gtgccgaaac gcaaatgggg aaacacccgc    720
ttttcggatg attatgcatt gtctccacat tgtatgcttc caagattctg gtgggaatac    780
tactgatagc ctaacgttca tgatcaatat caaactgttc taaccctac ttgaactgca     840
atatataaac aggaggaaac ttcccagtcg aaaaccttct ttcatcatca ttattagctt    900
actttcataa ttgtgactgg ttccaattga caagcttttg attctaacga cttttaacga    960
caatttgaga agatcaaaaa acaactaatt attcgaaacg                         1000
```

<210> SEQ ID NO 8
<211> LENGTH: 1000
<212> TYPE: DNA
<213> ORGANISM: Komagataella pastoris

<400> SEQUENCE: 8

```
gcttgcacga ctcagttacc tgaaaatttc agcctgtcct ctttaataaa atttcacccg     60
ttcctctgca tgtccactca gctctattca tctatccttg agccttctcg agcgtctaat    120
gaacagcctg cgaattcagg ttacaacccc tcatttttc gtctcggtcg atctctacaa    180
agtcaacagc caactttgat gttaagcgag tcatcaccag ccagcgatag tgaaaaactt    240
taagcataga ttgatggtgg gtttatgtca cttggcggct gcattagagt ttgaaactat    300
ggggtaatgc atcacatccg gaactgatcc gactcggaga tcatatgcaa accacgtgat    360
gtaccccgta aactgctcgg attactgttc caattcatcg tcttaaacag tataagaaac    420
ttattcatg ggtcattgga ctctgatgag gggcacattt ccccattgat ttttgggaca     480
gtaagccata aaaggactgt taagcgaagc agacaagaca acgaacagct agaataacaa    540
ctatctaccg ccttgtggac cgttgggagt ttccaattgg ttggttttgg atttctgagc    600
ccatgttgtg ttgtccatgc ttctccttgc acacaatgca agttgataag atatcacctt    660
ccaagatagg ctattttgt cgcataaatt ttggtctcag agtgaaaccc cctttatgt      720
gaacggatta gagaagcctc ctaccccttca ccggctgaga tggggagaaa ttaagcgatg    780
aggagacgat aattgctata aagaagcaa ccaaaacccc ttattgtctc tttctgatca     840
gcatcaaaga atattgtctt aaaacgggct tttaactaca ttgttcttac acattgcaaa    900
```

```
cctcctcctt caatttcgga tcagctgtat tgactacatt gatcttttt aacgaagttc    960
acgactact aaatccccat aaacaaacca actgagaaaa                          1000
```

<210> SEQ ID NO 9
<211> LENGTH: 663
<212> TYPE: PRT
<213> ORGANISM: Komagataella pastoris

<400> SEQUENCE: 9

```
Met Ala Ile Pro Glu Glu Phe Asp Ile Leu Val Leu Gly Gly Gly Ser
1               5                   10                  15

Ser Gly Ser Cys Ile Ala Gly Arg Leu Ala Asn Leu Asp His Ser Leu
            20                  25                  30

Lys Val Gly Leu Ile Glu Ala Gly Glu Asn Asn Leu Asn Asn Pro Trp
        35                  40                  45

Val Tyr Leu Pro Gly Ile Tyr Pro Arg Asn Met Lys Leu Asp Ser Lys
    50                  55                  60

Thr Ala Ser Phe Tyr Thr Ser Asn Pro Ser Pro His Leu Asn Gly Arg
65                  70                  75                  80

Arg Ala Ile Val Pro Cys Ala Asn Val Leu Gly Gly Ser Ser Ile
                85                  90                  95

Asn Phe Met Met Tyr Thr Arg Gly Ser Ala Ser Asp Tyr Asp Asp Phe
            100                 105                 110

Gln Ala Glu Gly Trp Lys Thr Lys Asp Leu Leu Pro Leu Met Lys Lys
        115                 120                 125

Thr Glu Thr Tyr Gln Arg Ala Cys Asn Asn Pro Asp Ile His Gly Phe
    130                 135                 140

Glu Gly Pro Ile Lys Val Ser Phe Gly Asn Tyr Thr Tyr Pro Val Cys
145                 150                 155                 160

Gln Asp Phe Leu Arg Ala Ser Glu Ser Gln Gly Ile Pro Tyr Val Asp
                165                 170                 175

Asp Leu Glu Asp Leu Val Thr Ala His Gly Ala Glu His Trp Leu Lys
            180                 185                 190

Trp Ile Asn Arg Asp Thr Gly Arg Arg Ser Asp Ser Ala His Ala Phe
        195                 200                 205

Val His Ser Thr Met Arg Asn His Asp Asn Leu Tyr Leu Ile Cys Asn
    210                 215                 220

Thr Lys Val Asp Lys Ile Ile Val Glu Asp Gly Arg Ala Ala Ala Val
225                 230                 235                 240

Arg Thr Val Pro Ser Lys Pro Leu Asn Pro Lys Lys Pro Ser His Lys
                245                 250                 255

Ile Tyr Arg Ala Arg Lys Gln Ile Val Leu Ser Cys Gly Thr Ile Ser
            260                 265                 270

Ser Pro Leu Val Leu Gln Arg Ser Gly Phe Gly Asp Pro Ile Lys Leu
        275                 280                 285

Arg Ala Ala Gly Val Lys Pro Leu Val Asn Leu Pro Gly Val Gly Arg
    290                 295                 300

Asn Phe Gln Asp His Tyr Cys Phe Phe Ser Pro Tyr Arg Ile Lys Pro
305                 310                 315                 320

Gln Tyr Glu Ser Phe Asp Asp Phe Val Arg Gly Asp Ala Glu Ile Gln
                325                 330                 335

Lys Arg Val Phe Asp Gln Trp Tyr Ala Asn Gly Thr Gly Pro Leu Ala
            340                 345                 350
```

```
            Thr Asn Gly Ile Glu Ala Gly Val Lys Ile Arg Pro Thr Pro Glu Glu
                    355                 360                 365
            Leu Ser Gln Met Asp Glu Ser Phe Gln Glu Gly Tyr Arg Glu Tyr Phe
                370                 375                 380
            Glu Asp Lys Pro Asp Lys Pro Val Met His Tyr Ser Ile Ile Ala Gly
            385                 390                 395                 400
            Phe Phe Gly Asp His Thr Lys Ile Pro Pro Gly Lys Tyr Met Thr Met
                            405                 410                 415
            Phe His Phe Leu Glu Tyr Pro Phe Ser Arg Gly Ser Ile His Ile Thr
                        420                 425                 430
            Ser Pro Asp Pro Tyr Ala Ala Pro Asp Phe Asp Pro Gly Phe Met Asn
                        435                 440                 445
            Asp Glu Arg Asp Met Ala Pro Met Val Trp Ala Tyr Lys Lys Ser Arg
            450                 455                 460
            Glu Thr Ala Arg Arg Met Asp His Phe Ala Gly Glu Val Thr Ser His
            465                 470                 475                 480
            His Pro Leu Phe Pro Tyr Ser Ser Glu Ala Arg Ala Leu Glu Met Asp
                            485                 490                 495
            Leu Glu Thr Ser Asn Ala Tyr Gly Gly Pro Leu Asn Leu Ser Ala Gly
                        500                 505                 510
            Leu Ala His Gly Ser Trp Thr Gln Pro Leu Lys Lys Pro Thr Ala Lys
                        515                 520                 525
            Asn Glu Gly His Val Thr Ser Asn Gln Val Glu Leu His Pro Asp Ile
                    530                 535                 540
            Glu Tyr Asp Glu Glu Asp Lys Ala Ile Glu Asn Tyr Ile Arg Glu
            545                 550                 555                 560
            His Thr Glu Thr Thr Trp His Cys Leu Gly Thr Cys Ser Ile Gly Pro
                            565                 570                 575
            Arg Glu Gly Ser Lys Ile Val Lys Trp Gly Val Leu Asp His Arg
                        580                 585                 590
            Ser Asn Val Tyr Gly Val Lys Gly Leu Lys Val Gly Asp Leu Ser Val
                    595                 600                 605
            Cys Pro Asp Asn Val Gly Cys Asn Thr Tyr Thr Ala Leu Leu Ile
            610                 615                 620
            Gly Glu Lys Thr Ala Thr Leu Val Gly Glu Asp Leu Gly Tyr Thr Gly
            625                 630                 635                 640
            Glu Ala Leu Asp Met Thr Val Pro Gln Phe Lys Leu Gly Thr Tyr Glu
                            645                 650                 655
            Lys Thr Gly Leu Ala Arg Phe
                        660

<210> SEQ ID NO 10
<211> LENGTH: 1992
<212> TYPE: DNA
<213> ORGANISM: Komagataella pastoris

<400> SEQUENCE: 10
atggctatcc ctgaagagtt tgatatcctt gttttaggtg gtggatccag tggatcctgt      60
attgccggaa gattggccaa cttggaccac tccttgaaag ttggtcttat cgaggcaggt     120
gagaacaacc tcaacaaccc atgggtttac cttccaggta tttacccaag aaacatgaag     180
ttggactcca agactgcatc cttctacact tctaaccctt ctcctcactt gaacggtaga     240
agagctattg ttccatgtgc taacgtcttg ggtggtggtt cttccattaa cttcatgatg     300
```

```
tacaccagag gttctgcttc tgattatgac gacttccaag ccgagggctg aaaaccaag    360
gacttgcttc cattgatgaa aaagaccgag acctaccaaa gagcttgcaa caaccctgac    420
attcacgggt tcgaaggtcc aatcaaggtt tctttcggta actacaccta cccagtttgc    480
caggacttct tgagagcttc tgaatcccaa ggtattccat acgttgacga cttggaagac    540
ttggttactg ctcacggtgc tgaacactgg ctgaaatgga tcaacagaga cactggtcgt    600
cgttccgact ccgctcatgc atttgtccac tctactatga aaaccacga caacttgtac     660
ttgatttgta acacaaaggt tgacaagatt attgtcgaag acggaagagc tgctgctgtt    720
agaactgttc caagcaagcc tttgaaccca aagaagccaa gtcacaagat ctaccgtgct    780
agaaagcaaa tcgttttgtc ttgtggtacc atctcatctc ctttggttct gcaaagatcc    840
ggtttcggtg acccaatcaa gttgagagcc gctggtgtta agcctttggt caacttgcct    900
ggtgtcggaa gaaacttcca agaccactac tgtttcttca gtccttacag aatcaagcct    960
cagtacgaat ctttcgatga cttcgtgcgt ggtgatgctg agatccaaaa gagagttttc   1020
gaccaatggt acgccaatgg tactggtcct cttgccacta cggtatcga agccggtgtc    1080
aagattagac caacaccaga ggaactgtct caaatggacg aatctttcca gaggggttac   1140
agagaatact tgaggacaa gccagacaag ccagttatgc actactccat tattgctggt   1200
ttcttcggtg accacaccaa gattcctcct ggaaagtaca tgaccatgtt ccacttttg   1260
gaataccat tctccagagg ttccattcac attacctctc cagatccata cgcagctcca   1320
gacttcgacc caggtttcat gaacgatgaa agagacatgg ctcctatggt ctgggcctac   1380
aagaagtcta gagagacagc tagaagaatg gaccactttg ccggtgaggt tacttctcac   1440
cacccattgt tcccatactc atccgaggcc agagctttgg agatggattt ggagacctcc   1500
aatgcctacg gtggaccttt gaacttgtct gctggtcttg cccacggttc ttggactcaa   1560
cctttgaaga agccaactgc aaagaacgaa ggccatgtta cctccaacca agtcgagctt   1620
catccagaca tcgagtacga cgaggaggac gacaaggcca ttgaaaacta catccgtgag   1680
cacactgaga ccacatggca ctgtctggga acctgttcca tcggtccaag agagggttcc   1740
aagatcgtca atggggtgg tgtttttggac cacagatcca acgtttacgg agtcaagggc   1800
ctgaaggttg gtgacttgtc tgtctgtcca gacaatgttg gttgtaacac ctacaccacc   1860
gctctttga tcggtgagaa gactgccact ttggttggag aagacttagg atacaccggt   1920
gaagccttag acatgactgt tcctcagttc aagttgggca cttacgagaa gaccggtctt   1980
gctagattct aa                                                       1992

<210> SEQ ID NO 11
<211> LENGTH: 663
<212> TYPE: PRT
<213> ORGANISM: Komagataella pastoris

<400> SEQUENCE: 11

Met Ala Ile Pro Glu Glu Phe Asp Ile Leu Val Leu Gly Gly Gly Ser
1               5                   10                  15

Ser Gly Ser Cys Ile Ala Gly Arg Leu Ala Asn Leu Asp His Ser Leu
            20                  25                  30

Lys Val Gly Leu Ile Glu Ala Gly Glu Asn Asn Leu Asn Asn Pro Trp
        35                  40                  45

Val Tyr Leu Pro Gly Ile Tyr Pro Arg Asn Met Lys Leu Asp Ser Lys
    50                  55                  60
```

```
Thr Ala Ser Phe Tyr Thr Ser Asn Pro Ser Pro His Leu Asn Gly Arg
 65                  70                  75                  80

Arg Ala Ile Val Pro Cys Ala Asn Ile Leu Gly Gly Gly Ser Ser Ile
             85                  90                  95

Asn Phe Met Met Tyr Thr Arg Gly Ser Ala Ser Asp Tyr Asp Asp Phe
            100                 105                 110

Glu Ala Glu Gly Trp Lys Thr Lys Asp Leu Leu Pro Leu Met Lys Lys
            115                 120                 125

Thr Glu Thr Tyr Gln Arg Ala Cys Asn Asn Pro Glu Ile His Gly Phe
            130                 135                 140

Glu Gly Pro Ile Lys Val Ser Phe Gly Asn Tyr Thr Tyr Pro Val Cys
145                 150                 155                 160

Gln Asp Phe Leu Arg Ala Thr Glu Ser Gln Gly Ile Pro Tyr Val Asp
                165                 170                 175

Asp Leu Glu Asp Leu Glu Thr Ala His Gly Ala Glu His Trp Leu Lys
            180                 185                 190

Trp Ile Asn Arg Asp Thr Gly Arg Arg Ser Asp Ser Ala His Ala Phe
            195                 200                 205

Val His Ser Thr Met Arg Asn His Asp Asn Leu Tyr Leu Ile Cys Asn
210                 215                 220

Thr Lys Val Asp Lys Ile Ile Val Glu Asp Gly Arg Ala Ala Gly Val
225                 230                 235                 240

Arg Thr Val Pro Ser Lys Pro Leu Asn Ala Lys Lys Pro Thr His Lys
                245                 250                 255

Val Tyr Arg Ala Arg Lys Gln Ile Val Leu Ser Cys Gly Thr Ile Ser
            260                 265                 270

Ser Pro Leu Val Leu Gln Arg Ser Gly Phe Gly Asp Pro Ile Lys Leu
            275                 280                 285

Arg Ala Ala Gly Val Lys Pro Leu Val Asn Leu Pro Gly Val Gly Arg
290                 295                 300

Asn Phe Gln Asp His Tyr Cys Phe Phe Ser Pro Tyr Arg Ile Lys Pro
305                 310                 315                 320

Gln Tyr Glu Ser Phe Asp Asp Phe Val Arg Gly Asp Ala Asn Ile Gln
                325                 330                 335

Lys Lys Val Phe Asp Gln Trp Tyr Ala Asn Gly Thr Gly Pro Leu Ala
            340                 345                 350

Thr Asn Gly Ile Glu Ala Gly Val Lys Ile Arg Pro Thr Pro Glu Glu
            355                 360                 365

Leu Ser Gln Met Asp Glu Ser Phe Gln Glu Gly Tyr Arg Glu Tyr Phe
            370                 375                 380

Glu Asp Lys Pro Asp Lys Pro Val Met His Tyr Ser Ile Ile Ala Gly
385                 390                 395                 400

Phe Phe Gly Asp His Thr Lys Ile Pro Pro Gly Lys Tyr Met Thr Met
                405                 410                 415

Phe His Phe Leu Glu Tyr Pro Phe Ser Arg Gly Ser Ile His Ile Thr
            420                 425                 430

Ser Pro Asp Pro Tyr Ala Thr Pro Asp Phe Asp Pro Gly Phe Met Asn
            435                 440                 445

Asp Glu Arg Asp Met Ala Pro Met Val Trp Ser Tyr Lys Lys Ser Arg
            450                 455                 460

Glu Thr Ala Arg Lys Met Asp His Phe Ala Gly Glu Val Thr Ser His
465                 470                 475                 480
```

His Pro Leu Phe Pro Tyr Ser Ser Glu Ala Arg Ala Tyr Glu Met Asp
            485                 490                 495

Leu Glu Thr Ser Asn Ala Tyr Gly Gly Pro Leu Asn Leu Thr Ala Gly
        500                 505                 510

Leu Ala His Gly Ser Trp Thr Gln Pro Leu Lys Lys Pro Ala Ala Arg
            515                 520                 525

Asn Glu Gly His Val Thr Ser Asn Gln Val Glu Leu His Pro Asp Ile
        530                 535                 540

Glu Tyr Asp Glu Glu Asp Lys Ala Ile Glu Asn Tyr Ile Arg Glu
545                 550                 555                 560

His Thr Glu Thr Thr Trp His Cys Leu Gly Thr Cys Ser Ile Gly Pro
                565                 570                 575

Arg Glu Gly Ser Lys Ile Val Lys Trp Gly Val Leu Asp His Arg
            580                 585                 590

Ser Asn Val Tyr Gly Val Lys Gly Leu Lys Val Gly Asp Leu Ser Val
        595                 600                 605

Cys Pro Asp Asn Val Gly Cys Asn Thr Tyr Thr Ala Leu Leu Ile
610                 615                 620

Gly Glu Lys Thr Ala Thr Leu Val Gly Glu Asp Leu Gly Tyr Thr Gly
625                 630                 635                 640

Asp Ala Leu Asp Met Thr Val Pro Gln Phe Lys Leu Gly Thr Tyr Glu
                645                 650                 655

Lys Thr Gly Leu Ala Arg Phe
            660

<210> SEQ ID NO 12
<211> LENGTH: 1992
<212> TYPE: DNA
<213> ORGANISM: Komagataella pastoris

<400> SEQUENCE: 12

```
atggctattc ctgaagaatt cgatattctt gtcctaggtg gtggatccag tggatcctgt      60
attgccggaa gattggccaa cttggaccac tctttgaaag ttggtcttat cgaggccggt     120
gagaacaatc ttaacaaccc tgggtctac cttccaggta tttacccaag aaacatgaaa     180
ttggactcca agaccgcttc tttctacacc tccaacccat ctcctcattt gaatggtaga     240
agagctattg tccatgtgc taacatcttg ggtggtggtt cttccatcaa cttcatgatg     300
tacaccagag gttccgcttc tgattacgat gacttcgaag ctgagggctg aaaaccaag     360
gatttgcttc ctttgatgaa gaagactgag acctaccaaa gagcttgcaa caaccctgag     420
atccacggtt tcgaaggtcc aatcaaggtt tctttcggta actacactta cccggttgt      480
caagacttct tgagagcaac tgaatcccaa ggtattccat acgttgacga cttggaagac     540
ttggagactg ctcatggtgc cgaacactgg ttgaaatgga tcaacagaga cactggtcgt     600
cgttccgact ctgctcatgc tttcgtccat tctactatga aaaccatga taacttgtac     660
ttgatctgca acaccaaggt tgacaagatt attgttgaag acggaagagc tgctggtgtc     720
agaaccgtcc caagtaaacc tttgaacgca aagaagccaa ctcacaaggt ttaccgtgct     780
agaaagcaga tcgttttgtc ttgtggtacc atttcttccc ctctggtttt gcaaagatcc     840
ggttttggtg atccaatcaa attgagagcc gctggtgtta agcctttggt caacttgcca     900
ggtgttggaa ggaacttcca ggaccattac tgcttcttct ctccttacag aatcaagccc     960
caatacgagt cttttgatga cttcgtccgt ggtgacgcta acatccaaaa gaaggtattc    1020
gaccaatggt acgctaacgg tactggtcca ttggccacca atggtattga agccggtgtc    1080
```

-continued

```
aagatcagac caactccaga ggaattatct caaatggacg agtcgttcca ggagggttac    1140
agagagtact ttgaagacaa accagacaaa ccagttatgc actattccat cattgctggt    1200
ttcttcggtg accacaccaa gattccgcct ggaaagtaca tgaccatgtt ccacttcttg    1260
gagtacccat tctccagagg ttctattcat atcacctctc cagacccata cgcaactcca    1320
gactttgacc caggtttcat gaatgatgaa agagacatgg ctcctatggt ttggtcttac    1380
aagaagtcca gagagactgc cagaaagatg gatcactttg ctggtgaggt tacttcccac    1440
caccctctgt tcccatactc atccgaggcc agagcttacg agatggactt ggagacctcc    1500
aacgcctacg gtggaccact gaacttgact gctggtcttg ctcacggttc ttggactcag    1560
cctttgaaga agcctgccgc aagaaacgaa ggacatgtta cctctaacca agttgagctt    1620
catccagaca ttgaatacga tgaggaggat gacaaggcca ttgagaacta catccgtgag    1680
cacactgaga ccacatggca ctgtctcgga acctgttcca tcggtccaag agaaggttcc    1740
aagatagtca atggggtgg tgttttggac cacagatcca acgtttacgg agtcaagggc    1800
ctgaaggttg gtgacttgtc tgtctgccca gacaatgttg gttgtaacac ctacaccacc    1860 gctctttttaa tcggtgaaaa gactgcaacc ttggtgggtg aagacttagg atacacaggt    1920
gatgccttag acatgactgt tcctcagttc aagttgggca cttacgagaa gactggtctt    1980
gctagattct ag                                                       1992
```

<210> SEQ ID NO 13
<211> LENGTH: 664
<212> TYPE: PRT
<213> ORGANISM: Ogataea methanolica

<400> SEQUENCE: 13

```
Met Ala Ile Pro Asp Glu Phe Asp Ile Ile Val Val Gly Gly Gly Ser
1               5                   10                  15

Thr Gly Cys Ala Leu Ala Gly Arg Leu Gly Asn Leu Asp Glu Asn Val
            20                  25                  30

Thr Val Ala Leu Ile Glu Gly Gly Glu Asn Asn Ile Asn Asn Pro Trp
        35                  40                  45

Val Tyr Leu Pro Gly Val Tyr Pro Arg Asn Met Arg Leu Asp Ser Lys
    50                  55                  60

Thr Ala Thr Phe Tyr Ser Ser Arg Pro Ser Pro His Leu Asn Gly Arg
65                  70                  75                  80

Arg Ala Ile Val Pro Cys Ala Asn Ile Leu Gly Gly Gly Ser Ser Ile
                85                  90                  95

Asn Phe Leu Met Tyr Thr Arg Ala Ser Ala Ser Asp Tyr Asp Asp Trp
            100                 105                 110

Glu Ser Glu Gly Trp Thr Thr Asp Glu Leu Leu Pro Leu Met Lys Lys
        115                 120                 125

Ile Glu Thr Tyr Gln Arg Pro Cys Asn Asn Arg Glu Leu His Gly Phe
    130                 135                 140

Asp Gly Pro Ile Lys Val Ser Phe Gly Asn Tyr Thr Tyr Pro Asn Gly
145                 150                 155                 160

Gln Asp Phe Ile Arg Ala Ala Glu Ser Gln Gly Ile Pro Phe Val Asp
                165                 170                 175

Asp Ala Glu Asp Leu Lys Cys Ser His Gly Ala Glu His Trp Leu Lys
            180                 185                 190

Trp Ile Asn Arg Asp Leu Gly Arg Ser Asp Ser Ala His Ala Tyr
        195                 200                 205
```

```
Ile His Pro Thr Met Arg Asn Lys Gln Asn Leu Phe Leu Ile Thr Ser
    210                 215                 220

Thr Lys Cys Glu Lys Ile Ile Glu Asn Gly Val Ala Thr Gly Val
225                 230                 235                 240

Lys Thr Val Pro Met Lys Pro Thr Gly Ser Pro Lys Thr Gln Val Ala
                245                 250                 255

Arg Thr Phe Lys Ala Arg Lys Gln Ile Ile Val Ser Cys Gly Thr Ile
                260                 265                 270

Ser Ser Pro Leu Val Leu Gln Arg Ser Gly Ile Gly Ser Ala His Lys
        275                 280                 285

Leu Arg Gln Val Gly Ile Lys Pro Ile Val Asp Leu Pro Gly Val Gly
    290                 295                 300

Met Asn Phe Gln Asp His Tyr Cys Phe Phe Thr Pro Tyr His Val Lys
305                 310                 315                 320

Pro Asp Thr Pro Ser Phe Asp Asp Phe Val Arg Gly Asp Lys Ala Val
                325                 330                 335

Gln Lys Ser Ala Phe Asp Gln Trp Tyr Ala Asn Lys Asp Gly Pro Leu
                340                 345                 350

Thr Thr Asn Gly Ile Glu Ala Gly Val Lys Ile Arg Pro Thr Glu Glu
        355                 360                 365

Glu Leu Ala Thr Ala Asp Asp Glu Phe Arg Ala Ala Tyr Asp Asp Tyr
    370                 375                 380

Phe Gly Asn Lys Pro Asp Lys Pro Leu Met His Tyr Ser Leu Ile Ser
385                 390                 395                 400

Gly Phe Phe Gly Asp His Thr Lys Ile Pro Asn Gly Lys Tyr Met Cys
                405                 410                 415

Met Phe His Phe Leu Glu Tyr Pro Phe Ser Arg Gly Phe Val His Val
                420                 425                 430

Val Ser Pro Asn Pro Tyr Asp Ala Pro Asp Phe Asp Pro Gly Phe Met
        435                 440                 445

Asn Asp Pro Arg Asp Met Trp Pro Met Val Trp Ser Tyr Lys Lys Ser
    450                 455                 460

Arg Glu Thr Ala Arg Arg Met Asp Cys Phe Ala Gly Glu Val Thr Ser
465                 470                 475                 480

His His Pro His Tyr Pro Tyr Asp Ser Pro Ala Arg Ala Ala Asp Met
                485                 490                 495

Asp Leu Glu Thr Thr Lys Ala Tyr Ala Gly Pro Asp His Phe Thr Ala
                500                 505                 510

Asn Leu Tyr His Gly Ser Trp Thr Val Pro Ile Glu Lys Pro Thr Pro
        515                 520                 525

Lys Asn Ala Ala His Val Thr Ser Asn Gln Val Glu Lys His Arg Asp
    530                 535                 540

Ile Glu Tyr Thr Lys Glu Asp Ala Ala Ile Glu Asp Tyr Ile Arg
545                 550                 555                 560

Glu His Thr Glu Thr Thr Trp His Cys Leu Gly Thr Cys Ser Met Ala
                565                 570                 575

Pro Arg Glu Gly Ser Lys Val Val Pro Thr Gly Gly Val Val Asp Ser
                580                 585                 590

Arg Leu Asn Val Tyr Gly Val Glu Lys Leu Lys Val Ala Asp Leu Ser
        595                 600                 605

Ile Cys Pro Asp Asn Val Gly Cys Asn Thr Tyr Ser Thr Ala Leu Leu
    610                 615                 620
```

```
Ile Gly Glu Lys Ala Ser Thr Leu Val Ala Glu Asp Leu Gly Tyr Ser
625                 630                 635                 640

Gly Asp Ala Leu Lys Met Thr Val Pro Asn Phe Lys Leu Gly Thr Tyr
            645                 650                 655

Glu Glu Ala Gly Leu Ala Arg Phe
            660

<210> SEQ ID NO 14
<211> LENGTH: 1995
<212> TYPE: DNA
<213> ORGANISM: Ogataea methanolica

<400> SEQUENCE: 14
atggctattc cagatgaatt tgatattatt gttgtcggtg gtggttccac cggttgtgct      60
cttgctggta gattaggtaa cttggacgaa aacgtcacag ttgctttaat cgaaggtggt     120
gaaaacaaca tcaacaaccc atgggtttac ttaccaggtg tttatccaag aaacatgaga     180
ttagactcaa agactgctac tttttactct tcaagaccat caccacactt gaacggtaga     240
agagctattg ttccatgtgc taacatcttg ggtggtggtt cttccatcaa cttcttgatg     300
tacaccagag cctctgcctc cgattacgat gattgggaat ctgaaggttg gactaccgat     360
gaattattac cactaatgaa gaagattgaa acttatcaaa gaccatgtaa cacagagaa      420 ttgcacggtt cgatggtcc aattaaggtt tcatttggta actatactta tccaaacggt      480
caagatttca ttagagctgc cgaatctcaa ggtattccat tgttgatga tgctgaagat      540 ttgaaatgtt cccacggtgc tgagcactgg ttgaagtgga tcaacagaga cttaggtaga     600
agatccgatt ctgctcatgc ttacattcac ccaaccatga gaaacaagca aaacttgttc     660
ttgattactt ccaccaagtg tgaaaagatt atcattgaaa acggtgttgc tactggtgtt     720
aagactgttc caatgaagcc aactggttct ccaaagaccc aagttgctag aactttcaag     780
gctagaaagc aaattattgt ttcttgtggt actatctcat caccattagt tttgcaaaga     840
tctggtatcg gttccgctca aagttgaga caagttggta ttaaaccaat tgttgactta     900
ccaggtgttg gtatgaactt ccaagatcac tactgtttct tcactccata ccatgtcaag     960
ccagatactc catcattcga tgactttgtt agaggtgata agctgttca aaaatctgct    1020 ttcgaccaat ggtatgctaa caaggatggt ccattaacca ctaatggtat tgaggcaggt    1080
gttaagatta gaccaactga agaagaatta gccactgctg atgacgaatt cagagctgct    1140
tatgatgact actttggtaa caagccagat aagccattaa tgcactactc tctaatttct    1200
ggtttctttg gtgaccacac caagattcca aacggtaagt acatgtgcat gttccacttc    1260
ttggaatatc cattctccag aggtttcgtt cacgttgttt ctccaaaccc atacgatgct    1320
cctgactttg atccaggttt catgaacgat ccaagagata tgtggccaat ggtttggtct    1380
tacaagaagt ccagagaaac tgccagaaga atggactgtt tgccggtga agttacttct    1440 caccacccac actacccata cgactcacca gccagctgct gacatgga cttgaaaact    1500 actaaagctt atgctggtcc agaccacttt actgctaact tgtaccacgg ttcatggact    1560
gttccaattg aaaagccaac tccaagaac gctgctcacg ttacttctaa ccaagttgaa    1620
aaacatcgtg acatcgaata caccaaggag gatgatgctc tatcgaaga ttacatcaga    1680 gaacacactg aaaccacatg gcattgtctt ggtacttgtt caatggctcc aagagaaggt    1740
tctaaggttg tcccaactgg tggtgttgtt gactccagat aaacgttta cggtgttgaa    1800 aagttgaagg ttgctgattt atcaatttgc ccagataatg ttggttgtaa cacttactct    1860
```

```
actgctttgt taatcggtga aaaggcttct accttagttg ctgaagactt gggctactct    1920
ggtgatgctt tgaagatgac tgttccaaac ttcaaattgg gtacttatga agaagctggt    1980
ctagctagat tctag                                                     1995
```

```
<210> SEQ ID NO 15
<211> LENGTH: 663
<212> TYPE: PRT
<213> ORGANISM: Ogataea methanolica

<400> SEQUENCE: 15
```

```
Met Ala Ile Pro Glu Glu Phe Asp Ile Ile Val Val Gly Gly Gly Ser
1               5                   10                  15

Ala Gly Cys Pro Thr Ala Gly Arg Leu Ala Asn Leu Asp Pro Asn Leu
            20                  25                  30

Thr Val Ala Leu Ile Glu Ala Gly Glu Asn Asn Ile Asn Asn Pro Trp
        35                  40                  45

Val Tyr Leu Pro Gly Val Tyr Pro Arg Asn Met Arg Leu Asp Ser Lys
    50                  55                  60

Thr Ala Thr Phe Tyr Ser Ser Arg Pro Ser Pro His Leu Asn Gly Arg
65                  70                  75                  80

Arg Ala Ile Val Pro Cys Ala Asn Ile Leu Gly Gly Gly Ser Ser Ile
                85                  90                  95

Asn Phe Met Met Tyr Thr Arg Gly Ser Ala Ser Asp Tyr Asp Asp Trp
            100                 105                 110

Glu Ser Glu Gly Trp Thr Thr Asp Glu Leu Leu Pro Leu Met Lys Arg
        115                 120                 125

Leu Glu Thr Tyr Gln Arg Pro Cys Asn Asn Pro Asp Leu His Gly Phe
    130                 135                 140

Asp Gly Pro Ile Lys Val Ser Phe Gly Asn Tyr Thr Tyr Pro Asn Cys
145                 150                 155                 160

Gln Asp Phe Leu Arg Ala Ala Glu Ser Gln Gly Ile Pro Phe Val Asp
                165                 170                 175

Asp Ala Glu Asp Leu Lys Thr Ser His Ala Ser Gln His Trp Leu Lys
            180                 185                 190

Trp Ile Asn Arg Asp Leu Gly Arg Arg Ser Asp Ala Ala His Ala Tyr
        195                 200                 205

Ile His Pro Thr Met Arg Asn Lys Ser Asn Leu Tyr Leu Ile Thr Ser
    210                 215                 220

Thr Lys Ala Asp Lys Val Ile Ile Glu Asp Gly Val Ala Ala Gly Ile
225                 230                 235                 240

Gln Val Val Pro Ser Lys Pro Leu Asn Pro Glu Lys Pro Ala Ala Lys
                245                 250                 255

Ile Tyr Lys Ala Arg Lys Gln Ile Ile Leu Ser Cys Gly Thr Ile Ser
            260                 265                 270

Thr Pro Leu Val Leu Gln Arg Ser Gly Ile Gly Ser Ala His Lys Leu
        275                 280                 285

Arg Gln Ala Gly Ile Lys Pro Ile Val Asp Leu Pro Gly Val Gly Met
    290                 295                 300

Asn Phe Gln Asp His Tyr Cys Phe Phe Thr Pro Tyr His Val Lys Pro
305                 310                 315                 320

Asp Thr Pro Ser Phe Asp Asp Phe Ala Arg Gly Asp Lys Ala Val Gln
                325                 330                 335

Lys Ser Ala Phe Asp Gln Trp Tyr Ala Asn Lys Asp Gly Pro Leu Thr
            340                 345                 350
```

```
Thr Asn Gly Ile Glu Ala Gly Val Lys Ile Arg Pro Thr Ala Glu Glu
        355                 360                 365

Leu Ala Thr Ala Asp Glu Asp Phe Gln Leu Gly Tyr Ala Ser Tyr Phe
    370                 375                 380

Glu Asn Lys Pro Asp Lys Pro Leu Met His Tyr Ser Leu Ile Ser Gly
385                 390                 395                 400

Phe Phe Gly Asp His Thr Lys Ile Pro Asn Gly Lys Tyr Met Thr Met
                405                 410                 415

Phe His Phe Leu Glu Tyr Pro Phe Ser Arg Gly Phe Val His Val Val
                420                 425                 430

Ser Pro Ser Pro Tyr Asp Ala Pro Asp Phe Asp Pro Gly Phe Met Asn
            435                 440                 445

Asp Pro Lys Asp Met Trp Pro Met Val Trp Ala Tyr Lys Met Ser Arg
        450                 455                 460

Glu Thr Ala Arg Arg Met Glu Cys Phe Ala Gly Glu Val Thr Ser His
465                 470                 475                 480

His Pro Lys Tyr Pro Tyr Asp Ser Pro Ala Arg Ala Lys Asp Leu Asp
                485                 490                 495

Leu Glu Thr Cys Lys Ala Tyr Ala Gly Pro Asp His Phe Thr Ala Asn
            500                 505                 510

Leu Tyr His Gly Ser Trp Thr Ile Pro Leu Glu Lys Pro Thr Pro Lys
        515                 520                 525

Asn Thr Ser His Val Thr Ser Asn Gln Val Glu Leu His Ala Gln Leu
    530                 535                 540

Glu Tyr Ser Lys Glu Asp Ile Ala Ile Glu Asn Tyr Ile Lys Glu
545                 550                 555                 560

His Val Glu Thr Thr Trp His Cys Leu Gly Thr Cys Ser Met Ala Pro
                565                 570                 575

Arg Glu Gly Ser Ser Ile Val Pro Thr Gly Val Val Asp Glu Arg
            580                 585                 590

Leu Asn Val Tyr Asp Val Ala His Leu Lys Cys Ala Asp Leu Ser Ile
        595                 600                 605

Cys Pro Asp Asn Val Gly Cys Asn Thr Tyr Ser Thr Ala Leu Leu Val
    610                 615                 620

Gly Glu Lys Ala Ser Met Ile Val Ala Glu Asp Leu Gly Tyr Ser Gly
625                 630                 635                 640

Ala Glu Leu Asp Met Thr Ile Pro Gly Phe Lys Leu Gly Thr Tyr Glu
                645                 650                 655

Ser Thr Gly Leu Gly Arg Phe
            660

<210> SEQ ID NO 16
<211> LENGTH: 1992
<212> TYPE: DNA
<213> ORGANISM: Ogataea methanolica

<400> SEQUENCE: 16
atggctattc ctgaagaatt cgatatcatt gttgtcggtg gtggttctgc cggctgtcct    60
actgctggta gattggctaa cttagaccca aatttaactg ttgctttaat cgaagctggt   120
gaaaacaaca ttaacaaccc atgggtctac ttaccaggcg tttacccaag aaacatgaga   180
ttagactcca aaactgcaac tttctactct tctagacctt ccccacattt aaatggtaga   240
agagctattg ttccatgtgc taatatctta ggtggtggtt cttcaattaa cttcatgatg   300
```

-continued

```
tacactagag gttcagcttc tgattatgat gactgggaat ccgaaggttg gactaccgat      360
gaattattgc cattgatgaa aagattagaa acttatcaaa gaccatgtaa caaccctgat      420
ttgcacggtt tcgacggccc tatcaaggtc tccttcggta actacactta tcctaactgt      480
caagatttct taagagccgc tgaatctcaa ggtattccat tgttgatga tgctgaagat       540 ttaaagactt ctcatgcttc ccaacactgg ctgaagtgga ttaacagaga cctgggtaga     600
agatctgatg ctgcgcatgc ttacattcac ccaactatga aaacaagtc aaacttatac      660 ttgatcactt ccactaaggc tgataaagtt ataattgaag atggagttgc agctggtatt     720
caagttgttc cttccaaacc attgaaccca gaaaagccgg ctgccaagat ctacaaggct     780
agaaagcaaa tcattctatc ctgtggtaca atttctaccc cgttggtcct acaaagatct    840
ggtattggct cagctcataa attaagacag gcaggcataa aaccgatcgt tgacttgcca     900
ggagttggta tgaacttcca agatcactac tgcttttca ccccatacca tgtcaagcca      960
gatactcctt cttttgatga ctttgccaga ggtgataagg ctgttcaaaa atcagctttt    1020
gatcaatggt atgctaacaa agatggtcct ttaaccacta cggtattga agctggtgtt    1080 aagattagac caactgctga gaactggct actgctgatg aagatttcca actaggctac    1140
gcttcttact ttgaaaacaa gccagataaa ccattgatgc attactcttt aatctctggt    1200
ttctttggtg atcacactaa gattccaaac ggtaaataca tgaccatgtt ccatttctta    1260
gaatacccat tctccagggg ttttgttcac gttgtttcgc caagcccata cgatgctcca    1320
gactttgacc caggtttcat gaacgaccca aaggacatgt ggccaatggt ttgggcttat   1380
aaaatgtcaa gagaaactgc tagaagaatg gaatgctttg ctggtgaagt tacttcccac    1440
catcctaaat atccatacga ttcacctgcc agagctaagg acttggactt ggaaacttgt    1500
aaagcttacg cgggtccaga tcactttact gcaaacttgt accacggttc gtggaccatt    1560
ccattggaga agccaactcc caagaacact tctcacgtta cttcgaatca gttgaatta    1620 catgctcaat tagaatattc taagaagat gacatcgcca tcgaaaacta tatcaaggaa    1680
cacgttgaaa ctacctggca ttgtcttggt acttgttcaa tggctccaag agaaggctca    1740
tcaattgtcc caacaggtgg tgttgttgat gaaagactaa acgtttatga tgttgctcac    1800
ttaaaatgtg ctgatttatc tatctgtcca gataatgtgg gttgtaacac ttactctact   1860
gcgttactgg ttggtgaaaa ggcttctatg attgttgctg aagatttagg ttactctgga   1920
gctgaattgg atatgaccat tcctggtttc aagttaggta cttacgaatc tactggatta   1980
ggtagattct aa                                                        1992
```

<210> SEQ ID NO 17
<211> LENGTH: 1000
<212> TYPE: DNA
<213> ORGANISM: Ogataea methanolica

<400> SEQUENCE: 17

```
gacaaagttt tgttaaatga ctatcgaaca agccatgaaa tagcacattt ctgccagtca      60
cttttaacac tttcctgctt gctggttgac tctcctcata caaacaccca aagggaaac     120 tttcagtgtg gggacacttg acatctcaca tgcaccccag attaatttcc ccagacgatg    180
cggagacaag acaaaacaac cctttgtcct gctcttttct ttctcacacc gcgtgggtgt    240
gtgcgcaggc aggcaggcag gcagcgggct gcctgccatc tctaatcgct gctcctcccc    300
cctggcttca aataacagcc tgctgctatc tgtgaccaga ttgggacacc cccctccct     360 ccgaatgatc catcacctt tgtcgtactc cgacaatgat ccttccctgt catcttctgg     420
```

```
caatcagctc cttcaataat taaatcaaat aagcataaat agtaaaatcg catacaaacg    480
tcatgaaaag ttttatctct atggccaacg gatagtctat ctgcttaatt ccatccactt    540
tgggaaccgt tctctcttta ccccagattc tcaaagctaa tatctgcccc ttgtctattg    600
tcctttctcc gtgtacaagc ggagcttttg cctcccatcc tcttgctttg tttcggttat    660 tttttttct tttgaaactc ttggtcaaat caaatcaaac aaaaccaaac cttctattcc    720
atcagatcaa ccttgttcaa cattctataa atcgatataa atataacctt atccctccct    780
tgttttttac caattaatca atcttcaaat ttcaaatatt ttctacttgc tttattactc    840
agtattaaca tttgtttaaa ccaactataa cttttaactg gctttagaag ttttatttaa    900
catcagtttc aatttacatc tttatttatt aacgaaatct ttacgaatta actcaatcaa    960
aacttttacg aaaaaaaaat cttactatta atttctcaaa                         1000

<210> SEQ ID NO 18
<211> LENGTH: 1000
<212> TYPE: DNA
<213> ORGANISM: Ogataea methanolica

<400> SEQUENCE: 18
cgaacttgcc cttgtggaat ttggttgtta atcaaactgt tctgtatttc atgtcatact     60
actattgata ttattaatgt tacttactca tctggccatt taacaggttt gaagctttaa    120
tgctcttaac taacagcaat ccatcaccgt caaccttaac cccctggtg cttgctgtct    180 ttatccttcg tatcttttc atgttgcacc gccctgttcc ttatacggtt gttcccccat    240
aggctaactt ctctgtttcc gaccatctct gcaataacaa agaattctat acgcttacac    300
tataatcata caatgactct catgccatt ttcactttac ttacttgcca tcggaagata    360
ctgaatcaga aagccatagt aactacataa cttcaaaaca cacccttttt acagattagt    420
tacaattttg tcaatgtttg tttgataacc caaggtggaa cgtttccagt tagacctgtt    480
taatccaact cactttacca ccccaaaact ttcctaccgt tagacaaata ctggctaaat    540
ctgacgaaaa caaccaatca acaattgaat ccactgggag gtatctctaa tccactgaca    600
aactttgcta aaacaagaaa aagtgggggc ctccgttgcg gagaagacgt gcgcaggctt    660
aaaaacacaa gagaacactt ggaagtaccc cagattttta gcttcctact attctgacac    720
cccctattca agcacgacgg tgattgattc attcaattt gctgctccaa tgataggata    780
aacccttttg gacttcaatc agacctctgt cctccatagc aatataaata ccttctagtt    840
gccccacttc ctctctcctg tactgcccca atgagtgact tattcaagtt actttctctc    900
ttttcctaac aattaaacaa gaagctttat tataacatta atatactatt ttataacagg    960
attgaaaatt atatttatct atctaaaact aaaattcaaa                         1000

<210> SEQ ID NO 19
<211> LENGTH: 664
<212> TYPE: PRT
<213> ORGANISM: Ogataea polymorpha

<400> SEQUENCE: 19

Met Ala Ile Pro Asp Glu Phe Asp Ile Ile Val Val Gly Gly Gly Ser
1               5                   10                  15

Thr Gly Cys Cys Ile Ala Gly Arg Leu Ala Asn Leu Asp Asp Gln Asn
                20                  25                  30

Leu Thr Val Ala Leu Ile Glu Gly Gly Glu Asn Asn Ile Asn Asn Pro
            35                  40                  45
```

```
Trp Val Tyr Leu Pro Gly Val Tyr Pro Arg Asn Met Arg Leu Asp Ser
     50                  55                  60

Lys Thr Ala Thr Phe Tyr Ser Ser Arg Pro Ser Lys Ala Leu Asn Gly
 65                  70                  75                  80

Arg Arg Ala Ile Val Pro Cys Ala Asn Ile Leu Gly Gly Gly Ser Ser
                 85                  90                  95

Ile Asn Phe Leu Met Tyr Thr Arg Ala Ser Ala Ser Asp Tyr Asp Asp
            100                 105                 110

Trp Glu Ser Glu Gly Trp Ser Thr Asp Glu Leu Leu Pro Leu Ile Lys
        115                 120                 125

Lys Ile Glu Thr Tyr Gln Arg Pro Cys Asn Asn Arg Asp Leu His Gly
130                 135                 140

Phe Asp Gly Pro Ile Lys Val Ser Phe Gly Asn Tyr Thr Tyr Pro Thr
145                 150                 155                 160

Cys Gln Asp Phe Leu Arg Ala Ala Glu Ser Gln Gly Ile Pro Val Val
                165                 170                 175

Asp Asp Leu Glu Asp Phe Lys Thr Ser His Gly Ala Glu His Trp Leu
            180                 185                 190

Lys Trp Ile Asn Arg Asp Leu Gly Arg Arg Ser Asp Ser Ala His Ala
        195                 200                 205

Tyr Val His Pro Thr Met Arg Asn Lys Gln Ser Leu Phe Leu Ile Thr
    210                 215                 220

Ser Thr Lys Cys Asp Lys Val Ile Ile Glu Asp Gly Lys Ala Val Ala
225                 230                 235                 240

Val Arg Thr Val Pro Met Lys Pro Leu Asn Pro Lys Lys Pro Val Ser
                245                 250                 255

Arg Thr Phe Arg Ala Arg Lys Gln Ile Val Ile Ser Cys Gly Thr Ile
            260                 265                 270

Ser Ser Pro Leu Val Leu Gln Arg Ser Gly Ile Gly Ala Ala His His
        275                 280                 285

Leu Arg Ser Val Gly Val Lys Pro Ile Val Asp Leu Pro Gly Val Gly
290                 295                 300

Glu Asn Phe Gln Asp His Tyr Cys Phe Phe Thr Pro Tyr Tyr Val Lys
305                 310                 315                 320

Pro Asp Val Pro Thr Phe Asp Asp Phe Val Arg Gly Asp Pro Val Ala
                325                 330                 335

Gln Lys Ala Ala Phe Asp Gln Trp Tyr Ser Asn Lys Asp Gly Pro Leu
            340                 345                 350

Thr Thr Asn Gly Ile Glu Ala Gly Val Lys Ile Arg Pro Thr Glu Glu
        355                 360                 365

Glu Leu Ala Thr Ala Asp Glu Asp Phe Arg Arg Gly Tyr Ala Glu Tyr
370                 375                 380

Phe Glu Asn Lys Pro Asp Lys Pro Leu Met His Tyr Ser Val Ile Ser
385                 390                 395                 400

Gly Phe Phe Gly Asp His Thr Lys Ile Pro Asn Gly Lys Phe Met Thr
                405                 410                 415

Met Phe His Phe Leu Glu Tyr Pro Phe Ser Arg Gly Phe Val Arg Ile
            420                 425                 430

Thr Ser Ala Asn Pro Tyr Asp Ala Pro Asp Phe Asp Pro Gly Phe Leu
        435                 440                 445

Asn Asp Glu Arg Asp Leu Trp Pro Met Val Trp Ala Tyr Lys Lys Ser
450                 455                 460
```

```
Arg Glu Thr Ala Arg Arg Met Glu Ser Phe Ala Gly Glu Val Thr Ser
465                 470                 475                 480

His His Pro Leu Phe Lys Val Asp Ser Pro Ala Arg Ala Arg Asp Leu
                485                 490                 495

Asp Leu Glu Thr Cys Ser Ala Tyr Ala Gly Pro Lys His Leu Thr Ala
            500                 505                 510

Asn Leu Tyr His Gly Ser Trp Thr Val Pro Ile Asp Lys Pro Thr Pro
            515                 520                 525

Lys Asn Asp Phe His Val Thr Ser Asn Gln Val Gln Leu His Ser Asp
            530                 535                 540

Ile Glu Tyr Thr Glu Glu Asp Asp Glu Ala Ile Val Asn Tyr Ile Lys
545                 550                 555                 560

Glu His Thr Glu Thr Thr Trp His Cys Leu Gly Thr Cys Ser Met Ala
                565                 570                 575

Pro Arg Glu Gly Ser Lys Ile Ala Pro Lys Gly Val Leu Asp Ala
            580                 585                 590

Arg Leu Asn Val Tyr Gly Val Gln Asn Leu Lys Val Ala Asp Leu Ser
            595                 600                 605

Val Cys Pro Asp Asn Val Gly Cys Asn Thr Tyr Ser Thr Ala Leu Thr
610                 615                 620

Ile Gly Glu Lys Ala Ala Thr Leu Val Ala Glu Asp Leu Gly Tyr Ser
625                 630                 635                 640

Gly Ser Asp Leu Asp Met Thr Ile Pro Asn Phe Arg Leu Gly Thr Tyr
                645                 650                 655

Glu Glu Thr Gly Leu Ala Arg Phe
            660
```

<210> SEQ ID NO 20
<211> LENGTH: 1995
<212> TYPE: DNA
<213> ORGANISM: Ogataea polymorpha

<400> SEQUENCE: 20

```
atggccattc ctgacgaatt cgatatcatt gttgttggtg gaggttccac cggctgctgc        60
attgcgggca gactcgcaaa cctcgacgac caaaacctca cagttgccct gatcgagggt       120
ggtgagaaca acatcaacaa cccttgggtc taccttcccg gagtgtatcc tagaaacatg       180
agactcgact ccaagacggc caccttctac tcgtccagac catcgaaggc tctgaacggc       240
agaagagcga tcgttccttg cgccaacatc cttggaggcg gctcgtcgat caactttctg       300
atgtacacca gagcctctgc ttccgactac gacgactggg agtccgaggg atggagcacc       360
gacgagttgc tacctctgat caaaaaaatc gaaacttacc agcgtccttg caacaacaga       420
gatctgcacg gctttgacgg cccaatcaag gtttcctttg aaaactacac gtatcctacg       480
tgccaggact tcctgagagc agcagagtcg cagggaattc ctgttgtgga cgacctggag       540
gacttcaaga catcgcatgg tgcagagcac tggctgaagt ggattaacag agacctgggc       600
agaagatcgg attctgcgca cgcctacgtc cacccaacta tgagaaacaa gcagagcctg       660
ttcctcatca cctccaccaa gtgtgacaag gtgatcatcg aggacggcaa ggctgtggcc       720
gtgagaacag tgccaatgaa gcctctgaac cctaagaagc tgtgtccag aaccttcaga       780
gccagaaagc agattgtgat ctcctgcgga accatctcgt ctcctctggt gctccagaga       840
tctggtattg gtgcagctca ccacttgaga tccgtggggg tcaagccaat cgtcgacctg       900
ccaggtgtgg gtgagaattt ccaggaccac tactgtttct tcactccata ctacgtcaag       960
```

| | |
|---|---:|
| cctgacgttc ctacgttcga cgactttgtc aggggtgacc cagttgccca gaaggccgct | 1020 |
| ttcgaccagt ggtactccaa caaggacggt ccattgacca ccaacggtat tgaagccgga | 1080 |
| gtcaagatca gacctaccga agaggagctg gctaccgcgg acgaggactt cagacgcggc | 1140 |
| tacgcagagt acttcgagaa caagccagac aagcctctga tgcactactc tgtcatctcc | 1200 |
| ggcttctttg gagaccacac caagattcct aacggcaagt tcatgaccat gttccacttc | 1260 |
| ctggagtatc cattctccag aggatttgtt agaatcacct cggcaaaccc atacgacgct | 1320 |
| cctgacttcg atcccggctt cctcaatgac gaaagagacc tgtggcctat ggtctgggca | 1380 |
| tacaagaagt ccagagagac ggccagaaga atggagagct ttgcaggaga ggtcacctcg | 1440 |
| caccacccat tgttcaaggt tgactcgcca gccagagcca gagacctgga cctcgagaca | 1500 |
| tgcagtgcat atgccggtcc taagcacctc actgccaacc tgtaccacgg ctcgtggacc | 1560 |
| gttcctatcg acaagccaac gcctaagaac gatttccacg tgacctccaa ccaagtccaa | 1620 |
| ctgcactccg acatcgagta caccgaggag gacgacgagg ccatcgtcaa ctacattaag | 1680 |
| gaacacaccg agaccacttg gcactgtctg ggtacctgct cgatggcccc aagagagggt | 1740 |
| agtaagattg ctcctaaggg aggtgtcttg gacgccagac tgaacgttta cggagtccag | 1800 |
| aacctcaagg ttgcggacct ttctgtttgt cccgacaacg ttggatgcaa cacctactct | 1860 |
| actgcattga ccatcggtga gaaggctgcc actcttgttg ctgaagatct tggctactca | 1920 |
| ggctccgacc tggacatgac gattccaaac ttcagactcg gaacttacga ggagaccgga | 1980 |
| cttgccagat tctaa | 1995 |

<210> SEQ ID NO 21
<211> LENGTH: 1000
<212> TYPE: DNA
<213> ORGANISM: Ogataea polymorpha

<400> SEQUENCE: 21

| | |
|---|---:|
| gctgcagctt gcgatctcgg atggttttgg aatggaagaa ccgcgacatc tccaacagct | 60 |
| gggccgtgtt gagaatgagc cggacgtcgt tgaacgaggg ggccacaagc cggcgtttgc | 120 |
| tgatggcgcg cgctcgtcc tcgatgtaga aggccttttc cagaggcagt ctcgtgaaga | 180 |
| agttgccaac gctcggaacc agctgcacga gccgagacaa ttcgggggtg ccggctttgg | 240 |
| tcatttcaat gttgtcgtcg atgaggagtt caaggtcgtg gaagatttcc gcgtagcggc | 300 |
| gttttgcctc agagtttacc atgaggtcgt ccactgcaga gatgccgttg ctcttcaccg | 360 |
| cgtacaggac gaacggcgtg gccagcaggc ccttgatcca ttctatgagg ccatctcgac | 420 |
| ggtgttcctt gagtgcgtac tccactctgt agcgactgga catctcgaga ctgggcttgc | 480 |
| tgtgctggat gcaccaatta attgttgccg catgcatcct tgcaccgcaa gtttttaaaa | 540 |
| cccactcgct ttagccgtcg cgtaaaactt gtgaatctgg caactgaggg ggttctgcag | 600 |
| ccgcaaccga acttttcgct tcgaggacgc agctggatgg tgtcatgtga ggctctgttt | 660 |
| gctggcgtag cctacaacgt gaccttgcct aaccggacgc cgctaccac tgctgtctgt | 720 |
| gcctgctacc agaaaatcac cagagcagca gagggccgat gtggcaactg gtggggtgtc | 780 |
| ggacaggctg tttctccaca gtgcaaatgc gggtgaaccg gccagaaagt aaattcttat | 840 |
| gctaccgtgc agtgactccg acatccccag ttttgccct acttgatcac agatggggtc | 900 |
| agcgctgccg ctaagtgtac ccaaccgtcc ccacacggtc catctataaa tactgctgcc | 960 |
| agtgcacggt ggtgacatca atctaaagta caaaaacaaa | 1000 |

```
<210> SEQ ID NO 22
<211> LENGTH: 20
<212> TYPE: PRT
<213> ORGANISM: Artificial Sequence
<220> FEATURE:
<223> OTHER INFORMATION: Signal sequence
<220> FEATURE:
<221> NAME/KEY: MISC_FEATURE
<222> LOCATION: (3)..(3)
<223> OTHER INFORMATION: X at position 3 is either F or L
<220> FEATURE:
<221> NAME/KEY: MISC_FEATURE
<222> LOCATION: (16)..(16)
<223> OTHER INFORMATION: X at position 16 is either A or T

<400> SEQUENCE: 22

Met Lys Xaa Ser Thr Asn Leu Ile Leu Ala Ile Ala Ala Ala Ser Xaa
1               5                   10                  15

Val Val Ser Ala
            20

<210> SEQ ID NO 23
<211> LENGTH: 36
<212> TYPE: PRT
<213> ORGANISM: Artificial Sequence
<220> FEATURE:
<223> OTHER INFORMATION: Leader sequence
<220> FEATURE:
<221> NAME/KEY: MISC_FEATURE
<222> LOCATION: (3)..(3)
<223> OTHER INFORMATION: X at position 3 is either F or L
<220> FEATURE:
<221> NAME/KEY: MISC_FEATURE
<222> LOCATION: (16)..(16)
<223> OTHER INFORMATION: X at position 16 is either A or T

<400> SEQUENCE: 23

Met Lys Xaa Ser Thr Asn Leu Ile Leu Ala Ile Ala Ala Ala Ser Xaa
1               5                   10                  15

Val Val Ser Ala Ala Pro Val Ala Pro Ala Glu Glu Ala Ala Asn His
            20                  25                  30

Leu His Lys Arg
        35

<210> SEQ ID NO 24
<211> LENGTH: 85
<212> TYPE: PRT
<213> ORGANISM: Saccharomyces cerevisiae

<400> SEQUENCE: 24

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
            85

<210> SEQ ID NO 25
<211> LENGTH: 1991
```

<212> TYPE: DNA
<213> ORGANISM: Artificial Sequence
<220> FEATURE:
<223> OTHER INFORMATION: AOX1 split marker cassette 1

<400> SEQUENCE: 25

| | | | | | |
|---|---|---|---|---|---|
| agggtccaa | gtaagaagct | tcttgctgta | gaatttgggc | atatgtgctg | gtgacaaagg | 60 |
| catctctgcc | ttgagtttct | gacggcggga | cagcattctt | accggatata | taacaccaat | 120 |
| tgccagcacc | accaatctca | gaggtacccc | taacaaactt | aataaaatct | tgggtatcaa | 180 |
| cttcattaag | ctttgtagtt | tgcaagtact | tataaacaaa | attccgtaag | gtgtcgtctt | 240 |
| gaggctggga | cttgacaaac | tgccaaaatg | gcaacaaatc | tactggcttg | gccataattt | 300 |
| tgacattcga | gtcatcaaag | gtaaattcaa | ccggagactt | gtattcttta | ttgataactt | 360 |
| tctcatatag | gacattgtca | ggaacacgat | gaaaccagga | tgcccccaaa | tccaatgaga | 420 |
| ctgaggtttc | atgagtcgca | accaacctac | ctccaatacg | gtccctaccc | tctaaaatca | 480 |
| acgcattcac | gccattgctt | ttgagatcga | ctgcagcttt | gatgcctgaa | atcccagcgc | 540 |
| ctacaatgat | gacatttgga | tttggttgac | tcatgttggt | attgtgaaat | agacgcagat | 600 |
| cgggaacact | gaaaataac | agttattatt | cgagatctaa | catccaaaga | cgaaaggttg | 660 |
| aatgaaacct | ttttgccatc | cgacatccac | aggtccattc | tcacacataa | gtgccaaacg | 720 |
| caacaggagg | ggatacacta | gcagcagacc | gttgcaaacg | caggacctcc | actcctcttc | 780 |
| tcctcaacac | ccacttttgc | catcgaaaaa | ccagcccagt | tattgggctt | gattggagct | 840 |
| cgctcattcc | aattccttct | attaggctac | taacaccatg | actttattag | cctgtctatc | 900 |
| ctggcccccc | tggcgaggtt | catgtttgtt | tatttccgaa | tgcaacaagc | tccgcattac | 960 |
| acccgaacat | cactccagat | gagggctttc | tgagtgtggg | gtcagtacgc | tgcaggtcga | 1020 |
| caacccttaa | tataacttcg | tataatgtat | gctatacgaa | gttattaggt | ctagatcggt | 1080 |
| accgacatgg | aggcccagaa | taccctcctt | gacagtcttg | acgtgcgcag | ctcaggggca | 1140 |
| tgatgtgact | gtcgcccgta | catttagccc | atacatcccc | atgtataatc | atttgcatcc | 1200 |
| atacattttg | atggccgcac | ggcgcgaagc | aaaaattacg | gctcctcgct | gcagacctgc | 1260 |
| gagcagggaa | acgctcccct | cacagacgcg | ttgaattgtc | cccacgccgc | gcccctgtag | 1320 |
| agaaatataa | aaggttagga | tttgccactg | aggttcttct | ttcatatact | ccttttaaa | 1380 |
| atcttgctag | gatacagttc | tcacatcaca | tccgaacata | aacaaccatg | ggtaaggaaa | 1440 |
| agactcacgt | ttcgaggccg | cgattaaatt | ccaacatgga | tgctgattta | tatgggtata | 1500 |
| aatgggctcg | cgataatgtc | gggcaatcag | gtgcgacaat | ctatcgattg | tatgggaagc | 1560 |
| ccgatgcgcc | agagttgttt | ctgaaacatg | gcaaaggtag | cgttgccaat | gatgttacag | 1620 |
| atgagatggt | cagactaaac | tggctgacgg | aatttatgcc | tcttccgacc | atcaagcatt | 1680 |
| ttatccgtac | tcctgatgat | gcatggttac | tcaccactgc | gatccccggc | aaaacagcat | 1740 |
| tccaggtatt | agaagaatat | cctgattcag | gtgaaaatat | tgttgatgcg | ctggcagtgt | 1800 |
| tcctgcgccg | gttgcattcg | attcctgttt | gtaattgtcc | ttttaacagc | gatcgcgtat | 1860 |
| ttcgtctcgc | tcaggcgcaa | tcacgaatga | ataacggttt | ggttgatgcg | agtgattttg | 1920 |
| atgacgagcg | taatgctggg | cctgttgaac | aagtctggaa | agaaatgcat | aagcttttgc | 1980 |
| cattctcacc | g | | | | | 1991 |

<210> SEQ ID NO 26
<211> LENGTH: 1853
<212> TYPE: DNA

<213> ORGANISM: Artificial Sequence
<220> FEATURE:
<223> OTHER INFORMATION: AOX1 split marker cassette 2

<400> SEQUENCE: 26

```
aagcccgatg cgccagagtt gtttctgaaa catggcaaag gtagcgttgc caatgatgtt      60
acagatgaga tggtcagact aaactggctg acggaattta tgcctcttcc gaccatcaag     120
cattttatcc gtactcctga tgatgcatgg ttactcacca ctgcgatccc cggcaaaaca     180
gcattccagg tattagaaga atatcctgat tcaggtgaaa atattgttga tgcgctggca     240
gtgttcctgc gccggttgca ttcgattcct gtttgtaatt gtccttttaa cagcgatcgc     300
gtatttcgtc tcgctcaggc gcaatcacga atgaataacg gtttggttga tgcgagtgat     360
tttgatgacg agcgtaatgg ctggcctgtt gaacaagtct ggaaagaaat gcataagctt     420
ttgccattct caccggattc agtcgtcact catggtgatt tctcacttga taaccttatt     480
tttgacgagg ggaaattaat aggttgtatt gatgttggac gagtcggaat cgcagaccga     540
taccaggatc ttgccatcct atggaactgc ctcggtgagt tttctccttc attacagaaa     600
cggcttttc aaaaatatgg tattgataat cctgatatga ataaattgca gtttcatttg     660
atgctcgatg agttttttcta atcagtactg acaataaaaa gattcttgtt ttcaagaact     720
tgtcatttgt atagtttttt tatattgtag ttgttctatt ttaatcaaat gttagcgtga     780
tttatatttt ttttcgcctc gacatcatct gcccagatgc gaagttaagt gcgcagaaag     840
taatatcatg cgtcaatcgt atgtgaatgc tggtcgctat actggtacca ttcgagaacc     900
cttaatataa cttcgtataa tgtatgctat acgaagttat taggtgatat cagatccact     960
gccatttgcc tgagagatgc aggcttcatt tttgatactt ttttatttgt aacctatata    1020
gtataggatt ttttttgtca ttttgtttct tctcgtacga gcttgctcct gatcagccta    1080
tctcgcagct gatgaatatc ttgtggtagg ggtttgggaa aatcattcga gtttgatgtt    1140
tttcttggta tttcccactc ctcttcagag tacagaagat taagtgagac gttcgtttgt    1200
gcaagcttca acgatgccaa aagggtataa taagcgtcat ttgcagcatt gtgaagaaaa    1260
ctatgtggca agccaagcct gcgaagaatg tattttaagt ttgactttga tgtattcact    1320
tgattaagcc ataattctcg agtatctatg attggaagta tgggaatggt gatcccgca    1380
ttcttcagtg tcttgaggtc tcctatcaga ttatgcccaa ctaaagcaac cggaggagga    1440
gatttcatgg taaatttctc tgacttttgg tcatcagtag actcgaactg tgagactatc    1500
tcggttatga cagcagaaat gtccttcttg gagacagtaa atgaagtccc accaataaag    1560
aaatccttgt tatcaggaac aaacttcttg tttcgaactt tttcggtgcc ttgaactata    1620
aaatgtagag tggatatgtc gggtaggaat ggagcgggca atgcttacc ttctggacct    1680
tcaagaggta tgtagggttt gtagatactg atgccaactt cagtgacaac gttgctattt    1740
cgttcaaacc attccgaatc cagagaaatc aaagttgttt gtctactatt gatccaagcc    1800
agtgcggtct tgaaactgac aatagtgtgc tcgtgttttg aggtcatctt tgt           1853
```

<210> SEQ ID NO 27
<211> LENGTH: 2038
<212> TYPE: DNA
<213> ORGANISM: Artificial Sequence
<220> FEATURE:
<223> OTHER INFORMATION: AOX2 split marker cassette 1

<400> SEQUENCE: 27

```
gtacgggttt actgatttga catatcttgg tactaacgtt accaatggtg ttccaaataa    60
cgcagatgat gagcgtggtt gcattgctgg atttgacaac actggtttcg tgctgggaac   120
ttcatcctcg ttgtttaatc agtttattct gcaactgaat acgagtgatc tttcaggagc   180
aatttaccaa atcattgagc attttctgac tggacttagc gaagacgaag acgacattgc   240
tatctattcc cccaaccctt tctacaaaag tacgtatgca ggagtaggtg ccattgcgga   300
aaatgacacc ctttacttgg ttgatggtgg agaggataac caaaacgtcc ctctgcagcc   360
tctacttcaa aaggagcgtg acgttgatat catctttgcg tttgacaaca gtgcagacac   420
tgacctctct tggccaaacg gttcatcatt agtcaacacc tacatgagac agttttcttc   480
tcaagcaaat ggaacaacgt tcccttatgt acctgatacc accactttcc taaacttgaa   540
tctttcgagt aagccaacct tctttggttg tgatgctaga aatttgacag acattgttga   600
aggcacggat cacattcctc ccctggttgt ttatctggcc aatagacctt tctcgtattg   660
gagtaacact tcaactttca agttagacta ctctgaatcc gagaagagag gaatgatcca   720
aaacggtttt gaagtgtcgt ctcgtttgaa catgactatt gatgaagaat ggcgtacttg   780
tgttggatgt gcaatcattc gtagacagca ggagagatcc aatgcaacac aaacagagca   840
atgtagaaga tgttttgaga attattgttg gaacggtgat attgcacttt ccaccgaaga   900
tatcccccgtt aattttacca ctactggagc aaccaatgag gagaatgaca actccacttc   960
aatatcatcg gccaattcgg tagcaccttc caaactttgg taccaagcac cattgctgtt  1020
ggtcggcctt gtcgcattct tcatctagta cgtacgctgc aggtcgacaa cccttaatat  1080
aacttcgtat aatgtatgct atacgaagtt attaggtcta gatcggtacc gacatggagg  1140
cccagaatac cctccttgac agtcttgacg tgcgcagctc aggggcatga tgtgactgtc  1200
gcccgtacat ttagcccata catccccatg tataatcatt tgcatccata cattttgatg  1260
gccgcacggc gcgaagcaaa aattacggct cctcgctgca gacctgcgag cagggaaacg  1320
ctcccctcac agacgcgttg aattgtcccc acgccgcgcc cctgtagaga aatataaaag  1380
gttaggattt gccactgagg ttcttctttc atatacttcc tttaaaatc ttgctaggat  1440
acagttctca catcacatcc gaacataaac aaccatgggt aaggaaaaga ctcacgtttc  1500
gaggccgcga ttaaattcca acatggatgc tgatttatat gggtataaat gggctcgcga  1560
taatgtcggg caatcaggtg cgacaatcta tcgattgtat gggaagcccg atgcgccaga  1620
gttgtttctg aaacatggca aaggtagcgt tgccaatgat gttacagatg agatggtcag  1680
actaaactgg ctgacggaat ttatgcctct tccgaccatc aagcatttta tccgtactcc  1740
tgatgatgca tggttactca ccactgcgat ccccggcaaa acagcattcc aggtattaga  1800
agaatatcct gattcaggtg aaaatattgt tgatgcgctg gcagtgttcc tgcgccggtt  1860
gcattcgatt cctgtttgta attgtccttt aacagcgat cgcgtatttc gtctcgctca  1920
ggcgcaatca cgaatgaata acggtttggt tgatgcgagt gattttgatg acgagcgtaa  1980
tggctggcct gttgaacaag tctggaaaga atgcataag cttttgccat tctcaccg   2038
```

<210> SEQ ID NO 28
<211> LENGTH: 1944
<212> TYPE: DNA
<213> ORGANISM: Artificial Sequence
<220> FEATURE:
<223> OTHER INFORMATION: AOX2 split marker cassette 2

<400> SEQUENCE: 28

```
aagcccgatg cgccagagtt gtttctgaaa catggcaaag gtagcgttgc caatgatgtt      60
acagatgaga tggtcagact aaactggctg acggaattta tgcctcttcc gaccatcaag     120
cattttatcc gtactcctga tgatgcatgg ttactcacca ctgcgatccc cggcaaaaca     180
gcattccagg tattagaaga atatcctgat tcaggtaaaa atattgttga tgcgctggca     240
gtgttcctgc gccggttgca ttcgattcct gtttgtaatt gtccttttaa cagcgatcgc     300
gtatttcgtc tcgctcaggc gcaatcacga atgaataacg gtttggttga tgcgagtgat     360
tttgatgacg agcgtaatgg ctggcctgtt gaacaagtct ggaaagaaat gcataagctt     420
ttgccattct caccggattc agtcgtcact catggtgatt tctcacttga taaccttatt     480
tttgacgagg ggaaattaat aggttgtatt gatgttggac gagtcggaat cgcagaccga     540
taccaggatc ttgccatcct atggaactgc ctcggtgagt tttctccttc attacagaaa     600
cggctttttc aaaaatatgg tattgataat cctgatatga ataaattgca gtttcatttg     660
atgctcgatg agttttctta atcagtactg acaataaaaa gattcttgtt ttcaagaact     720
tgtcatttgt atagtttttt tatattgtag ttgttctatt ttaatcaaat gttagcgtga     780
tttatatttt ttttcgcctc gacatcatct gcccagatgc gaagttaagt gcgcagaaag     840
taatatcatg cgtcaatcgt atgtgaatgc tggtcgctat actggtacca ttcgagaacc     900
cttaatataa cttcgtataa tgtatgctat acgaagttat taggtgatat cagatccact     960
tcctcttacg gctttctttc ccaaaaaatc attggggaaa tgtgcccctc atcagagtcc    1020
aatgacccat gaataaagtt tcttgtactg tttaagacga tgaattgcaa cgataatccg    1080
agcagtttac ggggtacatc acgtgctttg catatgatct cggagtcgga tcagttccgg    1140
atgtgatgta ttaccccata gtttcaaact ctaatgcagc cgccaagtgc atacaccct     1200
ccatcaatct atgcttaaag tttttcacca tcgttgggtg gtgatgatga ctcgcttagt    1260
ctctgctgtt cgatattaac tttgtaagga tcgcccttgg atggaaaatt gaggggttgt    1320
aacctgaatt tgcaggctac ttacattgga cttttgagaa ggctggacgg ttgatgaaga    1380
gggctgggtg cagaggaatg gaaaaaaatt tagttgagag gactgcttga aattttagga    1440
aatggagtcc tttaagctga caaaacttca aggatgggga ttttcatgta gcttttttcat   1500
gccttcgaca agctaaagga aggtaattga ttctggataa atggatattt gatctgcttt    1560
agcagatgtc aaagttctac tagtgatagt ctggtatctc gtagccttca attgggcgta    1620
tcttactcga agtgttatat ttttagctga cgagacgaag aacgagagag tattgacaca    1680
ttcagaggta agacaatatg tcgtattatc aaaataagta tcgaacctct attaggagcc    1740
tactggctca aatgtgcaac cttagtggtg attgtctctg cttcttgatc acaatctgtc    1800
gtgtttgaga gtgccgatgt atgattttta gtaaatgttt ttcagaaaag gcgctaagta    1860
aataaccagt aagtaataaa taacgtaaaa gtgatttgaa tcataaaaga atcaagatag    1920
aggtcaaagc atagataatc cccc                                           1944
```

<210> SEQ ID NO 29
<211> LENGTH: 22
<212> TYPE: DNA
<213> ORGANISM: Artificial Sequence
<220> FEATURE:
<223> OTHER INFORMATION: Primer sequence

<400> SEQUENCE: 29

```
ggctggaaat agatgtaggg ag                                               22
```

<210> SEQ ID NO 30
<211> LENGTH: 21
<212> TYPE: DNA
<213> ORGANISM: Artificial Sequence
<220> FEATURE:
<223> OTHER INFORMATION: Primer sequence

<400> SEQUENCE: 30
tcgcatctcc gcaaatttct c                                       21

<210> SEQ ID NO 31
<211> LENGTH: 21
<212> TYPE: DNA
<213> ORGANISM: Artificial Sequence
<220> FEATURE:
<223> OTHER INFORMATION: Primer sequence

<400> SEQUENCE: 31
gatcccattc cctatccatg t                                       21

<210> SEQ ID NO 32
<211> LENGTH: 20
<212> TYPE: DNA
<213> ORGANISM: Artificial Sequence
<220> FEATURE:
<223> OTHER INFORMATION: Primer sequence

<400> SEQUENCE: 32 ctctccccccc tcgtaatctt                                        20

<210> SEQ ID NO 33
<211> LENGTH: 720
<212> TYPE: DNA
<213> ORGANISM: Artificial Sequence
<220> FEATURE:
<223> OTHER INFORMATION: enhanced green fluorescent protein (eGFP)

<400> SEQUENCE: 33
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 34
<211> LENGTH: 1830
<212> TYPE: DNA
<213> ORGANISM: Artificial Sequence
<220> FEATURE:
<223> OTHER INFORMATION: Human serum albumin (HSA) with its native
      secretion leader

<400> SEQUENCE: 34

```
atgaagtggg ttactttcat ctccttgttg ttcttgttct cctcagctta ctccagaggt    60
gttttcagaa gagatgctca caagtccgag gttgctcaca gattcaagga cttgggtgaa   120
gagaacttca aggctttggt tttgatcgct ttcgctcagt acttgcagca gtgtccattc   180
gaggaccacg ttaagttggt taacgaggtt actgagttcg ctaagacttg tgttgctgac   240
gaatccgctg agaactgtga taagtccttg cacactttgt tcggtgacaa gttgtgtact   300
gttgctactt tgagagaaac ttacggtgag atggctgact gttgtgctaa gcaagagcct   360
gagagaaacg agtgtttctt gcaacacaag gacgacaacc caaacttgcc aagattggtt   420
agaccagagg ttgacgttat gtgtactgct ttccacgaca cgaagagac tttcttgaag    480
aagtacttgt acgagatcgc tagaagacac ccatacttct acgctccaga gttgttgttc   540
ttcgctaaga gatacaaggc tgctttcact gagtgttgtc aggctgctga taaggctgct   600
tgtttgttgc aaagttgga cgagttgaga tgagggta aggcttcttc cgctaagcag      660
agattgaagt gtgcttcctt gcagaagttc ggagagagag cttttaaggc ttgggctgtt   720
gctagattgt cccagagatt cccaaaggct gagttcgctg aggtttccaa gttggttact   780
gacttgacta aggttcacac agagtgttgt cacggtgact tgttggaatg tgctgatgac   840
agagctgact ggctaagta catctgtgag aaccaggatt ccatctcctc caagttgaaa    900
gaatgttgtg agaagccttt gttggagaag tcccactgta tcgctgaggt tgaaaacgac   960
gaaatgccag ctgacttgcc atctttggct gctgacttcg ttgaatccaa ggacgtctgc  1020
aagaactacg ctgaggctaa ggacgttttc ttgggtatgt tcttgtatga gtacgctaga  1080
agacatccag actactccgt tgttttgttg ttgagattgg ctaagactta cgagactact  1140
ttggagaagt gttgtgctgc tgctgaccca catgagtgtt acgctaaggt tttcgacgag  1200
ttcaagccat ggttgaagga accacagaac ttgatcaagc agaactgtga gttgttcgag  1260
cagttgggtg agtacaagtt ccagaacgct ttgttggtta gatacactaa gaaggttcca  1320
caggtttcca ctccaacttt ggttgaggtt tccagaaact tgggtaaggt tggttccaag  1380
tgttgtaagc acccagaggc taagagaatg ccatgtgctg aggactactt gtctgttgtt  1440
ttgaaccagt tgtgtgtctt gcacgaaaag acaccagttt ccgacagagt tactaagtgt  1500
tgtactgaat ccttggttaa cagaagacct tgtttctccg ctttggaggt tgacgagact  1560
tacgttccaa agagttcaa cgctgagact ttcactttcc acgctgacat ctgtactttg   1620
tccgagaaag agagacagat caagaagcag actgctttgg ttgagttggt taagcacaag  1680
ccaaaggcta caaagagca gttgaaggct gttatggacg acttcgctgc tttcgttgag   1740
aaatgttgta aggctgacga caaagagact tgtttcgctg aagagggtaa gaagttggtt  1800
gctgcttccc aagctgcttt gggtctgtaa                                   1830
```

<210> SEQ ID NO 35
<211> LENGTH: 1056
<212> TYPE: DNA
<213> ORGANISM: Artificial Sequence
<220> FEATURE:
<223> OTHER INFORMATION: variable region of a camelid antibody (VHH)
      with the S. cerevisiae alpha-mating factor leader

<400> SEQUENCE: 35

```
atgagattcc catctatttt caccgctgtc ttgttcgctg cctcctctgc attggctgcc    60
cctgttaaca ctaccactga agacgagact gctcaaattc cagctgaagc agttatcggt   120
```

-continued

| | |
|---|---:|
| tactctgacc ttgagggtga tttcgacgtc gctgttttgc ctttctctaa ctccactaac | 180 |
| aacggtttgt tgttcattaa caccactatc gcttccattg ctgctaagga agagggtgtc | 240 |
| tctctcgaga agagacaagc cggtggttca ttaagattgt cctgtgctgc ctctggtaga | 300 |
| actttcactt ctttcgcaat gggttggttt agacaagcac ctggaaaaga gagagagttt | 360 |
| gttgcttcta tctccagatc cggtacttta actagatacg ctgactctgc caagggtaga | 420 |
| ttcactattt ctgttgacaa cgccaagaac actgtttctt tgcaaatgga caaccttaac | 480 |
| ccagatgaca ccgcagtcta ttactgtgcc gctgacttgc acagaccata cggtccagga | 540 |
| acccaaagat ccgatgagta cgattcttgg ggtcagggaa ctcaagtcac tgtctcttca | 600 |
| ggtggtggat ctggtggtgg aggttcaggt ggtggaggat ccggtggtgg tggttctggt | 660 |
| ggtggtggat ctggtggagg tgaagttcaa cttgtcgaat ccggtggtgc acttgtccaa | 720 |
| cctggtggat ctcttagact ttcttgtgcc gcctccggtt ttcctgttaa ccgttactct | 780 |
| atgcgttggt acagacaagc ccctggaaaa gaacgtgaat gggttgccgg aatgtcctca | 840 |
| gctggtgaca gatcctccta cgaagattct gtgaagggac gtttcaccat ctccagagat | 900 |
| gacgcccgta acaccgttta ccttcaaatg aactccctta gcctgagga tactgccgtc | 960 |
| tactattgta acgtgaatgt cggatttgaa tactggggac agggaaccca agttactgtc | 1020 |
| tcttccggtg acatcacca ccaccatcac taatag | 1056 |

<210> SEQ ID NO 36
<211> LENGTH: 991
<212> TYPE: DNA
<213> ORGANISM: Pichia pastoris

<400> SEQUENCE: 36

| | |
|---|---:|
| gcaaggcaac tgagaaattg aatagtggtt tcaagcccgc tgacttttg tattatctca | 60 |
| atgtcggtgt ttcacagtcc ccagaagggg gctttgcctt caagggagac ggaagagaca | 120 |
| tcgtcaaccc tggggagaag tatttcaaat ggcgcaagtt cgctaatttt tacgattaag | 180 |
| cagtgctgta tggggtagtt aataaatcgg gaatatcctt ctgacgtgac tgtaacaaat | 240 |
| ctctttttac gtggtgcgca tactggacag aggcagagtc tcaatttctt cttttgagac | 300 |
| aggctactac agcctgtgat tcctcttggt acttggattt gcttttatct ggctccgttg | 360 |
| ggaactgtgc ctgggttttg aagtatcttg tggatgtgtt tctaacactt tttcaatctt | 420 |
| cttggagtga gaatgcagga ctttgaacat cgtctagctc gttggtaggt gaaccgtttt | 480 |
| accttgcatg tggttaggag tttttctgga taaccaagac cgtcttatca tcgccgtaaa | 540 |
| atcgctctta ctgtcgctaa taatcccgct ggaagagaag ttcgaacaga agtagcacgc | 600 |
| aaagctcttg tcaaatgaga attgttaatc gtttgacagg tcacactcgt gggctatgta | 660 |
| cgatcaactt gccggctgtt gctggagaga tgacaccagt tgtggcatgg ccaattggta | 720 |
| ttcagccgta ccactgtatg gaaaatgaga ttatcttgtt cttgatctag tttcttgcca | 780 |
| ttttagagtt gccacattcg taggtttcag taccaataat ggtaacttcc aaacttccaa | 840 |
| cgcagatacc agagatctgc cgatccttcc ccaacaatag gagcttacta cgccatacat | 900 |
| atagcctatc tattttcact ttcgcgtggg tgcttctata taaacggttc cccatcttcc | 960 |
| gtttcatact acttgaattt taagcactaa a | 991 |

<210> SEQ ID NO 37
<211> LENGTH: 864
<212> TYPE: DNA

<213> ORGANISM: Pichia pastoris

<400> SEQUENCE: 37

```
cttttctttg ggcaaggaaa aatcaagaaa aagcagaggt taaagttttc aggggaatgg      60
caattgcttt atatatggga gaaagttaac tacgtcggtg ctgtaggcgt agagagcgac     120
tggagaatgc gtgatgaggt cgtctctttt cgccccccct tggcggggta aaaattgcac     180
tactgcagaa ttactacacc cctattccga ggagacggag tgcgacaaaa atggtaaagt     240
tcaccctagt ctgcgacttt taattgacgg acaccggcgt ttacatgcga aaaaaactaa     300
agtgcgcgca tttcacggcc gagggggtc ccacttggga ctgagagggg gtgggatctg      360
aaatcgagga ggtatcaaga ccccccgttt ctcaactccc taatcaaaaa ttacgaagtc     420
ctcgttggaa aggagttaaa ataattaagc ggggtcggac gccataccga ggttatcttg     480
caggcatttt actaatattg gaattcggag ctcaacttgc aaccaggcag ggtttagcta     540
tgtaatcaat gtaatcaata taataaagca ctaccacatc gaaggtttgg gagggaggcc     600
aatagtgtcc cccacagggt gctgatatcg cgattcttgg gtgaggagac acatatttca     660
ctcctctcac caaccaacca agcggctcct cgcaagatga tttatccgat tatccggaca     720
ctatactccc atccagtttg atgccgattt catcgattgt cctaaataat ccttaaatat     780
gtatagaacg gtaccctggg gttacataat ccttatttaa taatccctcc cccaccgctt     840
ttctttttt ttcttcttat tgtc                                             864
```

<210> SEQ ID NO 38
<211> LENGTH: 1000
<212> TYPE: DNA
<213> ORGANISM: Pichia pastoris

<400> SEQUENCE: 38

```
aaatggcaga aggatcagcc tggacgaagc aaccagttcc aactgctaag taaagaagat      60
gctagacgaa ggagacttca gaggtgaaaa gtttgcaaga agagagctgc gggaaataaa     120
ttttcaattt aaggacttga gtgcgtccat attcgtgtac gtgtccaact gttttccatt     180
acctaagaaa aacataaaga ttaaaaagat aaacccaatc gggaaacttt agcgtgccgt     240
tcggattcc gaaaaacttt tggagcgcca gatgactatg gaaagaggag tgtaccaaaa      300
tggcaagtcg ggggctactc accggatagc caatacattc tctaggaacc agggatgaat     360
ccaggttttt gttgtcacgg taggtcaagc attcacttct taggaatatc tcgttgaaag     420
ctacttgaaa tcccattggg tgcggaacca gcttctaatt aaatagttcg atgatgttct     480
ctaagtggga ctctacggct caaacttcta cacagcatca tcttagtagt cccttcccaa     540
aacaccattc taggtttcgg aacgtaacga acaatgttc ctctcttcac attgggccgt      600
tactctagcc ttccgaagaa ccaataaaag ggaccggctg aaacgggtgt ggaaactcct     660
gtccagttta tggcaaaggc tacagaaatc ccaatcttgt cgggatgttg ctcctcccaa     720
acgccatatt gtactgcagt tggtgcgcat tttagggaaa atttaccccca gatgtcctga    780
ttttcgaggg ctaccccccaa ctccctgtgc ttatacttag tctaattcta ttcagtgtgc    840
tgacctacac gtaatgatgt cgtaacccag ttaaatggcc gaaaaactat ttaagtaagt    900
ttatttctcc tccagatgag actctccttc ttttctccgc tagttatcaa actataaacc    960
tattttacct caaatacctc caacatcacc cacttaaaca                          1000
```

<210> SEQ ID NO 39
<211> LENGTH: 549

<212> TYPE: DNA
<213> ORGANISM: Pichia pastoris

<400> SEQUENCE: 39

```
aatgatataa acaacaattg agtgacaggt ctactttgtt ctcaaaaggc cataaccatc      60
tgtttgcatc tcttatcacc acaccatcct cctcatctgg ccttcaattg tggggaacaa     120
ctagcatccc aacaccagac taactccacc cagatgaaac cagttgtcgc ttaccagtca     180
atgaatgttg agctaacgtt ccttgaaact cgaatgatcc cagccttgct gcgtatcatc     240
cctccgctat tccgccgctt gctccaacca tgtttccgcc ttttcgaac aagttcaaat      300
acctatcttt ggcaggactt ttcctcctgc ctttttagc ctcaggtctc ggttagcctc      360
taggcaaatt ctggtcttca tacctatatc aacttttcat cagatagcct ttgggttcaa     420
aaaagaacta agcaggatg cctgatatat aaatcccaga tgatctgctt ttgaaactat      480
tttcagtatc ttgattcgtt tacttacaaa caactattgt tgattttatc tggagaataa     540
tcgaacaaa                                                             549
```

<210> SEQ ID NO 40
<211> LENGTH: 1000
<212> TYPE: DNA
<213> ORGANISM: Pichia pastoris

<400> SEQUENCE: 40

```
attactgttt tgggcaatcc tgttgataag acgcattcta gagttgtttc atgaaagggt      60
tacgggtgtt gattggtttg agatatgcca gaggacagat caatctgtgg tttgctaaac     120
tggaagtctg gtaaggactc tagcaagtcc gttactcaaa aagtcatacc aagtaagatt     180
acgtaacacc tgggcatgac tttctaagtt agcaagtcac caagagggtc ctatttaacg     240
tttggcggta tctgaaacac aagacttgcc tatcccatag tacatcatat tacctgtcaa     300
gctatgctac cccacagaaa tacccaaaa gttgaagtga aaaatgaaa attactggta      360
acttcacccc ataacaaact taataatttc tgtagccaat gaaagtaaac cccattcaat     420
gttccgagat ttagtatact tgcccctata agaaacgaag gatttcagct tccttacccc     480
atgaacagaa atcttccatt tacccccac tggagagatc cgcccaaacg aacagataat      540
agaaaaaga aattcggaca aatagaaac tttctcagcc aattaaagtc attccatgca       600
ctccctttag ctgccgttcc atcccttgt tgagcaacac catcgttagc cagtacgaaa      660
gaggaaactt aaccgatacc ttggagaaat ctaaggcgcg aatgagttta gcctagatat     720
ccttagtgaa gggttgttcc gatacttctc cacattcagt catagatggg cagctttgtt     780
atcatgaaga gacggaaacg ggcattaagg gttaaccgcc aaattatata aagacaacat     840
gtccccagtt taaagttttt ctttcctatt cttgtatcct gagtgaccgt tgtgtttaat     900
ataacaagtt cgttttaact taagaccaaa accagttaca acaaattata acccctctaa     960
acactaaagt tcactcttat caaactatca aacatcaaaa                          1000
```

<210> SEQ ID NO 41
<211> LENGTH: 1000
<212> TYPE: DNA
<213> ORGANISM: Pichia pastoris

<400> SEQUENCE: 41

```
gtcaactgcg tactcttttg tcgaatggac tactgaatct gcctcgatag ccactatagg      60
aaggtccata gaggccagtt tttcaactag tcttggtgga aagaaaccga caaagccttt     120
```

```
catggagtca ccgatactga aaggttcaaa caaagaatgc ttgggtagtc tcttaatacc    180
catggcaacg aaaaagggt cttcattgtt caacatgaat tcgtatccac ctttaatgta    240
gtcataaagc tgctgaagtt ccgaatcagt gatggaactg tctacagtga caatatagga   300
gttctcaatc accttatatc cagtcgaata tatctggata gggtcgggtc tcactgtgga   360
agattcaaat gggttagatc cctgtaattt cagcgatgga gactcagtat gatgggcaa    420
ggaaaacggc aattggatat tcaattggtc aagagatggt atcaaaagcg agtgtgccag   480
ggtagccacg gtagccactg atgctaatct gataattttc atttctggag tgtcaaaaca   540
gtagtgataa aaggctatga aggaggttgt ctaggggctc gcggaggaaa gtgattcaaa   600
cagacctgcc aaaagagaa aaaagaggga atccctgttc tttccaatgg aaatgacgta    660
actttaactt gaaaaatacc ccaaccagaa gggttcaaac tcaacaagga ttgcgtaatt   720
cctacaagta gcttagagct gggggagaga caactgaagg cagcttaacg ataacgcggg   780
gggattggtg cacgactcga aaggaggtat cttagtcttg taacctcttt tttccagagg   840
ctattcaaga ttcataggcg atatcgatgt ggagaagggt gaacaatata aaaggctgga   900
gagatgtcaa tgaagcagct ggatagattt caaattttct agatttcaga gtaatcgcac   960
aaaacgaagg aatcccacca agcaaaaaaa aaaatctaag                        1000
```

<210> SEQ ID NO 42
<211> LENGTH: 704
<212> TYPE: DNA
<213> ORGANISM: Pichia pastoris

<400> SEQUENCE: 42

```
aaattaatcc ataagataag gcaaatgtgc ttaagtaatt gaaaacagtg ttgtgattat    60
ataagcatgg tatttgaata gaactactgg ggttaactta tctagtagga tggaagttga   120
gggagatcaa gatgcttaaa gaaaaggatt ggccaatatg aaagccataa ttagcaatac   180
ttatttaatc agataattgt ggggcattgt gacttgactt ttaccaggac ttcaaacctc   240
aaccatttaa acagttatag aagacgtacc gtcacttttg cttttaatgt gatctaaatg   300
tgatcacatg aactcaaact aaaatgtatat cttttactgg acaaaaatgt tatcctgcaa   360
acagaaagct ttcttctatt ctaagaagaa catttacatt ggtgggaaac ctgaaaacag   420
aaaataaata ctccccagtg acccctatgag caggatttttt gcatccctat tgtaggcctt   480
tcaaactcac acctaatatt tcccgccact cacactatca atgatcactt cccagttctc   540
ttcttcccct attcgtacca tgcaaccct acacgccttt tccatttcgg ttcggatgcg    600
acttccagtc tgtgggggtac gtagcctatt ctcttagccg gtatttaaac atacaaattc   660
acccaaattc taccttgata aggtaattga ttaatttcat aaat                    704
```

<210> SEQ ID NO 43
<211> LENGTH: 1000
<212> TYPE: DNA
<213> ORGANISM: Pichia pastoris

<400> SEQUENCE: 43

```
agctcagatt ggaaatgatt tttgatccta ccaagaagcc tttgatttcc agaatctccg    60
ctaagtaagt aaccccccgca aacgcatgca tccatgcaaa caaatactaa caatttttag   120
ccccgttgtt gagaaaccca gaaaattgaa tgttcaacca atccagacga tcaataagaa   180
aaaaggccca aaggctactt ccaaacctgc tgccgccaaa cctgctcctt caaaagccgg   240
tcccaaggga ggtaagaagg tgagaaagcc aaagaagaca gttgaagaat tggatcagga   300
```

```
aatggctgac tactttgaaa ataagaatta gcccaacaaa atatgtacaa gtattatata    360
aatgaatcta catggtgtgt tttatttaga tcctccaaac caaggaaaga aactaaactt    420
atctccggac ttacgagtca ataaactatc cgcagttcct tggaactcag actttcttcc    480
ataagcggtc atatcatctt tggactgtgg aatcctgga cgaatctttg aaatgtcata     540
atcttgctct ctatctccaa gcacagcgtc cggtaaatgc tggttcttct ttctcagatg    600
aatcttggat ttaacaaata aagccgtgcc tatggctaat gtactcaaaa acaaagtctg    660
cttccagaat ttcgcaaacg atggaatgcc atttcctgta aatgtactca ttgaacctat    720
gtttgattaa agttggtgtg aagtcatcaa acgagagtaa aatcagatac tcgtgcaccg    780
gccaaaattg actgagctaa tctctgcagg cttgacatcc gaacacaaca aataggcgac    840
aaatcttaac tatctaatcg taggctatgg tagaactttg tggggtaga ggaagactac     900 aacagcaaga caaacaaaa gagtcatagt ttgactctct gcttttttct tctttctctt     960 cttttcttc ctccatattc gttatttatt tcgaactgga                          1000

<210> SEQ ID NO 44
<211> LENGTH: 1000
<212> TYPE: DNA
<213> ORGANISM: Pichia pastoris

<400> SEQUENCE: 44
cagccattaa tctcacctca gtttttgaat cagtagaatt tttaatgaaa caaacggttg     60
gtatattatt tgatagagtt gccaaatttc caaagataaa ttttcatca ggtaatatcc     120 tgaataccgt aacatagtga ctattggaag acactgctat catattatat ttcggataaa    180
aatccaaacc ccagaccgac ctcttgagtc tcaactccaa gtcagccgca actttaatta    240
tccgtggatt gggagctagt ttggacaacg catcagtata atataacttt acggttccat    300
tatcagacgc tattgcaaga acttcctttc cattgatctc gccaatgcgg cagtaattga    360
tatcgtaggg taggtctgga aagacgctgg cgcttgtgtc ccattctgca ggaatctctg    420
gcacggtgct aatggtagtt atccaacgga gctgaggtag tcgatatatc tggatatgcc    480
gcctatagga taaaaacagg agagggtgaa ccttgcttat ggctactaga ttgttcttgt    540
actctgaatt ctcattatgg gaaactaaac taatctcatc tgtgtgttgc agtactattg    600
aatcgttgta gtatctacct ggagggcatt ccatgaatta gtgagataac agagttgggt    660
aactagagag aataatagac gtatgcatga ttactacaca acggatgtcg cactcttcc     720 ttagttaaaa ctatcatcca atcacaagat gcgggctgga aagacttgct cccgaaggat    780
aatcttctgc ttctatctcc cttcctcata tggtttcgca gggctcatgc cccttcttcc    840
ttcgaactgc ccgatgagga agtccttagc ctatcaaaga attcgggacc atcatcgatt    900
tttagagcct tacctgatcg caatcaggat ttcactactc atataaatac atcgctcaaa    960
gctccaactt tgcttgttca tacaattctt gatattcaca                         1000

<210> SEQ ID NO 45
<211> LENGTH: 1000
<212> TYPE: DNA
<213> ORGANISM: Pichia pastoris

<400> SEQUENCE: 45
tggttccctc tcgtccaat accaaaaata ttatcaccat acaggtctcc cttcgatacc      60
agtgcaaagt tgaaccgtgg gattaccttg gaatctacaa aaatagtgtc actcacaagt    120
```

```
ttgtcatcaa ccacgctgcc gcttgcaaag gagaactgaa catgaaggtt gttagggttt        180
gttatattgg aataagtggt ggatttgttg aaggcgaacg caccaaagct acatccgtcc        240
tgagcacact gtgaatttgt cacggaattg accaagaggt cagacgatcc tgtatcccat        300
tgagccgtta tgctttgtgg gggaaaccct atttctatcg tactaagaaa accaatggtg        360
aactcatatt cggtatcaat ggcgacgatt ccagcatagc ctgtagacag taacaacact        420
agggcaacag caactaacat atcttcattg atgaaacgtt gtgatcggtg tgactttat         480 agtaaaagct acaactgttt gaaataccaa gatatcattg tgaatggctc aaaagggtaa        540
tacatctgaa aaacctgaag tgtggaaaat tccgatggag ccaactcatg ataacgcaga        600
agtcccattt tgccatcttc tcttggtatg aaacggtaga aaatgatccg agtatgccaa        660
ttgatactct tgattcatgc cctatagttt gcgtagggtt taattgatct cctggtctat        720
cgatctggga cgcaatgtag accccattag tggaaacact gaaagggatc caacactcta        780
ggcggacccg ctcacagtca tttcaggaca atcaccacag gaatcaacta cttctcccag        840
tcttccttgc gtgaagcttc aagcctacaa cataacactt cttacttaat ctttgattct        900
cgaattgttt acccaatctt gacaacttag cctaagcaat actctggggt tatatatagc        960
aattgctctt cctcgctgta gcgttcattc catctttcta                              1000
```

<210> SEQ ID NO 46
<211> LENGTH: 1001
<212> TYPE: DNA
<213> ORGANISM: Pichia pastoris

<400> SEQUENCE: 46

```
gatatcgatc tacacttaat agtagatgac gaggcatctc tccaataggt accatatctg         60
gtgtttcttg taatttaaga atctgttggt ctatgaatgt agatttgtca tgaacaatga        120
tatatgggtc aggaggacaa gatggttttct ctgagttggg ttgttgaggt gcctggcaag       180
acttcggagc gttgatatcc ccaagacttg tagtgaccga tagttgaagc gtgtgtttgc        240
aggaacggca catcaatgca actttcgtaa ctttggaatt gagagttgat gcactgatga        300
cgatacccga aattttgacg attttaccaa tatgacttga agacaagtct ctcattgaaa        360
ccttattatc gttactaagc aaaacgagct gacaagaagg gaaggtggtc ggtatttcct        420
cgttgttcaa atatatgatt ctcctggcaa tatctgtgat ggcctgttca aaaagtggaa        480
tcatttctgc aggatcatct accaactttt tattgagctc ctcattgaat acgattaagt        540
ggtcattttg aatcgtcagt aagtacttgt ttacaagtaa attctgtctg agttgttctc        600
tgtagatgta ctgattttcc atacgaaact ccaaaatgaa cgaacggaat gccttaatga        660
cctcactgaa ctggtcatcg ttctgttctc cgggaaggac acttgtgtta aagactgatg        720
ctctatcaaa ggacattgca acaaagtata acggttgtg agcgggaaaa agatgtgtag        780
gtaattgtcg tagatgagac tgattcagta gaaaacgcgt cctgcactat ttttttcttt        840
cttcattaca tttcctaatc gggacaaaat gaatctaaag acgtggttat gtagtacacg        900
catcgatagg ctatccccat accaaaacac tattttaccc catccttgac aggttataaa        960
tatgcgatag tatgagtatc ttcaaattca gctgaaatat c                           1001
```

<210> SEQ ID NO 47
<211> LENGTH: 1000
<212> TYPE: DNA
<213> ORGANISM: Pichia pastoris

<400> SEQUENCE: 47

```
aataaaaaaa cgttatagaa agaaattgga ctacgatatg ctccaatcca aattgtcaaa      60
attgaccacc gaaaagaac aattggaatt tgacaagagg aacaactcac tagattctca     120
aacggagcgt cacctagagt cagtttccaa gtcaattaca gaaagtttgg aaacagaaga    180
ggagtatcta caattgaatt ccaaacttaa agtcgagctg tccgaattca tgtcgctaag    240
gctttcttac ttggacccca ttttgaaag tttcattaaa gttcagtcaa aaattttcat     300
ggacatttat gacacattaa agagcggact accttatgtt gattctctat ccaagagga    360
ttatcagtcc aagatcttgg actctagaat agataacatt ctgtcgaaaa tggaagcgct    420
gaaccttcaa gcttacattg atgattagag caatgatata acaacaatt gagtgacagg    480
tctactttgt tctcaaaagg ccataaccat ctgtttgcat ctcttatcac cacaccatcc    540
tcctcatctg gccttcaatt gtggggaaca actagcatcc caacaccaga ctaactccac    600
ccagatgaaa ccagttgtcg cttaccagtc aatgaatgtt gagctaacgt tccttgaaac    660
tcgaatgatc ccagccttgc tgcgtatcat ccctccgcta ttccgccgct gctccaacc     720
atgtttccgc ttttttcgaa caagttcaaa tacctatctt tggcaggact tttcctcctg    780
ccttttttag cctcaggtct cggttagcct ctaggcaaat tctggtcttc ataccctatat   840
caacttttca tcagatagcc tttgggttca aaaaagaact aaagcaggat gcctgatata    900
taaatcccag atgatctgct tttgaaacta ttttcagtat cttgattcgt ttacttacaa    960
acaactattg ttgattttat ctggagaata atcgaacaaa                         1000
```

<210> SEQ ID NO 48
<211> LENGTH: 1000
<212> TYPE: DNA
<213> ORGANISM: Pichia pastoris

<400> SEQUENCE: 48

```
attgttgtga atactctcct tcatttggat ttcttggact tcggactctc ttgatctctc     60
ttcgaaagtt ttaactctgt tcatgtataa ttttacccgc tgtaggtcgc tcataatacc    120
atgagtatgc acatctttta ctccattaac tttcaggtat gcaaaataca atgaagatag    180
tatatagctc aaagaattta gcattttgca ttgatctaat tgtgacattt tctctatgat    240
atcatctagc ttcttaaact cgagaatctc gtccaacgag gcagaaacat tgtccagtct    300
tacgtcaaga ttattcacga gtttctggac cgtatcaacg ttttccatct taagattaca    360
gtaagtatcg tccttttgaa ctgcaaaggt agaaaagtta attttgatt tggtagtaca     420
ctatgaaact tgctcacccc aatctttcct cctgacaggt tgatctttat ccctctacta    480
aattgcccca agtgtatcaa gtagactaga tctcgcgaaa gaacagccta ataaactccg    540
aagcatgatg gcctctatcc ggaaaacgtt aagagatgtg gcaacaggag ggcacataga    600
atttttaaag acgctgaaga atgctatcat agtccgtaaa aatgtgatag tacttttgtt    660
agtgcgtacg ccacttattc ggggccaata gctaaaccca ggtttgctgg cagcaaattc    720
aactgtagat tgaatctctc taacaataat ggtgttcaat cccctggctg gtcacgggga    780
ggactatctt gcgtgatccg cttggaaaat gttgtgtatc cctttctcaa ttgcggaaag    840
catctgctac ttcccatagg caccagttac ccaattgata tttccaaaaa agattaccat    900
atgttcatct agaagtataa atacaagtgg acattcaatg aatatttcat tcaattagtc    960
attgacactt tcatcaactt actacgtctt attcaacaat                         1000
```

<210> SEQ ID NO 49
<211> LENGTH: 1000
<212> TYPE: DNA
<213> ORGANISM: Pichia pastoris

<400> SEQUENCE: 49

```
tatacggtct atccactttg gaaacgatgt agttgaaacg gggaagtaat agtggttccc      60
aaacgacatg aagaggttat ataagtttgc aagagggtga caccatttta gttgtggttc     120
ccgggtattt ttttaatctt tttagtctaa gatagcctcc ccagatatta ccgagttggg     180
ccatttgggg cggtatcggt ggtatctgat ggtagcgcgt ttttacatgc ctgtgcattg     240
aactggcaaa gagtatacta tcgtggggcc ctgaaggagg cagcaaatgg accgtcaatt     300
ggttgatcag ggactcaaga caggtattga gcttttcaaa caaaaagagt ataggcgctg     360
ctacaaggca tttacttcta ctatcaattt cattgagaat gatcccgagt tggccgccag     420
ctgtgtatct caactgatat ctctgttaga ttgtagggca gcctgtttgg aaaagctaga     480
tcaattgaat atggccttga agatggtct taaaatgatc aagagagagt gccacaactg     540
caagggttat ttgagaactt gcaaaatttt agacctacaa gggaagatca gtgaggcttt     600
gtctacagca agagaaggga tctccataat agaaactaga agagatcagg ataatcaatt     660
tagatattcc aaggttcttt tggaacaatt aaaggaactg aaaaatgcac tgaaaatcaa     720
attggacaag aaaaatcagc tacacttcaa agttttaaag tttgacgcac cagtgccttg     780
tacaaagaaa ctaagattag tcactccaag aacaatagat ccttccattt ttttgccgat     840
agagctagtg aagctgatct ttcgcctgtt gaatttctca gacatgtatg cctgtttatt     900
ggtctcaaca aaatggaact caattatatc ctcatcaccg gaactgtttc gaaaacttca     960
gttgaaatcc caactgtcca acaaggcgtt aaacaattgt                          1000
```

<210> SEQ ID NO 50
<211> LENGTH: 350
<212> TYPE: PRT
<213> ORGANISM: Komagataella phaffii

<400> SEQUENCE: 50

```
Met Ser Pro Thr Ile Pro Thr Thr Gln Lys Ala Val Ile Phe Glu Thr
1               5                   10                  15

Asn Gly Gly Pro Leu Glu Tyr Lys Asp Ile Pro Val Pro Lys Pro Lys
            20                  25                  30

Ser Asn Glu Leu Leu Ile Asn Val Lys Tyr Ser Gly Val Cys His Thr
        35                  40                  45

Asp Leu His Ala Trp Lys Gly Asp Trp Pro Leu Asp Asn Lys Leu Pro
    50                  55                  60

Leu Val Gly Gly His Glu Gly Ala Gly Val Val Val Ala Tyr Gly Glu
65                  70                  75                  80

Asn Val Thr Gly Trp Glu Ile Gly Asp Tyr Ala Gly Ile Lys Trp Leu
                85                  90                  95

Asn Gly Ser Cys Leu Asn Cys Glu Tyr Cys Ile Gln Gly Ala Glu Ser
            100                 105                 110

Ser Cys Ala Lys Ala Asp Leu Ser Gly Phe Thr His Asp Gly Ser Phe
        115                 120                 125

Gln Gln Tyr Ala Thr Ala Asp Ala Thr Gln Ala Ala Arg Ile Pro Lys
    130                 135                 140

Glu Ala Asp Leu Ala Glu Val Ala Pro Ile Leu Cys Ala Gly Ile Thr
145                 150                 155                 160
```

```
Val Tyr Lys Ala Leu Lys Thr Ala Asp Leu Arg Ile Gly Gln Trp Val
            165                 170                 175

Ala Ile Ser Gly Ala Gly Gly Leu Gly Ser Leu Ala Val Gln Tyr
        180                 185                 190

Ala Lys Ala Leu Gly Leu Arg Val Leu Gly Ile Asp Gly Gly Ala Asp
        195                 200                 205

Lys Gly Glu Phe Val Lys Ser Leu Gly Ala Glu Val Phe Val Asp Phe
        210                 215                 220

Thr Lys Thr Lys Asp Val Val Ala Glu Val Gln Lys Leu Thr Asn Gly
225                 230                 235                 240

Gly Pro His Gly Val Ile Asn Val Ser Val Ser Pro His Ala Ile Asn
            245                 250                 255

Gln Ser Val Gln Tyr Val Arg Thr Leu Gly Lys Val Val Leu Val Gly
            260                 265                 270

Leu Pro Ser Gly Ala Val Val Asn Ser Asp Val Phe Trp His Val Leu
            275                 280                 285

Lys Ser Ile Glu Ile Lys Gly Ser Tyr Val Gly Asn Arg Glu Asp Ser
        290                 295                 300

Ala Glu Ala Ile Asp Leu Phe Thr Arg Gly Leu Val Lys Ala Pro Ile
305                 310                 315                 320

Lys Ile Ile Gly Leu Ser Glu Leu Ala Lys Val Tyr Glu Gln Met Glu
            325                 330                 335

Ala Gly Ala Ile Ile Gly Arg Tyr Val Val Asp Thr Ser Lys
            340                 345                 350

<210> SEQ ID NO 51
<211> LENGTH: 1053
<212> TYPE: DNA
<213> ORGANISM: Komagataella phaffii

<400> SEQUENCE: 51
atgtctccaa ctatcccaac tacacaaaag gctgttatct tcgagaccaa cggcggtccc      60
ctagagtaca aggacattcc agtcccaaag ccaaagtcaa cgaactttt gatcaacgtt      120 aagtactccg gtgtctgtca cactgatttg cacgcctgga agggtgactg gccattggac      180
aacaagcttc ctttggttgg tggtcacgaa ggtgctggtg tcgttgtcgc ttacggtgag      240
aacgtcactg gatgggagat cggtgactac gctggtatca aatggttgaa cggttcttgt      300
ttgaactgtg agtactgtat ccaaggtgct gaatccagtt gtgccaaggc tgacctgtct      360
ggtttcaccc acgacggatc tttccagcag tatgctactg ctgatgccac ccaagccgcc      420
agaattccaa aggaggctga cttggctgaa gttgccccaa ttctgtgtgc tggtatcacc      480
gtttacaagg ctcttaagac cgctgacttg cgtattggcc aatgggttgc catttctggt      540
gctggtggag actgggttc tcttgccgtt caatacgcca aggctctggg tttgagagtt      600
ttgggtattg atggtggtgc cgacaagggt gaatttgtca agtccttggg tgctgaggtc      660
ttcgtcgact tcactaagac taaggacgtc gttgctgaag tccaaaagct caccaacggt      720
ggtccacacg gtgttattaa cgtctccgtt tccccacatg ctatcaacca atctgtccaa      780
tacgttagaa ctttgggtaa ggttgttttg gttggtctgc catctggtgc cgttgtcaac      840
tctgacgttt tctggcacgt tctgaagtcc atcgagatca agggatctta cgttggaaac      900
agagaggaca gtgccgaggc catcgacttg ttcaccagag gtttggtcaa ggctcctatc      960
```

```
aagattatcg gtctgtctga acttgctaag gtctacgaac agatggaggc tggtgccatc    1020
atcggtagat acgttgtgga cacttccaaa taa                                 1053
```

<210> SEQ ID NO 52
<211> LENGTH: 350
<212> TYPE: PRT
<213> ORGANISM: Komagataella pastoris

<400> SEQUENCE: 52

```
Met Ser Pro Thr Ile Pro Ser Thr Gln Lys Ala Val Val Phe Glu Thr
1               5                   10                  15

Asn Gly Gly Pro Leu Glu Tyr Lys Asp Ile Pro Val Pro Lys Pro Lys
            20                  25                  30

Ser Asn Glu Ile Leu Ile Asn Val Lys Tyr Ser Gly Val Cys His Thr
        35                  40                  45

Asp Leu His Ala Trp Lys Gly Asp Trp Pro Leu Asp Asn Lys Leu Pro
    50                  55                  60

Leu Val Gly Gly His Glu Gly Ala Gly Val Val Val Ala Leu Gly Glu
65                  70                  75                  80

Asn Val Thr Gly Trp Asn Ile Gly Asp Tyr Ala Gly Ile Lys Trp Leu
                85                  90                  95

Asn Gly Ser Cys Leu Asn Cys Glu Tyr Cys Ile Gln Gly Ala Glu Ser
            100                 105                 110

Ser Cys Ala Lys Ala Asp Leu Ser Gly Phe Thr His Asp Gly Ser Phe
        115                 120                 125

Gln Gln Tyr Ala Thr Ala Asp Ala Thr Gln Ala Ala Arg Ile Pro Lys
    130                 135                 140

Glu Val Asp Leu Ala Glu Val Ala Pro Ile Leu Cys Ala Gly Ile Thr
145                 150                 155                 160

Val Tyr Lys Ala Leu Lys Thr Ala Asp Leu Arg Ile Gly Gln Trp Val
                165                 170                 175

Ala Ile Ser Gly Ala Gly Gly Leu Gly Ser Leu Ala Val Gln Tyr
            180                 185                 190

Ala Lys Ala Leu Gly Leu Arg Val Leu Gly Ile Asp Gly Gly Ala Asp
        195                 200                 205

Lys Gly Glu Phe Val Lys Ser Leu Gly Ala Glu Val Tyr Val Asp Phe
    210                 215                 220

Thr Lys Thr Lys Asp Val Val Ala Glu Val Gln Lys Ala Thr Asn Gly
225                 230                 235                 240

Gly Pro His Gly Val Ile Asn Val Ser Val Ser Pro His Ala Ile Asn
                245                 250                 255

Gln Ser Val Gln Tyr Ala Arg Thr Leu Gly Lys Ile Val Leu Val Gly
            260                 265                 270

Leu Pro Ser Gly Ala Val Val Asn Ser Asp Val Phe Trp His Val Leu
        275                 280                 285

Lys Ser Ile Glu Ile Lys Gly Ser Tyr Val Gly Asn Arg Glu Asp Ser
    290                 295                 300

Ala Glu Ala Ile Asp Leu Phe Ala Arg Gly Leu Val Lys Ala Pro Ile
305                 310                 315                 320

Lys Ile Ile Gly Leu Ser Glu Leu Ala Lys Val Tyr Glu Gln Met Glu
                325                 330                 335

Ala Gly Ala Ile Ile Gly Arg Tyr Val Val Asp Thr Ser Lys
            340                 345                 350
```

<210> SEQ ID NO 53
<211> LENGTH: 1053
<212> TYPE: DNA
<213> ORGANISM: Komagataella pastoris

<400> SEQUENCE: 53

```
atgtctccaa ctatcccatc tacacaaaag gctgttgtct tcgagaccaa cggcggtcct        60
ctcgagtaca aggacatccc tgtcccaaag ccaaagtcca acgaaatctt gatcaacgtt       120
aagtactccg gtgtctgtca cactgacttg cacgcctgga agggtgactg gccattggac       180
aacaagcttc ctttggtcgg tggtcacgaa ggtgctggtg tcgttgtcgc tttaggtgag       240
aacgtcactg gatggaacat cggtgactac gctggtatca aatggttgaa cggttcttgt       300
ttgaactgtg agtactgtat ccaaggtgct gaatccagtt gtgccaaggc tgacctgtct       360
ggtttcaccc acgacggatc tttccagcag tatgctactg ctgatgccac ccaagccgcc       420
agaattccaa aggaagttga cttggctgaa gttgccccaa ttttgtgtgc tggtatcacc       480
gtttacaagg ctcttaagac cgctgacttg cgtatcggcc aatggttgc catttccggt       540
gctggtggag gattaggttc tcttgccgtt caatacgcca aggctctggg tttgagagtt       600
ttgggtattg atggtggtgc cgacaagggt gagttcgtca agtccttggg tgctgaggtc       660
tacgtcgact tcactaagac taaggacgtc gttgctgagg tccaaaaggc caccaacggt       720
ggtccacacg tgttatcaa cgtctccgtt tccccacatg ctatcaacca atctgtccaa       780
tacgctagaa ctttgggtaa gattgttttg gttggtctgc catctggtgc cgttgtcaac       840
tctgacgttt tctggcacgt tctgaagtcc atcgagatca agggatctta cgttggaaac       900
agagaggaca gtgccgaagc catcgacttg ttcgctagag gcttagtcaa ggctcctatt       960
aagattattg gtctgtccga acttgctaag gtctacgagc agatggaggc tggtgccatc      1020
atcggtagat acgttgtgga cacttccaaa taa                                   1053
```

<210> SEQ ID NO 54
<211> LENGTH: 349
<212> TYPE: PRT
<213> ORGANISM: Ogataea parapolymorpha

<400> SEQUENCE: 54

```
Met Thr Ser Ile Pro Lys Thr Gln Lys Ala Val Val Phe Glu Thr Asn
1               5                   10                  15

Gly Gly Pro Leu Leu Tyr Lys Asp Ile Pro Val Pro Gln Pro Lys Pro
            20                  25                  30

Asn Glu Ile Leu Val Asn Val Lys Tyr Ser Gly Val Cys His Thr Asp
        35                  40                  45

Leu His Ala Trp Lys Gly Asp Trp Pro Leu Thr Lys Leu Pro Leu
    50                  55                  60

Val Gly His Glu Gly Ala Gly Val Val Ala Lys Gly Ala Asn
65                  70                  75                  80

Val Thr Asn Phe Glu Ile Gly Asp Tyr Ala Gly Ile Lys Trp Leu Asn
                85                  90                  95

Gly Ser Cys Met Gly Cys Glu Phe Cys Gln Gln Gly Ala Glu Pro Asn
            100                 105                 110

Cys Pro Glu Ala Asp Leu Ser Gly Tyr Thr His Asp Gly Ser Phe Gln
        115                 120                 125

Gln Tyr Ala Thr Ala Asp Ala Val Gln Ala Ala Lys Ile Pro Lys Gly
    130                 135                 140
```

| | | | | | | | | | | | | | | |
|---|---|---|---|---|---|---|---|---|---|---|---|---|---|---|
|Thr|Asn|Leu|Ala|Asp|Val|Ala|Pro|Ile|Leu|Cys|Ala|Gly|Val|Thr|Val|
|145| | | | |150| | | | |155| | | | |160|

| | | | | | | | | | | | | |
|---|---|---|---|---|---|---|---|---|---|---|---|---|
|Tyr|Lys|Ala|Leu|Lys|Thr|Ala|Glu|Leu|Ser|Pro|Gly|Gln|Trp|Val|Ala|
| | | | |165| | | | |170| | | | |175| |

Ile Ser Gly Ala Gly Gly Leu Gly Ser Leu Ala Val Gln Tyr Ala
            180                 185                 190

Val Ala Met Gly Leu Arg Val Leu Gly Ile Asp Gly Gly Asp Glu Lys
        195                 200                 205

Ala Lys Leu Phe Glu Ser Leu Gly Gly Glu Val Phe Ile Asp Phe Thr
    210                 215                 220

Lys Glu Lys Asp Ile Val Gly Ala Val Gln Lys Ala Thr Asn Gly Gly
225                 230                 235                 240

Pro His Gly Val Ile Asn Val Ser Val Ser Pro Ala Ala Ile Ser Gln
                245                 250                 255

Ser Cys Gln Tyr Val Arg Thr Leu Gly Lys Val Val Leu Val Gly Leu
                260                 265                 270

Pro Ala Gly Ala Val Cys Glu Ser Pro Val Phe Glu His Val Ile Lys
            275                 280                 285

Ser Ile Gln Ile Arg Gly Ser Tyr Val Gly Asn Arg Gln Asp Thr Ala
    290                 295                 300

Glu Ser Ile Asp Phe Phe Val Arg Gly Lys Val Lys Ala Pro Ile Lys
305                 310                 315                 320

Val Val Gly Leu Ser Glu Leu Pro Lys Val Phe Glu Leu Met Glu Gln
                325                 330                 335

Gly Lys Ile Ala Gly Arg Tyr Val Leu Asp Thr Ser Lys
            340                 345

<210> SEQ ID NO 55
<211> LENGTH: 1050
<212> TYPE: DNA
<213> ORGANISM: Ogataea parapolymorpha

<400> SEQUENCE: 55

```
atgacttcca ttccaaagac tcaaaaggcc gttgttttcg agaccaacgg tggtcctctt    60
ctctacaagg acatccctgt tccacaacca aagccaaatg agattcttgt caacgtcaag   120
tactccggtg tttgccacac cgatctccac gcttggaagg gtgactggcc attggacacc   180
aaacttccac tggtcggtgg tcacgagggt gctggtgttg ttgttgctaa gggtgccaac   240
gttaccaact tgaaatcggt gactacgct ggtatcaaat ggttgaacgg ctcgtgcatg   300
ggttgtgagt tctgtcaaca aggtgcagag ccaaactgtc ctgaggccga cctttccggt   360
tacacgcacg acggttcttt ccaacaatac gccactgctg atgctgtcca ggctgccaag   420
attccaaagg gaactaacct ggctgacgtt gctccaattc tctgtgctgg tgtcactgtg   480
tacaaggcat tgaagactgc cgaattgagc ccaggccaat gggttgctat ctctggtgct   540
ggtggaggat tgggttctct tgccgttcaa tacgctgtcg ccatgggcct gagagtcctg   600
ggtatcgatg gtggtgacga aaaggctaag ctcttcgaga gcttgggcgg agaagtcttc   660
atcgatttca ccaaggaaaa ggacattgtc gagccgtcc agaaggcaac caacggtggt   720
ccacacggtg ttatcaacgt ttctgtgtct ccagcagcta tctctcaatc ctgccaatac   780
gtgagaactc ttggtaaggt tgttcttgtt ggtcttccag ccggtgctgt tgcgagtct   840
ccagttttcg agcacgttat caagtctatc cagattagag gttcctacgt tggtaacaga   900
caggacactg ccgagtcgat tgacttcttc gtcagaggca aggttaaggc tccaatcaag   960
```

```
gttgttggcc tttctgagct gccaaaggtg ttcgagttga tggagcaagg aaagattgct   1020
ggaagatacg ttcttgacac ttccaaatag                                    1050
```

<210> SEQ ID NO 56
<211> LENGTH: 382
<212> TYPE: PRT
<213> ORGANISM: Ogataea parapolymorpha

<400> SEQUENCE: 56

```
Met Met Ser Ile Ser Arg Val Ala Ala Leu Arg Asn Gln Phe Ala Arg
1               5                   10                  15

Leu Ala Lys Pro Ala Val Val Gln Gln Val Phe Arg His Ser Thr Ala
            20                  25                  30

Ser Ala Pro Thr Ile Pro Lys Thr Gln Met Gly Cys Val Phe Glu Thr
        35                  40                  45

Asn Gly Gly Pro Ile Glu Tyr Lys Glu Ile Pro Val Pro Lys Pro Lys
    50                  55                  60

Pro Asn Glu Ile Leu Val His Val Lys Tyr Ser Gly Val Cys His Thr
65                  70                  75                  80

Asp Leu His Ala Trp Lys Gly Asp Trp Pro Leu Pro Val Lys Leu Pro
                85                  90                  95

Leu Val Gly Gly His Glu Gly Ala Gly Val Val Ala Lys Gly Glu
            100                 105                 110

Asn Val Lys Asn Phe Glu Ile Gly Asp Leu Ala Gly Ile Lys Trp Leu
        115                 120                 125

Asn Gly Ser Cys Met Gly Cys Glu Phe Cys Gln Gln Gly Ala Glu Pro
130                 135                 140

Asn Cys Pro Asp Ala Asp Leu Ser Gly Tyr Thr His Asp Gly Ser Phe
145                 150                 155                 160

Gln Gln Tyr Ala Thr Ala Asp Ala Val Gln Ala Ala Lys Leu Pro Pro
                165                 170                 175

Gly Thr Asp Leu Ala Ala Val Ala Pro Ile Leu Cys Ala Gly Val Thr
            180                 185                 190

Val Tyr Lys Ala Leu Lys Thr Ala Ala Leu Arg Pro Gly Gln Ile Val
        195                 200                 205

Ala Ile Ser Gly Ala Ala Gly Gly Leu Gly Ser Leu Ala Val Gln Tyr
    210                 215                 220

Ala Val Ala Met Gly Leu Arg Val Leu Gly Ile Asp Gly Gly Glu Gln
225                 230                 235                 240

Lys Gly Glu Phe Ile Lys Lys Leu Gly Ala Glu Phe Tyr Val Asp Phe
                245                 250                 255

Thr Lys Glu Lys Asp Ile Val Ser Ala Ile Gln Lys Ile Thr Asn Gly
            260                 265                 270

Gly Pro His Gly Val Ile Asn Val Ser Val Ser Pro Ala Ala Ile Ser
        275                 280                 285

Gln Ser Cys Gln Tyr Val Arg Thr Leu Gly Lys Val Val Leu Val Gly
    290                 295                 300

Leu Pro Ala Gly Ala Val Cys Glu Ser Pro Val Phe Glu His Val Val
305                 310                 315                 320

Lys Ser Ile Gln Ile Lys Gly Ser Tyr Val Gly Asn Arg Gln Asp Thr
                325                 330                 335

Ala Glu Ala Val Asp Phe Phe Thr Arg Gly Leu Val Lys Ser Pro Phe
            340                 345                 350
```

Gln Ile Ala Gly Leu Ser Glu Leu Pro Glu Val Phe Lys Lys Met Glu
            355                 360                 365

Glu Gly Lys Ile Leu Gly Arg Tyr Val Leu Asp Thr Ser Lys
    370                 375                 380

<210> SEQ ID NO 57
<211> LENGTH: 1149
<212> TYPE: DNA
<213> ORGANISM: Ogataea parapolymorpha

<400> SEQUENCE: 57

```
atgatgtcta tttcgagagt tgctgctttg agaaaccaat ttgctcggct agccaagccc      60
gctgttgtcc agcaggtctt cagacactct actgcctctg ctccaaccat cccaaagacc     120
cagatgggat gtgtttttga aaccaacggt ggtccaattg agtacaagga gatccctgtt     180
ccaaagccaa agcctaacga gattttggtc acgtcaagt actctggtgt gtgccacact      240
gacttgcacg cctggaaggg tgactggcca ctgcctgtca aactcccact tgtgggtggt     300
cacgagggtg ccggtgttgt cgttgccaag ggtgagaacg ttaaaaactt cgagatcggc     360
gacttggccg gtatcaagtg gctgaacggc tcgtgtatgg gttgtgagtt ctgtcaacag     420
ggtgccgaac caaactgtcc agacgctgac ctgtccggtt acacgcacga cggttctttc     480
caacaatacg ccactgctga cgctgtccag gccgctaagc tgcctcctgg aactgacctc     540
gctgctgttg ctcctatttt gtgtgctggt gtcactgttt acaaggcctt gaagactgct     600
gctctgcgtc aggacagat cgttgccatt tccggtgccg ccggtggatt gggttctctt      660
gccgttcaat acgctgtcgc catgggcctg agagttctgg gtattgacgg tggtgagcaa     720
aagggcgagt tcatcaagaa gctcggtgcc gaattctacg tcgacttcac caaggagaag     780
gacattgtgt ctgccatcca gaagatcacc aacggcggtc acacggtgt catcaacgtt      840
tctgtctctc agctgctat ctcccagtct tgtcaatacg tgagaaccct cggtaaggtt      900
gttctggtcg tcttccagc cggcgctgtt tgcgagtctc ctgtctttga gcacgtcgtc     960
aagtccatcc agatcaaggg atcttacgtt ggtaacagac aagacactgc cgaggccgtg    1020
gacttcttca ccagaggcct tgtcaagtct ccattccaga ttgctggtct ttccgagctg    1080
ccagaggtct tcaagaagat ggaggagggc aagatcttgg gcagatacgt ccttgacact    1140
tctaaatag                                                            1149
```

<210> SEQ ID NO 58
<211> LENGTH: 349
<212> TYPE: PRT
<213> ORGANISM: Ogataea polymorpha

<400> SEQUENCE: 58

Met Pro Ser Ile Pro Lys Thr Gln Lys Ala Ile Val Phe Glu Thr Asn
1               5                   10                  15

Gly Gly Pro Leu Leu Tyr Lys Asp Ile Pro Val Pro Gln Pro Lys Pro
            20                  25                  30

Asn Glu Ile Leu Val Asn Val Lys Tyr Ser Gly Val Cys His Thr Asp
        35                  40                  45

Leu His Ala Trp Lys Gly Asp Trp Pro Leu Ala Thr Lys Leu Pro Leu
    50                  55                  60

Val Gly Gly His Glu Gly Ala Gly Val Val Val Ala Lys Gly Ala Asn
65                  70                  75                  80

Val Thr Asn Phe Glu Ile Gly Asp Tyr Ala Gly Ile Lys Trp Leu Asn
                85                  90                  95

Gly Ser Cys Met Gly Cys Glu Phe Cys Gln Gln Gly Ala Glu Pro Asn
            100                 105                 110

Cys Pro Asp Ala Asp Leu Ser Gly Tyr Thr His Asp Gly Ser Phe Gln
            115                 120                 125

Gln Tyr Ala Thr Ala Asp Ala Val Gln Ala Ala Lys Ile Pro Lys Gly
        130                 135                 140

Thr Asn Leu Ala Asp Val Ala Pro Ile Leu Cys Ala Gly Val Thr Val
145                 150                 155                 160

Tyr Lys Ala Leu Lys Thr Ala Glu Leu Ser Pro Gly Gln Trp Val Ala
                165                 170                 175

Ile Ser Gly Ala Gly Gly Gly Leu Gly Ser Leu Ala Val Gln Tyr Ala
            180                 185                 190

Val Ala Met Gly Leu Arg Val Leu Gly Ile Asp Gly Gly Asp Glu Lys
            195                 200                 205

Ala Lys Leu Phe Glu Ser Leu Gly Gly Glu Val Phe Ile Asp Phe Thr
        210                 215                 220

Lys Glu Lys Asp Ile Val Gly Ala Val Gln Lys Ala Thr Asn Gly Gly
225                 230                 235                 240

Pro His Gly Val Ile Asn Val Ser Val Ser Pro Ala Ala Ile Ser Gln
                245                 250                 255

Ser Cys Gln Tyr Val Arg Thr Leu Gly Lys Val Val Leu Val Gly Leu
            260                 265                 270

Pro Ala Gly Ala Val Cys Glu Ser Pro Val Phe Glu His Val Ile Lys
            275                 280                 285

Ser Ile Gln Ile Arg Gly Ser Tyr Val Gly Asn Arg Gln Asp Thr Ala
        290                 295                 300

Glu Ser Ile Asp Phe Phe Val Arg Gly Lys Val Lys Ala Pro Ile Lys
305                 310                 315                 320

Val Val Gly Leu Ser Glu Leu Pro Lys Val Phe Glu Leu Met Glu Gln
                325                 330                 335

Gly Lys Ile Ala Gly Arg Tyr Val Leu Asp Thr Ser Lys
            340                 345

<210> SEQ ID NO 59
<211> LENGTH: 1050
<212> TYPE: DNA
<213> ORGANISM: Ogataea polymorpha

<400> SEQUENCE: 59
atgccttcca ttccaaagac tcaaaaggcc attgttttcg aaaccaacgg tggtcctctt      60
ctatacaagg acatccctgt tccacagcca aagccaaatg aaatccttgt caacgtcaag     120
tactctggtg tgtgccacac cgacttgcac gcctggaagg gtgactggcc attggccacc     180
aaacttccac tggtcggtgg tcacgagggt gctggtgttg ttgttgccaa gggtgccaac     240
gttaccaact tgagatcgg cgactacgct ggtatcaaat ggctgaacgg ctcgtgtatg     300
ggttgtgagt tctgtcaaca aggtgcagaa ccaaactgtc cagacgccga cctttccggt     360
tacacgcacg acggttcctt ccaacaatac gccactgctg atgctgtcca ggctgccaag     420
attccaaagg gaactaacct ggccgatgtt gctccaattc tctgtgctgg tgtcactgtg     480
tacaaggcat tgaagactgc cgaattgagc ccaggccagt gggtcgctat ctctggtgct     540
ggtggaggat tgggttctct tgccgttcaa tacgctgtcg ctatgggcct gagagttctg     600

```
ggtatcgatg gtggtgacga aaaggccaag ctcttcgaga gcttgggcgg agaagtcttc    660
atcgatttca caaaggaaaa ggacattgtc ggagccgtcc agaaggctac caacggtggt    720
ccacacggtg tcatcaacgt ttccgtgtct ccagcagcta tctctcaatc ctgccaatac    780
gtgagaactc ttggtaaggt tgttcttgtt ggtcttccag caggtgctgt ttgcgagtct    840
ccagttttcg agcacgttat caagtctatc cagattagag gttcctacgt tggtaacaga    900
caggacactg cggagtcgat cgacttcttc gtcagaggca aggttaaggc tccaatcaag    960
gttgttggtc tttctgagct gccaaaagtg ttcgagttga tggagcaagg aaagattgca   1020
ggaagatacg tcctcgacac ttccaaatag                                    1050
```

<210> SEQ ID NO 60
<211> LENGTH: 381
<212> TYPE: PRT
<213> ORGANISM: Ogataea polymorpha

<400> SEQUENCE: 60

```
Met Ser Ile Ser Arg Val Ala Ala Leu Arg Asn Gln Phe Ala Arg Leu
1               5                   10                  15

Ala Lys Pro Ala Val Gln Gln Val Phe Arg His Ser Thr Ala Ser
            20                  25                  30

Ala Pro Thr Ile Pro Lys Thr Gln Met Gly Cys Val Phe Glu Thr Asn
        35                  40                  45

Gly Gly Pro Ile Glu Tyr Lys Glu Ile Pro Val Pro Lys Pro Lys Pro
    50                  55                  60

Asn Glu Ile Leu Val His Val Lys Tyr Ser Gly Val Cys His Thr Asp
65                  70                  75                  80

Leu His Ala Trp Lys Gly Asp Trp Pro Leu Pro Val Lys Leu Pro Leu
                85                  90                  95

Val Gly Gly His Glu Gly Ala Gly Val Val Val Ala Lys Gly Glu Asn
            100                 105                 110

Val Lys Asn Phe Glu Ile Gly Asp Leu Ala Gly Ile Lys Trp Leu Asn
        115                 120                 125

Gly Ser Cys Met Gly Cys Glu Phe Cys Gln Gln Gly Ala Glu Pro Asn
    130                 135                 140

Cys Pro Asp Ala Asp Leu Ser Gly Tyr Thr His Asp Gly Ser Phe Gln
145                 150                 155                 160

Gln Tyr Ala Thr Ala Asp Ala Val Gln Ala Ala Lys Leu Pro Pro Gly
                165                 170                 175

Thr Asp Leu Ala Ala Val Ala Pro Ile Leu Cys Ala Gly Val Thr Val
            180                 185                 190

Tyr Lys Ala Leu Lys Thr Ala Ala Leu Arg Pro Gly Gln Ile Val Ala
        195                 200                 205

Ile Ser Gly Ala Ala Gly Gly Leu Gly Ser Leu Ala Val Gln Tyr Ala
    210                 215                 220

Val Ala Met Gly Leu Arg Val Leu Gly Ile Asp Gly Gly Glu Gln Lys
225                 230                 235                 240

Gly Glu Phe Ile Lys Lys Leu Gly Ala Glu Phe Tyr Val Asp Phe Thr
                245                 250                 255

Lys Glu Lys Asp Ile Val Ser Ala Ile Gln Lys Val Thr Asn Gly Gly
            260                 265                 270

Pro His Gly Val Ile Asn Val Ser Val Ser Pro Ala Ala Ile Ser Gln
        275                 280                 285
```

```
Ser Cys Gln Tyr Val Arg Thr Leu Gly Lys Val Val Leu Val Gly Leu
    290                 295                 300

Pro Ala Gly Ala Val Cys Glu Ser Pro Val Phe Glu His Val Val Lys
305                 310                 315                 320

Ser Ile Gln Ile Lys Gly Ser Tyr Val Gly Asn Arg Gln Asp Thr Ala
                325                 330                 335

Glu Ala Val Asp Phe Phe Thr Arg Gly Leu Val Arg Ser Pro Phe Gln
            340                 345                 350

Ile Ala Gly Leu Ser Glu Leu Pro Glu Val Phe Lys Lys Met Glu Glu
            355                 360                 365

Gly Lys Ile Leu Gly Arg Tyr Val Leu Asp Thr Ser Lys
        370                 375                 380

<210> SEQ ID NO 61
<211> LENGTH: 1146
<212> TYPE: DNA
<213> ORGANISM: Ogataea polymorpha

<400> SEQUENCE: 61
atgtctattt cgagagttgc tgcattgaga aaccaatttg ctcgtctagc caagccggct      60
gtagtccagc aggtcttcag acactccact gcctctgctc caaccatccc aaagacccag     120
atgggatgtg tttttgaaac caacggcggt ccaattgagt acaaggagat cccagttcca     180
aagccaaagc caaacgagat tctggtccac gtcaagtact ctggtgtgtg ccacaccgac     240
ttgcacgcct ggaagggtga ctggccactg cctgtcaaac tcccacttgt gggtggtcac     300
gagggtgccg tgttgtcgt tgccaagggt gagaacgtta aaaacttcga atcggcgac      360
ttggccggta tcaaatggct gaacggctcg tgtatgggtt gtgagttctg tcaacagggt     420
gccgaaccaa actgtcctga cgccgacctt tccggttaca cacgacgg ttcttcaa       480
caatacgcca ctgctgacgc tgtccaggcc gctaagctgc tccaggaac tgacctcgct     540
gctgttgctc aattttgtg tgctggtgtg actgtttaca aggccttgaa gactgctgct     600
ttgcgtccag gtcagattgt tgctatttcc ggtgccgccg gtggattggg ttctcttgcc     660
gttcaatacg ctgtcgccat gggtctgaga gttctgggta ttgacggtgg tgagcagaag     720
ggcgagttca tcaagaagct cggtgccgaa ttctacgtcg acttcaccaa ggagaaggac     780
attgtgtctg ccatccagaa ggtcaccaat ggcggtccac acggtgtcat caacgtgtct     840
gtgtctccag ctgctatctc ccagtcttgt caatacgtga aaccctcgg taaggttgtt     900
ctggttggtc ttccagccgg cgctgtttgc gaatctcctg tctttgagca cgtcgtcaag     960
tccatccaga tcaagggatc ttatgttggt aacagacaag acactgccga ggccgtggac    1020
ttcttcacca gaggccttgt ccgttctcca ttccaaattg ccggtctttc cgagctgcct    1080
gaggtcttca agaagatgga ggagggcaag atcttgggta gatatgtcct tgacacttct    1140
aaataa                                                              1146

<210> SEQ ID NO 62
<211> LENGTH: 348
<212> TYPE: PRT
<213> ORGANISM: Saccharomyces cerevisiae

<400> SEQUENCE: 62

Met Ser Ile Pro Glu Thr Gln Lys Ala Ile Ile Phe Tyr Glu Ser Asn
1               5                   10                  15

Gly Lys Leu Glu Tyr Lys Asp Ile Pro Val Pro Lys Pro Lys Ala Asn
            20                  25                  30
```

```
Glu Leu Leu Ile Asn Val Lys Tyr Ser Gly Val Cys His Thr Asp Leu
             35                  40                  45

His Ala Trp His Gly Asp Trp Pro Leu Pro Val Lys Leu Pro Leu Val
     50                  55                  60

Gly Gly His Glu Gly Ala Gly Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
             100                 105                 110

Pro His Ala Asp Leu Ser Gly Tyr Thr His Asp Gly Ser Phe Gln Gln
         115                 120                 125

Tyr Ala Thr Ala Asp Ala Val Gln Ala Ala His Ile Pro Gln Gly Thr
     130                 135                 140

Asp Leu Ala Glu Val Ala Pro Val Leu Cys Ala Gly Ile Thr Val Tyr
145                 150                 155                 160

Lys Ala Leu Lys Ser Ala Asn Leu Arg Ala Gly His Trp Val Ala Ile
                 165                 170                 175

Ser Gly Ala Ala Gly Gly Leu Gly Ser Leu Ala Val Gln Tyr Ala Lys
             180                 185                 190

Ala Met Gly Tyr Arg Val Leu Gly Ile Asp Gly Gly Pro Gly Lys Glu
         195                 200                 205

Glu Leu Phe Thr Ser Leu Gly Gly Glu Val Phe Ile Asp Phe Thr Lys
     210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
                 245                 250                 255

Thr Arg Tyr Cys Arg Ala Asn Gly Thr Val Val Leu Val Gly Leu Pro
             260                 265                 270

Ala Gly Ala Lys Cys Ser Ser Asp Val Phe Asn His Val Val Lys Ser
         275                 280                 285

Ile Ser Ile Val Gly Ser Tyr Val Gly Asn Arg Ala Asp Thr Arg Glu
     290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                 325                 330                 335

Gln Ile Ala Gly Arg Tyr Val Val Asp Thr Ser Lys
             340                 345

<210> SEQ ID NO 63
<211> LENGTH: 1047
<212> TYPE: DNA
<213> ORGANISM: Saccharomyces cerevisiae

<400> SEQUENCE: 63
atgtctattc cagaaactca aaaagccatt atcttctacg agtccaacgg taagttggaa      60
tacaaagata ttccagttcc aaagccaaag gccaacgaat gttgatcaa cgttaaatac     120 tctggtgtct gtcacactga cttgcacgct tggcacggtg actggccatt gccagttaag     180
ctaccattag tcggtggtca cgaaggtgcc ggtgtcgttg tcggcatggg tgaaaacgtt     240
aagggctgga agatcggtga ctacgccggt atcaaatggt tgaacggttc ttgtatggcc     300
```

```
tgtgaatact gtgaattggg taacgaatcc aactgtcctc acgctgactt gtctggttac    360
acccacgacg gttctttcca acaatacgct accgctgacg ctgttcaagc cgctcacatt    420
cctcaaggta ctgacttggc tgaagtcgcc ccagttttgt gtgctggtat caccgtctac    480
aaggctttga agtctgccaa cttgagagca ggccactggg tggccatttc tggtgctgct    540
ggtggtctag gttctttggc tgttcaatat gctaaggcga tgggttacag agtcttaggt    600
attgatggtg gtccaggaaa ggaagaattg tttacctcgc tcggtggtga agtattcatc    660
gacttcacca agagaaggac cattgttagc gcagtcgtta aggctaccaa cggcggtgcc    720
cacggtatca tcaatgtttc cgtttccgaa gccgctatcg aagcttctac cagatactgt    780
agggcgaacg gtactgttgt cttggttggt ttgccagccg gtgcaaagtg ctcctctgat    840
gtcttcaacc acgttgtcaa gtctatctcc attgtcggct cttacgtggg gaacagagct    900
gataccagag aagccttaga tttctttgcc agaggtctag tcaagtctcc aataaaggta    960
gttggcttat ccagtttacc agaaatttac gaaaagatgg agaagggcca aattgctggt   1020
agatacgttg ttgacacttc taaataa                                        1047
```

<210> SEQ ID NO 64
<211> LENGTH: 349
<212> TYPE: PRT
<213> ORGANISM: Candida maltosa

<400> SEQUENCE: 64

```
Met Ser Ser Ile Pro Thr Thr Gln Lys Ala Ile Ile Phe Glu Thr Asn
1               5                   10                  15

Gly Gly Lys Leu Glu Tyr Lys Asp Ile Pro Val Pro Lys Pro Lys Pro
            20                  25                  30

Asn Glu Leu Leu Ile Asn Val Lys Tyr Ser Gly Val Cys His Thr Asp
        35                  40                  45

Leu His Ala Trp Lys Gly Asp Trp Pro Leu Ala Thr Lys Leu Pro Leu
    50                  55                  60

Val Gly Gly His Glu Gly Ala Gly Val Val Val Ala Ile Gly Asp Asn
65                  70                  75                  80

Val Lys Asn Trp Lys Val Gly Asp Phe Ala Gly Val Lys Trp Leu Asn
                85                  90                  95

Gly Ser Cys Leu Asn Cys Glu Tyr Cys Gln Gln Gly Ala Glu Pro Asn
            100                 105                 110

Cys Ala Gln Ala Asp Leu Ser Gly Tyr Thr His Asp Gly Ser Phe Gln
        115                 120                 125

Gln Tyr Ala Thr Ala Asp Ala Val Gln Ala Ala Arg Ile Pro Ala Gly
    130                 135                 140

Thr Asp Leu Ala Thr Val Ala Pro Ile Leu Cys Ala Gly Val Thr Val
145                 150                 155                 160

Tyr Lys Ala Leu Lys Thr Ala Asn Leu Gln Pro Gly Gln Trp Val Ala
                165                 170                 175

Ile Ser Gly Ala Ala Gly Gly Leu Gly Ser Leu Ala Val Gln Tyr Ala
            180                 185                 190

Lys Ala Met Gly Tyr Arg Val Leu Ala Ile Asp Gly Gly Glu Asp Lys
        195                 200                 205

Gly Gln Phe Val Lys Ser Leu Gly Ala Glu Thr Phe Ile Asp Phe Thr
    210                 215                 220

Lys Glu Lys Asp Val Val Gly Ala Val Gln Lys Ala Thr Asn Gly Gly
225                 230                 235                 240
```

```
Pro His Gly Val Ile Asn Val Ser Val Ser Asp Arg Ala Ile Asn Gln
            245                 250                 255

Ser Val Glu Tyr Val Arg Thr Leu Gly Lys Val Leu Val Gly Leu
        260                 265                 270

Pro Ala Gly Ala Lys Val Thr Ala Pro Val Phe Asp Ser Val Val Lys
    275                 280                 285

Ser Ile Glu Ile Lys Gly Ser Tyr Val Gly Asn Arg Lys Asp Thr Ala
    290                 295                 300

Glu Ala Val Asp Phe Phe Ser Arg Gly Leu Ile Lys Cys Pro Ile Lys
305                 310                 315                 320

Ile Val Gly Leu Ser Glu Leu Pro Glu Val Tyr Lys Leu Met Glu Glu
                325                 330                 335

Gly Lys Ile Leu Gly Arg Tyr Val Leu Asp Thr Ser Lys
                340                 345
```

<210> SEQ ID NO 65
<211> LENGTH: 1050
<212> TYPE: DNA
<213> ORGANISM: Candida maltosa

<400> SEQUENCE: 65

```
atgtcttcta ttccaactac tcaaaaagct attatcttcg aaaccaacgg cggtaaatta      60
gaatacaaag atatcccagt cccaaaacca aaaccaaatg aattgttgat caatgttaaa     120
tactccggtg tttgtcacac tgatttgcac gcttggaaag gtgattggcc attagccacc     180
aaattaccat tggtcggtgg tcacgaaggt gctggtgttg tcgttgctat tggtgacaat     240
gtcaagaact ggaaagttgg tgatttcgcc ggtgtcaaat ggttgaatgg ttcttgtttg     300
aactgtgaat actgtcaaca aggtgctgaa ccaaactgtg ctcaagctga cttgtccggt     360
tacacccacg atggttcttt ccaacaatac gccactgccg atgcagttca agcggctaga     420
attccagctg gtactgattt agccaccgtt gctccaatct gtgtgctggt gttaccgtt      480
tacaaggctt tgaagactgc caacttacaa ccaggtcaat gggttgccat ttccggtgcc     540
gctggtggtt taggttcttt ggctgttcaa tacgctaaag ctatgggtta cagagtcttg     600
gccattgacg gtggtgaaga taaaggtcaa tttgttaaat ctttgggtgc tgaaactttt     660
atcgatttta ccaaagaaaa ggatgttgtt ggtgctgtcc aaaaagctac caacggtggt     720
ccacatggtg tcattaacgt ctctgtttcc gacagagcta tcaaccaatc cgttgaatac     780
gttagaactt taggtaaagt tgttttggtt ggtttaccag ctggtgctaa agtcactgct     840
ccagtctttg actccgtcgt taatccatt gaaattaaag gttcttatgt tggtaacaga      900
aaagacactg ccgaagccgt tgatttcttc tctagaggtt tgattaaatg tccaatcaag     960
attgttggtt tatctgaatt accagaagtt tacaaattga tggaagaagg taaaatcttg    1020
ggtagatacg ttttggacac ctccaaataa                                     1050
```

<210> SEQ ID NO 66
<211> LENGTH: 379
<212> TYPE: PRT
<213> ORGANISM: Kluyveromyces marxianus

<400> SEQUENCE: 66

```
Met Phe Arg Leu Ala Arg Ala Gln Thr Ser Ile Thr Thr Thr Ser Lys
1               5                   10                  15

Ala Leu Gly Gly Ser Arg Arg Leu Phe Val Arg Leu Asn Ser Ser Phe
            20                  25                  30
```

Ala Ile Pro Glu Ser Gln Lys Gly Val Ile Phe Tyr Glu Asn Gly Gly
35                  40                  45

Lys Leu Glu Tyr Lys Asp Leu Pro Val Pro Lys Pro Asn Glu
50                  55                  60

Ile Leu Ile Asn Val Lys Tyr Ser Gly Val Cys His Thr Asp Leu His
65                  70                  75                  80

Ala Trp Lys Gly Asp Trp Pro Leu Pro Val Lys Leu Pro Leu Val Gly
        85                  90                  95

Gly His Glu Gly Ala Gly Val Val Ala Lys Gly Glu Asn Val Thr
            100                 105                 110

Asn Phe Glu Ile Gly Asp Tyr Ala Gly Ile Lys Trp Leu Asn Gly Ser
        115                 120                 125

Cys Met Ser Cys Glu Leu Cys Glu Gln Gly Tyr Glu Ser Asn Cys Leu
130                 135                 140

Gln Ala Asp Leu Ser Gly Tyr Thr His Asp Gly Ser Phe Gln Gln Tyr
145                 150                 155                 160

Ala Thr Ala Asp Ala Val Gln Ala Ala Gln Ile Pro Lys Gly Thr Asp
                165                 170                 175

Leu Ala Glu Ile Ala Pro Ile Leu Cys Ala Gly Val Thr Val Tyr Lys
            180                 185                 190

Ala Leu Lys Thr Ala Asp Leu Gln Pro Gly Gln Trp Ile Ala Ile Ser
        195                 200                 205

Gly Ala Ala Gly Gly Leu Gly Ser Leu Ala Val Gln Tyr Ala Lys Ala
    210                 215                 220

Met Gly Leu Arg Val Leu Gly Ile Asp Gly Gly Pro Gly Lys Glu Glu
225                 230                 235                 240

Leu Phe Lys Ser Leu Gly Gly Glu Val Phe Ile Asp Phe Thr Lys Ser
                245                 250                 255

Lys Asp Met Val Ala Asp Ile Gln Glu Ala Thr Asn Gly Gly Pro His
            260                 265                 270

Gly Val Ile Asn Val Ser Val Ser Glu Ala Ala Ile Ser Met Ser Thr
        275                 280                 285

Glu Tyr Val Arg Pro Thr Gly Val Val Leu Val Gly Leu Pro Ala
    290                 295                 300

His Ala Tyr Val Lys Ser Glu Val Phe Ser His Val Val Lys Ser Ile
305                 310                 315                 320

Ser Ile Lys Gly Ser Tyr Val Gly Asn Arg Ala Asp Thr Arg Glu Ala
                325                 330                 335

Ile Asp Phe Phe Thr Arg Gly Leu Val Lys Ser Pro Ile Lys Val Val
            340                 345                 350

Gly Leu Ser Glu Leu Pro Lys Val Tyr Glu Leu Met Glu Ala Gly Lys
        355                 360                 365

Ile Leu Gly Arg Tyr Val Val Asp Thr Ser Lys
370                 375

<210> SEQ ID NO 67
<211> LENGTH: 1140
<212> TYPE: DNA
<213> ORGANISM: Kluyveromyces marxianus

<400> SEQUENCE: 67
atgttcagac tagcacgcgc tcagaccagc attaccacca ctagcaaggc tctaggtggc        60
tccagaagac tattcgtcag actaaactcc tctttcgcca tcccagaatc ccaaaagggt      120
gtgattttct acgaaaacgg cggtaagttg aatacaagg accttccagt tccaaagcca      180

-continued

```
aagccaaatg aaatcttgat caacgtcaag tactccggtg tgtgtcacac tgatttgcac    240
gcctggaagg gtgactggcc attgccagtt aagttgcctt tggtcggtgg tcacgaaggt    300
gccggtgtcg tcgttgccaa gggtgaaaac gttaccaact tcgagatcgg tgactacgca    360
ggtatcaagt ggttgaacgg ttcttgtatg tcttgtgaac tctgtgaaca aggttacgaa    420
tccaactgtt tgcaagctga cttgtctggt tacacccacg acggttcctt ccaacaatat    480
gccactgctg acgctgttca agctgcccaa attccaaagg gtaccgattt ggctgaaatc    540
gccccaatct tgtgtgccgg tgtcaccgtc tacaaggctc taaagaccgc tgacttgcaa    600
ccaggtcaat ggatcgctat ctccggtgct gccggtggtc ttggttccct agccgtgcaa    660
tacgccaagg caatgggtct aagagttcta ggtatcgacg gtggtccagg taaggaagaa    720
ttgttcaaga gcttgggtgg tgaagtcttc attgacttca caagtccaa ggacatggtc     780
gcagacatcc aggaagccac caacggtggt cctcacggtg tgatcaacgt ctccgtctcc    840
gaggccgcta tctccatgtc caccgagtac gtcagaccaa ccggtgtggt cgttctagtc    900
ggtttgccag cccacgctta cgtcaagtcc gaagtcttct cccacgtcgt caagtctatc    960
tctattaagg gttcttacgt cggtaacaga gcagacacca gagaagctat tgacttcttc    1020
accagaggtt tggtcaagtc tccaatcaag gttgttggtt tgtctgaatt gccaaaggtt    1080
tatgaattga tggaagctgg taagatcttg ggtagatacg tcgttgacac ttccaaataa    1140
```

<210> SEQ ID NO 68
<211> LENGTH: 350
<212> TYPE: PRT
<213> ORGANISM: Escherichia coli

<400> SEQUENCE: 68

```
Met Ser Glu Gln Ile Pro Lys Thr Gln Lys Ala Val Val Phe Asp Thr
1               5                  10                  15

Asn Gly Gly Gln Leu Val Tyr Lys Asp Tyr Pro Val Pro Thr Pro Lys
            20                  25                  30

Pro Asn Glu Leu Leu Ile Asn Val Lys Tyr Ser Gly Val Cys His Thr
        35                  40                  45

Asp Leu His Ala Trp Lys Gly Asp Trp Pro Leu Ala Thr Lys Leu Pro
    50                  55                  60

Leu Val Gly Gly His Glu Gly Ala Gly Val Val Gly Met Gly Glu
65                  70                  75                  80

Asn Val Lys Gly Trp Lys Ile Gly Asp Phe Ala Gly Ile Lys Trp Leu
                85                  90                  95

Asn Gly Ser Cys Met Ser Cys Glu Phe Cys Gln Gln Gly Ala Glu Pro
            100                 105                 110

Asn Cys Gly Glu Ala Asp Leu Ser Gly Tyr Thr His Asp Gly Ser Phe
        115                 120                 125

Glu Gln Tyr Ala Thr Ala Asp Ala Val Gln Ala Ala Lys Ile Pro Ala
    130                 135                 140

Gly Thr Asp Leu Ala Asn Val Ala Pro Ile Leu Cys Ala Gly Val Thr
145                 150                 155                 160

Val Tyr Lys Ala Leu Lys Thr Ala Asp Leu Ala Ala Gly Gln Trp Val
                165                 170                 175

Ala Ile Ser Gly Ala Gly Gly Gly Leu Gly Ser Leu Ala Val Gln Tyr
            180                 185                 190

Ala Arg Ala Met Gly Leu Arg Val Val Ala Ile Asp Gly Gly Asp Glu
        195                 200                 205
```

```
Lys Gly Glu Phe Val Lys Ser Leu Gly Ala Glu Ala Tyr Val Asp Phe
         210                 215                 220

Thr Lys Asp Lys Asp Ile Val Glu Ala Val Lys Lys Ala Thr Asp Gly
225                 230                 235                 240

Gly Pro His Gly Ala Ile Asn Val Ser Val Ser Glu Lys Ala Ile Asp
                245                 250                 255

Gln Ser Val Glu Tyr Val Arg Pro Leu Gly Lys Val Val Leu Val Gly
                260                 265                 270

Leu Pro Ala His Ala Lys Val Thr Ala Pro Val Phe Asp Ala Val Val
                275                 280                 285

Lys Ser Ile Glu Ile Lys Gly Ser Tyr Val Gly Asn Arg Lys Asp Thr
         290                 295                 300

Ala Glu Ala Ile Asp Phe Phe Ser Arg Gly Leu Ile Lys Cys Pro Ile
305                 310                 315                 320

Lys Ile Val Gly Leu Ser Asp Leu Pro Glu Val Phe Lys Leu Met Glu
                325                 330                 335

Glu Gly Lys Ile Leu Gly Arg Tyr Val Leu Asp Thr Ser Lys
                340                 345                 350

<210> SEQ ID NO 69
<211> LENGTH: 1053
<212> TYPE: DNA
<213> ORGANISM: Escherichia coli

<400> SEQUENCE: 69
atgtctgaac aaatcccaaa aactcaaaaa gccgttgtct ttgataccaa tggtggtcaa      60
ttagtctaca aggattaccc agttccaact ccaaagccaa tgaattgtt aatcaacgtc     120 aaatactctg gtgtctgtca cactgattta cacgcttgga aggtgactg gccattggct     180 actaaattgc cattagttgg tggtcacgaa ggtgccggtg tcgttgtcgg tatgggtgaa     240
aacgtcaaag gatggaaaat cggtgacttt gccggtatca aatggttgaa cggttcttgt     300
atgagttgtg aattctgtca acaaggtgct gaaccaaact gtggtgaagc tgacttgtct     360
ggttacactc acgatggttc attcgaacaa tacgctactg ctgatgctgt ccaagccgct     420
aaaattccag ctggtactga tttagccaat gtcgcaccaa tcttatgtgc tggtgttact     480
gtttacaaag cctaaagac tgctgactta gcagctggcc aatgggttgc tatctccggt     540
gctggtggtg gtttaggttc tttggccgtt caatacgcca gagccatggg tttgagagtt     600
gttgctattg acggtggtga cgaaaaaggt gaatttgtta aatcattggg tgctgaagct     660
tacgttgatt tcaccaaaga taagatatt gttgaagctg ttaagaaggc tactgatggt     720
ggtccacacg gtgctatcaa tgtctctgtt tctgaaaaag ccattgacca atctgttgaa     780
tatgttagac cattaggtaa agttgttttg gttggttac cagctcacgc taaagtcact     840
gctccagttt tcgatgctgt tgtcaaatcc attgaaatca aaggttctta cgttggtaac     900
agaaaagata ctgctgaagc tattgacttc ttctccagag gtttaatcaa atgcccaatc     960
aagattgtcg gttatctga cttgccagaa gtcttcaaat tgatggaaga aggtaaaatc    1020
ttgggtagat acgtcttgga caccagtaaa taa                                1053

<210> SEQ ID NO 70
<211> LENGTH: 353
<212> TYPE: PRT
<213> ORGANISM: Fusarium graminearum
```

<400> SEQUENCE: 70

```
Met Ala Ala Pro Gln Ile Pro Ser Gln Gln Trp Ala Gln Ile Phe Glu
1               5                   10                  15

Lys Thr Ala Gly Pro Ile Glu Tyr Lys Gln Ile Pro Val Gln Lys Pro
            20                  25                  30

Gly Pro Asp Glu Val Leu Val Asn Val Lys Phe Ser Gly Val Cys His
        35                  40                  45

Thr Asp Leu His Ala Trp Gln Gly Asp Trp Pro Leu Asp Thr Lys Leu
    50                  55                  60

Pro Leu Val Gly Gly His Glu Gly Ala Gly Val Val Ala Arg Gly
65                  70                  75                  80

Glu Leu Val Lys Asp Val Lys Ile Gly Glu Lys Val Gly Ile Lys Trp
                85                  90                  95

Leu Asn Gly Ser Cys Leu Ser Cys Ser Tyr Cys Gln Asn Ala Asp Glu
            100                 105                 110

Ser Leu Cys Ala Glu Ala Leu Leu Ser Gly Tyr Thr Val Asp Gly Ser
        115                 120                 125

Phe Gln Gln Tyr Ala Ile Ala Lys Ala Ile His Val Ala Arg Ile Pro
    130                 135                 140

Glu Glu Cys Asp Leu Glu Ala Ile Ser Pro Ile Leu Cys Ala Gly Ile
145                 150                 155                 160

Thr Val Tyr Lys Gly Ile Lys Glu Ser Gly Val Lys Ala Gly Gln Ser
                165                 170                 175

Leu Ala Ile Val Gly Ala Gly Gly Leu Gly Ser Ile Ala Val Gln
            180                 185                 190

Tyr Ala Lys Ala Met Gly Ile His Ala Ile Ala Ile Asp Gly Gly Glu
    195                 200                 205

Glu Lys Glu Lys Met Cys Met Ser Leu Gly Ala Gln Thr Phe Ile Asp
    210                 215                 220

Phe Thr Lys Thr Lys Asn Ile Val Ala Asp Val Lys Ala Thr Thr Asn
225                 230                 235                 240

Asp Gly Leu Gly Pro His Ala Ala Leu Leu Val Ala Ala Glu Lys
                245                 250                 255

Pro Phe Gln Gln Ala Thr Gln Tyr Ile Arg Ser Lys Gly Thr Val Val
            260                 265                 270

Cys Ile Gly Leu Pro Ala Gly Ala Gln Phe Ser Ala Pro Val Phe Asp
        275                 280                 285

Thr Val Val Arg Met Ile Gln Ile Lys Gly Ser Tyr Val Gly Asn Arg
    290                 295                 300

Ala Asp Thr Ala Glu Ala Ile Asp Phe Phe Arg Arg Gly Leu Ile Lys
305                 310                 315                 320

Val Pro Phe Lys Thr Val Gly Leu Ser Glu Leu Asn Glu Val Phe Lys
                325                 330                 335

Leu Met Lys Ala Gly Gln Val Ala Gly Arg Tyr Val Val Asp Thr Ser
            340                 345                 350

Arg
```

<210> SEQ ID NO 71
<211> LENGTH: 1062
<212> TYPE: DNA
<213> ORGANISM: Fusarium graminearum

<400> SEQUENCE: 71

```
atggccgctc cccagattcc ttcccagcag tgggctcaga tcttcgagaa gaccgccggt    60
cccatcgagt acaagcagat tcccgtccag aagcctggcc ccgatgaggt tctcgtcaac   120
gtcaagttct ccggtgtctg ccacactgac ctccacgcct ggcagggtga ctggcccctc   180
gacaccaagc tgccccttgt cggtggccac gagggtgccg tgttgtcgt tgcccgcggc    240
gagcttgtca aggatgtcaa gattggcgag aaggtcggta tcaagtggct caacggttct   300
tgcttgagct gctcttactg ccaaaacgcc gatgagtctc tctgcgctga ggctcttctc   360
tccggttaca ccgtcgatgg atcttccag caatacgcca tcgccaaggc tatccacgtt    420
gctcgcatcc ctgaggagtg tgaccttgag gccatctccc ccattctctg cgccggtatc   480
accgtctaca agggtatcaa ggagtccggt gtcaaggccg ccagtctct tgctatcgtc    540
ggtgctggtg gtggtctcgg ttccatcgct gttcagtacg ccaaggctat gggtatccat   600
gccattgcca ttgatggtgg tgaggagaag gagaagatgt gcatgtctct cggtgcccaa   660
accttcatcg acttcacaaa gactaagaac atcgtcgctg atgtcaaggc tactaccaac   720
gatggccttg ccctcacgc tgctctcctc gtcgctgctg ccgagaagcc cttccaacag    780
gctacccaat acatccgatc caagggtacc gtcgtctgca tcggtctccc cgctggtgct   840
cagttctctg cccccgtctt cgacactgtc gttcgcatga ttcagatcaa gggatcttat   900
gtcggtaacc gtgccgatac tgctgaggcc atcgacttct ccgccgtgg tctcatcaag    960
gttcccttca agactgttgg tctctctgag ctcaacgagg tcttcaagct catgaaggct  1020
ggccaagttg ctggtcgcta tgtcgttgac accagccgat aa                     1062
```

<210> SEQ ID NO 72
<211> LENGTH: 1966
<212> TYPE: DNA
<213> ORGANISM: Artificial Sequence
<220> FEATURE:
<223> OTHER INFORMATION: Adh2 split marker cassette 1

<400> SEQUENCE: 72

```
cgtatctacc gatgatggca ccagcctcca tctgttcgta gaccttagca agttcagaca    60
gaccgataat cttgatagga gccttgacca aacctctggt gaacaagtcg atggcctcgg   120
cactgtcctc tctgtttcca acgtaagatc ccttgatctc gatggacttc agaacgtgcc   180
agaaaacgtc agagttgaca acggcaccag atggcagacc aaccaaaaca accttaccca   240
aagttctaac gtattggaca gattggttga tagcatgtgg ggaaacggag acgttaataa   300
caccgtgtgg accaccgttg gtgagctttt ggacttcagc aacgacgtcc ttagtcttag   360
tgaagtcgac gaagacctca gcacccaagg acttgacaaa ttcacccttg tcggcaccac   420
catcaatacc caaaactctc aaacccagag ccttggcgta ttgaacggca agagaaccca   480
gtcctccacc agcaccagaa atggcaaccc attggccaat acgcaagtca gcggtcttaa   540
gagccttgta acggtgata ccagcacaca gaattggggc aacttcagcc aagtcagcct    600
cctttggaat tctggcggct tgggtggcat cagcagtagc atactgctgg aaagatccgt   660
cgtgggtgaa accagacagg tcagccttgg cacaactgga ttcagcacct ggatacagt    720
actcacagtt caaacaagaa ccgttcaacc atttgatacc agcgtagtca ccgatagtgg   780
atctgatatc acctaataac ttcgtatagc atacattata cgaagttata ttaagggttc   840
tcgaatggta ccttgctcac atgttgatct ccagcttgca aattaaagcc ttcgagcgtc   900
```

```
ccaaaaccttt ctcaagcaag gttttcagta taatgttaca tgcgtacacg cgtctgtaca    960
gaaaaaaaag aaaaatttga aatataaata acgttcttaa tactaacata actataaaaa   1020
aataaatagg gacctagact tcaggttgtc taactccttc cttttcggtt agagcggatg   1080
tgggggaggg gcgtgaatgt aagcgtgaca taactaatta catgatatcg acaaaggaaa   1140 aggggggacgg atctccgagg taaaatagaa caactacaat ataaaaaaac tatacaaatg   1200
acaagttctt gaaaacaaga atcttttttat tgtcagtact gattattcct ttgccctcgg   1260
acgagtgctg gggcgtcggt ttccactatc ggcgagtact tctacacagc catcggtcca   1320
gacggccgcg cttctgcggg cgatttgtgt acgcccgaca gtcccggctc cggatcggac   1380
gattgcgtcg catcgaccct gcgcccaagc tgcatcatcg aaattgccgt caaccaagct   1440
ctgatagagt tggtcaagac caatgcggag catatacgcc cggagccgcg gcgatcctgc   1500
aagctccgga tgcctccgct cgaagtagcg cgtctgctgc tccatacaag ccaaccacgg   1560
cctccagaag aagatgttgg cgacctcgta ttgggaatcc ccgaacatcg cctcgctcca   1620
gtcaatgacc gctgttatgc ggccattgtc cgtcaggaca ttgttggagc cgaaatccgc   1680
gtgcacgagg tgccggactt cggggcagtc ctcggcccaa gcatcagct catcgagagc   1740 ctgcgcgacg gacgcactga cggtgtcgtc catcacagtt tgccagtgat acacatgggg   1800
atcagcaatc gcgcatatga aatcacgcca tgtagtgtat tgaccgattc cttgcggtcc   1860
gaatgggccg aacccgctcg tctggctaag atcggccgca gcgatcgcat ccatggcctc   1920
cgcgaccggc tgcagaacag cgggcagttc ggtttcaggc aggtct              1966
```

<210> SEQ ID NO 73
<211> LENGTH: 2069
<212> TYPE: DNA
<213> ORGANISM: Artificial Sequence
<220> FEATURE:
<223> OTHER INFORMATION: Adh2 split marker cassette 2
<220> FEATURE:
<221> NAME/KEY: misc_feature
<222> LOCATION: (1099)..(1099)
<223> OTHER INFORMATION: n is a, c, g, or t

<400> SEQUENCE: 73

```
agatgttggc gacctcgtat tgggaatccc cgaacatcgc ctcgctccag tcaatgaccg     60
ctgttatgcg gccattgtcc gtcaggacat tgttggagcc gaaatccgcg tgcacgaggt    120
gccggacttc ggggcagtcc tcggcccaaa gcatcagctc atcgagagcc tgcgcgacgg    180
acgcactgac ggtgtcgtcc atcacagttt gccagtgata cacatgggga tcagcaatcg    240
cgcatatgaa atcacgccat gtagtgtatt gaccgattcc ttgcggtccg aatgggccga    300
acccgctcgt ctggctaaga tcggccgcag cgatcgcatc catggcctcc gcgaccggct    360
gcagaacagc gggcagttcg gtttcaggca ggtcttgcaa cgtgacaccc tgtgcacggc    420
gggagatgca ataggtcagg ctctcgctga attccccaat gtcaagcact tccggaatcg    480
ggagcgcggc cgatgcaaag tgccgataaa cataacgatc tttgtagaaa ccatcggcgc    540
agctatttac ccgcaggaca tatccacgcc ctcctacatc gaagctgaaa gcacgagatt    600
cttcgccctc cgagagctgc atcaggtcgg agacgctgtc gaacttttcg atcagaaact    660
tctcgacaga cgtcgcggtg agttcaggct ttttacccat ggtttagttc ctcaccttgt    720
cgtattatac tatgccgata tactatgccg atgattaatt gtcaacaccg cccttagatt    780
agattgctat gctttctttc taatgagcaa gaagtaaaaa agttgtaat agaacaagaa    840 aaatgaaact gaaacttgag aaattgaaga ccgtttatta acttaaatat caatgggagg    900
```

```
tcatcgaaag agaaaaaaat caaaaaaaaa aaattttcaa gaaaagaaa  cgtgataaaa      960
atttttattg ccttttaga  cgaagaaaaa gaaacgaggc ggtctctttt ttcttttcca     1020
aacctttagt acgggtaatt aacgacaccc tagaggaaga agagggaa  atttagtatg     1080
ctgtgcttgg gggttttgna aatggtacgg cgatgcgcgg aatccgagaa aatctggaag     1140
agtaaaaaag gagtagaaac attttgaagc tatggtgtgt ggtaccgatc tagacctaat     1200
aacttcgtat agcatacatt atacgaagtt atattaaggg ttgtcgacct gcagcgtacg     1260
gcacgaattc gcaccccgga gagcgctcac ccccgttttc aaacagcggg gggagcacaa     1320
aatgttgaaa actacacaga tcttttcgga caccggtcgc tttatgtagt cgacatgcag     1380
attctcccaa atggaaaacg agattggaca atttgtggag ttggaaaggg gggtgggaat     1440
caacgaaatt agcagattca tgggcaattg gcaggactgg gcagaagggg tgagaattgc     1500
aatcgaatgg aacaggcact cccgttgcga aatcaaaaaa gtctcgctat ctgaactgat     1560
ttttttaag  cagcaactta cggtcaatac atctccgatg gaggaatttt tcacccctcg     1620
ctaactagat gggccccttc taagaaattt gggtttaagg ttgggcagtc agtcagtgca     1680
ccaatgctaa ctgccatttg tccaaagagg ggtgcaagga tgaggaccg  ttgagaataa     1740
gatttggggt gttaatcggt gatactgatt tgtcaaagag tggggaggac tgctgggcat     1800
tgttcacccc cctagttgtt agagttcgat agccggccga atcaccccc  tcttcttaca     1860
taatcattgt cactatgtgg ggtctctaca gtctcaccct gcgatccggg acgacgccgc     1920
gaaattaggg ggcaagtctc ctccgggcat gcaatattgg taacaggatc aattgatgcg     1980
agaaaagttg gaggggggtgt aaaattcaag cccacaaagt cacacccttacgcctgtaga     2040
ggggcaatcg gagagcagcc atggggtgt                                        2069
```

<210> SEQ ID NO 74
<211> LENGTH: 1850
<212> TYPE: DNA
<213> ORGANISM: Artificial Sequence
<220> FEATURE:
<223> OTHER INFORMATION: Adh900 split marker cassette 1

<400> SEQUENCE: 74

```
cactccagtt gggccattac cgaacatttt gccattgtag gcgattagta agtattaaca       60
agacagctga ctatacgttt attctcaaac aatatttccc ttttggtttt tgacctcgct      120
ttaatcaatt tttcagacct gatcccacct acttttcttc ggcctcaact tcaatctgac      180
tcttctctct caattggtac caaccagcca gaaaatgtcc ttccgttact tgaaacggca      240
tttctctaca gctacaaacg caattgctct ccttagcaga cctgaattca aaataggtcg      300
aattgtggac gtcgtgaaac atccaaatgc agacaaactt tatgtctcgt cgatttctgt      360
gggaaacaat tatgcctcgg gtacatccaa caccctaacc gtttgcagcg gcttggtgga      420
ctacttttca gttcccgaat tgcttcagcg acgggtcgtt gtggtcacaa acctcaagcc      480
atcgaagatg agaggtgtaa catcggaggc aatgcttttg gcagggggaaa agtcggggaa      540
agtggaattg gtcgagccgc caatgtccgg gagagagggc gaatcactcc acttcgaagg      600
tgtagaaatt acatcagagg agagcgccaa tcaattgcat ttgcctgcta agcgattgaa      660
gaagtcagag tggagtcaac tggcggaagg tctacagaca aatgaccagc gtgaagtggt      720
cttccacagc caaattggct ccaaacgaat ttacgcttta gtaggagcga gtactgaaaa      780
atgcacgtta gcgactcttg cgcaggccgt cgtacgataa gggcaatatg gttgagaacg      840
```

```
ttcctcaccc aaataaaatc atcgtacgct gcaggtcgac aacccttaat ataacttcgt      900
ataatgtatg ctatacgaag ttattaggtc tagatcggta ccgacatgga ggcccagaat      960
accctccttg acagtcttga cgtgcgcagc tcaggggcat gatgtgactg tcgcccgtac     1020
atttagccca tacatcccca tgtataatca tttgcatcca tacattttga tggccgcacg     1080
gcgcgaagca aaaattacgg ctcctcgctg cagacctgcg agcagggaaa cgctcccctc     1140
acagacgcgt tgaattgtcc ccacgccgcg cccctgtaga gaaatataaa aggttaggat     1200
ttgccactga ggttcttctt tcatatactt ccttttaaaa tcttgctagg atacagttct     1260
cacatcacat ccgaacataa acaaccatgg gtaaggaaaa gactcacgtt tcgaggccgc     1320
gattaaattc caacatggat gctgatttat atgggtataa atgggctcgc gataatgtcg     1380
ggcaatcagg tgcgacaatc tatcgattgt atgggaagcc cgatgcgcca gagttgtttc     1440
tgaaacatgg caaaggtagc gttgccaatg atgttacaga tgagatggtc agactaaact     1500
ggctgacgga atttatgcct cttccgacca tcaagcattt tatccgtact cctgatgatg     1560
catggttact caccactgcg atccccggca aaacagcatt ccaggtatta gaagaatatc     1620
ctgattcagg tgaaaatatt gttgatgcgc tggcagtgtt cctgcgccgg ttgcattcga     1680
ttcctgtttg taattgtcct tttaacagcg atcgcgtatt cgtctcgct caggcgcaat     1740
cacgaatgaa taacggtttg gttgatgcga gtgattttga tgacgagcgt aatggctggc     1800
ctgttgaaca agtctggaaa gaaatgcata agcttttgcc attctcaccg                1850

<210> SEQ ID NO 75
<211> LENGTH: 1993
<212> TYPE: DNA
<213> ORGANISM: Artificial Sequence
<220> FEATURE:
<223> OTHER INFORMATION: Adh900 split marker cassette 2

<400> SEQUENCE: 75
aagcccgatg cgccagagtt gtttctgaaa catggcaaag gtagcgttgc caatgatgtt       60
acagatgaga tggtcagact aaactggctg acggaattta tgcctcttcc gaccatcaag      120
cattttatcc gtactcctga tgatgcatgg ttactcacca ctgcgatccc cggcaaaaca      180
gcattccagg tattagaaga atatcctgat tcaggtgaaa atattgttga tgcgctggca      240
gtgttcctgc gccggttgca ttcgattcct gtttgtaatt gtccttttaa cagcgatcgc      300
gtatttcgtc tcgctcaggc gcaatcacga atgaataacg gtttggttga tgcgagtgat      360
tttgatgacg agcgtaatgg ctggcctgtt gaacaagtct ggaaagaaat gcataagctt      420
ttgccattct caccggattc agtcgtcact catggtgatt tctcacttga taaccttatt      480
tttgacgagg gaaattaat aggttgtatt gatgttggac gagtcggaat cgcagaccga      540
taccaggatc ttgccatcct atggaactgc ctcggtgagt tttctccttc attacagaaa      600
cggctttttc aaaaatatgg tattgataat cctgatatga ataaattgca gtttcatttg      660
atgctcgatg agttttctta atcagtactg acaataaaaa gattcttgtt ttcaagaact      720
tgtcatttgt atagtttttt tatattgtag ttgttctatt ttaatcaaat gttagcgtga      780
tttatatttt ttttcgcctc gacatcatct gcccagatgc gaagttaagt gcgcagaaag      840
taatatcatg cgtcaatcgt atgtgaatgc tggtcgctat actggtacca ttcgagaacc      900
cttaatataa cttcgtataa tgtatgctat acgaagttat taggtgatat cagatccact      960
ctgtagtgag ggttggtggt ctgacgaaca tccagcaagg tgttccacct gaatttttc     1020
accttggagg gtaatgtgat gacgccattt cctgtgcaaa tgcttttcgt tttgaacagt     1080
```

```
gcaacttttg tatcagatct tcatctactt gatgccatct caacaaatcc ctcatttact    1140
agcgtgtgaa ggaatctaga ttttccactg ataagccaat ttgtcggaaa tcccccgcgc    1200
gggagttggc gttcagtacg agccacacac gtttcttttg gacaaccaaa gcatccgcct    1260
gaagggacaa cttgcattca acggcttcag ttggaaacgt cagagctgac ctatagtttg    1320
ctagaaccgt tttctctgtt tacgtttacg tctcctcaaa tttgcgctcg gtatgtcctt    1380
cctaattagc gggaaaagct gttcttagtt aatacggaga agtttcggg gttaccgttc     1440 cgggaagagg aggggtcatc tctctcatct catccaacca ttaagtttct tccaaaactt    1500
caggataatc agtttaacca ccgacaggag tcagatttga gattgacaga aagttttcc    1560 gtccatttcc tcatcttgtc gccgttatca gtcaatctct atggttatct ggaatttctt    1620
ttttctttta attcatcttc tttttatccc gcgcctttgg cgttctagct catctcatga    1680
aaacaaaacc ctctcatgtt cggataattc cagcggcttt cactttcaga tgacacatag    1740
attggactca accatggcta tctggggtat acggacgttg gcaagggcgt taatttttca    1800
ggacaaacgg aaatgccatg gctccaggga aaggcattcc tattgcaaac ctagaccgtc    1860
gaacctctcc tatcgcctac cagtcaccca gctatcccta ggcaactcat ctccttcaag    1920
cggattgcaa cctgctaagc caaattagat ctggccacag aaatgccgca atatttcttg    1980
gctctcccct ccc                                                        1993

<210> SEQ ID NO 76
<211> LENGTH: 23
<212> TYPE: DNA
<213> ORGANISM: Artificial Sequence
<220> FEATURE:
<223> OTHER INFORMATION: Primer sequence

<400> SEQUENCE: 76
gaattgagcc aaaaaaggag agg                                              23

<210> SEQ ID NO 77
<211> LENGTH: 23
<212> TYPE: DNA
<213> ORGANISM: Artificial Sequence
<220> FEATURE:
<223> OTHER INFORMATION: Primer sequence

<400> SEQUENCE: 77
gatggaatag gagactaggt gtg                                              23

<210> SEQ ID NO 78
<211> LENGTH: 20
<212> TYPE: DNA
<213> ORGANISM: Artificial Sequence
<220> FEATURE:
<223> OTHER INFORMATION: Primer sequence

<400> SEQUENCE: 78
tggttgagac gtttgtattg                                                  20

<210> SEQ ID NO 79
<211> LENGTH: 18
<212> TYPE: DNA
<213> ORGANISM: Artificial Sequence
<220> FEATURE:
<223> OTHER INFORMATION: Primer sequence
```

<400> SEQUENCE: 79
tgggttggga gtttagtg                                                18

<210> SEQ ID NO 80
<211> LENGTH: 1053
<212> TYPE: DNA
<213> ORGANISM: Artificial Sequence
<220> FEATURE:
<223> OTHER INFORMATION: ADH2 coding sequence

<400> SEQUENCE: 80
atgtctccaa ctatcccaac tacacaaaag gctgttatct tcgagaccaa cggcggtccc      60
ctagagtaca aggacattcc agtcccaaag ccaaagtcaa acgaactttt gatcaacgtt     120
aagtactccg gtgtctgtca cactgatttg cacgcctgga agggtgactg gccattggac     180
aacaagcttc ctttggttgg tggtcacgaa ggtgctggtg tcgttgtcgc ttacggtgag     240
aacgtcactg gatgggagat cggtgactac gctggtatca atggttgaa cggttcttgt      300 ttgaactgtg agtactgtat ccaaggtgct gaatccagtt gtgccaaggc tgacctgtct     360
ggtttcaccc acgacggatc tttccagcag tatgctactg ctgatgccac ccaagccgcc     420
agaattccaa aggaggctga cttggctgaa gttgccccaa ttctgtgtgc tggtatcacc     480
gtttacaagg ctcttaagac cgctgacttg cgtattggcc aatgggttgc catttctggt     540
gctggtggag gactgggttc tcttgccgtt caatacgcca aggctctggg tttgagagtt     600
ttgggtattg atggtggtgc cgacaagggt gaatttgtca agtccttggg tgctgaggtc     660
ttcgtcgact tcactaagac taaggacgtc gttgctgaag tccaaaagct caccaacggt     720
ggtccacacg tgttattaa cgtctccgtt tccccacatg ctatcaacca atctgtccaa     780
tacgttagaa ctttgggtaa ggttgttttg gttggtctgc atctggtgc cgttgtcaac     840 tctgacgttt tctggcacgt tctgaagtcc atcgagatca agggatctta cgttggaaac     900
agagaggaca gtgccgaggc catcgacttg ttcaccagag gtttggtcaa ggctcctatc     960
aagattatcg gtctgtctga acttgctaag gtctacgaac agatggaggc tggtgccatc    1020
atcggtagat acgttgtgga cacttccaaa taa                                 1053

<210> SEQ ID NO 81
<211> LENGTH: 1083
<212> TYPE: DNA
<213> ORGANISM: Artificial Sequence
<220> FEATURE:
<223> OTHER INFORMATION: ADH900 coding sequence

<400> SEQUENCE: 81
atgtctgtga tgaaagccct cgtgtacggt ggtaagaacg tcttcgcctg gaaaaacttc      60
cctaaaccaa ctatcttgca cccaacagat gtcatcgtta agacggtggc tactaccatc     120
tgcggaacag acttgcacat cttgaaaggt gatgttccag aggtcaaacc tgaaaccgtc     180
ttgggtcatg aagcaattgg agtcgtcgaa tctatcggtg ataacgtcaa aaacttcagc     240
attggtgata aggtgctggt ttcatgcatc accagttgtg gaagctgtta ctactgtaag     300
agaaacttgc agagtcattg caagaccggt ggatggaaat taggtcacga tttgaacggt     360
acgcaggctg agtttgtccg tatcccatat ggagacttct cattgcaccg tattcctcat     420
gaagcagatg aaaaggcagt tctgatgctg tctgacatct tacctactgc ttacgaagtt     480
ggtgttcttg ccggaaatgt ccaaaaggga gactcagttg ccattgtcgg cgccggtcca    540

```
gttggtcttg ccgctctgct gactgtcaaa gcctttgagc cttctgaaat tattatgatt     600
gacactaacg atgaaagact gagtgcctcc ttgaaattgg gagccaccaa ggcagtcaac     660
ccaaccaagg tcagcagtgt caaagatgct gtttatgata ttgtcaatgc cactgtccgc     720
gtcaaggaga acgacctgga gccaggtgtc gatgttgcca ttgagtgtgt tggtgttcct     780
gacacgtttg caacttgtga agagattatc gccccaggtg gccgtattgc caatgttggt     840
gttcacggca ctaaagtgga tttacaactg caagacctat ggatcaagaa cattgctatc     900
accaccggtt tggtagccac atactccact aaagacctgt tgaagcgagt ctctgacaag     960
tctctagacc ctacaccact ggttacacat gagttcaagt tcagtgaatt tgagaaggcc    1020
tatgagactt ctcaaaatgc tgccaccacc aaagccatca agattttctt atctgccgat    1080
taa                                                                 1083

<210> SEQ ID NO 82
<211> LENGTH: 1080
<212> TYPE: DNA
<213> ORGANISM: Artificial Sequence
<220> FEATURE:
<223> OTHER INFORMATION: Adh2_GG_cured

<400> SEQUENCE: 82
gataggtctc acatgtctcc aactatccca actacacaaa aggctgttat cttcgaaacc      60
aacggcggtc ccctagagta caaggacatt ccagtcccaa agccaaagtc aaacgaactt     120
ttgatcaacg ttaagtactc cggtgtctgt cacactgatt tgcacgcctg aagggtgac      180 tggccattgg acaacaagct tcctttggtt ggtggtcacg aaggtgctgg tgtcgttgtc     240
gcttacggtg agaacgtcac tggatgggag atcggtgact acgctggtat caaatggttg     300
aacggttctt gtttgaactg tgagtactgt atccaaggtg ctgaatccag ttgtgccaag     360
gctgacctgt ctggtttcac ccacgacgga tctttccagc agtatgctac tgctgatgcc     420
acccaagccg ccagaattcc aaaggaggct gacttggctg aagttgcccc aattctgtgt     480
gctggtatca ccgtttacaa ggctcttaag accgctgact tgcgtattgg ccaatgggtt     540
gccatttctg gtgctggtgg aggactgggt tctcttgccg ttcaatacgc caaggctctg     600
ggtttgagag ttttgggtat tgatggtggt gccgacaagg gtgaatttgt caagtccttg     660
ggtgctgagg tgttcgtcga cttcactaag actaaggacg tcgttgctga agtccaaaag     720
ctcaccaacg gtggtccaca cggtgttatt aacgtctccg tttccccaca tgctatcaac     780
caatctgtcc aatacgttag aactttgggt aaggttgttt tggttggtct gccatctggt     840
gccgttgtca actctgacgt tttctggcac gttctgaagt ccatcgagat caagggatct     900
tacgttggaa acagagagga cagtgccgag gccatcgact tgttcaccag aggttttggtc     960 aaggctccta tcaagattat cggtctgtct gaacttgcta aggtctacga acagatggag    1020
gctggtgcca tcatcggtag atacgttgtg gacacttcca ataagcttta gagaccgatc    1080

<210> SEQ ID NO 83
<211> LENGTH: 1110
<212> TYPE: DNA
<213> ORGANISM: Artificial Sequence
<220> FEATURE:
<223> OTHER INFORMATION: Adh900_GG_cured

<400> SEQUENCE: 83
gataggtctc acatgtctgt gatgaaagcc ctcgtgtacg gtggtaagaa cgtgttcgcc      60
tggaaaaact tccctaaacc aactatcttg cacccaacag atgtcatcgt taagacggtg     120
```

```
gctactacca tctgcggaac agacttgcac atcttgaaag gtgatgttcc agaggtcaaa    180
cctgaaaccg tcttgggtca tgaagcaatt ggagtcgtcg aatctatcgg tgataacgtc    240
aaaaacttca gcattggtga taaggtgctg gtttcatgca tcaccagttg tggaagctgt    300
tactactgta agagaaactt gcagagtcat tgcaagaccg gtggatggaa attaggtcac    360
gatttgaacg gtacgcaggc tgagtttgtc cgtatcccat atggagactt ctcattgcac    420
cgtattcctc atgaagcaga tgaaaaggca gttctgatgc tgtctgacat cttacctact    480
gcttacgaag ttggtgttct tgccggaaat gtccaaaagg gagactcagt tgccattgtc    540
ggcgccggtc cagttggtct tgccgctctg ctgactgtca aagcctttga gccttctgaa    600
attattatga ttgacactaa cgatgaaaga ctgagtgcct ccttgaaatt gggagccacc    660
aaggcagtca acccaaccaa ggtcagcagt gtcaaagatg ctgtttatga tattgtcaat    720
gccactgtcc gcgtcaagga gaacgacctg gagccaggtg tcgatgttgc cattgagtgt    780
gttggtgttc ctgacacgtt tgcaacttgt gaagagatta tcgccccagg tggccgtatt    840
gccaatgttg gtgttcacgg cactaaagtg gatttacaac tgcaagacct atggatcaag    900
aacattgcta tcaccaccgg tttggtagcc acatactcca ctaaagacct gttgaagcga    960
gtctctgaca agtctctaga ccctacacca ctggttacac atgagttcaa gttcagtgaa    1020
tttgagaagg cctatgagac ttctcaaaat gctgccacca ccaaagccat caagattttc    1080
ttatctgccg attaagctta gagaccgatc                                     1110

<210> SEQ ID NO 84
<211> LENGTH: 21
<212> TYPE: DNA
<213> ORGANISM: Artificial Sequence
<220> FEATURE:
<223> OTHER INFORMATION: Primer sequence

<400> SEQUENCE: 84
ttgatctttt ctacggggtg g                                              21

<210> SEQ ID NO 85
<211> LENGTH: 20
<212> TYPE: DNA
<213> ORGANISM: Artificial Sequence
<220> FEATURE:
<223> OTHER INFORMATION: Primer sequence

<400> SEQUENCE: 85
ggtgttttga agtggtacgg                                                20
```